US010844356B2

(12) United States Patent
Valamehr et al.

(10) Patent No.: US 10,844,356 B2
(45) Date of Patent: Nov. 24, 2020

(54) CELL CULTURE PLATFORM FOR SINGLE CELL SORTING AND ENHANCED REPROGRAMMING OF IPSCS

(71) Applicant: Fate Therapeutics, Inc., San Diego, CA (US)

(72) Inventors: Bahram Valamehr, San Diego, CA (US); Ramzey Abujarour, San Diego, CA (US); Peter Flynn, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/639,628

(22) Filed: Jun. 30, 2017

(65) Prior Publication Data

US 2017/0362569 A1 Dec. 21, 2017

Related U.S. Application Data

(62) Division of application No. 13/997,014, filed as application No. PCT/US2011/065900 on Dec. 19, 2011, now Pat. No. 9,732,319.

(60) Provisional application No. 61/496,991, filed on Jun. 14, 2011, provisional application No. 61/426,369, filed on Dec. 22, 2010.

(51) Int. Cl.
C12N 5/00 (2006.01)
C12N 5/074 (2010.01)

(52) U.S. Cl.
CPC ......... *C12N 5/0696* (2013.01); *C12N 5/0607* (2013.01); *C12N 2501/148* (2013.01); *C12N 2501/415* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2501/999* (2013.01); *C12N 2502/99* (2013.01); *C12N 2506/1307* (2013.01); *C12N 2533/52* (2013.01); *C12N 2533/54* (2013.01)

(58) Field of Classification Search
CPC .............. C12N 5/0696; C12N 5/0607
See application file for complete search history.

(56) References Cited

U.S. PATENT DOCUMENTS

| 4,797,368 A | 1/1989 | Carter et al. |
| 5,010,175 A | 4/1991 | Rutter et al. |
| 5,139,941 A | 8/1992 | Muzyczka et al. |
| 5,288,514 A | 2/1994 | Ellman |
| 5,384,253 A | 1/1995 | Krzyzek et al. |
| 5,478,838 A | 12/1995 | Arita et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,580,859 A | 12/1996 | Felgner et al. |
| 5,589,466 A | 12/1996 | Felgner et al. |
| 5,593,853 A | 1/1997 | Chen et al. |
| 5,656,610 A | 8/1997 | Shuler et al. |
| 5,702,932 A | 12/1997 | Hoy et al. |
| 5,736,524 A | 4/1998 | Huygen et al. |
| 5,780,448 A | 7/1998 | Davis |
| 5,789,215 A | 8/1998 | Berns et al. |
| 5,824,837 A | 10/1998 | Chen et al. |
| 5,843,780 A | 12/1998 | Thomson |
| 5,945,100 A | 8/1999 | Fick |
| 5,981,274 A | 11/1999 | Tyrrell et al. |
| 5,994,136 A | 11/1999 | Naldini et al. |
| 5,994,624 A | 11/1999 | Trolinder et al. |
| 6,013,516 A | 1/2000 | Verma et al. |
| 6,030,943 A | 2/2000 | Crumb et al. |
| 6,200,806 B1 | 3/2001 | Thomson |
| 6,534,476 B2 | 3/2003 | Miyazono et al. |
| 6,692,736 B2 | 2/2004 | Yu et al. |
| 6,696,440 B1 | 2/2004 | Bridges et al. |
| 6,703,420 B1 | 3/2004 | Hobbs, Jr. |
| 6,730,293 B1 | 5/2004 | Rothbard et al. |
| 6,875,608 B1 | 4/2005 | Smith et al. |
| 7,029,913 B2 | 4/2006 | Thomson |

(Continued)

FOREIGN PATENT DOCUMENTS

| CN | 101356270 A | 1/2009 |
| CN | 101563449 A | 10/2009 |

(Continued)

OTHER PUBLICATIONS

Sylvester et al. Arch Surg.139:93-99, 2004. (Year: 2004).*
Moon et al. Inter J Stem Cells 4(1):24-34, 2011 (Year: 2011).*
Bedel et al. Stem Cell Transplantation Medicine 6:382-393, 2017 (Year: 2017).*
Amit et al. Developmental Biology 227:271-278, 2000 (Year: 2000).*
Aasen et al., "Efficient and rapid generation of induced pluripotent stem cells from human keratinocytes", Nature Biotechnology, 26:1276-1284 (2008).
Adcock, "HDAC inhibitors as anti-inflammatory agents", British Journal of Pharmacology, 150(7):829-831 (2007).

(Continued)

*Primary Examiner* — Marcia S Noble
(74) *Attorney, Agent, or Firm* — Mintz Levin Cohn Ferris Glovsky and Popeo, P.C.

(57) ABSTRACT

The invention provides cell culture conditions for culturing stem cells, including feeder-free conditions for generating and culturing human induced pluripotent stem cells (iPSCs). More particularly, the invention provides a culture platform that allows long-term culture of pluripotent cells in a feeder-free environment; reprogramming of cells in a feeder-free environment; single-cell dissociation of pluripotent cells; cell sorting of pluripotent cells; maintenance of an undifferentiated status; improved efficiency of reprogramming; and generation of a naïve pluripotent cell.

20 Claims, 54 Drawing Sheets
Specification includes a Sequence Listing.

(56) References Cited

U.S. PATENT DOCUMENTS

| | | |
|---|---|---|
| 7,265,138 B2 | 9/2007 | Doherty et al. |
| 7,585,844 B2 | 9/2009 | Turner et al. |
| 8,044,201 B2 | 10/2011 | Xu et al. |
| 8,298,825 B1 | 10/2012 | Hochedlinger et al. |
| 8,524,498 B2 | 9/2013 | Geijsen et al. |
| 8,603,818 B1 | 12/2013 | Hochedlinger et al. |
| 8,906,677 B2 | 12/2014 | Li et al. |
| 9,005,968 B2 * | 4/2015 | Lin ............... C12N 5/0696 435/377 |
| 9,068,170 B2 | 6/2015 | Zhou et al. |
| 9,166,832 B1 | 10/2015 | Li et al. |
| 9,295,697 B2 * | 3/2016 | Yu ............... A61K 35/545 |
| 9,394,524 B2 | 7/2016 | Shi et al. |
| 9,534,205 B2 | 1/2017 | Shi et al. |
| 9,540,615 B2 | 1/2017 | Shi et al. |
| 9,732,319 B2 | 8/2017 | Valamehr et al. |
| 2002/0142457 A1 | 10/2002 | Umezawa et al. |
| 2003/0087919 A1 | 5/2003 | Nagarathnam et al. |
| 2003/0125344 A1 | 7/2003 | Nagarathnam et al. |
| 2003/0204862 A1 | 10/2003 | Kuehn et al. |
| 2004/0002507 A1 | 1/2004 | Nagarathnam et al. |
| 2004/0002508 A1 | 1/2004 | Nagarathnam et al. |
| 2004/0014755 A1 | 1/2004 | Nagarathnam et al. |
| 2004/0157324 A1 | 8/2004 | Spradling et al. |
| 2005/0075276 A1 | 4/2005 | Rudd |
| 2005/0119203 A1 | 6/2005 | Steinbrecher et al. |
| 2005/0130144 A1 | 6/2005 | Nakatsuji et al. |
| 2005/0192304 A1 | 9/2005 | Nagarathnam et al. |
| 2005/0209261 A1 | 9/2005 | Nagarathnam et al. |
| 2006/0182724 A1 | 8/2006 | Riordan |
| 2007/0032447 A1 | 2/2007 | Eilertsen |
| 2007/0128719 A1 | 6/2007 | Tseng et al. |
| 2007/0134215 A1 | 6/2007 | Fukuda et al. |
| 2007/0141703 A1 | 6/2007 | Xu et al. |
| 2007/0149484 A1 | 6/2007 | Claus et al. |
| 2007/0161107 A1 | 7/2007 | Mummery et al. |
| 2007/0172946 A1 | 7/2007 | Smith et al. |
| 2007/0196919 A1 | 8/2007 | Reh et al. |
| 2007/0254359 A1 | 11/2007 | Rezania et al. |
| 2007/0259423 A1 | 11/2007 | Odorico et al. |
| 2007/0264709 A1 | 11/2007 | Smith et al. |
| 2007/0269412 A1 | 11/2007 | Kopyov |
| 2007/0281355 A1 | 12/2007 | Dalton et al. |
| 2008/0004287 A1 | 1/2008 | Ma et al. |
| 2008/0066197 A1 | 3/2008 | Ying et al. |
| 2008/0242594 A1 | 10/2008 | McKay et al. |
| 2008/0268533 A1 | 10/2008 | Dalton et al. |
| 2009/0068742 A1 | 3/2009 | Yamanaka |
| 2009/0117439 A1 | 5/2009 | Fujinami et al. |
| 2009/0203690 A1 | 8/2009 | Akritopoulou-Zanze et al. |
| 2009/0227032 A1 | 9/2009 | Yamanaka et al. |
| 2009/0299763 A1 | 12/2009 | Sakurada |
| 2009/0304646 A1 | 12/2009 | Sakurada et al. |
| 2010/0009442 A1 | 1/2010 | Sasai et al. |
| 2010/0093090 A1 | 4/2010 | Deng et al. |
| 2010/0233804 A1 | 9/2010 | Zhou et al. |
| 2010/0267141 A1 | 10/2010 | Shi et al. |
| 2010/0303775 A1 | 12/2010 | Raya |
| 2011/0033931 A1 | 2/2011 | Schwartz et al. |
| 2011/0039332 A1 | 2/2011 | Sakurada et al. |
| 2011/0039338 A1 | 2/2011 | Yamanaka et al. |
| 2011/0110899 A1 | 5/2011 | Shi et al. |
| 2011/0306516 A1 | 12/2011 | Kahler et al. |
| 2012/0009676 A1 * | 1/2012 | Mack ............... C12N 5/0696 435/372 |
| 2012/0058562 A1 * | 3/2012 | Thomson ............. C12N 5/0696 435/455 |
| 2012/0122212 A1 | 5/2012 | Grskovic et al. |
| 2012/0129172 A1 | 5/2012 | Okano et al. |
| 2012/0196360 A1 | 8/2012 | Okita et al. |
| 2012/0220034 A1 | 8/2012 | Ahlfors et al. |
| 2012/0264218 A1 | 10/2012 | Lin et al. |
| 2013/0273536 A1 | 10/2013 | Shi et al. |
| 2013/0323833 A1 | 12/2013 | Zhu et al. |
| 2014/0220681 A1 | 8/2014 | Valamehr et al. |
| 2014/0369973 A1 | 12/2014 | Bernstein et al. |
| 2015/0079675 A1 | 3/2015 | Li et al. |
| 2015/0240214 A1 | 8/2015 | Lin et al. |
| 2016/0369244 A1 | 12/2016 | Shi et al. |
| 2017/0073643 A1 | 3/2017 | Valamehr et al. |
| 2018/0155717 A1 | 6/2018 | Valamehr et al. |
| 2019/0218520 A1 | 7/2019 | Valamehr et al. |

FOREIGN PATENT DOCUMENTS

| | | |
|---|---|---|
| CN | 102597221 A | 7/2012 |
| EP | 1970446 A1 | 9/2008 |
| EP | 1992360 A1 | 11/2008 |
| EP | 3 371 314 A1 | 9/2018 |
| GB | 2 436 737 A | 10/2007 |
| GB | 2 450 603 A | 12/2008 |
| JE | 2012-510526 A | 5/2012 |
| JP | 2007/508026 A | 4/2007 |
| JP | 2008-099662 A | 5/2008 |
| JP | 2008/307007 A | 12/2008 |
| JP | 2010-504090 A | 2/2010 |
| JP | 2010/529851 A | 9/2010 |
| JP | 2013-507932 A | 3/2013 |
| JP | 2013-509864 A | 3/2013 |
| WO | WO 1991/019735 A1 | 12/1991 |
| WO | WO 1992/000091 A1 | 1/1992 |
| WO | WO 1993/020242 A1 | 10/1993 |
| WO | WO 1997/000271 A1 | 3/1997 |
| WO | WO 1998/006433 A1 | 2/1998 |
| WO | WO 1999/001426 A1 | 1/1999 |
| WO | WO 2000/078351 A1 | 12/2000 |
| WO | WO 2001/017562 A1 | 3/2001 |
| WO | WO 2002/006213 A2 | 1/2002 |
| WO | WO 2002/076976 A2 | 10/2002 |
| WO | WO 2002/076977 A2 | 10/2002 |
| WO | WO 2002/088346 A2 | 11/2002 |
| WO | WO 2003/059913 A1 | 7/2003 |
| WO | WO 2003/062225 A1 | 7/2003 |
| WO | WO 2003/062227 A1 | 7/2003 |
| WO | WO 2003/077914 A1 | 9/2003 |
| WO | WO 2003/082808 A1 | 10/2003 |
| WO | WO 2003/095628 A2 | 11/2003 |
| WO | WO 2004/039796 A1 | 5/2004 |
| WO | WO 2004/045617 A1 | 6/2004 |
| WO | WO 2005/035506 A1 | 4/2005 |
| WO | WO 2005/051301 A2 | 6/2005 |
| WO | WO 2005/074643 A2 | 8/2005 |
| WO | WO 2005/084158 A2 | 9/2005 |
| WO | WO 2007/016566 A2 | 2/2007 |
| WO | WO 2007/044084 A2 | 4/2007 |
| WO | WO 2007/069666 A1 | 6/2007 |
| WO | WO 2007/085827 A2 | 8/2007 |
| WO | WO 2007/113505 A2 | 10/2007 |
| WO | WO 2007/123667 A2 | 11/2007 |
| WO | WO 2008/006583 A1 | 1/2008 |
| WO | WO 2008/011093 A2 | 1/2008 |
| WO | WO 2009/006422 A1 | 1/2008 |
| WO | WO 2008/015418 A2 | 2/2008 |
| WO | WO 2008/035110 A1 | 3/2008 |
| WO | WO 2008/056173 A2 | 5/2008 |
| WO | WO 2008/088882 A2 | 7/2008 |
| WO | WO 2008/089351 A1 | 7/2008 |
| WO | WO 2008/094597 A2 | 8/2008 |
| WO | WO 2008/105630 A1 | 9/2008 |
| WO | WO 2008/108741 A1 | 9/2008 |
| WO | WO 2008/126932 A2 | 10/2008 |
| WO | WO 2008/129554 | 10/2008 |
| WO | WO 2009/007851 A2 | 1/2009 |
| WO | WO 2009/007852 A1 | 1/2009 |
| WO | WO 2009/032194 A1 | 3/2009 |
| WO | WO 2009/032456 A2 | 3/2009 |
| WO | WO 2009/057831 A1 | 5/2009 |
| WO | WO 2009/061442 A1 | 5/2009 |
| WO | WO 2009/067756 A1 | 6/2009 |
| WO | WO 2009/067757 A1 | 6/2009 |
| WO | WO 2009/073523 A2 | 6/2009 |
| WO | WO 2009/115295 A1 | 9/2009 |
| WO | WO 2009/117439 A1 | 9/2009 |
| WO | WO 2010/053472 A1 | 5/2010 |

(56) References Cited

FOREIGN PATENT DOCUMENTS

| WO | WO 2010/065721 A1 | 6/2010 |
|---|---|---|
| WO | WO 2010/077955 A1 | 7/2010 |
| WO | WO 2010/120785 A2 | 10/2010 |
| WO | WO 2011/047300 A1 | 4/2011 |
| WO | WO 2011/056971 A2 | 5/2011 |
| WO | WO-2011/090221 A1 | 7/2011 |
| WO | WO 2011/109695 A1 | 9/2011 |
| WO | WO-2011/159692 A1 | 12/2011 |
| WO | WO 2012/087965 A2 | 6/2012 |
| WO | WO 2013/070852 A2 | 5/2013 |
| WO | WO 2015/134652 A1 | 9/2015 |
| WO | WO-2017/066634 A1 | 4/2017 |

OTHER PUBLICATIONS

Adhikary and Eilers, "Transcriptional regulation and transformation by Myc proteins", Nat Rev Mol Cell Biol., 6(8): 635-645 (2005).
Alessi et al., "Characterization of a 3-phosphoinositide-dependent protein kinase which phosphorylates and activates protein kinase Bα", Current Biology, 7(4): 261-269 (1997).
Aoi et al., "Generation of Pluripotent Stem Cells from Adult Mouse Liver and Stomach Cells," Science Express, Feb. 2008 (Corrected Aug. 2008), DOI 10.1126/science.1154884, 8 pages.
Artyomov et al., "A model for genetic and epigenetic regulatory networks identifies rare pathways for transcription factor induced pluripotency", PLoS Computational Biology, 6(5): e1000785, 1-14 (2010).
Barrett et al., "The discovery of the benzhydromate MEK inhibitors CI-1040 and PD 0325901," Bioorganic & Medicinal Chemistry Letters, 18(24):6501-6504 (2008).
Beaujean et al., "Induction of early transcription in one-cell mouse embryos by microinjection of the nonhistone chromosomal protein HMG-I", Developmental Biology, 221(2): 337-354 (2000).
Bertrand, "Structural Characterization of the GSK-3β Active Site Using Selective and Non-selective ATP-mimetic Inhibitors", Journal of Molecular Biology, 333(2): 393-407 (2003).
Blelloch et al., "Reprogramming efficiency following somatic cell nuclear transfer is influenced by the differentiation and methylation state of the donor nucleus", Stem Cells, 24(9): 2007-2013 (2006).
Blömer et al., "Highly efficient and sustained gene transfer in adult neurons with a lentivirus vector", Journal of Virology, 71(9):6641-6649 (1997).
Brambrink et al., "Sequential expression of pluripotency markers during direct reprogramming of mouse somatic cells", Cell Stem Cell, 2(2): 151-159 (2008).
Brons et al., "Derivation of pluripotent epiblast stem cells from mammalian embryos", Nature, 448: 191-195 (2007).
Brueckner, et al., "Epigenetic reactivation of tumor suppressor genes by a novel small-molecule inhibitor of human DNA methyltransferases", Cancer Research, 65(14): 6305-6311 (2005).
Byfield et al., "SB-505124 is a selective inhibitor of transforming growth factor-β type I receptors ALK4, ALK5, and ALK7", Molecular Pharmacology, 65(3):744-752 (2004).
Callahan et al., "Identification of novel inhibitors of the transforming growth factor β1 (TGF-β1) Type 1 receptor (ALK5)", J. Med Chem., 45(5): 999-1001 (2002). (Abstract).
Chahine et al., "Modulation of L-type Ca2+ channels in neonatal rat heart by a novel Ca2+ channel agonist", Canadian Journal of Physiology and Pharmacology, 81(2): 135-141 (2003).
Chambers et al., "Nanog safeguards pluripotency and mediates germline development", Nature, 450: 1230-1234 (2007).
Chang et al., "Transforming growth factor-beta signaling in breast cancer", Frontiers in Bioscience, 12: 4393-4401 (2007).
Chen and Okayama, "High-efficiency transformation of mammalian cells by plasmid DNA", Molecular and Cellular Biology, 7(8): 2745-2752 (1987).
Chen et al., ""Analogous" Organic Synthesis of Small-Compound Libraries: Validation of Combinatorial Chemistry in Small-Molecule Synthesis", J. Amer. Chem. Soc., 116(6): 2661-2662 (1994).

Chen et al., "Reversine increases the plasticity of lineage-committed mammalian cells", PNAS, 104(25): 10482-10487 (2007).
Chen et al., "Self-renewal of embryonic stem cells by a small molecule," PNAS, 103(46): 17266-17271 (2006).
Chin et al., "Induced pluripotent stem cells and embryonic stem cells are distinguished by gene expression signatures," Cell Stem Cell 5, Jul. 2009, pp. 111-123.
Chin et al., "Inhibition of GSK3β is a common event in neuroprotection by different survival factors", Molecular Brain Research, 137(1-2):193-201 (2005).
Chin et al., "Molecular analyses of human induced pluripotent stem cells and embryonic stem cells," Cell Stem Cell 7, Aug. 2010, pp. 263-269.
Cho et al., "An unnatural biopolymer", Science, 261(5126): 1303-1305 (1993).
Chou et al., "The growth factor environment defines distinct pluripotent ground states in novel blastocyst-derived stem cells", Cell, 135(3): 449-461 (2008).
Chow, et al., "Measurement of MAP kinase activation by flow cytometry using phospho-specific antibodies to MEK and ERK: Potential for pharmacodynamic monitoring of signal transduction inhibitors", Cytometry (Communications in Clinical Cytometry), 46(2): 72-78 (2001).
Christen et al., "Regeneration and reprogramming compared", BMC Biol, 8: 5, 14 pages (2010).
Claassen et al., "ROCK inhibition enhances the recovery and growth of cryopreserved human embryonic stem cells and human induced pluripotent stem cells", Molecular Reproduction and Development, 76(8): 722-732 (2009).
Collas et al., "On the way to reprogramming cells to pluripotency using cell-free extracts", Reproductive BioMedicine Online, 12(6): 762-770 (2006).
Colman and Dreesen, "Induced pluripotent stem cells and the stability of the differentiated state", EMBO Reports,10(7): 714-721 (2009).
Condorelli, G. et al., "Cardiomyocytes induce endothelial cells to trans-differentiate into cardiac muscle: Implications for myocardium regeneration," PNAS, 98(19): 10733-10738 (2001).
Conti et al., "Niche-independent symmetrical self-renewal of a mammalian tissue stem cell", PLoS Biol., 3(9): e283, 1594-1606 (2005).
Cotten et al., "High-efficiency receptor-mediated delivery of small and large (48 kilobase gene constructs using the endosome-disruption activity of defective or chemically inactivated adenovirus particles", PNAS, 89(13): 6094-6098 (1992).
Cui et al., "Selective inhibition of TGF-β responsive genes by Smad-interacting peptide aptamers from FoxH1, Lef1 and CBP", Oncogene, 24: 3864-3874 (2005).
D'Amour et al., "Efficient differentiation of human embryonic stem cells to definitive endoderm", Nat Biotechnol, 23(12): 1534-1541 (2005).
Dang et al., "The biology of the mammalian Krüppel-like family of transcription factors", The International Journal of Biochemistry & Cell Biology, 32(11-12): 1103-1121 (2000).
Darenfed, et al., "Molecular characterization of the effects of Y-27632", Cell Motil Cytoskeleton, 64(2): 97-109 (2007).
De Gouville and Huet, "Inhibition of ALK5 as a new approach to treat liver fibrotic diseases", Drug News Perspective, 19(2): 85-90 (2006).
Debs et al., "Regulation of gene expression in vivo by liposome-mediated delivery of a purified transcription factor", The Journal of Biological Chemistry, 265: 10189-10192 (1990).
Demers et al., "Rat embryonic stem-like (ES-like) cells can contribute to extraembryonic tissues in vivo", Cloning Stem Cells, 9(4): 512-522 (2007).
Djuric and Ellis, "Epigenetics of induced pluripotency, the seven-headed dragon", Stem Cell Research and Therapy, 1(1):3, 7 pages (2010).
Dimos et al., "Induced pluripotent stem cells generated from patients with ALS can be differentiated into motor neurons", Science, 321(5893): 1218-1221 (2008).
Do and Schöler, "Nuclei of embryonic stem cells reprogram somatic cells", Stem Cells, 22(6): 941-949 (2004).

(56) References Cited

OTHER PUBLICATIONS

Do, J. T. et al., "Erasure of cellular memory by fusion with pluripotent cells", Stem Cells, 25(4): 1013-1020 (2007).
Dravida, S. et al., "The transdifferentiation potential of limbal fibroblast-like cells," Developmental Brain Research, 160(2): 239-251 (2005).
Dvorak et al., "Expression and potential role of fibroblast growth factor 2 and its receptors in human embryonic stem cells", Stem Cells, 23(8): 1200-1211 (2005).
Efe, Jem E. et al., "Conversion of mouse fibroblasts into cardiomyocytes using a direct reprogramming strategy," Nature Cell Biology, 13(3): 215-222 (2011).
Egler et al., "Histone Deacetylase Inhibition and Blockade of the Glycolytic Pathway Synergistically Induce Glioblastoma Cell Death", Clin. Cancer Res., 14(10): 3132-3140 (2008).
Elliott and O'Hare, "Intercellular trafficking and protein delivery by a herpesvirus structural protein", Cell, 88(2): 223-233 (1997).
Emre et al., "The ROCK inhibitor Y-27632 improves recovery of human embryonic stem cells after fluorescence-activated cell sorting with multiple cell surface markers", PLoS One, 5(8): e12148 (2010).
Engel et al., "Allosteric activation of the protein kinase PDK1 with low molecular weight compounds", The EMBO Journal, 25(23): 5469-5480 (2006).
English and Cobb, "Pharmacological inhibitors of MAPK pathways", Trends in Pharmaceutical Sciences, 23(1): 40-45 (2002).
EP Application No. 09721278.1, Extended European Search Report dated Jun. 1, 2011, 11 pages.
EP Application No. 10824189.4, Extended European Search Report dated May 29, 2013, 8 pages.
EP Application No. 11852133.5, Extended European Search Report dated Aug. 13, 2014, 7 pages.
EP Application No. 15177122.7, Extended European Search Report dated Oct. 27, 2015.
Epsztejn-Litman, et al., "De novo DNA methylation promoted by G9a prevents reprogramming of embryonically silenced genes", Nature Structural & Molecular Biology, 15(11): 1176-1183, 9 pages(2008).
Ernst et al., "gp130-mediated Signal Transduction in Embryonic Stem Cells Involves Activation of Jak and Ras/Mitogen-activated Protein Kinase Pathways", J. Biol. Chem., 271(47): 30163-30143 (1996).
Esteban et al., "Vitamin C enhances the generation of mouse and human induced pluripotent stem cells", Cell Stem Cell, 6(1): 71-79 (2010). Epub Dec. 31, 2009.
Fang et al., "Tea polyphenol (−)-epigallocatechin-3-gallate inhibits DNA methyltransferase and reactivates methylation-silenced genes in cancer cell lines", Cancer Research, 63: 7563-7570 (2003).
Feldman et al., "G9a-mediated irreversible epigenetic inactivation of Oct-3/4 during early embryogenesis", Nature Cell Biology, 8(2): 188-194 (2006).
Feng et al, "Molecules that Promote or Enhance Reprogramming of Somatic Cells to Induced pluripotent stem cells", Cell Stem Cell, 4(4):301-312 (2009).
Fernandes et al., "A dermal niche for multipotent adult skin-derived precursor cells", Nature Cell Biology, 6: 1082-1093 (2004).
Frame and Cohen, "GSK3 takes centre stage more than 20 years after its discovery", Biochemical Journal, 359(Pt 1): 1-16 (2001).
Frankel and Pabo, "Cellular uptake of the tat protein from human immunodeficiency virus", Cell, 55(6): 1289-1193 (1988).
Franzén et al., "Cloning of a TGFβ type I receptor that forms a heteromeric complex with the TGFβ type II receptor", Cell, 75(4): 681-692 (1993).
Furumai et al., "Potent histone deacetylase inhibitors built from trichostatin A and cyclic tetrapeptide antibiotics including trapoxin", PNAS, 98(1): 87-92 (2001).
Gellibert et al., "Discovery of 4-{4-[3-(Pyridin-2-yl)-1H-pyrazol-4-yl]pyridin-2-yl}-N-(tetrahydro-2H-pyran-4-yl)benzamide (GW788388): A Potent, Selective, and Orally Active Transforming Growth Factor-β Type I Receptor Inhibitor", Journal Medicinal Chemistry, 49(7): 2210-2221 (2006).
Gonzalez et al., "Generation of mouse-induced pluripotent stem cells by transient expression of a single nonviral polycistronic vector", PNAS, 106(22): 8918-8922 (2009).
Gopal, "Gene transfer method for transient gene expression, stable transformation, and cotransformation of suspension cell cultures", Molecular and Cellular Biology, 5(5):1188-1190 (1985).
Gore, "Combination therapy with DNA methyltransferase inhibitors in hematologic malignancies", Nature Clinical Practice Oncology, 2(Suppl 1): S30-S35 (2005).
Gore, et al., "Combined DNA methyltransferase and histone deacetylase inhibition in the treatment of myeloid neoplasms", Cancer Research, 66(12): 6361-6369 (2006).
Gould et al., "Effects of a glycogen synthase kinase-3 inhibitor, lithium, in adenomatous polyposis coli mutant mice", Pharmacological Research, 48(1): 49-53 (2003).
Gould, et al., "AR-A014418, a selective GSK-3 inhibitor, produces antidepressant-like effects in the forced swim test", The International Journal of Neuropsychopharmacology, 7(4): 387-390 (2004).
Graf and Enver, "Forcing cells to change lineages", Nature, 462(7273): 587-594 (2009).
Graham and Van Der Eb, "A new technique for the assay of infectivity of human adenovirus 5 DNA", Virology, 52(2): 456-467 (1973).
Green and Lowenstein, "Autonomous functional domains of chemically synthesized human immunodeficiency virus tat trans-activator protein", Cell, 55(6): 1179-1188 (1988).
Grunhaus et al., "Association of vaccinia virus-expressed adenovirus E3-19K glycoprotein with class I MHC and its effects on virulence in a murine pneumonia model", Seminar in Virology, 200(2):535-546 (1992).
Gump et al., "TAT transduction: the molecular mechanism and therapeutic prospects", (2007) Trends Mol Med. Oct;13(10):443-8 (2007).
Guo et al., "Klf4 reverts developmentally programmed restriction of ground state pluripotency", Development, 136: 1063-1069 (2009).
Hakelien et al., "Transient alteration of cell fate using a nuclear and cytoplasmic extract of an insulinoma cell line," BBRC, 316: 834-841 (2004).
Han and Sidhu, "Current concepts in reprogramming somatic cells to pluripotent state", Curr Stem Cell Res Ther, 3: 66-74 (2008).
Han and Yoon, "Induced pluripotent stem cells: emerging techniques for nuclear reprogramming", Antioxidants & Redox Signaling, 15(7): 1799-1820 92011).
Han et al., "Direct reprogramming of fibroblasts into epiblast stem cells", Nat Cell Biol, 13(1): 66-71 (2011).
Han et al., "HDAC inhibitors TSA and sodium butyrate enhanced the human IL-5 expression by altering histone acetylation status at its promoter region", Immunology Letters, 108(2):143-150 (2007).
Hanna et al, "Treatment of Sickle Cell Anemia Mouse Model with iPS Cells Generated from Autologous Skin," Science, 318: 1920-1922 (2007).
Hanna et al., "Direct cell reprogramming is a stochastic process amenable to acceleration", Nature, 462: 595-601 (2009).
Hanna et al., "Direct reprogramming of terminally differentiated mature B lymphocytes to pluripotency", Cell, 133: 250-264 (2008).
Hay, "An overview of epithelio-mesenchymal transformation", Acta Anat. (Basel) 154: 8-20 (1995).
Hayashi et al., "Dynamic equilibrium and heterogeneity of mouse pluripotent stem cells with distinct functional and epigenetic states", Cell Stem Cell, 3(4): 391-401 (2008).
Heo et al., "EGF stimulates proliferation of mouse embryonic stem cells: involvement of Ca2+ influx and p44/42 MAPKs", Am J Physiol Cell Physiol, 290(1): C123-133 (2006).
Hindie et al., "Structure and allosteric effects of low-molecular-weight activators on the protein kinase PDK1," Nat Chem Biol, 5(10): 758-764 (2009).
Ho et al., "Synthetic Protein Transduction Domains. Enhanced Transduction Potential in Vitro and in Vivo", Cancer Res., 61: 474-477 (2001).
Hochedlinger et al., "Epigenetic reprogramming and induced pluripotency", Development, 136(4): 509-23 (2009).

(56) References Cited

OTHER PUBLICATIONS

Hochedlinger, et al., "Ectopic expression of Oct-4 blocks progenitor-cell differentiation and causes dysplasia in epithelial tissues", Cell, 121(3): 465-477 (2005).
Hochedlinger, et al., "Nuclear reprogramming and pluripotency," Nature, 441: 1061-1067 (2006).
Hong et al., "Suppression of induced pluripotent stem cell generation by the p53-p21 pathway", Nature, 460: 1132-1135 (2009).
Hou, et al., "VEGI-192, a New Isoform of TNFSF15, Specifically Eliminates Tumor Vascular Endothelial Cells and Suppresses Tumor Growth", Clinical Cancer Research, 11: 5595-5602 (2005).
Huangfu et al., "Induction of pluripotent stem cells by defined factors is greatly improved by small-molecule compounds", Nature Biotechnology, 26: 795-797 (2008).
Huangfu et al., "Induction of pluripotent stem cells from primary human fibroblasts with only Oct4 and Sox2", Nature Biotechnology, 26(11): 1269-1275 (2008).
Hudecz et al., "Medium-sized peptides as built in carriers for biologically active compounds," Medicinal Research Reviews, 25(6):679-736 (2005).
Ichida et al., "A small-molecule inhibitor of tgf-Beta signaling replaces sox2 in reprogramming by inducing nanog", Cell Stem Cell, 5(5): 491-503(2009).
Ieda et al., "Direct reprogramming of fibroblasts into functional cardiomyocytes by defined factors", Cell, 142, 375-86 (2010).
Inman et al., "SB-431542 is a potent and specific inhibitor of transforming growth factor-β Superfamily Type I Activin Receptor-Like Kinase (ALK) Receptors ALK4, ALK5, and ALK7", Molecular Pharmacology, 62(1): 65-74 (2002).
Ishizaki et al., "Pharmacological properties of Y-27632, a specific inhibitor of rho-associated kinases", Mol. Pharmacol., 57: 976-983 (2000).
Jia et al., "A nonviral minicircle vector for deriving human iPS cells", Nat Methods, 7(3): 197-199 (2010).
Joliot et al., "alpha-2,8-Polysialic acid is the neuronal surface receptor of antennapedia homeobox peptide", New Biol., 3(11): 1121-1134 (1991).
Joliot et al., "Antennapedia homeobox peptide regulates neural morphogenesis", Proc. Natl. Acad. Sci. USA, 88(5): 1864-1868 (1991).
Kaji, et al., "Virus-free induction of pluripotency and subsequent excision of reprogramming factors", Nature, 458(7239): 771-775 (2009).
Kaminska, et al., "TGF beta signalling and its role in tumour pathogenesis", Acta Biochimica Polonica, 52(2): 329-337 (2005).
Kanatsu-Shinohara et al., "Generation of pluripotent stem cells from neonatal mouse testis", Cell, 119(7): 1001-1012 (2004).
Kelly, et al., "Drug insight: Histone deacetylase inhibitors—development of the new targeted anticancer agent suberoylanilide hydroxamic acid", Nature Clinical Practice Oncology, 2(3): 150-157 (2005).
Kennedy and Henderson, "Chronic exposure to morphine does not induce dependence at the level of the calcium channel current in human SH-SY5Y cells", Neuroscience, 49(4): 937-44 (1992).
Kim et al. "Pluripotent stem cells induced from adult neural stem cells by reprogramming with two factors", Nature, 454(7204): 646-651 (2008).
Kim et al., "ct4-induced pluripotency in adult neural stem cells", Cell, 136(3): 411-419, (2009).
Kim et al., "Direct reprogramming of human neural stem cells by OCT4," Nature, 461(7264):649-653 (2009).
Kim et al., "Direct reprogramming of mouse fibroblasts to neural progenitors", Proc. Natl. Acad. Sci., USA, 108(9): 7838-7843 (2011).
Kim et al., "Generation of Human Induced Pluripotent Stem Cells by Direct Delivery of Reprogramming Proteins," Cell Stem Cell, 4(6): 472-476 (2009).
Kim et al., Eur J Biochem, "Enzymic properties of recombinant BACE2", Eur. J. Biochem., 269(22): 5668-5677 (2002).
Kim, et al., "Pharmacokinetics and tissue distribution of 3-((5-(6-methylpyridin-2-yl)-4-(quinoxalin-6-yl)-1H-imidazol-2-yl)methyl)benzamide; a novel ALK5 inhibitor and a potential anti-fibrosis drug", Xenobiotica, 38(3): 325-339 (2008).
Klein et al., "The effects of a novel MEK inhibitor PD184161 on MEK-ERK signaling and growth in human liver cancer", Neoplasia, 8: 1-8 (2006).
Krippl et al., "Functions of purified E1A protein microinjected into mammalian cells", Proc. Natl. Acad. Sci. USA, 81(22): 6988-6992 (1984).
Kubicek et al., "Reversal of H3K9me2 by a Small-Molecule Inhibitor for the G9a Histone Methyltransferase," Molecular Cell, 25(3): 473-481 (2007).
Kuzmenkin et al., "Functional characterization of cardiomyocytes derived from murine induced pluripotent stem cells in vitro", FASEB J., 23(12): 4168-4180 (2009).
Lafevre, et al., "Recombinant, refolded tetrameric p53 and gonadotropin-releasing hormone-p53 slow proliferation and induce apoptosis in p53-deficient cancer cells", Molecular Cancer Therapeutics, 7(6): 1420-1429 (2008).
Leroux et al., "Neurotrophic activity of the Antennapedia homeodomain depends on its specific DNA-binding properties", Proc. Natl. Acad. Sci. USA, 90(19): 9120-9124 (1993).
Levenson, "DNA (cytosine-5) methyltransferase inhibitors: a potential therapeutic agent for schizophrenia", Molecular Pharmacology, 71(3): 635-637 (2007).
Li and Ding, "Generation of novel rat and human pluripotent stem cells by reprogramming and chemical approaches," Methods in Molecular Biology, 636:293-300 (2010).
Li et al., "Generation of Human-induced Pluripotent Stem Cells in the Absence of Exogenous Sox2", Stem Cells, 27: 2992-3000 (2009).
Li et al., "MEK/ERK signaling contributes to the maintenance of human embryonic stem cell self-renewal", Differentiation, 75(4): 299-307 (2007).
Li et al., "Generation of rat and human induced pluripotent stem cells by combining genetic reprogramming and chemical inhibitors," Cell Stem Cell, 4(1): 16-19 (2009).
Li et al., "Small molecules that modulate embryonic stem cell fate and somatic cell reprogramming," Trends Pharmacal Sci, 31(1): 36-45 (2010).
Liang et al., "Cyclic adenosine 3',5'-monophosphate-dependent activation of mitogen-activated protein kinase in cumulus cells is essential for germinal vesicle breakdown of porcine cumulus-enclosed oocyte", Endocrinology, 146(10): 4437-4444 (2005).
Lin et al., "A chemical platform for improved induction of human iPSCs", Nat Methods, 6(11): 805-808 (2009).
Lin et al., "A chemical platform for improved induction of human iPSCs", Nat Methods, 6:805-808, Supplemental Information, 7 pages (2009).
Lin et al., "Relationships of human immunodeficiency virus protease with eukaryotic aspartic proteases", Methods Enzymol, 241:195-224 (1994).
Liu, et al., "The calcium channel ligand FPL 64176 enhances L-type but inhibits N-type neuronal calcium currents", Neuropharmacology, 45(2): 281-292 (2003).
Loh et al., "Generation of induced pluripotent stem cells from human blood," Blood, 113(22): 5476-5479 (2009).
Lowry et al., "Generation of human induced pluripotent stem cells from dermal fibroblasts", Proc Natl Acad Sci USA, 105: 2883-2888 (2008).
Lyssiotis et al.,"Reprogramming of murine fibroblasts to induced pluripotent stem cells with chemical complementation of Klf4", PNAS, 106:8912-8917 (2009).
Ma et al., "G9a and Jhdm2a regulate embryonic stem cell fusion-induced reprogramming of adult neural stem cells", Stem Cells, 26(8):2131-2141 (2008).
Maeda et al., "Endogenous TGF-β signaling suppresses maturation of osteoblastic mesencymal cells," The EMBO Journal, vol. 23, No. 3, Jan. 2004, pp. 552-563.
Maherali et al., "A high-efficiency system for the generation and study of human induced pluripotent stem cells", Cell Stem Cell, 3(3):340-345 (2008).

(56) References Cited

OTHER PUBLICATIONS

Maherali et al., "Guidelines and techniques for the generation of induced pluripotent stem cells", Cell Stem Cell, 3(6):595-605 (2008).
Maherali et al., "Directly Reprogrammed Fibroblasts Show Global Epigenetic Remodeling and Widespread Tissue Contribution," Cell Stem Cell, 1:55-70 (2007).
Maherali et al., "Tgfβ Signal Inhibition Cooperates in the Induction of iPSCs and Replaces Sox2 and cMyc," Curr. Biology, 19: 1718-1723 (2009).
Mali et al., "Improved efficiency and pace of generating induced pluripotent stem cells from human adult and fetal fibroblasts", Stem Cells, 26(8): 1998-2005 (2008).
Manning et al., "AKT/PKB signaling: navigating downstream", Cell, 129(7): 1261-1274 (2007).
Marson et al., "Wnt signaling promotes reprogramming of somatic cells to pluripotency", Cell Stem Cell, 3(2): 132-135 (2008).
Martin et al., "Toll-like receptor-mediated cytokine production is differentially regulated by glycogen synthase kinase 3", Nature Immunology, 6(8): 777-784 (2005).
Massagué and Chen, "Controlling TGF-beta signaling", Genes Dev, 14(6): 627-644 (2000).
Massagué, J. "TGF-beta signal transduction", Annu Rev Biochem, 67: 753-791 (1998).
Mattingly et al., "The mitogen-activated protein kinase/extracellular signal-regulated kinase kinase inhibitor PD184352 (CI-1040) selectively induces apoptosis in malignant schwannoma cell lines", The Journal of Pharmacology and Experimental Therapeutics, 316(1): 456-465 (2006).
Meissner et al., "Direct reprogramming of genetically unmodified fibroblasts into pluripotent stem cells," Nature Biotechnology, 25(10): 1177-1181 (2007).
Mikkelsen et al., "Dissecting direct reprogramming through integrative genomic analysis", Nature, 454(7200) :49-55 (2008).
Miller et al., "Radiation resistance in a doxorubicin-resistant human fibrosarcoma cell line", Am. J. Clin. Oncol., 15(3): 216-221 (1992).
Mi et al., "Characterization of a class of cationic peptides able to facilitate efficient protein transduction in vitro and in vivo", Mol. Ther., 2(4): 339-347 (2000).
Muller et al., "Upping the Ante: Recent Advances in Direct Reprogramming," Mol. Ther., 17: 947-953 (2009).
Munster et al., "Phase I/II trial combining the HDAC inhibitor, valproic acid (VPA) and FEC100 (5-fluorouracil, epirubicin and cyclophosphamide) in locally advanced/metastatic breast cancer", Journal of Clinical Oncology, 25(18S):1065 (2007).
Nabel et al., "An inducible transcription factor activates expression of human immunodeficiency virus in T cells", Nature 326(6114):711-713 (1987).
Nagata, Shogo et al., "Generation of Ground State Human Induced Pluripotent Stem Cells with Kinase Inhibitors", 83th Japanese Association of Biochemistry Annual Meeting, 33th Japanese Association of Molecular Biology Abstract (CD-ROM), Nov. 19, 2010, Abstract No. 4P-0877 (with English Summary).
Nakagawa et al., "Generation of induced pluripotent stem cells without Myc from mouse and human fibroblasts", Nat Biotechnol,26(1): 101-106 (2008).
Nakajima et al., "Effect of Wf-536, a novel ROCK inhibitor, against metastasis of B16 melanoma", Cancer Chemother Pharmacol. 52(4): 319-324 (2003).
Narumiya, et al., "Use and properties of ROCK-specific inhibitor Y-27632", Methods Enzymol., 325: 273-284 (2000).
Noble et al., "Inhibition of glycogen synthase kinase-3 by lithium correlates with reduced tauopathy and degeneration in vivo", PNAS, 102(9): 6990-6995 (2005).
Noggle et al., "A Molecular Basis for Human Embryonic Stem Cell Pluripotency," Stem Cell Reviews and Reports, 1(2): 1550-8943 (2005). DOI: 10.1385/scr:1:2:111.
Ohori, M., "ERK inhibitors as a potential new therapy for rheumatoid arthritis", Drug News Perspective, 21(5): 245-250 (2008).

Okada et al., "Effective culture conditions for the induction of pluripotent stem cells", Biochem Biophys Acta, 1800(9): 956-63 (2010).
Okita et al., "Generation of germline-competent induced pluripotent stem cells", Nature, 448(7151): 313-317 (2007).
Okita et al., "Generation of Mouse Induced Pluripotent Stem Cells Without Viral Vectors," Science, 322: 949-953 (2008).
Oliveri et al., "Epigenetic dedifferentiation of somatic cells into pluripotency: cellular alchemy in the age of regenerative medicine? ", Regenerative Medicine, 2(5): 795-816 (2007).
Pan et al., "Identification of a nuclear localization signal in OCT4 and generation of a dominant negative mutant by its ablation", J. Biol. Chem., 279(35): 37013-37020 (2004).
Paskind et al., "Dependence of Moloney murine leukemia virus production on cell growth", Virology, 67(1): 242-248 (1975).
PCT/US2009/037429, International Preliminary Report on Patentability dated Sep. 21, 2010, 7 pages.
PCT/US2009/037429, International Search Report dated Aug. 12, 2009, 4 pages.
PCT/US2009/037429, Written Opinion dated Aug. 12, 2009, 6 pages.
PCT/US2010/052896, International Preliminary Report on Patentability dated Apr. 17, 2012, 6 pages.
PCT/US2010/052896, International Search Report dated Mar. 15, 2011, 4 pages.
PCT/US2010/052896, Written Opinion dated Mar. 15, 2011, 5 pages.
PCT/US2011/065900, International Preliminary Report on Patentability dated Jun. 25, 2013.
PCT/US2011/065900, International Search Report and Written Opinion dated Jul. 19, 2012.
PCT/US2015/018801, International Preliminary Report on Patentability, dated Sep. 6, 2016.
PCT/US2015/018801, International Search Report and Written Opinion dated May 20, 2015.
Peerani et al., "Niche-mediated control of human embryonic stem cell self-renewal and differentiation", EMBO J., 26(22): 4744-4755 (2007).
Pesce et al., "Differential expression of the Oct-4 transcription factor during mouse germ cell differentiation", Mechanisms of Development, 71: 89-98 (1998).
Plath et al., "Progress in understanding reprogramming to the induced pluripotent state", Nature Reviews, 12(4): 253-265 (2011).
Plews et al., "Activation of pluripotency genes in human fibroblast cells by a novel mRNA based approach", PLoS One, 5(12): e14397, pp. 1-10 (2010).
Plews et al., "Activation of Pluripotency Genes in Human Fibroblast Cells by a Novel mRNA Based Approach," PLoS ONE, 5(12): 1-10 (2010).
Potter et al., "Enhancer-dependent expression of human kappa immunoglobulin genes introduced into mouse pre-B lymphocytes by electroporation", Proc. Nat'l Acad. Sci. USA, 81(22): 7161-7165 (1984).
Riento and Ridley, "Rocks: multifunctional kinases in cell behaviour", Nat. Rev. Mol. Cell. Biol., 4(6): 446-456 (2003).
Rinehart et al., "Multicenter phase II study of the oral MEK inhibitor, CI-1040, in patients with advanced non-small-cell lung, breast, colon, and pancreatic cancer", Journal of Clinical Oncology, 22(22): 4456-4462 (2004).
Roberts et al., "PD98059 Enhanced Insulin, Cytokine, and Growth Factor Activation of Xanthine Oxidoreductase in Epithelial Cells Involves STAT3 and the Glucocoticoid Receptor", Journal of Cellular Biochemistry, 101: 1567-1587 (2007).
Ruhnke et al., "Long-term culture and differentiation of rat embryonic stem cell-like cells into neuronal, glial, endothelial, and hepatic lineages", Stem Cells, 21(4): 428-436 (2003).
Ryan et al., "POU domain family values: flexibility, partnerships, and developmental codes", Genes Dev., 11(10): 1207-1225 (1997).
Saha et al., "TGFbeta/Activin/Nodal pathway in inhibition of human embryonic stem cell differentiation by mechanical strain", Biophys. J., 94(10): 4123-4133 (2008).
Saha et al., "Technical challenges in using human induced pluripotent stem cells to model disease", Cell Stem Cell, 5(6): 584-595 (2009).

(56) References Cited

OTHER PUBLICATIONS

Sasaki et al., "The novel and specific Rho-kinase inhibitor (S)-(+)-2-methyl-1-[(4-methyl-5-isoquinoline)sulfonyl]-homopiperazine as a probing molecule for Rho-kinase-involved pathway", Pharmacol. Ther., 93(2-3): 225-232 (2002).
Sato et al., "Molecular signature of human embryonic stem cells and its comparison with the mouse", Dev. Biol., 260(2): 404-413 (2003).
Schenke-Layland, et al., "Reprogrammed mouse fibroblasts differentiate into cells of the cardiovascular and hematopoietic lineages", Stem Cell, 26(6): 1537-1546 (2008).
Schermelleh et al., "Trapped in action: direct visualization of DNA methyltransferase activity in living cells", Nature Methods, 2(10): 751-756 (2005).
Schramm et al., "Novel dihydropyridines with positive inotropic action through activation of Ca2+ channels", Nature, 303: 535-537 (1983).
Schugar et al., "Small molecules in stem cell self-renewal and differentiation", Gene Ther, 15(2): 126-135 (2008).
Schulze et al., "Derivation, maintenance, and characterization of rat embryonic stem cells in vitro", Methods Mol Biol, 329: 45-58 (2006).
Seaberg et al., "Clonal identification of multipotent precursors from adult mouse pancreas that generate neural and pancreatic lineages", Nature Biotechnol., 22(9): 1115-1124 (2004).
Sells et al., "Delivery of protein into cells using polycationic liposomes" BioTechniques, 19(1): 72-78 (1995).
Shi "Induction of Pluripotent Stem Cells from Mouse Embryonic Fibroblasts by Oct4 and Klf4 with Small-Molecule Compounds", Cell Stem Cell, 3: 568-574 (2008).
Shi and Whetstine, "Dynamic regulation of histone lysine methylation by demethylases", Molecular Cell, 25: 1-14 (2007).
Shi et al., "A Combined Chemical and Genetic Approach for the Generation of Induced Pluripotent Stem Cells", Cell Stem Cell, 2(6): 525-528 (2008).
Shields et al., "Two potent nuclear localization signals in the gut-enriched Krüppel-like factor define a subfamily of closely related Krüppel proteins", J. Biol. Chem., 272: 18504-18507 (1997).
Shimanuki et al., "Modulation of the functional binding sites for TGF-beta on the type II receptor leads to suppression of TGF-beta signaling", Oncogene, 26: 3311-3320 (2007).
Silva et al., "Nanog is the gateway to the pluripotent ground state", Cell, 138(4): 722-737 (2009).
Silva et al., "Promotion of reprogramming to ground state pluripotency by signal inhibition", PLoS Biology, 6(10):253, pp. 2237-2247 (2008).
Singh et al., "A heterogeneous expression pattern for Nanog in embryonic stem cells", Stem Cells, 25(10): 2534-2542 (2007).
Soldner, et al., "Parkinson's disease patient-derived induced pluripotent stem cells free of viral reprogramming factors", Cell, 136: 964-977 (2009).
Sridharan et al., "Role of the murine reprogramming factors in the induction of pluripotency", Cell, 136(2): 364-377 (2009).
Stacey et al., "Microinjection of transforming ras protein induces c-fos expression", Mol. Cell. Biol., 7: 523-527 (1987).
Stadtfeld et al., "A reprogrammable mouse strain from gene-targeted embryonic stem cells", Nat Methods, 7: 53-55 (2010).
Stadtfeld et al., "Defining molecular cornerstones during fibroblast to iPS cell reprogramming in mouse", Cell Stem Cell, 2: 230-240 (2008).
Stadtfeld et al., "Induced Pluripotent Stem Cells Generated Without Viral Integration," Science, 322: 945-949 (2008).
Stadtfeld et al., "Reprogramming of Pancreatic β Cells into Pluripotent Stem Cells," Curr. Biol., 18(12): 890-894 (2008). doi: 10.1016/j.cub.2008.05.010.
Studier, FW, "Protein production by auto-induction in high density shaking cultures", Protein Expr Purif., 41(1): 207-234 (2005).
Sullivan et al., "Elucidating nuclear reprogramming mechanisms: taking a synergistic approach", Reproductive BioMed. Online, 16(1): 41-50 (2008).
Suzuki et al., "A novel small-molecule inhibitor of transforming growth factor beta type I receptor kinase (SM16) inhibits murine mesothelioma tumor growth in vivo and prevents tumor recurrence after surgical resection", Cancer Research, 67(5): 2351-2359 (2007).
Sylvester and Longaker, "Stem cells: review and update",Arch Surg. 136:93-99, (2004).
Szabo et al., "Direct conversion of human fibroblasts to multilineage blood progenitors", Nature, 468(7323): 521-526 (2010).
Szymczak et al., "Correction of multi-gene deficiency in vivo using a single 'self-cleaving' 2A peptide-based retroviral vector," Nature Biotechnology, 22(5): 589-594 (2004).
Tada, et al., "Nuclear reprogramming of somatic cells by in vitro hybridization with ES cells," Curr. Biology, 11: 1553-1558 (2001).
Takahashi et al., "Induction of pluripotent stem cells from fibroblast cultures", Nat Protoc, 2: 3081-3089 (2007).
Takahashi, et al., "Induction of Pluripotent Stem Cells from Mouse Embryonic and Adult Fibroblast Cultures by Defined Factors," Cell, 126(4): 663-676 (2006).
Takahashi,et al., "Induction of Pluripotent Stem Cells from Adult Human Fobroblasts by Defined Factors", Cell, 131:861-872 (2007).
Takei, et al., "Bone morphogenetic protein-4 promotes induction of cardiomyocytes from human embryonic stem cells in serum-based embryoid body development," Am J Physiol Heart Circ Physiol, 296(6): H1793-H1803 (2009).
Takeuchi and Bruneau, "Directed transdifferentiation of mouse mesoderm to heart tissue by defined factors," Nature, 459(7247): 708-711 (2009).
Taranger et al., "Induction of Dedifferentiation, Genomewide Transcriptional Programming, and Epigenetic Reprogramming by Extracts of Carcinoma and Embryonic Stem Cells," Molecular Biology of the Cell, 16: 5719-5735 (2005).
Tesar et al., "New cell lines from mouse epiblast share defining features with human embryonic stem cells", Nature, 448: 196-199 (2007).
Thiery, J.P. et al., "Complex networks orchestrate epithelial-mesenchymal transitions", Nat. Rev. Mol. Cell Biol., 7: 131-142 (2006).
Thompson et al., "Recent progress in targeting the Raf/MEK/ERK pathway with inhibitors in cancer drug discovery", Curr. Opin. Pharmacology, 5(4): 350-356 (2005).
Tighe et al., "GSK-3 inhibitors induce chromosome instability", BMC Cell Biol. 8:34 doi///:www.biomedcentral.com/1471-2121/8/34, printout pp. 1-17 (2007).
Tojo, et al., "The ALK-5 inhibitor A-83-01 inhibits Smad signaling and epithelia-to-mesenchymal transition by transforming growth factor-β," Cancer Sci, 96(11): 791-800 (2005).
Tosti E., "Calcium ion currents mediating oocyte maturation events", Reprod Biol Endocrinol, 4: 26 (2006).
Toyooka,Yayoi, et al., "Identification and characterization of subpopulations in undifferentiated ES cell culture," Development, 135(5):909-918 (2008).
Tur-Kaspa et al., "Use of electroporation to introduce biologically active foreign genes into primary rat hepatocytes", Mol. Cell Biol., 6: 716-718 (1986).
Ueda et al., "Establishment of rat embryonic stem cells and making of chimera rats", PLoS ONE, 3: e2800 (2008).
Uehata et al., "Calcium sensitization of smooth muscle mediated by a Rho-associated protein kinase in hypertension", Nature, 389: 990-994 (1997).
Valamehr et al., "Developing defined culture systems for human pluripotent stem cells," Regenerative Medicine, 6(5):623-634 (2011).
Vallier et al., "Activin/Nodal and FGF pathways cooperate to maintain pluripotency of human embryonic stem cells," Journal of Cell Science, Oct. 2005, vol. 118(19), pp. 4495- 4509, DOI: 10.1111/J.1432-0436.2006.00143.X.
Vierbuchen et al., "Direct conversion of fibroblasts to functional neurons by defined factors," Nature, 463(7284): 1035-1042 (2010).
Wadia and Dowdy, "Protein transduction technology", Curr. Opin. Biotechnol., 13: 52-56 (2002).
Wagman et al., "Discovery and development of GSK3 inhibitors for the treatment of type 2 diabetes",Current Pharmaceutical Design, 10(10): 1105-1137 (2004).

(56) References Cited

OTHER PUBLICATIONS

Wang et al., "Clinical experience of MEK inhibitors in cancer therapy", Biochimica et Biophysica Acta 1773, pp. 1248-1255 (2007).
Wang et al., "The Immunophilin FKBP12 Functions as a Common Inhibitor of the TGFβ Family Type 1 Receptors", Cell, 86: 435-444 (1996).
Warren et al., "Highly efficient reprogramming to pluripotency and directed differentiation of human cells with synthetic modified mRNA", Cell Stem Cell, 7(5): 618-630 (2010).
Watabe et al., "TGF-β receptor kinase inhibitor enhances growth and integrity of embryonic stem cell-derived endothelial cells", The Journal of Cell Biology, 163(6): 1303-1311 (2003).
Watabe et al.,"Roles of TGF-beta family signaling in stem cell renewal and differentiation", Cell Res., 19: 103-115 (2009).
Watanabe et al., "Activation of Akt signaling is sufficient to maintain pluripotency in mouse and primate embryonic stem cells", Oncogene, 25: 2697-2707 (2006).
Watanabe et al., "A ROCK inhibitor permits survival of dissociated human embryonic stem cells," Nature Biotechnology, 25(6):681-868 (2007).
Wenlin et al., "Generation of novel rat and human pluripotent stem cells by reprogramming and chemical approaches," Methods in Molecular Biology, 636: 293-300 (2010).
Wernig et al., "c-Myc is Dispensable for Direct Reprogramming of Mouse Fibroblasts," Cell Stem Cell, 2: 10-12 (2008).
Wernig et al.,"A drug-inducible transgenic system for direct reprogramming of multiple somatic cell types", Nat Biotechnol, 26: 916-924 (2008).
Wernig, et al., "In vitro reprogramming of fibroblasts into a pluripotent ES-cell-like state," Nature, 448(7151): 318-324 (2007).
Willis et al.,"TGF-beta-induced EMT: mechanisms and implications for fibrotic lung disease", Am. J Physiol. Lung Cell Physiol., 293: L525-L534 (2007).
Wilson et al., "Implantation of vascular grafts lined with genetically modified endothelial cells", Science, 244(4910): 1344-1346 (1989).
Wissman et al., "Cooperative demethylation by JMJDC2 and LSD1 promotes androgen receptor-dependent gene expression", Nature Cell Biology, 9(3): 347-353; and Supplementary Information (12 pages) (2007).
Woltjen et al., "piggyBac transposition reprograms fibroblasts to induced pluripotent stem cells", Nature, 458(7239): 766-770 (2009).
Wong et al., "Appearance of beta-lactamase activity in animal cells upon liposome-mediated gene transfer", Gene, 10: 87-94 (1980).
Wrzesinski, et al., "Transforming growth factor-beta and the immune response: implications for anticancer therapy", Clinical Cancer Research, 13(18): 5262-5270 (2007).
Wu and Wu, "Evidence for targeted gene delivery to Hep G2 hepatoma cells in vitro", Biochemistry, 27: 887-892 (1988).
Wu and Wu, "Receptor-mediated in vitro gene transformation by a soluble DNA carrier system", J Biol. Chem., 262(10): 4429-4432 (1987).
Wu et al., "Cellular senescence is an important mechanism of tumor regression upon c-Myc inactivation," PNAS, 104(32): 13028-13033 (2007).
Xiong et al., "Histone deacetylase inhibitors DNA methyltransferase-3B messenger RNA stability and down-regulate de novo DNA methyltransferase activity in human endometrial cells," Cancer Res., 65(7): 2684-2689 (2005).
Xu et al., "A chemical approach to stem-cell biology and regenerative medicine", Nature, 453: 338-344 (2008).
Xu et al., "BMP4 initiates human embryonic stem cell differentiation to trophoblas", Nat. Biotechnol, 20(12): 1261-1264 (2002).
Xu et al., "Revealing a core signaling regulatory mechanism for pluripotent stem cell survival and self-renewal by small molecules," PNAS, 107(8): 8129-8134 (2010).
Yamanaka, "Strategies and New Developments in the Generation of Patient-Specific Pluripotent Stem Cells," Cell Stem Cell, 1(1): 39-49 (2007).
Yamanaka, et. al. "Induction of pluripotent stem cells from mouse embryonic and adult fibroblast cultures by defined factors", Cell, 126: 663-676 (2006).
Ying et al., "BMP induction of Id proteins suppresses differentiation and sustains embryonic stem cell self-renewal in collaboration with STAT3", Cell, 115(3): 281-292 (2003).
Ying et al., "Changing potency by spontaneous fusion", Nature, 416: 545-548 (2002).
Ying et al., "The ground state of embryonic stem cell self-renewal", Nature, 453:519-523 (2008).
Yu et al., "Human induced pluripotent stem cells free of vector and transgene sequences", Science, 324(5928): 797-801 (2009).
Yu et al., "Induced pluripotent stem cell lines derived from human somatic cells", Science, 318: 1917-1920 (2007).
Zhang et al., "Sall4 modulates embryonic stem cell pluripotency and early embryonic development by the transcriptional regulation of Pou5f1", Nat. Cell Biol., 8(10): 1114-1123 (2006).
Zhao et al., "Granzyme K cleaves the nucleosome assembly protein Set to induce single-stranded DNA nicks of target cells", Cell Death and Differentiation, 14(3): 489-499 (2007).
Zhao et al., "Resorcylic Acid Lactones: Naturally Occurring Potent and Selective Inhibitors of MEK", The Journal of Antibiotics, 52(12): 1086-1094 (1999).
Zhao et al., "Two supporting factors greatly improve the efficiency of human iPSC generation",Cell Stem Cell, 3(5): 475-479 (2008).
Zhao, et al., "Inhibition of transforming growth factor-betal-induced signaling and epithelial-to-mesenchymal transition by the Smad-binding peptide aptamer Trx-SARA", Molecular Biology of the Cell, 17(9): 3819-3831 (2006).
Zheng et al., "Lipid-mediated protein delivery of suicide nucleoside kinases",Cancer Res., vol. 63(20): 6909-6913 (2003).
Zhou et al., "In vivo reprogramming of adult pancreatic exocrine cells to beta-cells", Nature, 455(7213): 627-632 (2008).
Zhou et al., "Conversion of Mouse Epiblast Stem Cells to an Earlier Pluripotency State by Small Molecules," Journal of Biological Chemistry, 285(39): 29676-29680 (2010). DOI: 10.1074/jbc.C110.150599.
Zhou Hongyan et al., "Generation of Induced Pluripotent Stem Cells Using Recombinant Proteins", Cell Stem Cell, 4: 381-384 (2009).
Zhu and Otterson et al., "The interaction of histone deacetylase inhibitors and DNA methyltransferase inhibitors in the treatment of human cancer cells", Current Medicinal Chemistry, 3(3): 187-199 (2003).
Zhu et al., "Induction of S-phase arrest and p21 overexpression by a small molecule 2[[,3-(2,3-dichlorophenoxy)propyl] amino]ethanol in correlation with activation of ERK", Oncogene, 23: 4984-4992 (2004).
Zhu et al., "Reprogramming of human primary somatic cells by OCT4 and chemical compounds," Cell Stem Cell, 7(6): 651-655 (2010).
Bru et al., "Rapid induction of pluripotency genes after exposure of human somatic cells to mouse ES cell extracts," Exp. Cell Res., 314:2634-2642 (2008).
De Felipe, "Polycistronic viral vectors," Curr. Gene Ther., 2:355-378 (2002).
Radcliffe et al., "Multiple gene products from a single vector: 'self-cleaving' 2A peptides," Gene Therapy, 11:1673-1674 (2004).
Valamehr et al., "Platform for induction and maintenance of transgene-free hiPSCs resembling ground state pluripotent stem cells," Stem Cell Reports, 2:366-381 (2014).
Gonzalez, F. et al. (Apr. 2011, e-published Feb. 22, 2011). "Methods for making induced pluripotent stem cells: reprogramming a la carte," Nat Rev Genet 12(4):231-242.
Kitajima, H. et al. (Jun. 11, 2010, e-published May 9, 2010). "Clonal expansion of human pluripotent stem cells on gelatin-coated surface," Biochem Biophys Res Commun 396(4):933-938.
Munoz et al., "Conventional pluripotency markers are unspecific for bovine embryonic-derived cell-lines," Theriogenology, 69:1159-1164 (2008).
Pakzad, M. et al. (Mar. 2010). "Presence of a ROCK inhibitor in extracellular matrix supports more undifferentiated growth of feeder-

(56) References Cited

OTHER PUBLICATIONS free human embryonic and induced pluripotent stem cells upon passaging," Stem Cell Rev Rep 6(1):96-107.

Tan, F. et al. (Feb. 13, 2015, e-published Dec. 29, 2014). "Inhibition of transforming growth factor β (TGF-β) signaling can substitute for Oct4 protein in reprogramming and maintain pluripotency," J Biol Chem 290(7):4500-4511.

Hanna et al., "Human embryonic stem cells with biological and epigenetic characteristics similar to those of mouse ESCs," Proc. Natl. Acad. Sci. USA, 107(20):9222-9227 (2010).

Hanna et al., "Pluripotency and cellular reprogramming: facts, hypotheses, unresolved issues," Cell, 143:508-525 (2010).

Park et al., "Reprogramming of human somatic cells to pluripotency with defined factors," Nature, 451(7175):141-146 (2008).

Brevini et al., "Embryonic stem cells in domestic animals. No shortcuts to pig embryonic stem cells," Theriogenology, 74:544-550 (2010).

Buta et al., "Reconsidering pluripotency tests: do we still need teratoma assays?," Stem Cell Research, 11:552-562 (2013).

Declercq et al., "Zic3 enhances the generation of mouse induced pluripotent stem cells," Stem Cells Development, 22(14):2017-2026 (2013).

Gomez et al., "Derivation of cat embryonic stem-like cells from in vitro-produced blastocysts on homologous and heterologous feeder cells," Theriogenology, 74:498-515 (2010).

Hiraki et al., Culturing human IPS cells under non-feeder conditions alters their basic pluripotent status, Biochemical, 4P-0894 (2010) Abstract only.

Ivashchenko et al., "Human-induced pluripotent stem cell-derived cardiomyocytes exhibit temporal changes in phenotype," Am. J. Physiol. Heart Circ. Physiol., 305:H913-H922 (2013).

Jean et al., "Pluripotent genes in avian stem cells," Develop. Growth Differ. 55:41-51 (2013).

Kurosawa, "Application of Rho-associated protein kinase (ROCK) inhibitor to human pluripotent stem cells," J. Bioscience Bioengineering, 114(6):577-581 (2012).

Leitch et al., "Naive pluripotency is associated with global DNA hypomethylation," Nature Structural Molecular Biology, 20(3):311-316 (2013).

Lim et al., "The pluripotency regulator zic3 is a direct activator of the nanog promoter in ESCs," Stem Cells, 28:1961-1969 (2010).

Nissenbaum et al., "Global indiscriminate methylation in cell-specific gene promoters following reprogramming into human induced pluripotent stem cells," Stem Cell Reports, 1:509-517 (2013).

Ohgushi, "Role of cell-cell adhesion in the survival regulation of human pluripotent stem cells," Experimental Medicine, 30(10):88-94 (2012).

Paris et al., "Equine embryos and embryonic stem cells: defining reliable markers of pluripotency," Theriogenology, 74:516-524 (2010).

Planello et al., "Aberrant DNA methylation reprogramming during induced pluripotent stem cell generation is dependent on the choice of reprogramming factors," Cell Regeneration, 3:4 (2014).

\* cited by examiner

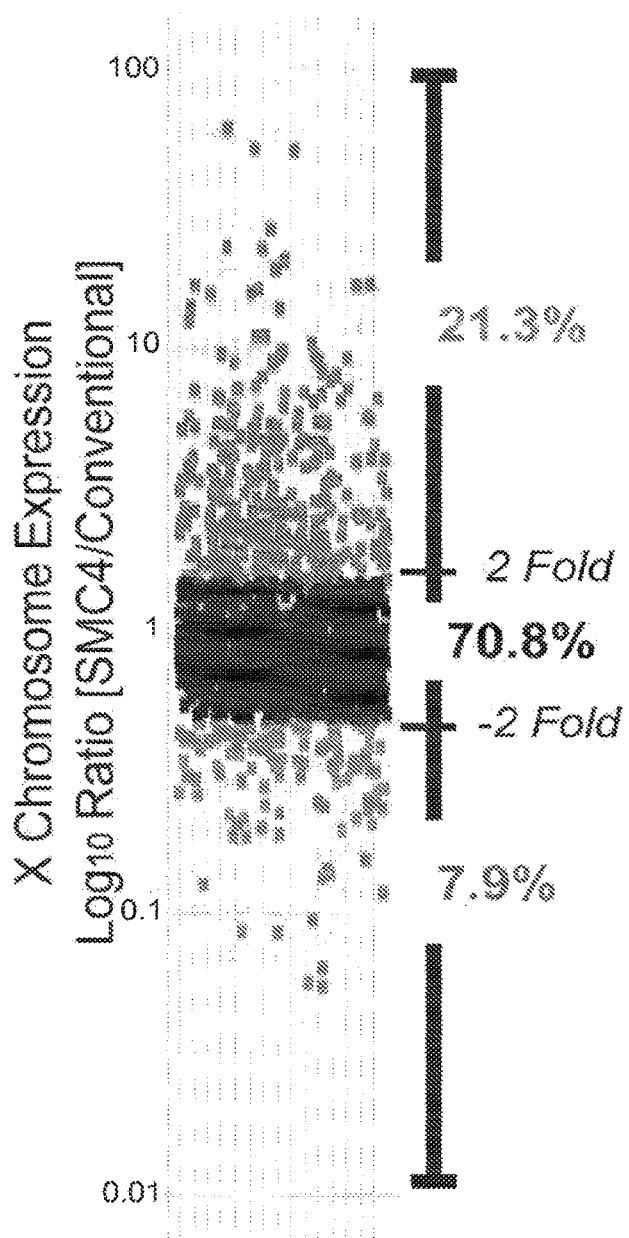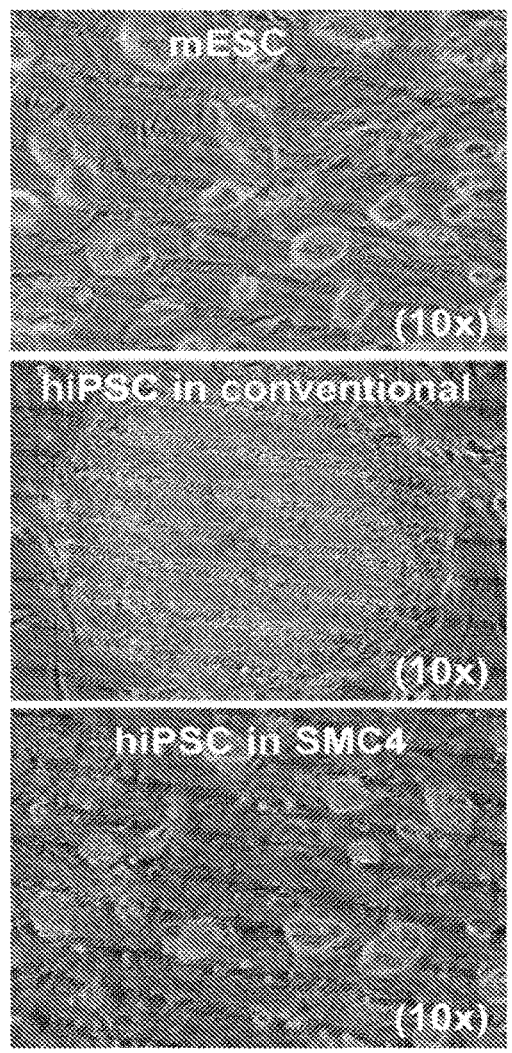
*FIG. 6D*  *FIG. 6E*

| Clone | CD30 expression | Nanog Expression |
|---|---|---|
| FTC8 clone 1 | + | + |
| FTi31 | + | + |
| FTC10 clone 3 | - | - |
| FTC10 clone 9 | - | - |

| Karyotype Report | Karyotype | Conclusion |
|---|---|---|
| FTC1 p2 | 46, XY | Normal Male Karyotype |
| FTi91 p20 | 46, XY | Normal Male Karyotype |
| FTi93 p20 | 46, XY | Normal Male Karyotype |

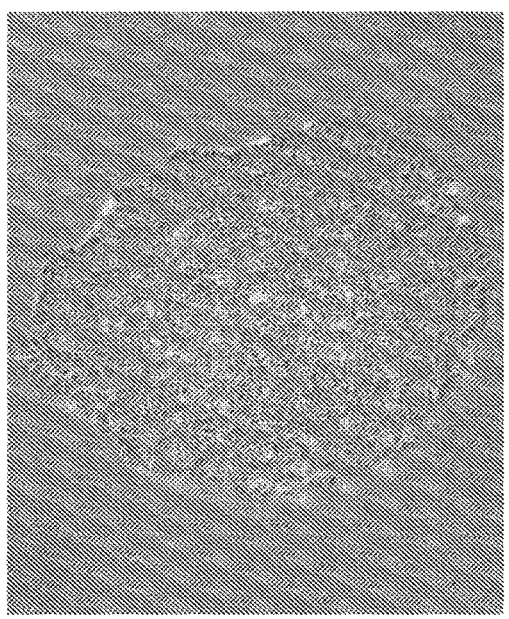
FIG. 21A
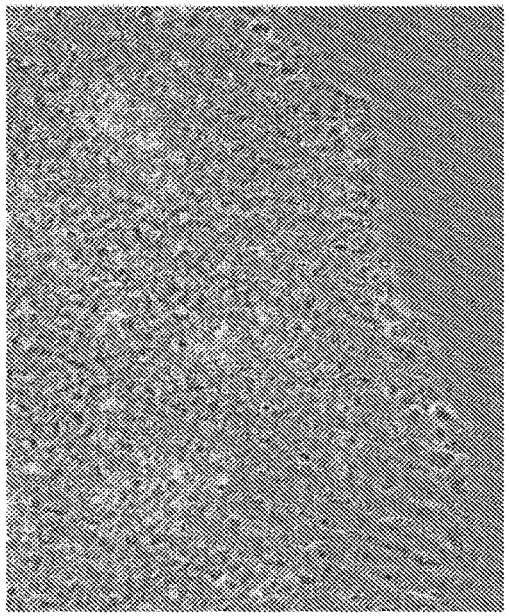
FIG. 21B
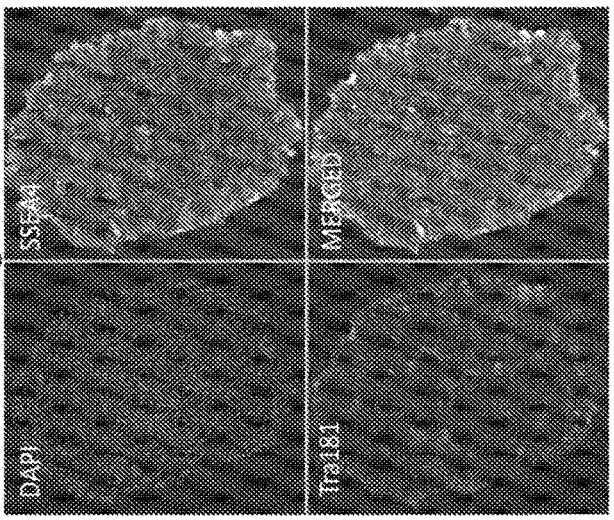
FIG. 21C
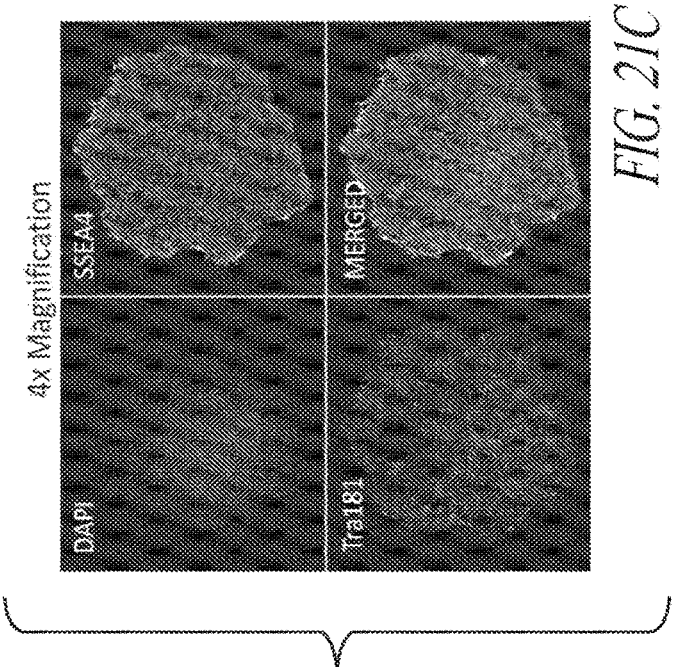

SEQUENCE LISTING

```
<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Transgenic Oct4 forward primer

<400> SEQUENCE: 1
ctggttggag ggaaggtaat ctag                                          24

<210> SEQ ID NO 2
<211> LENGTH: 26
<212> TYPE: DNA
<213> ORGANISM: Artificial Sequence
<220> FEATURE:
<223> OTHER INFORMATION: Transgenic Oct4, Klf4, Myc, Lin28, Sox2 and
      Nanog reverse primer

<400> SEQUENCE: 2
ttttgtaatc cagaggttga ttgttc                                        26

<210> SEQ ID NO 3
<211> LENGTH: 13
<212> TYPE: DNA
<213> ORGANISM: Artificial Sequence
<220> FEATURE:
<223> OTHER INFORMATION: Transgenic Oct4, Klf4, Myc, Lin28, Sox2 and
      Nanog Probe

<400> SEQUENCE: 3
```
ccccgacgcg tct                                                              13

<210> SEQ ID NO 4
<211> LENGTH: 23
<212> TYPE: DNA
<213> ORGANISM: Artificial Sequence
<220> FEATURE:
<223> OTHER INFORMATION: Transgenic Klf4 forward primer

<400> SEQUENCE: 4
gccttacaca tgaagaggca ttt                                                   23

<210> SEQ ID NO 5
<211> LENGTH: 25
<212> TYPE: DNA
<213> ORGANISM: Artificial Sequence
<220> FEATURE:
<223> OTHER INFORMATION: Transgenic Myc forward primer

<400> SEQUENCE: 5
tcttgtgcgt aactcgagtc tagag                                                 25

<210> SEQ ID NO 6
<211> LENGTH: 19
<212> TYPE: DNA
<213> ORGANISM: Artificial Sequence
<220> FEATURE:
<223> OTHER INFORMATION: Transgenic Lin28 forward primer

<400> SEQUENCE: 6
ccggaggcac agaattgac                                                        19

<210> SEQ ID NO 7
<211> LENGTH: 20
<212> TYPE: DNA
<213> ORGANISM: Artificial Sequence
<220> FEATURE:
<223> OTHER INFORMATION: Transgenic Sox2 forward primer

<400> SEQUENCE: 7
cactgcccct ctcacacatg                                                       20

<210> SEQ ID NO 8
<211> LENGTH: 22
<212> TYPE: DNA
<213> ORGANISM: Artificial Sequence
<220> FEATURE:
<223> OTHER INFORMATION: Transgenic Nanog forward primer

<400> SEQUENCE: 8
catgcaacct gaagacgtgt aa                                                    22

<210> SEQ ID NO 9
<211> LENGTH: 24
<212> TYPE: DNA
<213> ORGANISM: Artificial Sequence
<220> FEATURE:
<223> OTHER INFORMATION: Endogenous Oct4 forward primer

<400> SEQUENCE: 9
gggtttttgg gattaagttc ttca                                                  24

<210> SEQ ID NO 10
<211> LENGTH: 18
<212> TYPE: DNA

```
<213> ORGANISM: Artificial Sequence
<220> FEATURE:
<223> OTHER INFORMATION: Endogenous oct4 reverse primer

<400> SEQUENCE: 10
gcccccaccc tttgtgtt                                                 18

<210> SEQ ID NO 11
<211> LENGTH: 18
<212> TYPE: DNA
<213> ORGANISM: Artificial Sequence
<220> FEATURE:
<223> OTHER INFORMATION: Endogenous Oct4 probe

<400> SEQUENCE: 11
tcactaagga aggaattg                                                 18

<210> SEQ ID NO 12
<211> LENGTH: 22
<212> TYPE: DNA
<213> ORGANISM: Artificial Sequence
<220> FEATURE:
<223> OTHER INFORMATION: Endogenous Klf4 forward primer

<400> SEQUENCE: 12
agcctaaatg atggtgcttg gt                                            22

<210> SEQ ID NO 13
<211> LENGTH: 23
<212> TYPE: DNA
<213> ORGANISM: Artificial Sequence
<220> FEATURE:
<223> OTHER INFORMATION: Endogenous Klf4 reverse primer

<400> SEQUENCE: 13
ttgaaaactt tggcttcctt gtt                                           23

<210> SEQ ID NO 14
<211> LENGTH: 21
<212> TYPE: DNA
<213> ORGANISM: Artificial Sequence
<220> FEATURE:
<223> OTHER INFORMATION: Endogenous Klf4 probe

<400> SEQUENCE: 14
agtcttggtt ctaaaggtac c                                             21

<210> SEQ ID NO 15
<211> LENGTH: 21
<212> TYPE: DNA
<213> ORGANISM: Artificial Sequence
<220> FEATURE:
<223> OTHER INFORMATION: Endogenous Nanog forward primer

<400> SEQUENCE: 15
tgatgcccat ccagtcaatc t                                             21

<210> SEQ ID NO 16
<211> LENGTH: 20
<212> TYPE: DNA
<213> ORGANISM: Artificial Sequence
<220> FEATURE:
<223> OTHER INFORMATION: Endogenous nanog reverse primer

<400> SEQUENCE: 16
cctcgctgat taggctccaa                                               20
```

```
<210> SEQ ID NO 17
<211> LENGTH: 17
<212> TYPE: DNA
<213> ORGANISM: Artificial Sequence
<220> FEATURE:
<223> OTHER INFORMATION: Endogenous nanog probe

<400> SEQUENCE: 17
atggagggtg gagtatg                                              17
```

CELL CULTURE PLATFORM FOR SINGLE CELL SORTING AND ENHANCED REPROGRAMMING OF IPSCS

CROSS REFERENCE TO RELATED APPLICATIONS

This application claims the benefit under 35 U.S.C. § 119(e) of U.S. Provisional Application No. 61/426,369, filed Dec. 22, 2010, and U.S. Provisional Application No. 61/496,991, filed Jun. 14, 2011, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FATE_094_00WO_ST25.txt. The text file is 4 KB, was created on Dec. 15, 2011, and is being submitted electronically via EFS-Web.

BACKGROUND OF THE INVENTION

Technical Field

The present invention relates generally to cell culture conditions, media, and culture platforms for culturing stem cells, including feeder-free conditions for generating and culturing human induced pluripotent stem cells (iPSCs).

Description of Related Art

The application of pluripotent stem cell biology opens new doors for regenerative medicine. The derivation of human embryonic stem cells (hESC) by culturing pre-implantation blastocysts in cocktails of growth factors has led to many promising cell therapy approaches where the expanded self renewing population of cells can be differentiated to the therapy-relevant cell lineage in vitro or in vivo. In a further application of ESC biology and by using pre-implantation genetic analysis it has been possible to derive ESC lines from several genetic disease backgrounds, and thus, model these diseases in the tissue culture dish. There are, however, some limitations to ESC technology: the range of genetic backgrounds from which ESC can be derived are both technically and politically limited, the genetic background of the ESCs are not always known and the use of ESC-derived cell therapy is essentially an allograft, running the same rejection risks as traditional tissue/organ transplants.

In a major advance, pluripotent cell populations were generated from adult, terminally differentiated cells: such derived cells are called induced pluripotent stem cells (iPSC). iPSC technology allows cells from any donor to be reprogrammed into a pluripotent, self renewing state and thus allow the expansion of a homogeneous population of cells from any genetic background. iPSCs overcome ethical considerations pertaining to ESCs and can be used to derive models of any genetic human disease for high throughput drug screening or hepatocytes and cardiomyocytes for xenobiotic drug toxicity screening. Further, iPSCs may ultimately result in cell therapies generated from the patient's own cells in an autologous transplantation that may prevent graft rejection. Expression and differentiation analysis has shown iPSCs to be very close to ESCs at the molecular level with variations between clonal iPSC cultures of similar magnitude to those seen when comparing multiple ESC lines.

iPSCs have generally been generated by ectopic expression of several key genes shown to be required for full reprogramming, namely combinations of: Oct4, Sox2, Klf4, c-Myc, Lin28 and Nanog. iPSCs were originally generated using integrating viral systems to express key transcription factors. Retroviral and lentiviral systems including polycistronic and inducible systems have now been successfully employed in iPSC generation. However, permanent genomic changes due to insertional mutagenesis and the potential for exogenous gene reactivation post iPSC differentiation may present potential problems for subsequent drug screening and therapeutic applications of cells generated by these methods. Indeed, significant differences between iPSC clones generated using the same viral systems have been reported, with a large percentage of clones forming tumors in rodents when transplanted as differentiated neurospheres. Research suggests that iPSCs generated using the same viral methods may behave differently once differentiated. Differences in ectopic gene integration site may result in different insertional mutagenesis and epigenetic regulation of transgene expression. For iPSC generation methods that include integrating systems, many clones may need to be derived and screened to identify those that are stable in both pluripotent and differentiated states. Thus, a method for the rapid derivation of clonal iPSCs from a given donor cell source would be beneficial. The use of non-integrating systems for iPSC generation such as adenoviral or episomal transient expression have also been demonstrated, albeit with lower efficiency. These systems may overcome safety and stability issues in iPSC generation, however there is a potential for genomic integration when using any DNA-based reprogramming method and this would need to be assessed prior to their use in development of an iPSC-derived cell therapy.

Excisable viral systems and genome wide expression profiling show that iPSCs with integrated expression cassettes are less like ESCs than the same clones with the viral factors excised. Further, protein-only reprogramming has now been demonstrated in which the most commonly used transcription factors were expressed in *E. coli* as fusion proteins with cell penetrating peptides. Multiple doses of the purified proteins were applied to murine fibroblasts resulting in iPSC generation. The efficiency of reprogramming using this protein-only system was very low. This may be due to the efficiency of the protein transduction, the specific activity of the protein and/or the stability of the proteins.

The process of differentiated cell reprogramming by the ectopic expression of pluripotency genes or their introduction via protein transduction or mRNA requires several months and the knowledge of a skilled stem-cell biologist. The identification of reprogrammed cells is initially by eye: screening for of ESC-like colony morphology. Such colonies must be picked by hand, are usually mechanically passaged and expanded. The introduction of the pluripotency factors also produces transformed cell colonies as well as incompletely reprogrammed cells. A researcher may be able to identify the true iPSC colonies from the background of transformed cells, but this is not an efficient process. Further characterization and recognition as a true pluripotent population is then required and usually includes immunocytochemistry staining for markers of pluripotentcy, gene expression and epigenetic analysis and the ability of the pluripotent population to differentiate to the three germ layers (ectoderm, mesoderm and endoderm). Once pluripotent cells are identified and selected, such cells are generally grown as colonies and require manual passaging by picking and mechanically dissociating cells prior to replating to maintain cells long-term.

Embryonic stem cells derived from various pre- and post-implantation stages display distinct states of pluripotency. For example, cells derived from the inner cell mass of a blastocyst are considered more "naïve" and have key properties that are quite different from the postimplantation derived cells that are considered more "primed" with higher propensity to randomly differentiate. Naïve cells appear to be in a more "grounded state" and do not require extrinsic signaling to maintain their undifferentiated status. On the other hand, primed cells require extrinsic signaling of key cytokines including TGFβ, Activin and bFGF and are quite dependent on the ERK/MAPK cellular pathway for maintaining their undifferentiated status.

Improvements to the iPSC generation process could dramatically lower the technical barriers, speed-up the process and enable subsequent scale-up and differentiation of cells for industrial applications of the technology such as drug screening and cell therapy. Methods for more efficient production of iPSCs without the use of exogenous material, and more efficient identification and selection of reprogrammed cells are required. Methods of generating iPSCs that promote the naïve state of human pluripotent stem cells would be greatly advantageous for future applications in regenerative medicine, such as disease correction, directed differentiation and manufacturing-scale expansion. Further, methods for more efficient production of iPSCs in defined culture conditions that enable single cell passage and scalability are required.

BRIEF SUMMARY OF THE INVENTION

One embodiment of the invention provides a method of culturing a pluripotent cell in a feeder-free environment comprising: culturing a pluripotent cell that is not a murine embryonic stem cell in a feeder-free environment in a culture medium comprising at least one agent that maintains pluripotency of the cell, wherein the agent is selected from the group consisting of: i) a TFGβ inhibitor; ii) a GSK3 inhibitor; iii) a MEK inhibitor, and iv) a Rock inhibitor, while maintaining pluripotency of the cell during culturing.

In a particular embodiment the culture medium comprises a sufficient amount of the agent to allow for at least one cell division while maintaining pluripotency of the cell. In an additional embodiment, the culture medium comprises at least two agents that maintain pluripotency of the cell. In a particular embodiment, the culture medium comprises at least three agents or four agents that maintain pluripotency of the cell.

In another particular embodiment, the agent that maintains pluripotency of the cell comprises a Rock inhibitor. In a particular embodiment, the Rock inhibitor is thiazovivin or Y27632.

In one embodiment, the agent that maintains pluripotency of the cell comprises a TFGβ inhibitor, and in a particular embodiment the TFGβ inhibitor is A-83-01 or SB431542.

In a certain embodiment, the agent that maintains pluripotency of the cell comprises a GSK3 inhibitor, and in a particular embodiment the GSK3 inhibitor is CHIR99021 or BIO.

In one embodiment of the invention, the agent that maintains pluripotency of the cell comprises a MEK inhibitor. In a particular embodiment, the MEK inhibitor is PD98059 or PD032901.

In a particular embodiment, the culture medium comprises a TFGβ inhibitor, a GSK3 inhibitor, a MEK inhibitor, and a Rock inhibitor. In a more particular embodiment of the invention, the TFGβ inhibitor is SB431542, the GSK3 inhibitor is CHIR99021, the MEK inhibitor is PD0325901, and the Rock inhibitor is thiazovivin.

In some embodiments of the invention, the pluripotency of the cell is maintained for at least five cell divisions. In other embodiments, pluripotency of the cell is maintained for at least ten cell divisions.

In some embodiments, the cells are cultured in the absence of growth factors and cytokines, optionally in the presence of soluble fibronectin. In a further embodiment, the cells are cultured in the absence of Matrigel™, and in yet another embodiment the culture medium is substantially free of bFGF.

In particular embodiments of the invention, the pluripotent cells are human embryonic stem cells or human induced pluripotent stem cells.

Another embodiment of the invention provides a method of culturing a pluripotent cell comprising culturing a pluripotent cell that is not a murine embryonic stem cell in the absence of growth factors and cytokines.

In certain embodiments, the method comprises culturing the pluripotent cell in a culture medium comprising at least one agent that maintains pluripotency of the cell to allow for at least one cell division while maintaining pluripotency of the cell, wherein the agent is selected from the group consisting of i) a TFGβ inhibitor; ii) a GSK3 inhibitor; iii) a MEK inhibitor, and iv) a Rock inhibitor.

In one embodiment, the pluripotent cell is a human embryonic stem cell or a human induced pluripotent stem cell.

In further embodiments, the culture medium comprises at least two, at least three, or four agents selected from the group consisting of i) a TFGβ inhibitor; ii) a GSK3 inhibitor; iii) a MEK inhibitor, and iv) a Rock inhibitor; in particular embodiments, the culture medium comprises a TFGβ inhibitor, a GSK3 inhibitor, a MEK inhibitor, and a Rock inhibitor; in other particular embodiments the TFGβ inhibitor is SB431542, the GSK3 inhibitor is CHIR99021, the MEK inhibitor is PD0325901, and the Rock inhibitor is thiazovivin.

Yet another embodiment of the invention provides a method of obtaining dissociated human pluripotent cells comprising dissociating human pluripotent cells to obtain dissociated cells and contacting the dissociated cells with a culture medium comprising at least one agent that enhances viability of the dissociated cells, wherein the agent is selected from the group consisting of i) a TFGβ inhibitor; ii) a GSK3 inhibitor; iii) a MEK inhibitor, and iv) a Rock inhibitor, whereby viability of the dissociated cells is enhanced. In particular embodiments, viability of the dissociated cells is enhanced by at least 10%, at least 50%, at least 100%, at least 200%, or at least 500%.

In other embodiments, the method of the invention further comprises culturing the dissociated cells in the culture medium for at least one, at least two, at least five, or at least ten passages while maintaining pluripotency of the dissociated cells.

In certain embodiments, the karyotype of the dissociated cells after culturing is substantially similar to the karyotype of the population of cells prior to dissociation.

In some embodiments, the method comprises dissociating in the presence of the agent. In yet other embodiments, the method comprises contacting the pluripotent cells with the agent prior to dissociating. In particular embodiments, contacting the dissociated cells with the culture medium comprises suspending the dissociated cells in the culture medium.

In other embodiments, the invention provides a method of increasing the potency of a cell in a feeder-free environment comprising contacting a cell in a feeder-free environment with a culture medium comprising at least one small molecule agent to obtain a cell having increased potency as compared to the cell prior to contacting with the culture medium, wherein the small molecule agent is selected from the group consisting of i) a TFGβ inhibitor; ii) a GSK3 inhibitor; iii) a MEK inhibitor, and iv) a Rock inhibitor. In particular embodiments, the culture medium comprises a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In one embodiment, contacting comprises culturing the cell under conditions sufficient to increase the potency of the cell.

In some embodiments, the cell is selected from the group consisting of an embryonic stem cell; a pluripotent cell; a multipotent cell; a non-pluripotent cell; and a somatic cell.

In particular embodiments, the cell is not a murine embryonic stem cell. In other particular embodiments, the cell is a human cell, and in certain embodiments the cell is an induced pluripotent stem cell.

In some embodiments, the method further comprises contacting the cell with at least one pluripotency factor. In some embodiments, the pluripotency factor comprises a polynucleotide, polypeptide, or small molecule. In some embodiments, the pluripotency factor is an exogenous transcription factor. In particular embodiments, the exogenous transcription factor comprises an Oct4, Sox, Klf, Myc, Lin28, or Nanog polypeptide, or a polynucleotide encoding Oct4, Sox, Klf, Myc, Lin28, or Nanog. In other embodiments, the polypeptide comprises an amino acid sequence that allows transport across cell membranes. In other particular embodiments, the exogenous transcription factor comprises an Oct4, a Sox2, and a Klf4 polynucleotide.

In yet other embodiments, the cell having increased potency is characterized by one or more of the following: expression of at least one pluripotent stem cell marker selected from the group consisting of Oct4, Nanog, KLF4, SSEA4 and TRA 1-81; pluripotent stem cell morphology; ability to contribute to germline transmission; teratoma formation, ability to differentiate or transdifferentiate into a lineage different from the starting lineage, and in vitro trilineage differentiation. In some embodiments, the cell having increased potency expresses at least a two-fold higher level of Oct4 as compared to the cell prior to contacting with the culture medium. In yet other embodiments, the cell having increased potency has Xist activity that is at least two fold lower compared to conventionally cultured iPSCs. In further embodiments, the cell having increased potency has a compact, domed colony morphology.

In some embodiments, the cell having increased potency replicates and maintains pluripotency in the absence of exogenous stimulation of the TFGβ, activin, and MEK signaling pathways, and optionally in the absence of exogenous stimulation of the bFGF pathway.

In other embodiments, the method further comprises culturing the cell having increased potency in a feeder-free environment in the presence of at least one of i) a TFGβ inhibitor; ii) a GSK3 inhibitor; iii) a MEK inhibitor, or iv) a Rock inhibitor to allow for at least one cell division while maintaining the potency of the cell. In particular embodiments, cells are cultured in the presence of a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

The invention also provides a cell having increased potency made by any of the above embodiments.

The invention further provides a method of improving the efficiency of reprogramming of a population of cells in a feeder-free environment comprising contacting a population of cells in a feeder-free environment with at least one small molecule agent selected from the group consisting of i) a TFGβ inhibitor; ii) a GSK3 inhibitor; iii) a MEK inhibitor, and iv) a Rock inhibitor, under conditions sufficient to induce reprogramming, whereby the efficiency of reprogramming is improved by at least 10%, at least 50%, at least 100%, at least 300%, or at least 500% as compared to the efficiency of reprogramming without contacting the population of cells with the small molecule agent.

In particular embodiments, the cells are contacted with a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In some embodiments, the population of cells prior to reprogramming comprises non-pluripotent cells. In other embodiments, the efficiency of reprogramming is measured by time required for reprogramming or number of cells reprogrammed.

In yet other embodiments, the conditions sufficient to induce reprogramming comprise contacting the population of cells with at least one exogenous transcription factor selected from the group consisting of an Oct4, Sox, Klf, Myc, Lin28, or Nanog polypeptide, or a polynucleotide encoding Oct4, Sox, Klf, Myc, Lin28, or Nanog. In particular embodiments, the conditions comprise contacting the population of cells with an Oct4, Sox2, and Klf4 polypeptide or a polynucleotide encoding Oct4, Sox2, and Klf4.

Yet another embodiment of the invention provides a method of sorting a population of cells in a feeder-free environment to obtain a population of cells enriched for pluripotent cells comprising obtaining a suspension of dissociated cells comprising a mixed population of cells in a feeder-free environment and sorting the cells in the suspension to obtain cells expressing one or more markers of pluripotency, thereby obtaining an enriched population of cells enriched for pluripotent cells. In some embodiments, the suspension comprises at least one of i) a TFGβ inhibitor; ii) a GSK3 inhibitor; iii) a MEK inhibitor, or iv) a Rock inhibitor. In further embodiments, the sorting is by magnetic beads or flow cytometry. In particular embodiments, the sorting is by magnetic beads. In other particular embodiments, the sorting is by flow cytometry.

In some embodiments, the method further comprises culturing the enriched population of cells in a culture medium comprising at least one of i) a TFGβ inhibitor; ii) a GSK3 inhibitor; iii) a MEK inhibitor, or iv) a Rock inhibitor, optionally in combination with soluble fibronectin.

In particular embodiments, the mixed population of cells in the suspension is contacted before sorting with at least one of i) a TFGβ inhibitor; ii) a GSK3 inhibitor; iii) a MEK inhibitor, or iv) a Rock inhibitor. In certain embodiments, the mixed population of cells is contacted with a TFGβ inhibitor, a GSK3 inhibitor, a MEK inhibitor, and a Rock inhibitor;

in other certain embodiments the TFGβ inhibitor is SB431542, the GSK3 inhibitor is CHIR99021, the MEK inhibitor is PD0325901, and the Rock inhibitor is thiazovivin.

In particular embodiments, the mixed population of cells comprises cells expressing one or more markers of pluripotency. In particular embodiments, the one or more markers of pluripotency comprises SSEA4, TRA160, TRA181, TRA1-85, TRA2-54, GCTM-2, TG343, TG30, CD9, CD29, CD30, CD50, CD133/prominin, CD140a, CD56, CD73, CD105, CD31, CD34, OCT4, Nanog or Sox2. In specific embodiments, the marker of pluripotency is selected from the group consisting of SSEA4, TRA181, TRA160, and CD30

In particular embodiments, the method comprises contacting the mixed population of cells with one or more pluripotency factors to induce reprogramming. In some embodiments, contacting comprises introducing one or more pluripotency factors into the cells in the mixed population of cells. In certain embodiments, the pluripotency factor comprises an Oct4, Sox, Klf, Myc, Lin28, or Nanog polypeptide, or a polynucleotide encoding Oct4, Sox, Klf, Myc, Lin28, or Nanog. In other particular embodiments, the pluripotency factor comprises an Oct4, a Sox2, and a Klf4 polypeptide, or polynucleotides encoding an Oct4, a Sox2, and a Klf4 polypeptide.

In certain particular embodiments, the pluripotent cells are induced pluripotent cells.

In some embodiments, the enriched population of cells is enriched by at least 20%, at least 50%, at least 100%, at least 200%, or at least 500% with respect to cells expressing one or more markers of pluripotency.

In another embodiment the invention provides a method of obtaining induced pluripotent stem cells comprising: treating a population of cells to induce reprogramming; preparing a suspension of dissociated cells comprising the population of cells; sorting the cells in the suspension to obtain sorted cells expressing one or more markers of pluripotency; culturing the sorted cells expressing one or more markers of pluripotency, wherein iPSCs are obtained. In particular embodiments, the sorted cells are cultured in the absence of cytokines and growth factors, optionally in a feeder-free environment, and optionally in the presence of soluble fibronectin.

In some embodiments, the population of cells is contacted with at least one of i) a TGFβ inhibitor; ii) a GSK3 inhibitor; iii) a MEK inhibitor, or iv) a Rock inhibitor. In particular embodiments, the population of cells is contacted with a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In other embodiments, treating the population of cells to induce reprogramming comprises contacting the population of cells with one or more pluripotency factors. In particular embodiments, the pluripotency factor comprises an Oct4, Sox, Klf, Myc, Lin28, or Nanog polypeptide, or a polynucleotide encoding Oct4, Sox, Klf, Myc, Lin28, or Nanog. In certain embodiments, the pluripotency factor comprises an Oct4, a Sox2, and a Klf4 polypeptide, or polynucleotides encoding an Oct4, a Sox2, and a Klf4 polypeptide.

In other embodiments, treating the population of cells to induce reprogramming further comprises contacting the population of cells with at least one of i) a TFGβ inhibitor; ii) a GSK3 inhibitor; iii) a MEK inhibitor, or iv) a Rock inhibitor. In particular embodiments, the cells are contacted with a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In other embodiments, the suspension comprises at least one of i) a TFGβ inhibitor; ii) a GSK3 inhibitor; iii) a MEK inhibitor, or iv) a Rock inhibitor. In particular embodiments, the suspension comprises a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In some embodiments, sorting is by flow cytometry or magnetic beads. In particular embodiments, cells are sorted to obtain cells expressing at least one, two, three, four, or more marker of pluripotency. In other particular embodiments, the one or more markers of pluripotency comprises SSEA4, TRA160, TRA181, TRA1-85, TRA2-54, GCTM-2, TG343, TG30, CD9, CD29, CD30, CD50, CD133/prominin, CD140a, CD56, CD73, CD105, CD31, CD34, OCT4, Nanog or Sox2. In other particular embodiments, the one or more markers of pluripotency is selected from the group consisting of SSEA4, TRA160, TRA181, and CD30. In some embodiments, the one or more markers of pluripotency are SSEA4, CD30, and TRA160 or TRA181. In another embodiment cells are sorted using specific markers to deplete non-reprogrammed cells from a reprogramming population.

In some embodiments, culturing comprises culturing the cells in a culture medium comprising at least one small molecule agent selected from the group consisting of
i) a TFGβ inhibitor; ii) a GSK3 inhibitor; iii) a MEK inhibitor, and iv) a Rock inhibitor. In particular embodiments, the culture medium comprises a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In particular embodiments, the cells are cultured in a feeder-free environment. In certain embodiments, the cells are treated, suspended, sorted, and cultured in a feeder-free environment.

In some embodiments, induced pluripotent stem cells are obtained in about 2 to 22 days. In particular embodiments, induced pluripotent stem cells are obtained in about 4 to about 18 days.

In other embodiments, induced pluripotent stem cells are obtained within about 4 to about 22 days after treating the population of cells to induce reprogramming. In certain embodiments, induced pluripotent stem cells are obtained within about 6 to about 18 days after treating the population of cells to induce reprogramming, and in other certain embodiments, induced pluripotent stem cells are obtained within about 10 to about 16 days after treating the population of cells to induce reprogramming.

The invention also provides in another embodiment an induced pluripotent stem cell obtained by any of the above methods.

The invention further provides a method of depleting pluripotent cells from a population of cells comprising: obtaining a suspension of dissociated cells comprising a mixed population of cells having pluripotent cells, and sorting the cells in the suspension to remove cells expressing one or more markers of pluripotency, thereby depleting pluripotent cells from a population of cells.

In some embodiments, the mixed population of cells comprises multipotent cells or (adult) somatic cells.

In other embodiments, the mixed population of cells in the suspension is cultured prior to obtaining the suspension in a culture medium comprising at least one small molecule agent selected from the group consisting of i) a TFGβ inhibitor; ii) a GSK3 inhibitor; iii) a MEK inhibitor, and iv) a Rock inhibitor. In particular embodiments, the culture medium comprises a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In further embodiments of the invention, the suspension comprises at least one small molecule agent selected from the group consisting of i) a TFGβ inhibitor; ii) a GSK3 inhibitor; iii) a MEK inhibitor, and iv) a Rock inhibitor. In particular embodiments, the suspension comprises a TFGβ inhibitor, a GSK3 inhibitor, a MEK inhibitor, and a Rock inhibitor; in certain embodiments the TFGβ inhibitor is SB431542, the GSK3 inhibitor is CHIR99021, the MEK inhibitor is PD0325901, and the Rock inhibitor is thiazovivin.

In some embodiments, sorting is by flow cytometry. In other embodiments sorting is by antibody-coated magnetic bead enrichment.

Some embodiments of the invention provide a method of obtaining a pluripotent cell having genomic stability comprising contacting a cell in a feeder-free environment with at least one small molecule agent selected from the group consisting of i) a TFGβ inhibitor; ii) a GSK3 inhibitor; iii) a MEK inhibitor, and iv) a Rock inhibitor; in the absence of c-myc under conditions sufficient to obtain a pluripotent cell having genomic stability.

In some embodiments the cell is an embryonic stem cell, a pluripotent cell, a multipotent cell; a non-pluripotent cell; and a somatic cell. In some specific embodiments, the cell comprises a non-pluripotent cell.

In certain embodiments, the conditions comprise contacting the cell with at least one pluripotency factor. In some embodiments, the pluripotency factor is an exogenous transcription factor selected from the group consisting of an Oct4, Sox, Klf, Myc, Lin28, or Nanog polypeptide, or a polynucleotide encoding Oct4, Sox, Klf, Myc, Lin28, or Nanog. In particular embodiments, the pluripotency factor comprises an Oct4, a Sox2, and a Klf4 polynucleotide.

In some embodiments of the invention, the small molecule agent comprises a Rock inhibitor. In particular embodiments, the Rock inhibitor is thiazovivin or Y27632, and in more particular embodiments the Rock inhibitor is thiazovivin.

In other embodiments of the invention, the small molecule agent comprises a TFGβ inhibitor. In some embodiments, the TFGβ inhibitor is A-83-01 or SB431542.

In some embodiments, the small molecule agent comprises a GSK3 inhibitor, and in particular embodiments the GSK3 inhibitor is CHIR99021 or BIO.

In other embodiments of the invention, the small molecule agent comprises a MEK inhibitor. In some particular embodiments, the MEK inhibitor is PD98059 or PD032901.

In some embodiments of the invention, the small molecule agent comprises a TFGβ inhibitor, a GSK3 inhibitor, a MEK inhibitor, and a Rock inhibitor. In particular embodiments, the TFGβ inhibitor is SB431542, the GSK3 inhibitor is CHIR99021, the MEK inhibitor is PD0325901, and the Rock inhibitor is thiazovivin.

The invention additionally comprises a method of culturing a pluripotent cell to maintain genomic stability of the cell comprising culturing a pluripotent cell in a feeder-free environment in a culture medium comprising at least one agent that maintains genomic stability of the pluripotent cell, wherein the agent is selected from the group consisting of: i) a TFGβ inhibitor; ii) a GSK3 inhibitor; iii) a MEK inhibitor, and iv) a Rock inhibitor, while maintaining genomic stability of the pluripotent cell during culturing.

In certain embodiments, the conditions comprise contacting the cell with at least one pluripotency factor. In some embodiments, the pluripotency factor is an exogenous transcription factor selected from the group consisting of an Oct4, Sox, Klf, Myc, Lin28, or Nanog polypeptide, or a polynucleotide encoding Oct4, Sox, Klf, Myc, Lin28, or Nanog. In particular embodiments, the pluripotency factor comprises an Oct4, a Sox2, and a Klf4 polynucleotide.

In some embodiments, the culture medium comprises at least two, at least three, or four agents.

In some embodiments of the invention, the agent comprises a Rock inhibitor. In particular embodiments, the Rock inhibitor is thiazovivin or Y27632, and in more particular embodiments the Rock inhibitor is thiazovivin.

In other embodiments of the invention, the agent comprises a TFGβ inhibitor. In some embodiments, the TFGβ inhibitor is A-83-01 or SB431542.

In some embodiments, the agent comprises a GSK3 inhibitor, and in particular embodiments the GSK3 inhibitor is CHIR99021 or BIO.

In other embodiments of the invention, the agent comprises a MEK inhibitor. In some particular embodiments, the MEK inhibitor is PD98059 or PD032901.

In some embodiments of the invention, the agent comprises a TFGβ inhibitor, a GSK3 inhibitor, a MEK inhibitor, and a Rock inhibitor. In particular embodiments, the TFGβ inhibitor is SB431542, the GSK3 inhibitor is CHIR99021, the MEK inhibitor is PD0325901, and the Rock inhibitor is thiazovivin.

In some embodiments of the invention, the pluripotent cell is cultured in the culture medium for at least one, at least two, at least five, at least ten, or at least 15 passages while maintaining genomic stability of the pluripotent cell.

BRIEF DESCRIPTION OF THE DRAWINGS

FIG. 1A. Different morphologies were evident when single cell dissociated human pluripotent stem cells were treated with various combinations of small molecules in a feeder free environment. Medium containing a combination of ROCKi/MEKi/TGFβi/GSKi delivered robust growth and viability of human pluripotent stem cells. FIG. 1B. While some small molecules supported maintenance of pluripotent stem cells, i.e., MEKi/TGFβi/GSKi, and others facilitated single cell dissociation of pluripotent stem cells, i.e., Rocki, the unique combination of these small molecules, i.e., ROCKi/MEKi/TGFβi/GSKi, supported single cell dissociation while maintaining undifferentiated status as indicated by highly proliferative colonies that were positive for pluripotent marker Tra181. Tra181, red; DAPI, blue. FIG. 1C. The combination of MEKi/TGFβi/GSKi/ROCKi supported viability and proliferation when hiPSCs were seeded at $1 \times 10^5$ cells on Matrigel and scored 4 days later for number of viable cells and percent viability as measured by trypan blue. FIG. 1D. When combined with MEKi/TGFβi/GSKi, colonies cultured with Thiazovivin appear to be more compact in morphology relative to culture supported by MEKi/TFGβi/GSKi with Y27632. FIG. 1E. Flow-cytometry analysis for surface expression of SSEA4 and Tra181 of hiPSCs cultured in Y27632 or Thiazovivin in combination with MEKi/TFGβi/GSKi shows that Thiazovivin better supports the maintenance of cells in an undifferentiated state compared to the combination having Y27632.

FIG. 2A. iPSCs generated on feeder cells were readily adapted to feeder free and single cell culture conditions with the utilization of SMC4 medium. Cell survival is perturbed and limited cell attachment and growth is seen, however, upon single cell dissociation and culture in conventional culture conditions. FIG. 2B. Once adapted to a feeder free environment, iPSCs were routinely cultured as single cells on a feeder free surface when continuously maintained in SMC4 medium.

FIG. 3A. Single cell dissociated human pluripotent stem cells maintained in SMC4 medium in a feeder free culture for 10 passages expressed pluripotent markers Nanog and Tra181 by immunoflourescence analysis. FIG. 3B shows the percent of 7 Aminoactinomysin D (7AAD) staining cells four hours after human pluripotent stem cells were dissociated into single cells and placed into either conventional culture medium or SMC4 medium. Single cell dissociated human pluripotent stem cells displayed significantly increased viability when cultured in SMC4 medium rather than conventional culture medium as seen by 7AAD staining and flow-cytometry analysis. FIG. 3C. Quantitative population analysis by flow cytometry revealed that nearly all the cells dissociated into single cells and maintained in SMC4 medium expressed multiple markers of undifferentiated status. FIG. 3D. Global expression analysis revealed a high correlation between iPSCs passaged as single cells and maintained in a SMC4 medium free of feeder cells and human ESCs cultured on feeder cells and maintained as cell clumps during passaging, including H1 cells. FIG. 3E. iPSCs cultured in a feeder cell-free system using SMC4 medium and passaged as single cells, but not their original source fibroblast cells, expressed an array of pluripotent markers, similar to human ESCs, including H1 and HuES9. FIG. 3F. Exogenous expression of reprogramming factors was effectively shutdown in iPSCs maintained in a feeder-free environment, unlike exogenous factor positive controls (fibroblast cells infected with lentivirus expressing reprogramming factors post 4 days). Endogenous expression of the reprogramming factors in feeder free iPSCs was similar to ESCs, including H1 and HuES9. FIG. 3G. After 11 passages as single cells in feeder free environment, human pluripotent stem cells retained normal karyotype. FIG. 3H. 14 days post replacement of SMC4 medium with conventional differentiation medium, cells maintained in a feeder free environment displayed gene expression indicative of ectoderm, endoderm and mesoderm germ layers, in addition to extraembryonic markers, which are normally expressed by only naïve and totipotent stem cells. FIG. 3I. Immuno-flourescence analysis: iPSCs cultured in a feeder cell-free system using SMC4 medium and passaged as single cells readily developed into all three somatic cell types upon transfer to conventional differentiation medium. Mesoderm, alpha smooth muscle actin (αSMA); Ectoderm, beta tubulin III (β TUB III); Endoderm, Sox17. FIG. 3J. Teratoma formation analysis demonstrating that human pluripotent stem cells cultured in SMC4 medium give rise to cell types representative of the three germ layers, and thus retain their pluripotent potential.

FIG. 4A. Prior to sorting, the human pluripotent stem cells were dissociated into single cells and labeled with antibody markers to SSEA4 and Tra-181. Cells were sorted using FACs technology based on surface marker expression of pluripotent markers, SSEA4 and TRA181. Post sort cells were seeded initially in SMC4+ fibronectin medium which was exchanged for SMC4 medium 24-72 hrs later. One day post sorting, sorted cells were dividing and by day 5, large colonies consisting of hundreds of cells were present. FIG. 4B. Sorted cells retained their expression of pluripotency marker Tra160. Tra160, red; DAPI, blue. FIG. 4C. After 5 passages post sort, approximately 1 month in culture, quantitative flow cytometry analysis revealed that the majority of the sorted iPSCs retained their pluripotent status based on SSEA4 and Tra181 staining. FIG. 4D. Various densities derived from SSEA4+ and Tra181+ human pluripotent stem cells were plated, including clonal densities of 500 events per well of a 6-well plate, approximately 52 events per $cm^2$, on feeder-free surface and supplemented with SMC4+ fibronectin medium. After 7 days post sort, many alkaline phosphatase positive colonies appeared in each of the seeded wells. FIG. 4E. The derived alkaline phosphatase positive colonies were scored. Approximately 8-10% of the seeded events had produced colonies with 16,000 events per well producing a nearly confluent well. N.C., not counted due to confluency preventing accurate counts. FIG. 4F. SSEA4+ and Tra181+ human pluripotent stem cells were sorted directly into 96 well-plates at various densities including 1 event per well, approximately 3 events per $cm^2$. Wells were stained for alkaline phosphatase 8 days post sort. FIG. 4G. Each well was scored for alkaline phosphatase colonies on day 8.

FIG. 5A. Seven days after the initiation of reprogramming by the ectopic expression of Oct4, Sox2, Klf4 and cMyc, the cells were either maintained in conventional medium or switched to SMC4 medium. After 20 days of reprogramming, few if any iPSC-like colonies were formed in the conventional medium culture, while many iPSC-like colonies appeared in the cells switched to SMC4 medium. FIG. 5B. Many iPSC-like colonies in SMC4 medium expressed alkaline phosphatase while few colonies in the conventional culture expressed alkaline phosphatase.

FIGS. 6A-6E. Culture in SMC4 medium promotes naïve characteristics. FIG. 6A. Schematic illustration of the adaptation of human pluripotent stem cells to SMC4 medium and its comparison to conventionally maintained human pluripotent stem cells. FIG. 6B. Hierarchical clustering based on Affymetrix global gene expression and Pearson Coefficient between hiPSCs derived from IMR90 parental cells (conventionally derived hiPSC (Cony) and SMC4 medium-adapted hiPSCs (SMC4 medium)), both cultured for 11 passages in respective media, demonstrating that both hiPSCs are similar to each other and different from their parental IMR90 cells. FIG. 6C. While Xist expression was modestly repressed in hiPSCs cultured in conventional format compared to their parental IMR90 cell line, it was significantly repressed in hiPSCs cultured in SMC4 medium and was similar to levels of female hESC, HUES9. FIG. 6D. X-chromosome located genes were more highly expressed in hiPSCs cultured in SMC4 medium as compared to expression in conventionally cultured hiPSCs. FIG. 6E. When transferred back onto feeder-cells, hiPSCs maintained in SMC4 medium exhibit a morphology that is more like mouse ESCs as seen by a more three-dimensional shape and less of a flat morphology as compared with hiPSCs cultured in conventional medium.

FIG. 7A. Schematic illustration of parallel generation of clones FTi91 and 93, generated in SMC4 medium and maintained in SMC4 medium in FF culture, and clone FTi99, generated in conventional medium and maintained on feeder cells. FIG. 7B. Hierarchical clustering based on Affymetrix global gene expression and Pearson Coefficient depicting a close relationship between the derived pluripotent lines and distant relationship from the starting cell line (FTC1). FIG. 7C. Hierarchical clustering based on all 4-fold differentially expressed genes amongst Hues9, H1, FTi99, FTi91 and FTi93 demonstrating a separation between pluripotent lines cultured in conventional system versus those cultured in SMC4 medium. FIG. 7D. Affymetrix gene expression of selected genes associated with naïve and lineage differentiation compared between the SMC4 medium group (FTi91 and 93) versus conventional culture group (H1, Hues9 and FTi99) showing an increase in expression of many genes associated with pluripotency and significant reduction in lineage-specific gene expression in the SMC4 medium set. FIG. 7E. Schematic illustration of various methods of deriving hiPSCs with naïve status. Bottom panel describes the advantages of naïve state over primed state.

FIG. 8A. A typical cell population early in the reprogramming process: immune staining showed that the majority of fast growing cells formed colonies that were SSEA4 negative and inevitably non-pluripotent cells. These cells were transformed and highly proliferative, grew quickly, and dominated the culture. Colony 1 shows a SSEA4 positive colony with the potential of becoming an iPSC colony while colony 2 shows a transformed population with a high proliferation rate but negative for pluripotentcy marker staining. FIG. 8B. Many non-iPSC colonies displayed expression of a single pluripotent marker, while true iPSC colonies displayed expression of multiple pluripotent markers. At a later stage of reprogramming, various colonies were formed with some colonies being double positive for both SSEA4 and Tra181, i.e., colony 1, while other colonies were only positive for one of the markers or none, e.g., colonies 4 and 5.

FIG. 11A. Representative flow profile of SSEA4/Tra181 expression of various hiPSC lines demonstrating that all derived clones are representative of the majority population expressing both SSEA4 and Tra181. FIG. 11B. Based on the gating seen in (A), CD30 and CD9 flow profile of each cell line was assessed. Only clones FTC8 clone 1 and FTi31 appear to express CD30 while all clones express CD9. FIG. 11C. Relative Nanog expression of various lines was also assessed. FIG. 11D. Summary table demonstrating that only CD30 expression correlates with Nanog expression.

FIG. 13A. A population of cells early in the reprogramming process was enriched by single cell sorting of SSEA4+ cells. The starting population of cells, containing reprogrammed and non-reprogrammed cells, was enzymatically dissociated into single cells, stained for unique markers of pluripotency and sorted based on surface marker expression by immunoconjugated magnetic beads to obtain a cell population positive for SSEA4. After this enrichment for SSEA$^{4+}$ cells, 10,000 SSEA4+ cells were seeded onto Matrigel™ coated dishes and cultured in either conventional medium or SMC4 medium in a FF environment. AP staining was conducted 8 days post sorting. The smaller inserted panels in the right-hand corners of these are images of representative cell morphologies. No alkaline phosphatase positive colonies were detected in conventional culture while many alkaline phosphatase positive colonies were derived with SMC4 medium. FIG. 13B. The number of SSEA$^{4+}$/Tra181$^+$ colonies derived from cellular reprogramming on Matrigel™ in the presence or absence of SMC4 medium were scored. FIG. 13C. iPSC clones derived from either IMR90 fibroblast cells or adipose stem cells in feeder free conditions and single cell culture using SMC4 medium expressed markers of pluripotency. FIG. 13D. Whole population flow cytometry analysis of iPSC clones derived using single cell sorting methods revealed that the majority of cells were positive for key pluripotent markers. FIG. 13E. iPSCs generated using single cell sorting for SSEA4 and feeder-free culture, but not their original source fibroblast or adipose stem cells, expressed an array of pluripotent markers, similar to human ESCs, including H1 and HuES9. FIG. 13F. Exogenous expression of reprogramming factors was effectively silenced in the iPSCs generated using single cell sorting and feeder-free culture, unlike control fibroblast cells that were infected with lentivirus expressing reprogramming factors post 3 days. FIG. 13G. iPSCs generated using single cell sorting based on SSEA4 readily developed into all three somatic cell types upon differentiation. Endoderm, FoxA2; Mesoderm, alpha smooth muscle actin (αSMA); Ectoderm, beta tubulin III (β TUB III).

FIG. 14A. Using FACS sorting, a unique and rare population of cells that were SSEA4+/Tra181+ early in the reprogramming process was selected and transferred to feeder free culture supplemented with SMC4+ fibronectin medium which was exchanged for SMC4 medium after 24-72 hours. After an additional 6 days of culture, SSEA4+/Tra181+ derived iPSC colonies appeared to be growing in feeder free culture. However, when SSEA4−/Tra181− colonies were transferred and maintained in feeder free culture, no alkaline phosphatase expressing colonies were detected after 14 days of culture. FIG. 14B. Various SSEA4+/Tra181+ sorted cells developed into colonies while maintaining their SSEA4 and Tra181 expression.

FIG. 16A. Clones FTi91 and FTi93 derived from the above strategy were stained for expression of pluripotent markers. FIG. 16B. qRT-PCR of endogenous expression of pluripotent markers for FTC1 (foreskin fibroblast), H1 and Hues9 (hESC lines), FTi 91 and 93 (FTC1 derived hiPSC clones) and Day 4 P.I. (Day 4 post infection). Expression was normalized to Gapdh and relative within each gene group. FIG. 16C. Oct4 promoter methylation status. Open circles represent unmethylated CpG islands while dark circles represent methylated CpG islands. FIG. 16D. EB formation and differentiation of clones FTi91 and 93 after 28 days of differentiation. Endoderm, FoxA2; Mesoderm, alpha smooth muscle actin (αSMA); Ectoderm, Tuj 1. FIG. 16E. Histological sections of teratoma derived from hiPSC clone generated and maintained in FF culture and SMC4 medium. Black arrows point to areas of interest: Mesoderm, white adipose tissue; Ectoderm, neurons; Endoderm, glands.

FIG. 17A. Copy number variation as assessed by array comparative genomic hybridization. Bottom table is an interpretation summary of the data demonstrating minimal copy number variation between the SMC4 medium-cultured human pluripotent stem cells and their parental cell line. FIG. 17B. Cytogenic analysis of G-banded metaphase cells. Bottom table is a summary of the data depicting genomic stability after long-term feeder free culture in SMC4 medium.

FIG. 18A. Representative immunofluorecence staining of pluripotent markers Oct4, Tra181, Nanog and Tra160 expressed in individual FTC5 and FTC7 derived hiPSC clones induced with OKS and generated using multiplex platform. FIG. 18B. Representative lineage specific staining of FTC5 and FTC7 derived hiPSCs 28 days post induction of differentiation. Endoderm, FoxA2; Mesoderm, alpha smooth muscle actin (αSMA); Ectoderm, Tuj 1. FIG. 18C. Cytogenetic analysis of G-banded metaphase cells from FTC5 and FTC7 derived hiPSC clones after long-term FF and single cell culture in various passages.

FIG. 19A. A population of pluripotent stem cells was further enriched during culturing as demonstrated by Tra181 enrichment in feeder free and SMC4 platform. FIG. 19B. During culture of a pluripotent cell population, some proportion of cells within the population may begin to differentiate and lose their pluripotency. Using selection methods for pluripotency, i.e., Tra181 enrichment, a homogeneous culture of undifferentiated cells was attained.

FIGS. 21A-21C. Cytokine free culture of human pluripotent stem cells on feeder free culture. FIG. 21A. Human pluripotent stem cells maintained their growth and morphology when cultured on a gelatin coated surface and supplemented with SMC4 medium in the absence of any cytokines, including bFGF. FIG. 21B. Magnified image depicting individual cells within a human pluripotent stem cell colony. FIG. 21C. SSEA4 and Tra181 co-expression at passage 3 provided further evidence that the cytokine-free cultured human pluripotent stem cells maintained their undifferentiated status.

DETAILED DESCRIPTION OF THE INVENTION

Figure 1A:
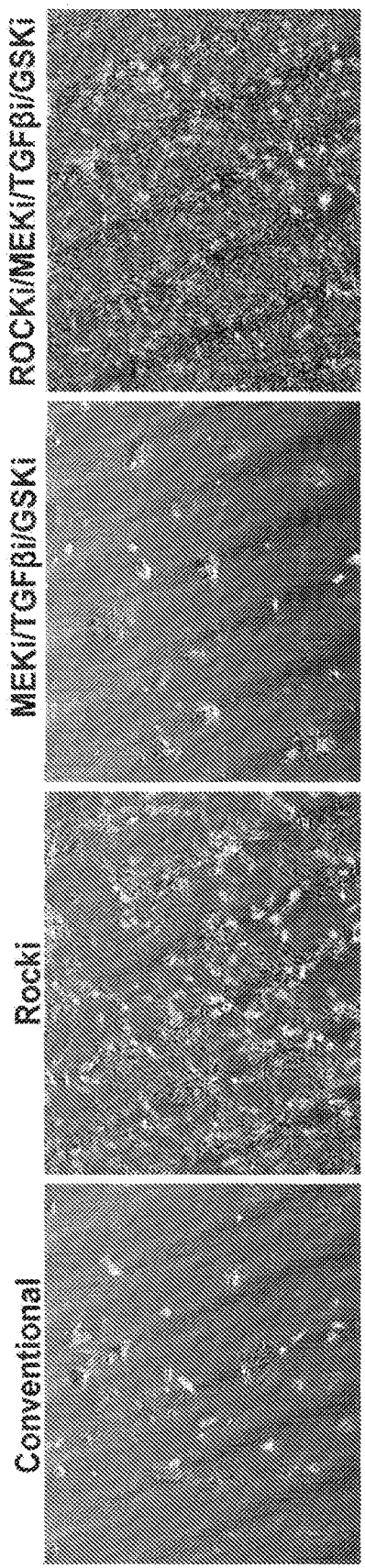
FIGS. 1A-1E. The effects of various small molecule cocktails on single cell culture of human pluripotent stem cells on feeder free substratum.
Figure 1B:
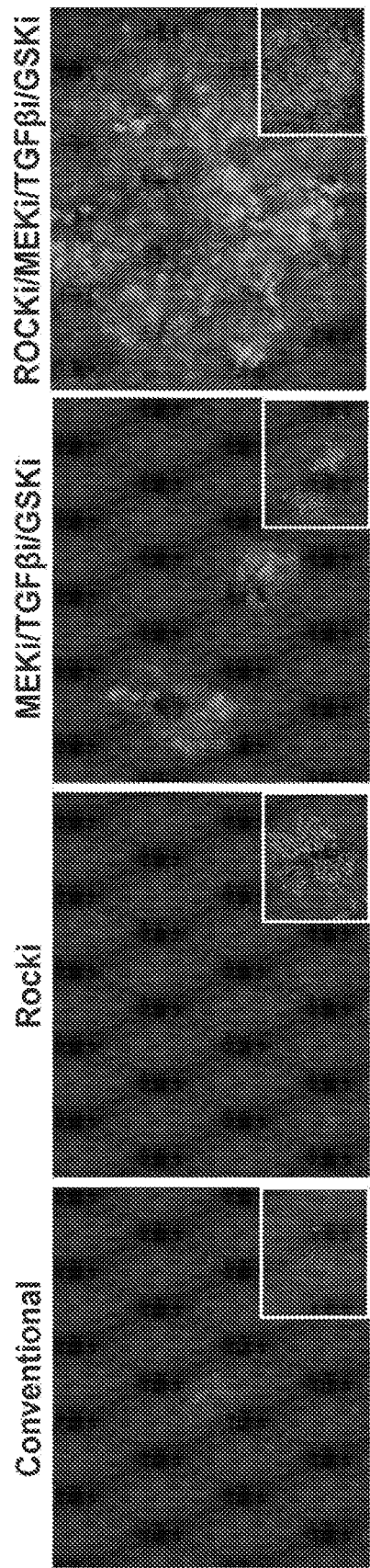
Figure 1C:
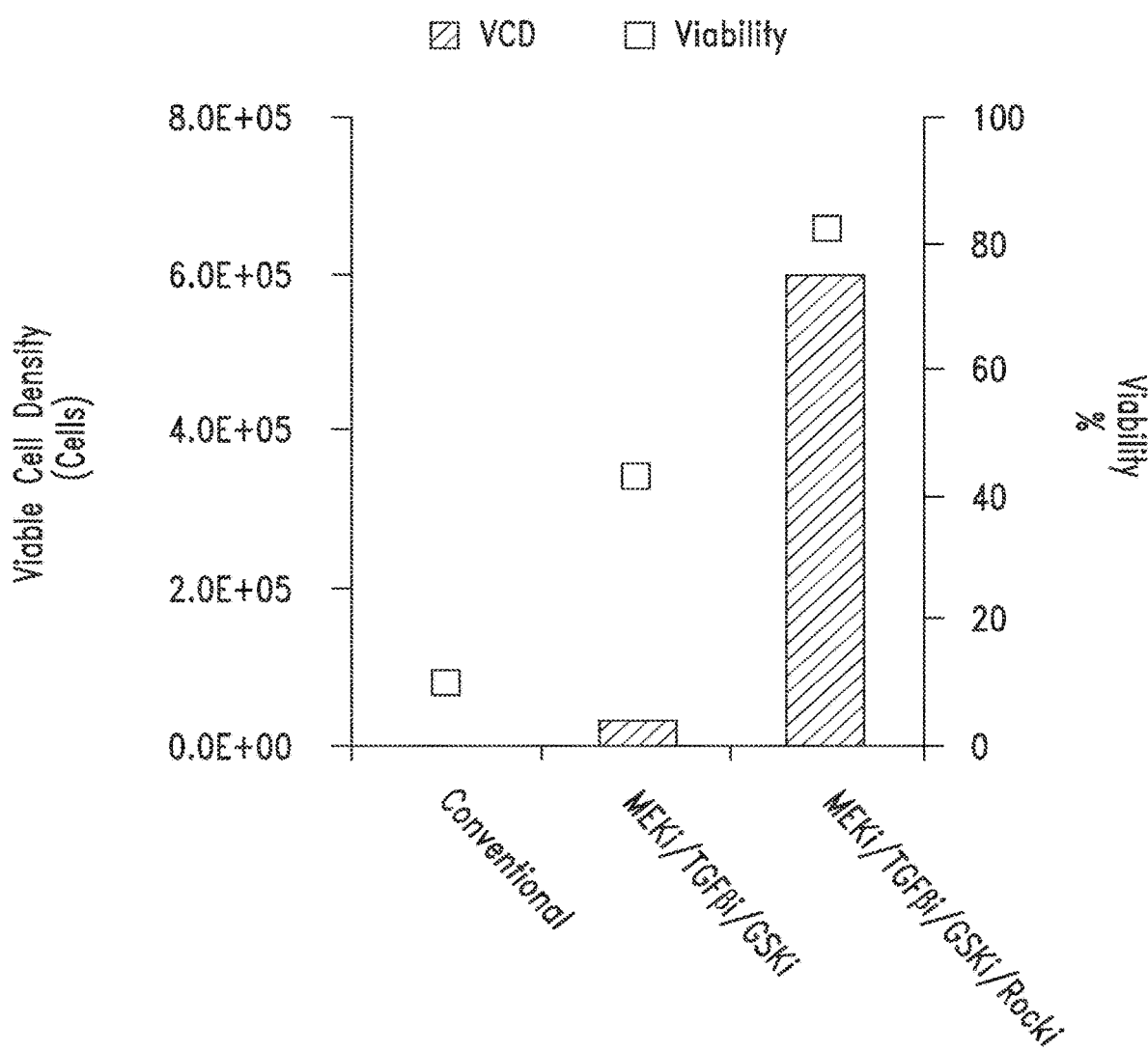
Figure 1D:
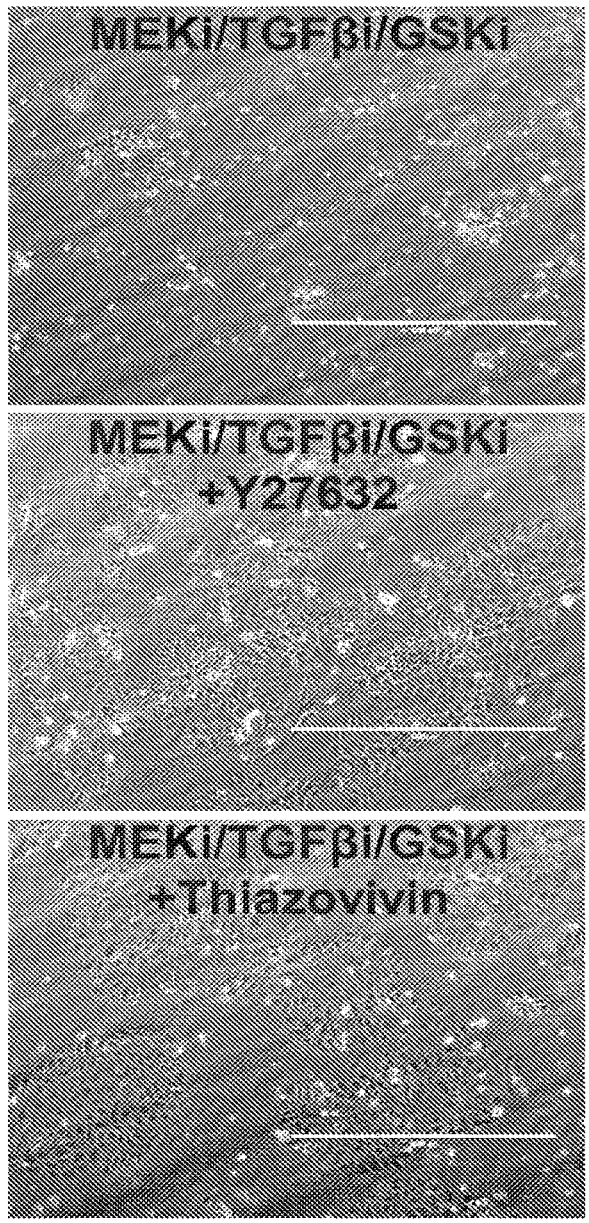
Figure 1E:
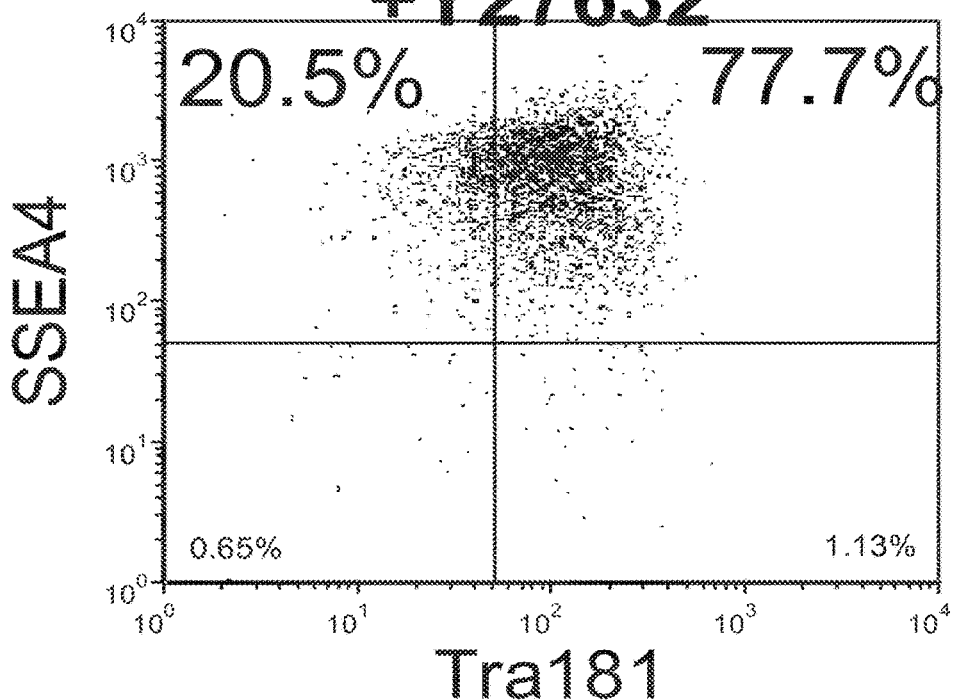
Figure 1E:
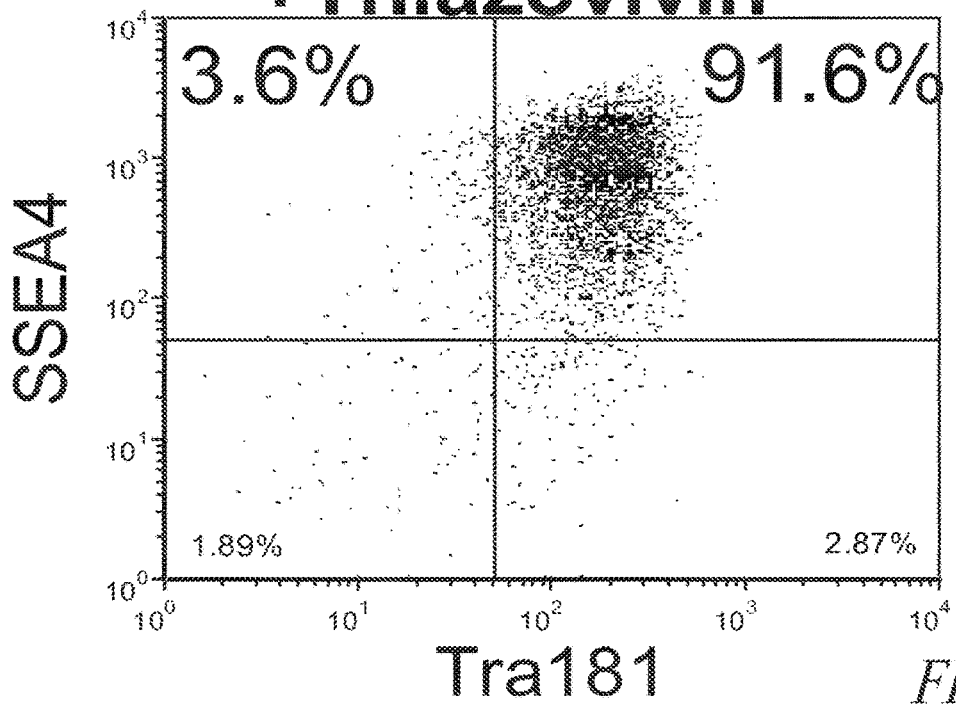

The invention provides a robust culture system for culturing stem cells, including feeder-free conditions for generating and culturing human induced pluripotent stem cells (iPSCs). Specifically, the invention provides a culture platform that allows long-term culture of pluripotent cells in a feeder-free environment; reprogramming of cells in a feeder-free environment; single-cell dissociation of pluripotent cells; cell sorting of pluripotent cells; improved efficiency of reprogramming; generation of a naïve pluripotent cell; and identification markers for the identification and selection of pluripotent cells. The media and culture methods of the invention support the viability and survival of single cell dissociated human stem cells, and maintain the undifferentiated status of stem cells to allow for cultivation and passaging of dissociated single cells without differentiation.

Definitions

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "potency" refers to the sum of all developmental options accessible to the cell (i.e., the developmental potency). One having ordinary skill in the art would recognize that cell potency is a continuum, ranging from the most plastic cell, a totipotent stem cell, which has the most developmental potency to the least plastic cell, a terminally differentiated cell, which has the least developmental potency. The continuum of cell potency includes, but is not limited to, totipotent cells, pluripotent cells, multipotent cells, oligopotent cells, unipotent cells, and terminally differentiated cells. In the strictest sense, stem cells are pluripotent; thus, being able to give rise to any mature cell type. However, multipotent, oligopotent or unipotent progenitor cells are sometimes referred to as lineage restricted stem cells (e.g., mesenchymal stem cells, adipose tissue derived stem cells, etc.) and/or progenitor cells.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell). The level of cell pluripotency can be determined by assessing pluripotency characteristics of the cells. Pluripotency characteristics include, but are not limited to: i) pluripotent stem cell morphology; ii) expression of pluripotent stem cell markers including, but not limited to SSEA1 (mouse only), SSEA3/4; TRA1-60/81; TRA1-85, TRA2-54, GCTM-2, TG343, TG30, CD9, CD29, CD133/prominin, CD140a, CD56, CD73, CD105, CD31, CD34, OCT4, Nanog and/or Sox2, and as described in the present invention, CD30 and CD50; iii) ability of pluripotent mouse stem cells to contribute to germline transmission in mouse chimeras; iv) ability of pluripotent stem cells to contribute to the embryo proper using tetraploid embryo complementation assays; v) teratoma formation of pluripotent stem cells; vi) formation of embryoid bodies: and vii) inactive X chromosome reactivation.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical intercell spacing.

As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

"Adhere" refers to cells attaching to a vessel, for example, a cell attaching to a sterile plastic (or coated plastic) cell culture dish or flask in the presence of an appropriate culture medium. Certain classes of cells are not sustained or do not grow in a culture unless they adhere to the cell culture vessel. Certain classes of cells ("non-adherent cells") are maintained and/or proliferate in culture without adhering.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate" refers to the sustaining, propagating (growing) and/or differentiating of cells outside of tissue or the body, for example in a sterile plastic (or coated plastic) cell culture dish or flask. "Cultivation" may utilize a culture medium as a source of nutrients, hormones and/or other factors helpful to propagate and/or sustain the cells.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, the terms "enrich" and "enriching" refer to increasing the amount of a specified component in a composition, such as a composition of cells, and "enriched", when used to describe a composition of cells such as a cell population, refers to a population of cells having an increased amount proportionally of a specified component as compared to the proportion of such component in the population of cells prior to being enriched. For example, a composition such as a population of cells may be enriched with respect to a target cell type (i.e., cells having specified characteristics), thus having an increased proportion or percent of the target cell type as compared to the proportion of the target cells present in the population of cells before being enriched. A population of cells may be enriched for a target cell type by cell selection and sorting methods known in the art. In some embodiments of the invention, a population of cells is enriched by a sorting or selection process as described in the examples herein. In a particular embodiment of the invention, a method that enriches for a target cell population, enriches the cell population with respect to the target cell population by at least about 20%, meaning that the enriched cell population comprises proportionately about 20% more of the target cell type than in the population before the population was enriched. In one embodiment, a method that enriches for a target cell population enriches the cell population with respect to the target cell population proportionately by at least about 30+%, 40+%, 50+%, 60+%, 70+%, 80%, 85%, 90%, 95%, 97%, 98% or 99%, or at least about 98%, or in particular embodiments, about 99%.

In certain aspects of the invention, a population of cells is enriched with respect to the amount of pluripotent cells or cells exhibiting pluripotency characteristics. In particular embodiments of the invention, a population of cells undergoing reprogramming is enriched for target cells having characteristics of pluripotency, such as expression of pluripotency markers including, without limitation, SSEA4, TRA 1-60, TRA-1-81, CD30 or CDS50. In another particular embodiment of the invention, a population of cells, such as a population of cells undergoing reprogramming, is depleted of nonpluripotent cells using surface markers specific to differentiating or nonpluripotent cells, which may include, for example, CD13, CD26, CD34, CD45, CD31, CD46, or CD7. The resulting cell population can thus be described as a population of cells enriched for pluripotent cells. In certain aspects of the invention, the cells in an enriched population of cells are enriched for target cells have a distinct gene or protein expression profile, for example, cell surface expression of at least two pluripotency markers such as SSEA4, TRA 1-60, TRA-1-81, CD30 and CD50. In some embodiments, the cell population is enriched for target cells expressing two or more pluripotency markers. In particular embodiments, the cell population is enriched for target cells expressing SSEA4 in combination with either Tra-181 or Tra-160. In more particular embodiments, the cell population is enriched for target cells expressing SSEA4, Tra181, and CD30. In one embodiment, at least about 5%, 10%, 15%, 20%, 25%, 30%, 40%, 50%, 70%, 75%, 80%, 90%, 95%, 97%, 98%, or 99% of the cells in an enriched population of cells are the target cell type, such as pluripotent cells.

Thus, in some embodiments the invention provides methods of enriching a population of cells for pluripotent cells by sorting the cell population based on cell surface expression of pluripotency markers, such as SSEA4, TRA 1-60, TRA-1-81, CD30 and CD50, and collecting the fraction of cells expressing such markers to obtain a population of cells that is enriched for pluripotent cells. In other embodiments of the invention, a population of cells is enriched for pluripotent cells by sorting the cell population based on cell surface expression of markers of differentiating or differentiated cells, such as CD13, CD26, CD34, CD45, CD31, CD46, and CD7, and depleting the cell population of such cells to obtain a population of cells that is enriched for pluripotent cells. In particular embodiments, the cell population is sorted based on the expression of CD13, and CD13+ cells are removed from the cell population to obtain a population of cells enriched for pluripotent cells.

As used herein, "feeder cells" or "feeders" are terms used to describe cells of one type that are co-cultured with cells of a second type to provide an environment in which the cells of the second type can grow, as the feeder cells provide growth factors and nutrients for the support of the second cell type. The feeder cells are optionally from a different species as the cells they are supporting. For example, certain types of human cells, including stem cells, can be supported by primary cultures of mouse embryonic fibroblasts, and immortalized mouse embryonic fibroblasts. The feeder cells may typically be inactivated when being co-cultured with other cells by irradiation or treatment with an anti-mitotic agent such as mitomycin c, to prevent them from outgrowing the cells they are supporting. Without limiting the foregoing, one specific feeder cell type may be a human feeder, such as a human skin fibroblast or a human embryonic stem cell. Another feeder cell type may be mouse embryonic fibroblasts (mEF).

As used herein, a "feeder-free" (FF) environment refers to an environment such as a cell culture or culture medium essentially free of feeder cells and which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, such as growth factors and cytokines, that are secreted by the feeder cells cultivated in the medium.

In some embodiments of the invention, the feeder free environment is essentially free of human feeder cells, including without limitation human fibroblasts, keratinocytes, and embryonic stem cells, and in particular embodiments additionally is not pre-conditioned by feeder cells. In further embodiments of the invention, the feeder free environment is essentially free of animal feeder cells, and further, in particular embodiments is not pre-conditioned with feeder cells. In certain embodiments of the invention, the feeder free environment is essentially free of both human and animal feeder cells, and in other certain embodiments the feeder free environment is essentially free of both human and animal feeder cells and is not pre-conditioned with feeder cells.

Genomic stability refers to the ability of a cell to faithfully replicate DNA and maintain integrity of the DNA replication process. As used herein to describe cells of the invention, "genomically stable cells" and "cells having genomic stability" refer to cells that exhibit a frequency of mutations and chromosomal aberrations (such as translocations, aneuploidy, copy number variations and duplications) that is substantially similar to the frequency of mutations and chromosomal aberrations relative to normal somatic human cells.

"Ingredient" refers to any compound or other material, whether chemical or biological in origin that may be used in cell culture media to maintain and/or promote the growth and/or differentiation of cells. The terms "component" "nutrient" and "ingredient" may be used interchangeably. Conventional ingredients used for cell culture media may include but are not limited to amino acids, salts, metals, sugars, lipids, nucleic acids, hormones, vitamins, fatty acids, proteins and the like. Other ingredients that promote and/or maintain cultivation of cells ex vivo may be selected by those persons of ordinary skill in the art as required for a desired effect.

"Isolate" or "isolating" refers to separating and collecting a composition or material from its natural environment, such as the separating of individual cell or cell cultures from tissue or the body. In one aspect, a population or composition of cells is substantially free of cells and materials with which it can be associated in nature.

"Isolated" or "purified" or "substantially pure", with respect to a target population of cells, refers to a population of cells that is at least about 50%, at least about 75%, at least about 85%, at least about 90%, and in particular embodiments, at least about 95% pure, with respect to the target cells making up a total cell population. Purity of a population or composition of cells can be assessed by appropriate methods that are well known in the art. For example, a substantially pure population of pluripotent cells refers to a population of cells that is at least about 50%, at least about 75%, at least about 85%, at least about 90%, and in particular embodiments at least about 95%, and in certain embodiments about 98% pure, with respect to pluripotent cells making up the total cell population. The term "essentially pure" is used interchangeably herein with "substantially pure".

"Passage" or "passaging" refers to the act of subdividing and plating cells into multiple cell culture surfaces or vessels when the cells have proliferated to a desired extent. In some embodiments "passage" or "passaging" refers to subdividing, diluting and plating the cells. As cells are passaged from the primary culture surface or vessel into a subsequent set of surfaces or vessels, the subsequent cultures may be referred to herein as "secondary culture" or "first passage," etc. Each act of subdividing and plating into a new culture vessel is considered one passage.

"Plating" refers to placing a cell or cells into a culture vessel such that the cells adhere to and spread on a cell culture vessel.

A "pluripotency factor" refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents. Transcription factors may refer to proteins (i.e., polypeptides) as well as the polynucleotides encoding the proteins unless the usage herein indicates otherwise. Examplary transcription factors include, for example, Oct, Klf, Myc, and Sox polypeptides, as well as polynucleotides encoding these polypeptides. Examples of additional transcription factors are provided herein.

As used herein, the terms "polypeptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. Polypeptides used in the methods of the invention may be prepared using any of a variety of well known recombinant and/or synthetic techniques.

The methods of the invention, in certain embodiments, employ active fragments of polypeptides described herein (e.g., Sox-2, c-Myc, Oct3/4, Klf4, Lin28, Nanog, etc., or a substrate, cofactor and/or downstream effector thereof), for example, comprising at least about 10, 15, 20, 25, 50, 75, 100, 200, 300, 400, 500, 1000, etc., contiguous amino acids, or more, including all intermediate lengths, of a polypeptide described herein. In a particular embodiment, the fragment or combination of fragments employed retain the ability to modulate, induce and/or maintain pluripotency when used in the methods described herein.

In another aspect, the present invention employs variants of the polypeptide compositions described herein (e.g., Sox-2, c-Myc, Oct3/4, Klf4, Lin28, Nanog, etc., or a substrate, cofactor and/or downstream effector thereof). Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein. In a particular embodiment, the variant or combination of variants employed retain the ability to induce pluripotency as described herein.

In another aspect, the present invention employs polypeptide variants which exhibit at least about 70%, 75%, 80%, 85%, 90%, 91%, 92%, 93%, 94%, 95%, 96%, 97%, 98%, or 99% or more identity (determined as described below), along its length, to the corresponding region of a wild-type mammalian polypeptide used according to the present disclosure.

A polypeptide variant may differ from a naturally occurring polypeptide in one or more substitutions, deletions, additions and/or insertions. Such variants may be naturally occurring or may be synthetically generated, for example, by modifying one or more of the above polypeptide sequences used in the methods of the invention and evaluating their effects using any of a number of techniques well known in the art.

"Proliferate" refers to the property of one cell dividing into two essentially identical cells or a population of cells increasing in number (e.g., to reproduce).

"Propagation" refers to growing (e.g., reproducing via cell proliferation) cells outside of tissue or the body, for example, in a sterile container such as a plastic (or coated plastic) cell culture dish or flask.

"Primary culture" refers to cells, tissue and/or culture where the isolated cells are placed in a first culture vessel with culture medium. The cells, tissue and/or culture may be sustained and/or may proliferate, however, as long as the cells, tissue and/or culture remain in the first vessel the cells, tissue and/or culture are referred to as the primary culture.

The terms "small molecule reprogramming agent" or "small molecule reprogramming compound" are used interchangeably herein and refer to small molecules that can increase developmental potency of a cell, either alone or in combination with other pluripotency factors. A "small molecule" refers to an agent that has a molecular weight of less than about 5 kD, less than about 4 kD, less than about 3 kD, less than about 2 kD, less than about 1 kD, or less than about 0.5 kD. Small molecules can be nucleic acids, peptidomimetics, peptoids, carbohydrates, lipids or other organic or inorganic molecules. Libraries of chemical and/or biological mixtures, such as fungal, bacterial, or algal extracts, are known in the art and can be screened with any of the assays of the invention. In particular embodiments, the small molecule reprogramming agent used herein has a molecular weight of less than 10,000 daltons, for example, less than 8000, 6000, 4000, 2000 daltons, e.g., between 50-1500, 500-1500, 200-2000, 500-5000 daltons.

As used herein, the terms "substantially free of" and "essentially free of" are used interchangeably, and when used to describe a composition, such as a cell population or culture media, refer to a composition that is free of a specified substance, such as, 95% free, 96% free, 97% free, 98% free, 99% free of the specified substance, or is undetectable as measured by conventional means. Similar meaning can be applied to the term "absence of," where referring to the absence of a particular substance or component of a composition.

Cells for Use in the Invention

A starting population of cells for use in the invention may be derived from essentially any suitable source, and may be heterogeneous or homogeneous with respect to cell types or state of pluripotency. In one embodiment, the cells are mammalian cells, and in particular embodiments, the cells are isolated from a mammal selected from the group consisting of: a rodent, a cat, a dog, a pig, a goat, a sheep, a horse, a cow, or a primate. In a certain embodiment, the mammal is a human. In other certain embodiments, the cells to be used or treated according to the invention are adult cells, including essentially any accessible adult cell types.

The cells may be somatic, non-pluripotent, incompletely or partially pluripotent stem cells, multipotent cells, oligopotent cells, unipotent cells, terminally differentiated cells, or a mixed population of cells comprising any combination of the foregoing. Pluripotent cells used in the methods of the invention may be naturally-occurring stem cells, including embryonic stem cells, or can be induced pluripotent stem cells. A "mixed" population of cells is a population of cells of varying degrees of developmental potency. For example, a mixed population of cells may comprise cells undergoing reprogramming, so that the mixed population comprises pluripotent cells, partially pluripotent cells, and non-pluripotent cells, such as fully differentiated cells.

In one embodiment, the starting population of cells is selected from adult or neonatal stem/progenitor cells. In particular embodiments, the starting population of stem/progenitor cells is selected from the group consisting of: mesodermal stem/progenitor cells, endodermal stem/progenitor cells, and ectodermal stem/progenitor cells.

In another embodiment, the starting population of stem/progenitor cells is a mesodermal stem/progenitor cell. Illustrative examples of mesodermal stem/progenitor cells include, but are not limited to: mesodermal stem/progenitor cells, endothelial stem/progenitor cells, bone marrow stem/progenitor cells, umbilical cord stem/progenitor cells, adipose tissue derived stem/progenitor cells, hematopoietic stem/progenitor cells (HSCs), mesenchymal stem/progenitor cells, muscle stem/progenitor cells, kidney stem/progenitor cells, osteoblast stem/progenitor cells, chondrocyte stem/progenitor cells, and the like.

In other related embodiments, the starting population of stem/progenitor cells is an ectodermal stem/progenitor cell. Illustrative examples of ectodermal stem/progenitor cells include, but are not limited to neural stem/progenitor cells, retinal stem/progentior cells, skin stem/progenitor cells, and the like.

In other related embodiments, the starting population of stem/progenitor cells is an endodermal stem/progenitor cell. Illustrative examples of endodermal stem/progenitor cells include, but are not limited to liver stem/progenitor cells, pancreatic stem/progenitor cells, epithelial stem/progenitor cells, and the like.

In certain embodiments, the starting population of cells may be a heterogeneous or homogeneous population of cells selected from the group consisting of: pancreatic islet cells, CNS cells, PNS cells, cardiac muscle cells, skeletal muscle cells, smooth muscle cells, hematopoietic cells, bone cells, liver cells, an adipose cells, renal cells, lung cells, chondrocyte, skin cells, follicular cells, vascular cells, epithelial cells, immune cells, endothelial cells, and the like.

Inducing Reprogramming and Increasing Potency of Cells

Various strategies are being pursued to induce pluripotency, or increase potency, in cells (Takahashi, K., and Yamanaka, S., *Cell* 126, 663-676 (2006); Takahashi et al., *Cell* 131, 861-872 (2007); Yu et al., *Science* 318, 1917-1920 (2007); Zhou et al., *Cell Stem Cell* 4, 381-384 (2009); Kim et al., *Cell Stem Cell* 4, 472-476 (2009); Yamanaka et al., 2009; Saha, K., Jaenisch, R., *Cell Stem Cell* 5, 584-595 (2009)), and improve the efficiency of reprogramming (Shi et al., *Cell Stem Cell* 2, 525-528 (2008a); Shi et al., *Cell Stem Cell* 3, 568-574 (2008b); Huangfu et al., *Nat Biotechnol* 26, 795-797 (2008a); Huangfu et al., *Nat Biotechnol* 26, 1269-1275 (2008b); Silva et al., *Plos Bio* 6, e253. doi: 10.1371/journal. pbio. 0060253 (2008); Lyssiotis et al., *PNAS* 106, 8912-8917 (2009); Ichida et al., *Cell Stem Cell* 5, 491-503 (2009); Maherali, N., Hochedlinger, K., *Curr Biol* 19, 1718-1723 (2009b); Esteban et al., *Cell Stem Cell* 6, 71-79 (2010); and Feng et al., *Cell Stem Cell* 4, 301-312 (2009)).

Generally, techniques for reprogramming involve modulation of specific cellular pathways, either directly or indirectly, using polynucleotide-, polypeptide- and/or small molecule-based approaches. The developmental potency of a cell may be increased, for example, by contacting a cell with one or more pluripotency factors. "Contacting", as used herein, can involve culturing cells in the presence of a pluripotency factor (such as, for example, small molecules, proteins, peptides, etc.) or introducing pluripotency factors into the cell. Pluripotency factors can be introduced into cells by culturing the cells in the presence of the factor, including transcription factors such as proteins, under conditions that allow for introduction of the transcription factor into the cell. See, e.g., Zhou H et al., *Cell Stem Cell*. 2009 May 8; 4(5):381-4; WO/2009/117439. Introduction into the cell may be facilitated for example, using transient methods, e.g., protein transduction, microinjection, non-integrating gene delivery, mRNA transduction, etc., or any other suitable technique. In some embodiments, the transcription factors are introduced into the cells by expression from a recombinant vector that has been introduced into the cell, or by incubating the cells in the presence of exogenous transcription factor polypeptides such that the polypeptides enter the cell.

In particular embodiments, the pluripotency factor is a transcription factor. Exemplary transcription factors that are associated with increasing, establishing, or maintaining the potency of a cell include, but are not limited to Oct-3/4, Cdx-2, Gbx2, Gsh1, HesX1, HoxA10, HoxA11, HoxB1, Irx2, Isl1, Meis1, Meox2, Nanog, Nkx2.2, Onecut, Otx1, Oxt2, Pax5, Pax6, Pdx1, Tcf1, Tcf2, Zfhxlb, Klf-4, Atbf1, Esrrb, Gcnf, Jarid2, Jmjd1a, Jmjd2c, Klf-3, Klf-5, Mel-18, Myst3, Nac1, REST, Rex-1, Rybp, Sa114, Sa111, Tif1, YY1, Zeb2, Zfp281, Zfp57, Zic3, Coup-Tf1, Coup-Tf2, Bmi1, Rnf2, Mta1, Pias1, Pias2, Pias3, Piasy, Sox2, Lef1, Sox15, Sox6, Tcf-7, Tcf711, c-Myc, L-Myc, N-Myc, Hand1, Mad1, Mad3, Mad4, Mxi1, Myf5, Neurog2, Ngn3, Olig2, Tcf3, Tcf4, Foxc1, Foxd3, BAF155, C/EBPβ, mafa, Eomes, Tbx-3; Rfx4, Stat3, Stella, and UTF-1. Exemplary transcription factors include Oct4, Sox2, Klf4, c-Myc, and Nanog.

Small molecule reprogramming agents are also pluripotency factors and may also be employed in the methods of the invention for inducing reprogramming and maintaining or increasing cell potency. In some embodiments of the invention, one or more small molecule reprogramming agents are used to induce pluripotency of a somatic cell, increase or maintain the potency of a cell, or improve the efficiency of reprogramming.

In some embodiments, small molecule reprogramming agents are employed in the methods of the invention to improve the efficiency of reprogramming. Improvements in efficiency of reprogramming can be measured by (1) a decrease in the time required for reprogramming and generation of pluripotent cells (e.g., by shortening the time to generate pluripotent cells by at least a day compared to a similar or same process without the small molecule), or alternatively, or in combination, (2) an increase in the number of pluripotent cells generated by a particular process (e.g., increasing the number of cells reprogrammed in a given time period by at least 10%, 30%, 50%, 100%, 200%, 500%, etc. compared to a similar or same process without the small molecule). In some embodiments, a 2-fold to 20-fold improvement in reprogramming efficiency is observed. In some embodiments, reprogramming efficiency is improved by more than 20 fold. In some embodiments, a more than 100 fold improvement in efficiency is observed over the method without the small molecule reprogramming agent (e.g., a more than 100 fold increase in the number of pluripotent cells generated).

Several classes of small molecule reprogramming agents may be important to increasing, establishing, and/or maintaining the potency of a cell. Exemplary small molecule reprogramming agents include, but are not limited to: agents that inhibit H3K9 methylation or promote H3K9 demethylation; agents that inhibit H3K4 demethylation or promotes H3K4 methylation; agents that inhibit histone deacetylation or promote histone acetylation; L-type Ca channel agonists; activators of the cAMP pathway; DNA methyltransferase (DNMT) inhibitors; nuclear receptor ligands; GSK3 inhibitors; MEK inhibitors; TGFβ receptor/ALK5 inhibitors; HDAC inhibitors; Erk inhibitors; ROCK inhibitors; FGFR inhibitors; and PARP inhibitors. Exemplary small molecule reprogramming agents include GSK3 inhibitors; MEK inhibitors; TGFβ receptor/ALK5 inhibitors; HDAC inhibitors; Erk inhibitors; and ROCK inhibitors. Each of these classes of small molecule agents is described more fully below.

In some embodiments of the invention, small molecule reprogramming agents are used to replace one or more transcription factors in the methods of the invention to induce pluripotency, improve the efficiency of reprogramming, and/or increase or maintain the potency of a cell. For example, in some embodiments, a cell is contacted with one or more small molecule reprogramming agents, wherein the agents are included in an amount sufficient to improve the efficiency of reprogramming. In other embodiments, one or more small molecule reprogramming agents are used in addition to transcription factors in the methods of the invention. In one embodiment, a cell is contacted with at least one pluripotency transcription factor and at least one small molecule reprogramming agent under conditions to increase, establish, and/or maintain the potency of the cell or improve the efficiency of the reprogramming process.

In another embodiment, a cell is contacted with at least one pluripotency transcription factor and at least two, at least three, at least four, at least five, at least six, at least seven, at least eight, at least nine, or at least ten small molecule reprogramming agents under conditions and for a time sufficient to increase, establish, and/or maintain the potency of the cell or improve the efficiency of reprogramming. The state of potency or differentiation of cells can be assessed by monitoring the pluripotency characteristics described elsewhere herein.

In one embodiment, cells are contacted with a composition comprising one or more pluripotency factors and/or a combination of small molecule reprogramming agents, wherein the pluripotency factors and small molecules increase or induce the pluripotency of a cell. It is contemplated that the cells of the invention may be contacted in vitro, ex vivo, or in vivo.

Characterizing Pluripotent Cells

Following induction of reprogramming, reprogrammed cells can be selected based on relevant and detectable morphological, molecular and/or biochemical changes associated with pluripotency. Specific characteristics of cell pluripotency which may be monitored, separately or in combination, in assessing the potency of a cell include, but are not limited to, gene expression, methylation, and in vivo and in vitro characteristics such as: i) pluripotent stem cell morphology that is round and flat; ii) expression of pluripotent stem cell markers including S SEA1 (mouse pluripotent stem cells), SSEA3/4 (human pluripotent stem cells); TRA1-60/81; TRA1-85, TRA2-54, GCTM-2, TG343, TG30, CD9, CD29, CD133/prominin, CD140a, CD56, CD73, CD105, CD31, CD34, OCT4, Nanog and/or Sox2, and, as provided by the present invention, CD30 and CD50, and combinations of the foregoing; iii) ability of pluripotent stem cells to contribute to germline transmission in mouse chimeras; iv) ability of pluripotent stem cells to contribute to the embryo proper using tetraploid embryo complementation assays; v) teratoma formation of pluripotent stem cells; vi) formation of embryoid bodies and in vitro trilineage differentiation; and vii) inactive X chromosome reactivation. In certain embodiments, a subset of any of the above characteristics is used for monitoring cell potency. In one embodiment, pluripotent cells are characterized by having a flat, round colony morphology, expression of SSEA4 and Oct4, and the ability to form chimeras and teratomas.

As discussed herein, pluripotency exists as a continuum and induced pluripotent stem cells appear to exist in both a "primed" state and a "naïve" state, with a cell in a naïve state possibly having greater differentiation potential. Induced pluripotent stem cells generated in conventional culture medium exist in a primed state and more closely resemble cells derived from a post-implantation blastocyst, while naïve iPSCs display pluripotency characteristics that more closely resemble mouse embryonic stem cells or cells derived from a pre-implantation blastocyst. The primed and naïve cell states can be defined by various differences, including differences in colony morphology, cellular response to inhibition or activation of key signaling pathways, gene expression signature, and ability to reactivate genes associated with extraembryonic cells. For example, conventional iPSCs, representing a primed pluripotent state, exhibit a colony morphology that is flat, while naïve iPSCs exhibit a compact domed colony morphology that is similar to mouse embryonic stem cells. Further, conventional iPSCs require extrinsic signaling of key cytokines, such as TGFβ, Activin, and bFGF and are dependent on ERK/MEK cellular signaling for maintenance of an undifferentiated state, and differentiate when these pathways are inhibited by contacting cells with, for example, a TGFβ or MEK inhibitor. In contrast, naïve cells do not require extrinsic signaling and maintain pluripotency even when treated with inhibitors of the TGFβ and MEK signaling pathways.

Additionally, gene expression analysis reveals significant differences between naïve and prime pluripotent cells. For example, naïve iPSCs have significantly repressed Xist expression while conventional iPSCS show only modest repression of Xist expression; naïve cells show significant X chromosome reactivation and increased expression of genes located on the X chromosome over the expression seen in conventional iPSCs; and naïve cells express extraembryonic stem cell markers, including without limitation Gata6, CDX2, and CGB. In contrast, early markers of differentiation, such as lineage specific genes such as Foxa2, Sox17, and Brachyury, are more highly expressed in conventional iPSCs over naïve iPSCs. Additional markers useful for identifying cells in a naïve state of pluripotency include an increase in Klf4, Tbx3, Gbx2, Lin28, Soc3 or a decrease in Otx2, Sox17, Cer1, FoxA2, Zic1, Lhx2, Xist.

In particular embodiments of the invention, naïve cells show Xist expression that is decreased by at least two-fold, at least five-fold, or at least ten-fold as compared to conventional iPSCs. In some embodiments of the invention, cells in a naïve state of pluripotency have Xist expression 2-fold lower than conventional iPSCs and expression of at least five genes located on the X chromosome at levels three-fold higher than conventional iPSCs.

X chromosome reactivation can be shown by increased expression of at least five genes, at least 10 genes, or in particular embodiments, at least 100 genes located on the X chromosome at levels at least two-fold, three-fold, five-fold, or more over levels of such genes in conventional iPSCs.

In particular embodiments of the invention, the pluripotent cells of the invention retain characteristics of pluripotency for multiple cell passages, such as for example, at least 1, 3, 5, 7, 10, 15, 20 or more passages.

Culture Media Platforms for Use in the Methods of the Invention

The culture media of the invention (i.e., culture platforms) comprise a chemically defined stock basal media and various combinations of small molecules, including small molecule inhibitors, that allow:

long-term culture of pluripotent cells in a feeder-free environment;
reprogramming of cells in a feeder-free environment;
single-cell dissociation of pluripotent cells;
cell sorting of pluripotent cells;
maintenance of an undifferentiated status;
improved efficiency of reprogramming; and
generation of a naïve pluripotent cell.

The chemically defined stock basal media for use in the culture medium of the invention may be any defined basal media suitable for supporting the maintenance, growth, and/or differentiation of stem cells, such as conventional human embryonic stem cell media. Examples of defined basal media which may be used in accordance with the invention include, but are not limited to: Dulbecco's Modified Eagle Medium ("DMEM"), Basal Media Eagle (BME), DMEM/F-12 (1:1 DMEM and F-12 vol:vol); Medium 199; F-12 (Ham) Nutrient Mixture; F-10 (Ham) Nutrient Mixture; Minimal Essential Media (MEM), Williams' Media E; and RPMI 1640, all of which are available from Gibco-BRL/Life Technologies, Inc., Gaithersburg, Md., among others. Several versions of many of these media are available, and those that are particularly useful to construct the culture media of the invention include, but are not limited to: DMEM 11966, DMEM 10314, MEM 11095, Williams' Media E 12251, Ham F12 11059, MEM-alpha 12561, and Medium-199 11151 (all available from Gibco-BRL/Life Technologies (1995-1996 catalog)). The culture media may include, for example, one or more of the following: amino acids, vitamins, organic salts, inorganic salts, trace elements, buffering salts, sugars, ATP, and the like (suitable basal media ingredients are available from Sigma-Aldrich of Saint Louis, Mo.).

Small molecules, and classes thereof, for use in the cell culture media of the invention are described more fully below. In particular embodiments, the culture media of the invention comprises one or more, two or more, or three or more of a TGFβ inhibitor, a GSK3 inhibitor, a MEK inhibitor, and a ROCK inhibitor. In certain embodiments, the culture media of the invention comprises a TGFβ inhibitor, a GSK3 inhibitor, a MEK inhibitor, and a ROCK inhibitor. Exemplary TGFβ inhibitors, GSK3 inhibitors, MEK inhibitors, and ROCK inhibitors for use in the cell culture media and methods of the invention are described below. The culture media may additionally comprise a PARP inhibitor, such as Olaparib (AZD-2281).

GSK-3β Inhibitors

Inhibitors of GSK-3β include, but are not limited to, antibodies that bind GSK-3β, dominant negative GSK-3β variants, and siRNA and antisense nucleic acids that target GSK-3β. Other exemplary GSK-3β inhibitors include, but are not limited to, Kenpaullone, 1-Azakenpaullone, CHIR99021, CHIR98014, AR-A014418, CT 99021, CT 20026, SB216763, AR-A014418, lithium, SB 415286, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl]-4-pyrazin-2-yl-pyrrole-2,5-dione; TWS1 19 pyrrolopyrimidine compound, L803 H-KEAPPAPPQSpP-NH2 or its myristoylated form; 2-Chloro-1-(4,5-dibromo-thiophen-2-yl)-ethanone, SB216763, and SB415286. Exemplary GSK3 inhibitors for use in the cell culture media of the invention include CHIR99021, BIO, and Kenpaullone, while CHIR99021 is preferred in particular embodiments.

ERK/MEK Inhibitors

Exemplary inhibitors of the ERK/MEK pathway include, but are not limited to antibodies to MEK or ERK, dominant negative MEK or ERK variants, and siRNA and antisense nucleic acids that suppress expression of MEK and/or ERK. Other exemplary ERK/MEK inhibitors include, but are not limited to, PD0325901, PD98059, U0126, SL327, ARRY-162, PD184161, PD184352, sunitinib, sorafenib, Vandetanib, pazopanib, Axitinib, GSK1 120212, ARRY-438162, R05126766, XL518, AZD8330, RDEA1 19, AZD6244, FR180204 and PTK787.

Additional MEK/ERK inhibitors include those compounds disclosed in International Published Patent Applications WO 99/01426, WO 02/06213, WO 03/077914, WO 05/051301 and WO2007/044084.

Further illustrative examples of MEK/ERK inhibitors include the following compounds:—6-(4-Bromo-2-chloro-phenylamino)-7-fluoro-3-methyl-3H-benzoimidazol-e-5-carboxylic acid (2,3-dihydroxy-propoxy)-amide; 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimida-zol-5-yl]-2-hydroxy-ethanone, 6-(4-Bromo-2-chloro-phenylamino)-7-fluoro-3-methyl-3H-benzoimidazol-e-5-carboxylic acid (2-hydroxy-1,1-dimethyl-ethoxy)-amide, 6-(4-Bromo-2-chloro-phenylamino)-7-fluoro-3-(tetrahydro-furan-2-ylm-ethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazol-e-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazol-e-5-carboxylic acid (2-hydroxy-ethoxy)-amide, referred to hereinafter as MEK inhibitor 1; 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2; and 4-(4-bromo-2-fluorophenylamino)-N-(2-hydroxyethoxy)-1,5-dimethyl-6-oxo-1,6-dihydropyridazine-3-carboxamide or a pharmaceutically acceptable salt thereof. In certain embodiments, the MEK/ERK inhibitor for use in the cell culture medium of the invention is PD98059.

TGFβ Receptor/ALK5 Inhibitors

Exemplary ALK5 inhibitors include antibodies to ALK5, dominant negative variants of ALK5, and antisense nucleic acids that suppress expression of ALK5. Other exemplary ALK5 inhibitors include, but are not limited to, SB431542, A-83-01, 2-(3-(6-Methylpyridin-2-yl)-1H-pyrazol-4-yl)-1, 5-naphthyridine, Wnt3a/BIO, BMP4, GW788388, SM16, IN-1130, GW6604, SB-505124, and pyrimidine derivatives, see, e.g., WO2008/006583, herein incorporated by reference.

Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., *J Mol. Phamacol.* 62 (1): 65-74 (2002).

In view of the data herein showing the effect of inhibiting ALK5, it is believed that inhibition of the TGFβ/activin pathway will have similar effects. Thus, any inhibitor, e.g., upstream or downstream of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGFβ receptor inhibitors can include antibodies to, dominant negative variants of and siRNA or antisense nucleic acids that target TGFβ receptors. Specific examples of inhibitors include but are not limited to SU5416; 2-(5-benzo [1,3]dioxol-5-yl-2-tert-butyl-3H-imidazol-4-yl)-6-methyl-pyridine hydrochloride (SB-505124); lerdelimumb (CAT-152); metelimumab (CAT-192); GC-1008; ID1 1; AP-12009; AP-11014; LY550410; LY580276; LY364947; LY2109761; SB-505124; SB-431542; SD-208; SM16; NPC-30345; Ki26894; SB-203580; SD-093; Gleevec; 3,5, 7,2',4'-pentahydroxyflavone (Morin); activin-M108A; P144; soluble TBR2-Fc; and antisense transfected tumor cells that target TGFβ receptors. (See, e.g., Wrzesinski, et al., *Clinical Cancer Research* 13 (18):5262-5270 (2007); Kaminska, et al., *Acta Biochimica Polonica* 52 (2):329-337 (2005); and Chang, et al., *Frontiers in Bioscience* 12:4393-4401 (2007).

Exemplary TGFβ receptor inhibitors for use in the cell culture media of the invention include SB431542, A-83-01, and RepSox. In particular embodiments, the TGFβ inhibitor is SB431542.

ROCK Inhibitors

ROCKs are serine/threonine kinases that serve as target proteins for Rho (of which three isoforms exist—RhoA, RhoB and RhoC). Exemplary ROCK inhibitors include, but are not limited to antibodies to ROCK, dominant negative ROCK variants, and siRNA and antisense nucleic acids that suppress expression of ROCK. Other exemplary ROCK inhibitors include, but are not limited to: thiazovivin, Y27632, Fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl) urea, 3-(4-Pyridyl)-1H-indole, and (R)-(+)-trans-N-(4-Pyridyl)-4-(1-aminoethyl)-cyclohexanecarboxamide.

Exemplary ROCK inhibitors for use in the cell culture medium of the invention include thiazovivin, Y27632, pyrintegrin, and Blebbistatin. In certain embodiments, the ROCK inhibitor is thiazovivin.

FGFR Inhibitors

Exemplary FGFR inhibitors include, but are not limited to antibodies to FGFR, dominant negative FGFR variants, and siRNA and antisense nucleic acids that suppress expression of FGFR. Other exemplary FGFR inhibitors include, but are not limited to RO-4396686, CHIR-258, PD 173074, PD 166866, ENK-834, ENK-835, SU5402, XL-999, SU6668, R04383596, and BIBF-1120.

PARP Inhibitors

PARP inhibitors inhibit Poly (ADP-ribose) polymerase ("PARP"). The PARP protein is a DNA repair enzyme which functions to regulate DNA repair pathways in cells. PARP is involved with base excision repair (BER) pathway, and PARP inhibition may promote genomic stability of cells during reprogramming or maintenance of pluripotent cells. Exemplary PARP inhibitors for use in the cell culture mediums of the invention include, without limitation, iniparib, veliparib, and olaparib (AZD-2281).

The amount of the small molecules in the cell culture media of the invention can vary and may be optimized according to the specific culture conditions, including the specific molecules and combinations used, the type of cell being cultured in the media, and the specific application of use for the culture medium of the invention. In some embodiments, a small molecule is present in the media at a concentration sufficient to induce pluripotency, improve the efficiency of reprogramming, or increase or maintain the potency of a cell.

In particular embodiments, preferred concentrations and combinations of the small molecules in the cell culture media of the invention are shown in Table 1. In particular embodiments of the cell culture media of the invention, the cell culture medium is "SMC4" medium, as described in Table 1. SMC4 medium comprises conventional human ESC media and the specific pathway modulators and additives as shown in Table 1. The components of the medium may be present in the medium in amounts within the optimal range for such components shown in Table 1, and are present at the optimal concentrations shown in Table 1. Embodiments of SMC4 medium may optionally comprise any one or more of the alternative medium and pathway modulators and activators shown in Table 2, in concentrations within the optimal ranges shown in Table 2, and in certain embodiments, in concentrations within the optimal concentration shown in Table 2. In particular embodiments of the media, SMC4 medium comprises soluble fibronectin, and is referred to throughout as "SMC4+fibronectin".

In some embodiments, the culture medium of the invention further comprises one or more of an Oct polypeptide, a Klf polypeptide, a Myc polypeptide, and a Sox polypeptide. In some embodiments, the culture medium does not comprise cells. In some embodiments, the culture medium further comprises cells, e.g., non-pluripotent cells, partially pluripotent cells, pluripotent cells, or mixed cell populations containing cells of various states of potency.

TABLE 1

Cell culture components and additives. The table below lists examples of molecules, and the signaling pathways they affect, that can be used to enhance the viability and pluripotency of cells undergoing single cell passage and cell sorting and enrichment procedures, and to enhance the reprogramming process as well as maintain pluripotent stem cells in an undifferentiated state.

| SMC4 MEDIUM | Optimal Concentration | Optimal Concentration Range |
|---|---|---|
| CONVENTIONAL/BASAL HUMAN ESC MEDIUM FORMULATION | | |
| DMEM/F12 (or DMEM, or HIGH GLUCOSE DMEM, or KNOCK-OUT DMEM) | 1× | 1× |
| L-GLUTAMINE | 2 mM | 1 to 10 mM |
| NON-ESSENTIAL AMINO ACIDS | 1× | 0.5 to 5× |
| 2-MERCAPTOETHANOL | 100 μM | 10 to 500 μM |
| bFGF | 10 ng/mL | 1 to 100 ng/mL |
| SPECIFIC PATHWAY INHIBITORS AND ADDITIVES | | |
| ERK/MEK/MAPK | | |
| PD0325901 | 0.4 μM | .01 to 100 μM |
| Wnt/βcatenin/GSK | | |
| CHIR99021 | 1 μM | .01 to 100 μM |
| Rho/ROCK/Myosin II | | |
| THIAZOVIVN | 5 μM | .01 to 500 μM |
| TGFB/ALK | | |
| SB431542 | 2 μM | .01 to 100 μM |
| EXTRACELLULAR MATRIX | | |
| MATRIGEL ™ | As per manufacturer's recommendations | |
| GELATIN | As per manufacturer's recommendations | |

SMC4+ Fibronectin refers to SMC4 medium, as described above, with soluble fibronectin in a concentration of about 5 μg/mL. Fibronectin may be present in the SMC4 medium in a concentration range of about 05 to 500 μg/mL.

TABLE 2

Particular alternative cell culture components and additives to enhance cellular pluripotency and viability on single cell passaging, cell sorting and culture on feeder-free systems
EXAMPLES OF PARTICULAR ALTERNATIVE MEDIUM AND PATHWAY MODULATORS AND ADDITIVES

| | Optimal Concentration | Optimal Range |
|---|---|---|
| ERK/MEK/MAPK | | |
| PD98059 | 10 μM | .01 to 500 μM |
| Wnt/βcatenin/GSK | | |
| Bio | 2 μM | .01 to 100 μM |
| Kenpaullone | 5 μM | .01 to 100 μM |
| XAV939 | 1 μM | .01 to 100 μM |
| Rho/ROCK/Myosin II | | |
| Y27632 | 10 μM | .01 to 500 μM |
| Blebbistatin | 5 μM | .01 to 500 μM |
| Pyrintegrin | 1 μM | .01 to 100 μM |
| TGFB/ALK | | |
| A-83-01 | 1 μM | .01 to 100 μM |
| RepSox | 1 μM | .01 to 100 μM |
| TFGβ | 250 ng/mL | 1 to 25,000 ng/mL |
| PI3K/AKT/PTEN | | |
| Insulin | 10 μg/mL | 1 to 100 μg/mL |
| IGF | 10 ng/mL | 1 to 100 ng/mL |
| PDK2 Agonist | 1 μM | .01 to 100 μM |
| PDK1 Agonist PS48 | 5 uM | .01 to 500 uM |

TABLE 2-continued

Particular alternative cell culture components and additives to enhance
cellular pluripotency and viability on single cell passaging, cell sorting and culture
on feeder-free systems
EXAMPLES OF PARTICULAR ALTERNATIVE MEDIUM AND
PATHWAY MODULATORS AND ADDITIVES

|  | Optimal Concentration | Optimal Range |
|---|---|---|
| FGF/FGFR |  |  |
| bFGF | 10 ng/mL | 1 to 100 ng/mL |
| PD173074 | 0.1 µM | .001 to 10 µM |
| SU5401 | 2 µM | .01 to 100 µM |
| EGF/EGFR |  |  |
| EGF | 10 ng/mL | 1 to 100 ng/mL |
| AG1478 | 1 µM | .01 to 100 µM |
| p53 |  |  |
| Pifithrin-α | 5 µM | .01 to 500 µM |
| Pifithrin-µ | 2 µM | .01 to 500 µM |
| Hedgehog |  |  |
| Cyclopamine | 1 µM | .01 to 100 µM |
| Notch/Delta |  |  |
| DAPT | 1 µM | .01 to 100 µM |
| Chromatin & Histone Modifier/Acetylation/Methylation |  |  |
| VALPROIC ACID | 0.5 mM | 0.05 to 5 mM |
| 5 AZA | 1 mM | .01 to 100 mM |
| Butyrate | 1 mM | .01 to 100 mM |
| Parnate | 2 µM | .01 to 200 µM |
| BIX01294 | 1 µM | .01 to 200 µM |
| RG108 | 1 µM | .01 to 200 µM |
| Tranylcypromine hydrochloride | 100 µM | .001 to 10 mM |
| trichostatin A | 100 nM | .01 to 1000 nM |
| Antioxidant |  |  |
| Ascorbic Acid | 10 µg/mL | 0.01 to 1000 µg/mL |
| Reduced Oxygen | 5% | 1 to 20% |
| Tocotrienols | 25 µM | .1 to 1000 µM |
| JAK/STAT |  |  |
| LIF | 1,000 U/mL | 10 to 10,000 U/mL |
| IL6 | 10 ng/mL | .1 to 1000 ng/mL |
| BMP |  |  |
| BMP | 10 ng/mL | .01 to 1000 ng/mL |
| Dorsommphin | 1 µM | .01 to 100 µM |
| LDN-193189 | 2 µM | .01 to 500 µM |
| PARP |  |  |
| Olaparib (AZD2281) | 1 µM | .01 to 100 µM |
| KLF |  |  |
| Forskolin | 10 µM | .01 to 100 µM |
| AICAR | 0.5 mM | .001 to 100 mM |
| Ca2+ channel activator |  |  |
| Bay K 8644 | 1 µM | .01 to 100 µM |
| KNOCKOUT SERUM REPLACEMENT | 20% v/v | 2 to 80% v/v |
| XENO-FREE KNOCKOUT SERUM REPLACEMENT | 20% v/v | 2 to 80% v/v |
| Transferrin | 1 mg/mL | .01 to 100 mg/mL |
| Albumin | .5 mg/mL | .1 to 10 mg/mL |
| N2 | 1× | .1× to 10× |
| B27 | 1× | .1× to 10× |

Cytokines and Growth Factors

In some embodiments of the invention, the cell culture media of the invention is substantially free of cytokines and/or growth factors, and optionally is a feeder-free environment. In other embodiments, the cell culture media contains supplements such as serums, extracts, growth factors, hormones, cytokines and the like.

Various growth factors and their use in culture media are well known in the art and include, for example, ECM proteins, laminin 1, fibronectin, collagen IV isotypes, proteases, protease inhibitors, cell surface adhesion proteins, cell-signaling proteins, cadherins, chloride intracellular channel 1, transmembrane receptor PTK7, insulin-like growth factor, Inhibin beta A, inducers of the TGFβ/Activin/nodal signaling pathway, and Activin A. Cytokines used in the culture media may include, for example, one or more of the following: growth factors such as epidermal growth factor (EGF), acidic fibroblast growth factor (aFGF), basic fibroblast growth factor (bFGF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-.gamma.) and other cytokines having effects upon stem cells such as stem cell factor (SCF) and erythropoietin (Epo). These cytokines may be obtained commercially, for example from R&D Systems, Minneapolis, Minn., and may be either natural or recombinant. In some embodiments, for culture of a wide variety of mammalian cells, the basal media will contain FGF at a concentration of about 0.01-100 ng/ml, about 0.2-20 ng/ml, and in particular embodiments about 0.5-10 ng/ml. Other cytokines, if used, may be added at concentrations that are determined empirically or as guided by the established cytokine art.

Additional components that may be included in the present media are insulin (especially as insulin $Zn^{++}$) and transferrin. These additional ingredients, available commercially (for example, from Sigma-Aldrich, St. Louis, Mo.), may be formulated into the present media at concentration ranges of about 0.1 to about 100 μg/ml or about 1 to about 10 μg/ml. Additionally, recombinant insulin or zinc based salt of insulin may be substituted for animal- or human-derived insulin. Other ingredients or substitutes may be added to the supplement compositions as are known to those persons of ordinary skill in the art.

Cytokines and like components of the supplements may instead (or in addition) be included in the basal media. Such components are typically included with the supplement compositions as the supplement compositions are conventionally stored at about −20° C. rather than the about 4° C. temperature regularly used for storing basal media. Cytokines and like components may fair better at temperatures closer to −20° C.

Substrates for Use in the Methods of the Invention

Any suitable vessel or cell culture container may be used as a support for cell cultures in the basal media and/or the cell culture supplements. No substrate coating on the support is necessary. Coating the surface of a culture vessel with adhesion-promoting substrata (for example, collagens, fibronectins, RGD-containing polypeptides, gelatins, and the like) however promotes attachment of the cells and thereby may enhance the effect of the cell culture media and supplements disclosed herein. Suitable substrates for culturing and passaging cells are known in the art and include, without limitation, gelatin, Laminin, Fibronectin, Collagen, Elastin, osteopontin, mixtures of naturally occurring cell line-produced matrices such as Matrigel™ and synthetic or man-made surfaces such as Polyamine monolayers and carboxy-terminated monolayers.

Feeder Free Environments

While cells have typically been cultured on feeder cells or in a culture environment pre-conditioned with feeder cells and containing fetal bovine serum, such environments may be unsuitable for producing cells for clinical and therapeutic use. For example, cells cultivated in such xeno-contaminated environments are generally considered unsuitable for human cell transplantation because the exposure to animal components may present a serious risk of immune rejection and transmitting unidentified pathogens to the treated patients, and could potentially reactivate animal retroviruses. Culture systems using animal-free culture medium, such as the feeder free environment of the invention, facilitate the production of clinical-grade cell lines, particulary hESC and iPSC cell lines.

In some embodiments of the invention, the feeder free environment of the invention is essentially free of human feeder cells, including without limitation human fibroblasts, keratinocytes, and embryonic stem cells, and is not pre-conditioned by feeder cells. In further embodiments of the invention, the feeder free environment is essentially free of animal feeder cells, and further, in some embodiments is not pre-conditioned with feeder cells. In particular embodiments of the invention, the feeder free environment is essentially free of both human and animal feeder cells, and in more particular embodiments the feeder free environment is essentially free of both human and animal feeder cells and is not pre-conditioned with feeder cells.

The feeder free cell culture media of the invention are used in the methods of the invention, including culturing of pluripotent cells, reprogramming of cells, single-cell dissociation of pluripotent cells, cell sorting of pluripotent cells, generation of a naïve pluripotent cell, and maintenance of an undifferentiated status of cells. In particular methods of the invention, the feeder free environment is used in methods to induce pluripotency, improve the efficiency of reprogramming, and/or increase or maintain the potency of a cell. In certain embodiments, the feeder free environment is substantially free of cytokines and growth factors, including bFGF.

Dissociation

Dissociation of cells into single cells, such as into a single cell suspension, can be accomplished by enzymatic or mechanical means. Any enzymatic agent known in the art to allow dissociation of cells into single cells may be used in the methods of the invention. In one embodiment of the invention, the dissociation agent is selected from Trypsin/EDTA, TrypLE-Select, Collagenase IV and Dispase.

A chelator, such as EDTA, Accutase, or AccuMax, may also be used, alone or in combination with an enzymatic agent, in dissociating cells in accordance with the methods of the invention. The dissociation agent may be dissolved in calcium and magnesium free PBS to facilitate dissociation to single cells.

To enhance the survival of the cells during and after dissociation, a survival promoting substance can be added (e.g., growth factor, inhibitors of cellular pathways involved in cell death and apoptosis, or conditioned media). In some embodiments, cells cultured in conventional medium are dissociated and the single cells are placed in a cell culture of the invention having one or more small molecule inhibitors, such as the SMC4 media or SMC4+ fibronectin. The dissociated single cells may optionally be placed in a feeder free environment. In other embodiments, cells are cultured in a feeder free environment before dissociating and placed in a cell culture of the invention having one or more small molecule inhibitors, such as the SMC4 media or SMC4+ fibronectin, which may optionally be a feeder free environment.

Enzymatic dissociation to single cells may be supported by mechanical force. Alternatively, the dissociation agent may be only a mechanical force, such as by using a mechanical tool, such as a pipette or a sharpened micro capillary to detach the cells.

General techniques in cell culture and media collection are outlined in Large Scale Mammalian Cell Culture (Hu et al., *Curr. Opin. Biotechnol.* 8:148, 1997); Serum-free Media (K. Kitano, Biotechnology 17:73, 1991); Large Scale Mammalian Cell Culture (*Curr. Opin. Biotechnol.* 2:375, 1991); and Suspension Culture of Mammalian Cells (Birch et al., *Bioprocess Technol.* 19:251, 1990). Other reading of interest includes Understanding Media (M. McLuhan, Mentor N.Y., 1964) and The Medium is the Massage (M. McLuhan & Q. Fiore, Bantam N.Y., 1967).

For further elaboration of general techniques useful in the practice of this invention, the practitioner can refer to standard textbooks and reviews in cell biology, tissue culture, and embryology. Included are "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cell Differentiation in vitro" (M. V. Wiles, Meth. Enzymol. 225:900, 1993); "Properties and uses of Embryonic Stem Cells: Prospects for Application to Human Biology and Gene Therapy" (P. D. Rathj en et al., al., 1993). Differentiation of stem cells is reviewed in Robertson, *Meth. Cell Biol.* 75:173, 1997; and Pedersen, Reprod. Fertil. Dev. 10:31,1998.

Enrichment and Depletion Strategies

The invention also provides strategies for enriching a population of cells for pluripotent cells as a method of increasing the efficiency of generating iPSCs. The enrichment strategy provides a method of deriving clonal iPSC colonies in a relatively short time, improving the efficiency of iPSC generation. The enrichment methods of the invention comprise sorting a population of cells that have been induced to reprogram to identify and obtain cells expressing markers of pluripotency, thereby obtaining a population of cells enriched for pluripotent cells. The cells to be sorted may have been induced to reprogram and may comprise a mixed population of cells undergoing reprogramming, so that the population comprises pluripotent cells, partially pluripotent cells, and non-pluripotent cells, such as fully differentiated cells. In one embodiment, the population of cells to be sorted has been induced to reprogram and expresses markers of pluripotency. In some embodiments, the cells are cultured after reprogramming is induced for about 4 to 30 days, about 4 to 24 days, about 6 to 22 days, or about 8 to about 12 days. An additional enrichment methodology involves the depletion of cells expressing markers of differentiation or non-pluripotency to obtain an enriched population of pluripotent cells.

The enrichment strategy of the invention includes obtaining a single cell suspension of the population of cells to be sorted. In one embodiment of the invention, a single cell suspension is obtained by dissociating the cells in the population and resuspending the cells. The dissociated cells may be resuspended in any suitable solution or media for maintaining cells or performing cell sorting. In particular embodiments, the single cell suspension contains one or more of a TFGβ inhibitor, a GSK3 inhibitor, a MEK inhibitor, and a Rock inhibitor. In certain embodiments, the single cell suspension comprises a TFGβ inhibitor, a GSK3 inhibitor, a MEK inhibitor, and a Rock inhibitor, and in certain particular embodiments, the TFGβ inhibitor is SB431542, the GSK3 inhibitor is CHIR99021, the MEK inhibitor is PD0325901, and the Rock inhibitor is thiazovivin.

In the enrichment process of the invention, cells are sorted to obtain pluripotent cells, or cells are depleted of non-reprogrammed or non-pluripotent cells, thereby obtaining a population of cells enriched for pluripotent cells. In one embodiment, a single cell suspension is prepared, and then the single cells are prepared for sorting, such as by staining for markers of pluripotency using, e.g., appropriate antibodies. Cells may be sorted by any suitable method of sorting cells, such as by magnetic bead or flow cytometry (FACS) sorting.

Cells may be sorted based on various markers of pluripotency, including expression of Oct, Sox, Nanog, SSEA3/4; TRA1-60/81; TRA1-85, TRA2-54, GCTM-2, TG343, TG30, CD9, CD29, CD133/prominin, CD140a, CD56, CD73, CD105, CD31, CD34, OCT4, KLF4, SSEA1 (Mouse), and as demonstrated in the present invention, CD30 and CD50. In various embodiments, cells are sorted based on at least two, at least three, or at least four markers of pluripotency. In certain embodiments, cells are sorted based on expression of SSEA4, and in certain particular embodiments based on expression of SSEA4 in combination with TRA181 or TRA160. In certain embodiments cells are sorted based on SSEA4, Tra181 or Tra160 and CD30. In certain embodiments, cells are initially depleted for non-reprogrammed cells using surface markers of differentiating cells, which may include but are not limited to, CD13, CD26, CD34, CD45, CD31, CD46, or CD7, and and then enriched for pluripotent markers such as SSEA4, Tra181 and CD30.

After sorting to obtain cells positive for pluripotency markers, the desired cell fraction is a population of cells enriched for pluripotent cells. The population enriched for pluripotent cells may be placed in a cell culture system, such as conventional hESC media or the cell culture media of the invention. The cell culture system may be supplemented with feeder cells, or optionally be a feeder free environment. In some embodiments, the sorted cells expressing markers of pluripotency are placed in a feeder cell supplemented culture system and then transferred to a feeder free environment. The cell culture system may be supplemented with one or more of the specific pathway modulators and additives shown in Table 1. In one embodiment, the cell culture medium is a feeder free environment and comprises at least one of a TFGβ inhibitor, a GSK3 inhibitor, a MEK inhibitor, and a Rock inhibitor; in particular embodiments, the cell culture media comprises a TFGβ inhibitor, a GSK3 inhibitor, a MEK inhibitor, and a Rock inhibitor; and in certain embodiment, the TFGβ inhibitor is SB431542, the GSK3 inhibitor is CHIR99021, the MEK inhibitor is PD0325901, and the Rock inhibitor is thiazovivin. In other particular embodiments of the invention, the cell culture system is a feeder free environment comprising a Matrigel™ coated tissue plate, conventional hESC medium, and the specific pathway modulators shown in Table 1. In one embodiment, the cell culture system comprises the SMC4 medium described in Table 1, optionally combined with any of the alternative medium and pathway modulators shown in Table 2.

The enriched cell population may be cultured in the cell culture systems described herein to obtain iPSC colonies, typically appearing about 3 to about 25 days after sort; about 5-9 days post sort, or about 5-7 days post sort. iPSC colonies can be picked or sorted for clonal expansion. Using the enrichment strategy of the invention, the cell population is enriched 3-fold for pluripotent cells.

The invention also provides methods of depleting a population of cells of undesirable cells. In some embodiments, a population of cells, such as a population of cells undergoing reprogramming or a population of pluripotent cells, is depleted of differentiated cells. In the method of the invention, a population of pluripotent cells or cells induced to reprogram can be depleted of cells having cells surface markers of differentiated cells. The population of cells can be sorted based on surface markers of differentiating cells, such as CD13, CD26, CD34, CD45, CD31, CD46, or CD7, and cells expressing the markers of differentiating cells can be removed from the cell population to obtain a cell population enriched in pluripotent cells. CD13 is used as a surface marker of differentiating cells in particular embodiments of the invention.

In other embodiments, a population of cells induced to differentiate, such as a population of cells induced to differentiate into a desired lineage, is depleted of pluripotent cells to obtain a population of differentiating or differentiated cells. In some embodiments, the population of differentiated cells comprises a population of cells, such as ESCs or iPSCs, that has been induced to differentiate into a specific lineage. A population of cells may be depleted of pluripotent cells using the sorting techniques described above, such as sorting cells in the population according to magnetic beads or FACs based on markers of pluripotency. In some embodiments, a population of cells comprising differentiated cells is sorted by FACs using pluripotency markers, and a fraction is obtained that is depleted of cells expressing pluripotency markers. In other embodiments, a population of cells is sorted by FACs based on markers of differentiation, such as lineage-specific markers like CD13, CD26, CD34, CD45, CD31, CD46, or CD7, to obtain a fraction depleted of markers of pluripotency. CD13 is used as a surface marker of differentiating cells in particular embodiments of the invention.

The practice of the present invention will employ, unless indicated specifically to the contrary, conventional methods of chemistry, biochemistry, organic chemistry, molecular biology, microbiology, recombinant DNA techniques, genetics, immunology, cell biology, stem cell protocols, cell culture and transgenic biology that are within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2001); Sambrook, et al., *Molecular Cloning: A Laboratory Manual* (2$^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-interscience; Glover, *DNA Cloning: A Practical Approach*, vol. I & II (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Fire et al., *RNA Interference Technology: From Basic Science to Drug Development* (Cambridge University Press, Cambridge, 2005); Schepers, *RNA Interference in Practice* (Wiley-VCH, 2005); Engelke, *RNA Interference (RNAi): The Nuts & Bolts of siRNA Technology* (DNA Press, 2003); Gott, *RNA Interference, Editing, and Modification: Methods and Protocols* (Methods in Molecular Biology; Human Press, Totowa, N.J., 2004); Sohail, *Gene Silencing by RNA Interference: Technology and Application* (CRC, 2004); Clarke and Sanseau, *microRNA: Biology, Function & Expression* (Nuts & Bolts series; DNA Press, 2006); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008); Hogan et al., *Methods of Manipulating the Mouse Embryo* (2$^{nd}$ Edition, 1994); Nagy et al., *Methods of Manipulating the Mouse Embryo* (3$^{rd}$ Edition, 2002), and *The zebrafish book. A guide for the laboratory use of zebrafish* (Danio rerio), 4th Ed., (Univ. of Oregon Press, Eugene, Oreg., 2000).

As used in this specification and the appended claims, the singular forms "a," "an" and "the" include plural references unless the content clearly dictates otherwise.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the claims below, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

Experimental Methods

A. Cell Culture of Pluripotent Stem Cells

Prior to feeder-free adaptation, human induced pluripotent stem cells (hiPSCs) were maintained on feeder cells (mitomycin C treated mouse embryonic fibroblast (MEF) cells (Millipore)), and cultured with conventional medium. As used in this application, "conventional medium" refers to basal human embryonic stem cell (hESC) medium containing DMEM/F12 (Mediatech), 10 ng/mL bFGF (Invitrogen), 20% v/v knockout serum replacement (Invitrogen), 1% v/v non-essential amino acids (Mediatech), 2 mM L-glutamine (Mediatech) and 100 µM β-mercaptoethanol (Invitrogen). Conventional medium is also described in the first sections of Table 1. hiPSCs were passaged every 5-7 days by mechanically cutting and scrapping colonies into small pieces using a fine tip glass pipette (clump passaging), collected and dilute passaged 1:3-1:6 onto freshly seeded mitomycin C treated MEF cells with daily addition of hESC medium. Cell cultures were maintained in a humidified incubator set at 37° C. and 5% CO2. Culturing cells in conventional medium with feeder cells and using clump passaging is referred to herein as "conventional culture".

For single cell dissociation, hiPSCs were washed once with phosphate buffered saline (PBS) (Mediatech) and treated with Accutase (Millipore) or TrypL (Invitrogen) for 3-5 min at 37° C. followed by pipetting to break into single cells. The single cell suspension was then mixed in equal volume with conventional medium as described above, spun down at 300 g for 5 min and resuspended in SMC4 medium or SMC4+ fibronectin medium. In most cases, the single cell dissociated cells were maintained in SMC4 medium composed of conventional hESC medium supplemented with various small molecules and additives, including 0.4 µM PD0325901, 1 µM CHIR99021, 5 µM Thiazovivin and 2 µM SB431542 (all Biovision). Small molecules were maintained at a stock concentration of 5-25 µM in DMSO at −20° C. prior to the addition to media. All working media were maintained in 4° C. for up to 4 weeks. Of the ROCK inhibitors, culture with Thiazovivin was preferred over Y27632 for maintaining cells in an undifferentiated state.

After resuspension in the appropriate medium, the cells were transferred to feeder-free tissue culture plates (BD Falcon) that were previously coated with Matrigel™ (1:25 dilution; BD Biosciences) for 1-2 hrs in 37° C. In this format, cells routinely received fresh medium every other day and were passaged when confluency had reached 66-75%, which normally occurred 4-5 days post passage. With each passage cells were re-dissociated into single cells and transferred to a new tissue culture plate coated with Matrigel™ (BD Biosciences) at a dilution passage of 1:5-1:10. For defined, growth-factor-free culture, cell suspensions were added to tissue culture plates previously coated with 1% Gelatin (Mediatech). Cells were maintained and passaged as described above, except that the SMC4 medium was substantially free of all cytokines and growth factors, including bFGF.

For the purpose of freezing, cells were dissociated into single cells, resuspended in SMC4+ fibronectin supplemented with 10% v/v DMSO (Mediatech) and placed into cryovials (Nalgene). Once capped, cryovials were placed inside a Mr. Frosty (Nalgene) and kept overnight at −80° C. The next day cryovials were transferred to liquid nitrogen for long-term storage. To thaw, frozen cryovials were placed in 37° C. water bath for approximately 1-2 min, until most of the ice had melted. The thawed cell solution was then gently mixed with fresh conventional hESC medium and spun down at 300 g for 5 min. The cell solution was resuspended in SMC4+fibronectin medium and transferred onto Matrigel™ (BD Biosciences) coated tissue culture plate. As with all other cell culture incubations, cells were maintained in a humidified incubator set at 37° C. and 5% CO2.

B. Induction of Reprogramming

To initiate the reprogramming process, ectopic expression of reprogramming factors (in variable combinations of human Oct4, Sox2, Klf4, c-Myc, Lin28, and Nanog) was achieved using lentiviral transduction or other methods such as protein only treatment. In most cases, the starting cells were plated at 10% confluency (i.e., 1×10$^5$ cells per well of a 6-well plate) on a gelatin (Mediatech) coated surface. For the method of viral infection, freshly collected lentivirus was added to the starting cells at a dilution of 1:2, supplemented with 4 µg/mL polybrene (Millipore), and spin-infected at 650 g at 32° C. for 1.5 hrs. The culture was transferred to 37° C. and 5% CO2 for an additional 7 hrs. After the completion of the incubation, the cells were washed three times with PBS and fed with fresh medium. With difficult to infect cells, such as IMR90 fibroblasts in feeder-free culture systems, this process was repeated one more time, 48 hrs post the initial infection. For non-genetic methods of inducing reprogramming such as the use of direct protein application to the cells, protein mixtures, or cocktails, consisting of reprogramming factors at 8 µg/mL were added to cell solution and maintained for 24 hrs prior to medium change. This step was repeated for an additional two to four times. All starting cells were cultured in their own respective somatic cell medium until day 4 post initial protein addition, at which point the medium was switched to one part somatic cell medium and one part conventional hESC medium. Upon confluency (usually between days 4-6) the cells were trypsinized, mixed with equal part culture medium, spun down at 300 g for 5 min, resuspended in 1:1 somatic/conventional hESC medium and expanded 1:4-1:6 into a larger culture plate. For example, cells in two wells of a 6-well plate are usually expanded onto a 10 cm dish. The next day following the expansion, the medium is completely switched to conventional hESC medium. Once the expanded cells reach confluency (usually between days 8-12) they will be processed for enrichment (see Unique Population Enrichment). In all cases the medium was routinely changed every other day.

C. Unique Population Enrichment

After the starting cells have been induced to reprogram with various strategies including individual lentivirus constructs or polycistronic vectors containing Oct4 and/or Klf4 and/or Sox2 and/or Myc and cultured for approximately 8-12 days (see above), cells are dissociated into single cells (see Cell Culture Of Pluripotent Stem Cells) and stained with various surface markers of pluripotency, markers of somatic cells and/or markers of incomplete reprogramming. Briefly, dissociated cells were resuspended in staining solution containing Hanks' Balanced Salt Solution (Invitrogen), 4% fetal bovine serum (Invitrogen) and 10 mM Hepes (Invitrogen) and kept on ice. Per recommended manufacturers' dilution, conjugated primary antibodies were added to the cell solution and the solution was incubated on ice for 15 min. The cell solution was washed and resuspended in staining buffer and maintained on ice. At this point, various enrichment/depletion strategies were taken, including Fluorescent Activated Cell Sorting (BD Biosciences, see below) and Magnetic Cell Sorting (Miltenyi Biotec, see below).

Flow cytometry sorting was performed on FACS Aria (BD, Biosciences). Primary antibodies used included SSEA4 (BD Biosciences), Tra-181 (Biosciences), Tra-161 (BD Biosciences), CD30 (BD Biosciences), and CD50 (BD Biosciences), as specified. The sorted cells were then spun down and resuspended in SMC4+ fibronectin medium and transferred to Matrigel™ coated tissue culture plates. When sorted into microwells, i.e., 96 well plates, the plates were spun down for 2 min at 300 g. The SMC4+fibronectin medium was replaced every other day for 3-4 days. After 3-4 days SMC4+ fibronectin medium was typically replaced with SMC4 medium for the remaining time in culture. Colony formation was typically seen 7-9 days post sort. Flow cytometry analysis was performed on Guava EasyCyte 8HT (Millipore).

MACS Microbeads (Miltenyi Biotec) separation was performed according to protocol. Briefly, cells were dissociated into single cells (See Cell Culture of Pluripotent Stem Cells) and stained with appropriate FITC-conjugated primary antibodies, including SSEA4 (BD Biosciences), Tra-1-81 (BD Biosciences), Tra-160 (BD Biosciences), CD30 (BD Biosciences), and CD50 (BD Biosciences), as specified. Cells were then magnetically labeled with Anti-FITC Microbeads (Miltenyi Biotec). The labeled cell suspension was then loaded onto a LS MACS Column (Miltenyi Biotec). The collected cells from either positively or negatively selected fractions were spun down at 300 g for 5 min and resuspended in SMC4+ fibronectin and transferred to Matrigel™ (BD Biosciences) coated tissue culture plates. The following day, fresh medium was added to the culture and subsequently replaced every other day. After 3-4 days, SMC4+ fibronectin medium was typically replaced with SMC4 media for the remaining time in culture. The colonies typically appeared 5-7 days post sort.

D. Alkaline Phosphatase Staining Cells were fixed in 4% v/v paraformaldehyde (Alfa Aesar) for 30 sec, washed three times with PBS and stained with Alkaline Phosphatase Staining Kit (Sigma-Aldrich). Briefly, 1 mL Sodium Nitrite Solution was added to 1 mL FRV-Alkaline Solution, mixed and incubated at 25° C. for 2 min. The solution was then mixed with 45 mL of $H_2O$ followed by the addition of 1 mL Naphthol AS-BI Alkaline Solution. The alkaline-dye mixture was added to the fixed cells and incubated at 25° C. for 15 min followed by a PBS wash. The cells were then scored for the presence of alkaline phosphatase.

E. Immunofluorescence Staining

Cells were fixed using 4% v/v paraformaldehyde (Alfa Aesar) for 15 min, washed three times with PBS containing 0.2% v/v Tween (PBST) (Fisher Scientific) and permeablized using 0.15% v/v TritonX-100 (Sigma-Aldrich) in PBS for 1 hr at 25° C. After permeabilization, cells were blocked with 1% v/v BSA (Invitrogen) in PBST (PBSTB) (Fisher Scientific) for 30 min at 25° C. After gentle removal of PBSTB, cells were incubated with primary antibody in PBSTB overnight at 4° C. Primary antibodies used in this study include Nanog (Abcam), Tra-1-60 (BD Biosciences), Tra-181 (BD Biosciences), SSEA4 (BD Biosciences), β-III Tubulin (R&D Systems), α-Smooth Muscle Actin (Sigma) and Sox17 (R&D Systems). After the overnight incubation, cells were washed three times with PBST and stained with secondary antibody (Alexa 488 or 555; Invitrogen) diluted 1:200 in PBSTB for 1 hr at 25° C. The cells were washed three times in PBST and stained with Hoechst dye (Invitrogen). Images of the stained cells were captured using fluorescence microscopy and CCD camera.

F. Induction of Differentiation and Teratoma Formation

Feeder-free iPSCs were differentiated as both monolayers and as embryoid bodies. For monolayer differentiation, iPSCs were allowed to reach near confluency prior to switching to differentiation medium as cells usually reduce their proliferation upon differentiation. Briefly, upon confluency, SMC4 medium was switched to differentiation medium containing DMEM/F12 (Mediatech), 20% fetal bovine serum (Invitrogen), 1% non-essential amino acids (Mediatech), 2 mM L-glutamine (Mediatech) and 100 μM β-mercaptoethanol. Once the medium was switched, the iPSCs were allowed to differentiate for 14 days. Medium was changed every 2-3 days. For embryoid body ("EB") formation and differentiation, hiPSCs were single cell dissociated with Accutase (Millipore) and resuspended in differentiation medium to a final concentration of 75,000 cells/mL and 5 uM Thiazovivan was added. Cells were seeded in 100 μL/well to V-bottom 96-well non-tissue culture plate (Nunc) and centrifuged at 950 g for 5 min. The following day compact "ball-like clumps" were transfer to ultra-low binding 6-well plate (Corning) using P1000 at approximately 30-40 EBs/well. After 7 days, transfer EBs were transferred at 1:1 to Matrigel coated 6-well plate. After 3 weeks in culture, cells were fixed and stained.

Teratoma grafting and analyses was conducted by Applied Stem Cells (Menlo Park, Calif.). Briefly, 1-2 million single cell dissociated hiPSCs were mixed in 100 uL SMC4 media supplemented medium and 100 uL Matrigel and introduced to the renal capsule and testis of Beige SCID mice. The developed teratomas were harvested, sectioned and analyzed for various differentiated cell types and structures.

G. RT-qPCR and qPCR Analysis

RNA was isolated using the PicoPure RNA Isolation kit (MDS Analytical Technologies), and 0.5 μg RNA was used to generate first strand cDNA using the iScript cDNA Synthesis Kit (Bio-Rad). Relative gene expression levels were determined using the TaqMan Fast Universal PCR Master Mix (Applied Biosystems) and the FAM-labeled TaqMan probes listed below in Table 3.

TABLE 3

ABI Primers and Probes.

| Symbol | Assay ID |
| --- | --- |
| Endogenous SOX2 | Hs00602736_s1 |
| Endogenous LIN28 | Hs00702808_s1 |
| Endogenous MYC | Hs00905030_m1 |
| ZFP42 (REX1) | Hs00399279_m1 |
| DPPA2 | Hs00414521_g1 |
| DPPA4 | Hs00216968_m1 |
| DNMT3B | Hs01003405_m1 |
| GAPDH | Hs99999905_m1 |

Custom-Made Primers and Probes

| Gene | Forward Primer | Reverse Primer | Probe |
| --- | --- | --- | --- |
| Transgenic Oct4 | CTGGTTGGAGGGAAGGTAATCTAG (SEQ ID NO: 1) | TTTTGTAATCCAGAGGTTGATTGTTC (SEQ ID NO: 2) | CCCCGACGCGTCT (SEQ ID NO: 3) |
| Transgenic Klf4 | GCCTTACACATGAAGAGGCATTT (SEQ ID NO: 4) | TTTTGTAATCCAGAGGTTGATTGTTC (SEQ ID NO: 2) | CCCCGACGCGTCT (SEQ ID NO: 3) |
| Transgenic Myc | TCTTGTGCGTAACTCGAGTCTAGAG (SEQ ID NO: 5) | TTTTGTAATCCAGAGGTTGATTGTTC (SEQ ID NO: 2) | CCCCGACGCGTCT (SEQ ID NO: 3) |
| Transgenic Lin28 | CCGGAGGCACAGAATTGAC (SEQ ID NO: 6) | TTTTGTAATCCAGAGGTTGATTGTTC (SEQ ID NO: 2) | CCCCGACGCGTCT (SEQ ID NO: 3) |
| Transgenic Sox2 | CACTGCCCCTCTCACACATG (SEQ ID NO: 7) | TTTTGTAATCCAGAGGTTGATTGTTC (SEQ ID NO: 2) | CCCCGACGCGTCT (SEQ ID NO: 3) |
| Transgenic Nanog | CATGCAACCTGAAGACGTGTAA (SEQ ID NO: 8) | TTTTGTAATCCAGAGGTTGATTGTTC (SEQ ID NO: 2) | CCCCGACGCGTCT (SEQ ID NO: 3) |
| Endogenous Oct4 | GGGTTTTTGGGATTAAGTTCTTCA (SEQ ID NO: 9) | GCCCCCACCCTTTGTGTT (SEQ ID NO: 10) | TCACTAAGGAAGGAATTG (SEQ ID NO: 11) |
| Endogenous Klf4 | AGCCTAAATGATGGTGCTTGGT (SEQ ID NO: 12) | TTGAAAACTTTGGCTTCCTTGTT (SEQ ID NO: 13) | AGTCTTGGTTCTAAAGGTACC (SEQ ID NO: 14) |
| Endogenous Nanog | TGATGCCCATCCAGTCAATCT (SEQ ID NO: 15) | CCTCGCTGATTAGGCTCCAA (SEQ ID NO: 16) | ATGGAGGGTGGAGTATG (SEQ ID NO: 17) |

H. Gene Expression Analysis

Total RNA was isolated from cells using a Pico Pure RNA Isolation Kit (Molecular Devices, Sunnyvale, Calif.). In brief, biotinylated aRNA was prepared using the standard protocol for MessageAmp II aRNA Amplification Kit (Applied Biosystems/Ambion, Austin, Tex.) utilizing the optional Second Round Amplification and then transcribed into biotin labeled aRNA using MessageAmp II Biotin Enhanced Kit (Applied Biosystems/Ambion, Austin, Tex.) using the standard protocol. Biotin labeled aRNA was purified and fragmented according to Affymetrix recommendations. 20 µg of fragmented aRNA were used to hybridize to the Human Genome U133 Plus 2.0 chips (Affymetrix Inc. Santa Clara, Calif.) for 16 hrs at 45° C. The arrays were washed and stained in the Affymetrix Fluidics Station 450 and scanned using the Affymetrix GeneChip Scanner 3000 7G. The image data were analyzed using Affymetrix Expression Console software using default analysis settings. Arrays were normalized by log scale robust multi-array analysis (RMA) and visualized in Spotfire for Genomics 3.1 (Tibco Spotfire, Palo Alto, Calif.).

I. Karyotype Analysis and Copy Number Variation Analysis

Cytogenetic analysis was performed on twenty G-banded metaphase cells by Cell Line Genetics located in Madison, Wis.

High resolution comparative genomic hybridization (NimbleGen 12x135k) and subsequent copy number variation analysis was conducted by WiCell (Madison, Wis.).

Example 2

Cell Culture Conditions and Methods to Enable Feeder-Free Culture Environments and Enzymatic Single Cell Dissociation and Passaging of Pluripotent Stem Cells The present example relates to the culturing and dissociation of pluripotent cell populations. Such cell populations include but are not limited to, embryonic stem cells (ESC) and induced pluripotent cells such as those generated through somatic cell nuclear transfer (SCNT) or via the introduction of pluripotency factors—induced pluripotent stem cells (iPSC). Pluripotent stem cell culture conditions have traditionally included the use of feeder-cells that are rendered mitotically inactive via irradiation or mitomycin-C treatment but provide growth factors and nutrients required for the support of stem cell cultures. The culturing of stem cell populations without the use of feeder cells would be advantageous for research and industrial applications where homogeneous populations of the stem cells are required or where scaled, industrial activities require xenogeneic-free, defined culture conditions for a stem cell product. In the present example several small molecule modulators of specific cell signaling pathways were tested to establish if individual or combinations ("cocktails") of small molecules could be used to enhance the culturing of pluripotent cells in feeder-free systems.

When pluripotent cell populations were cultured without the use of feeders but instead using more defined extracellular matrix such as Matrigel™ in conventional hESC cell culture media (such as the conventional/basal medium formulation described in the first section of Table 1) cell viability and pluripotency was not supported (FIG. 1). However, the use of a small molecule inhibitor of Rock kinase improved the cell viability under these conditions. Further, the use of small molecule inhibitors of the MAP Kinase, TGFβ and Wnt/β-catenin pathways maintained the pluripotent nature of cells in the absence of feeders, although changes in cell viability may be noticed. The combination of Rock kinase inhibitor, in combination with MEK, TGFβ and GSK3 inhibitors maintained both viability and pluripotency of pluripotent stem cells when cultured in feeder-free environments.

Pluripotent cells such as ESC or iPSCs typically grow as clumps. Traditionally these cells have been expanded and passaged by manually picking colonies with the morphology recognized by a researcher skilled in the art. Such procedures are described in Example 1 of this document (described as clump passaging). The picked colony is then mechanically broken up and the dissociated cells are replated. Rapid expansion of a pluripotent cell population would benefit from the use of enzymatic, single-cell passaging. Enzymes such as trypsin and accutase are commonly used for the single cell dissociation of cells during passaging.

Figure 3A:
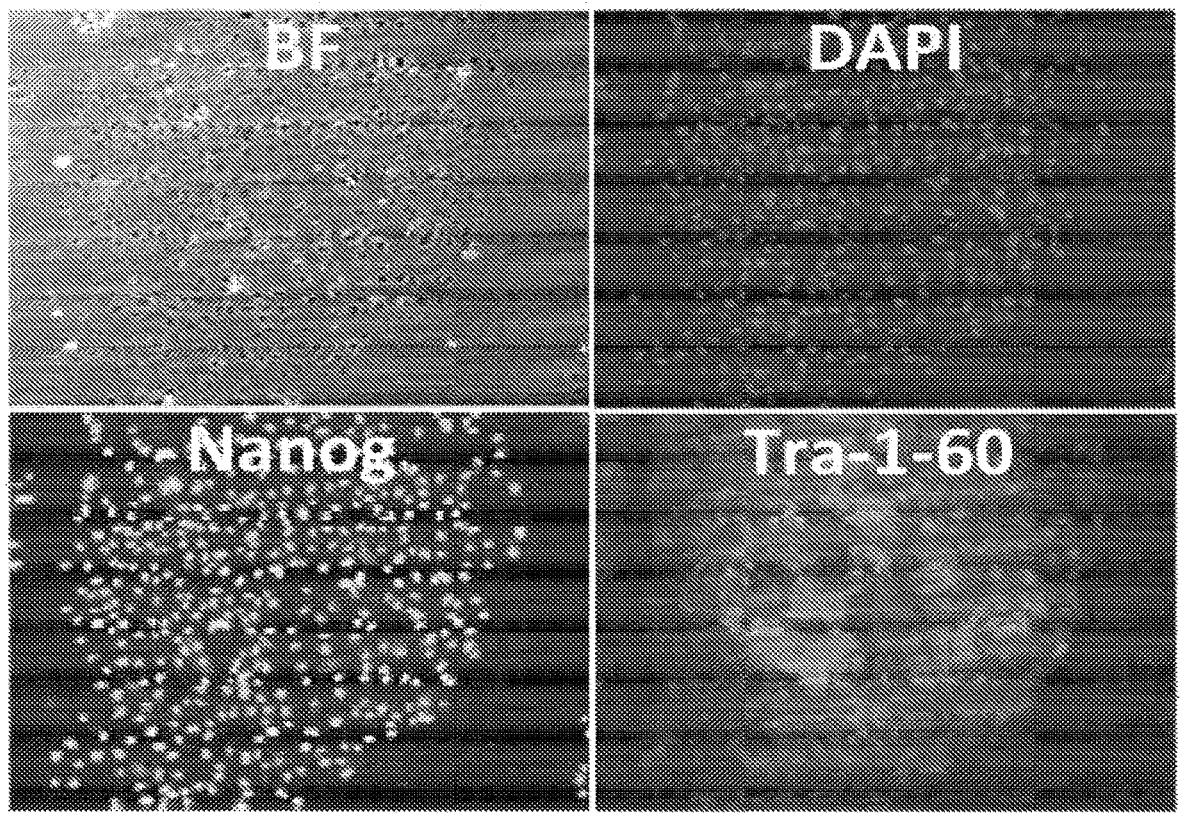
FIGS. 3A-3J. Long-term maintenance of single cell and feeder free human pluripotent stem cell culture.
Figure 3B:
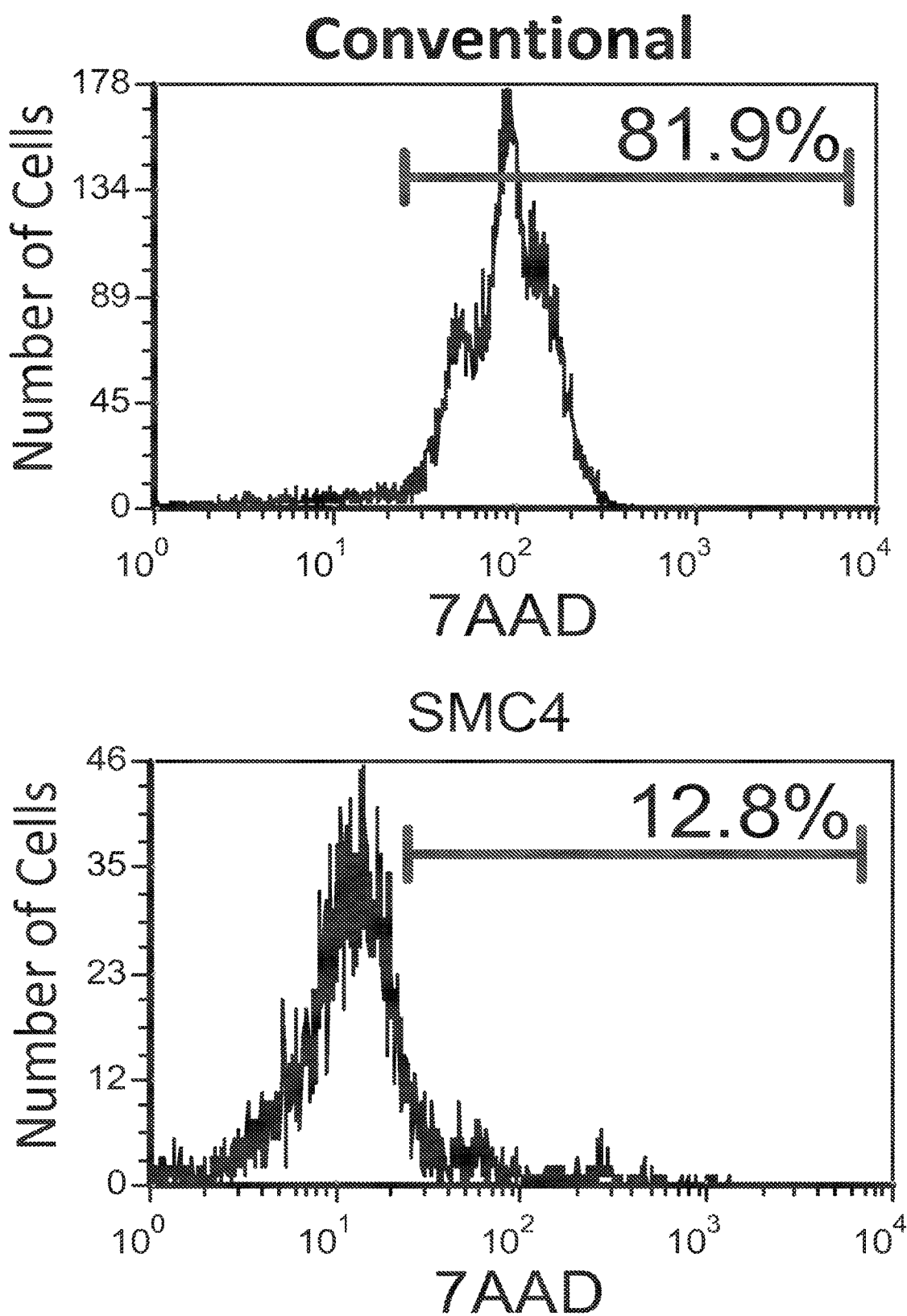
Figure 3C:
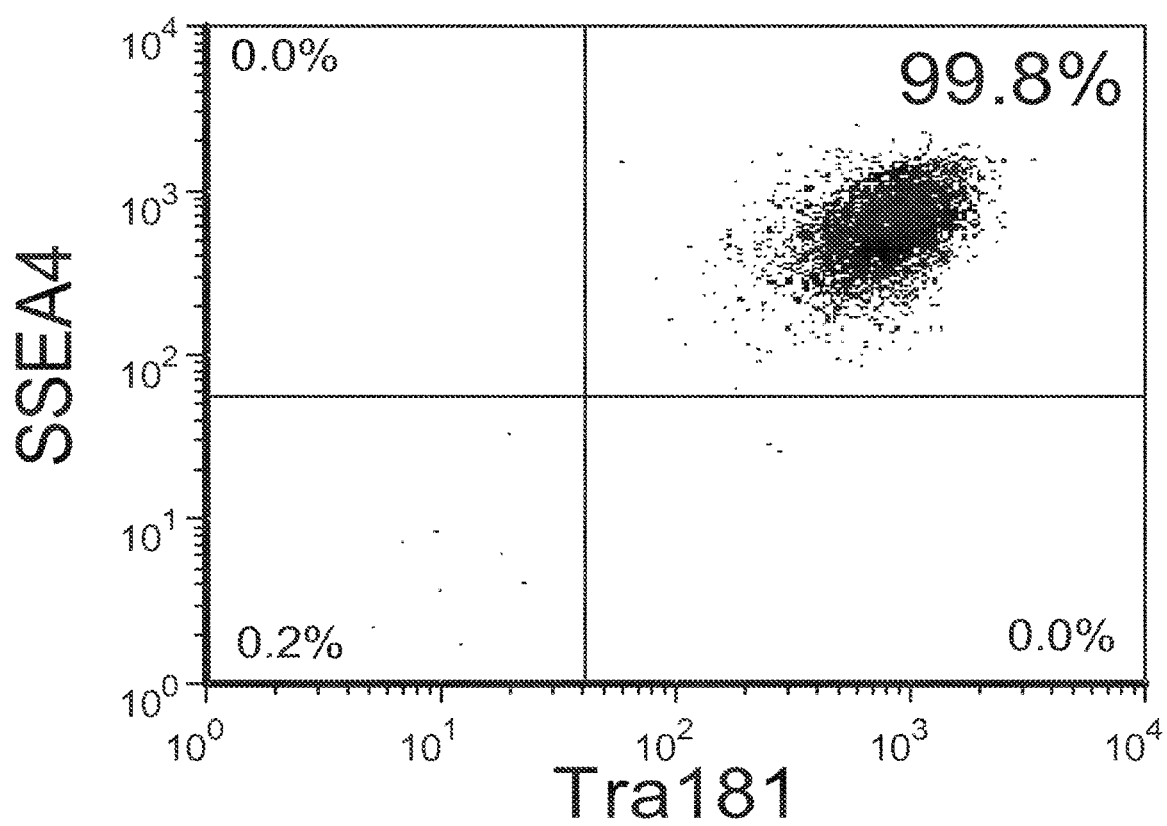
Figure 3D:
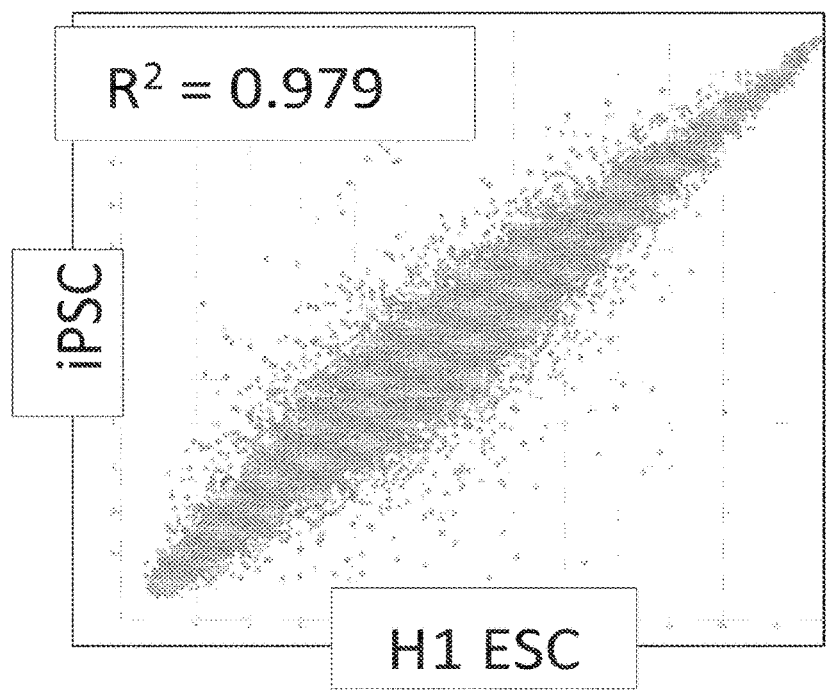
Figure 3E:
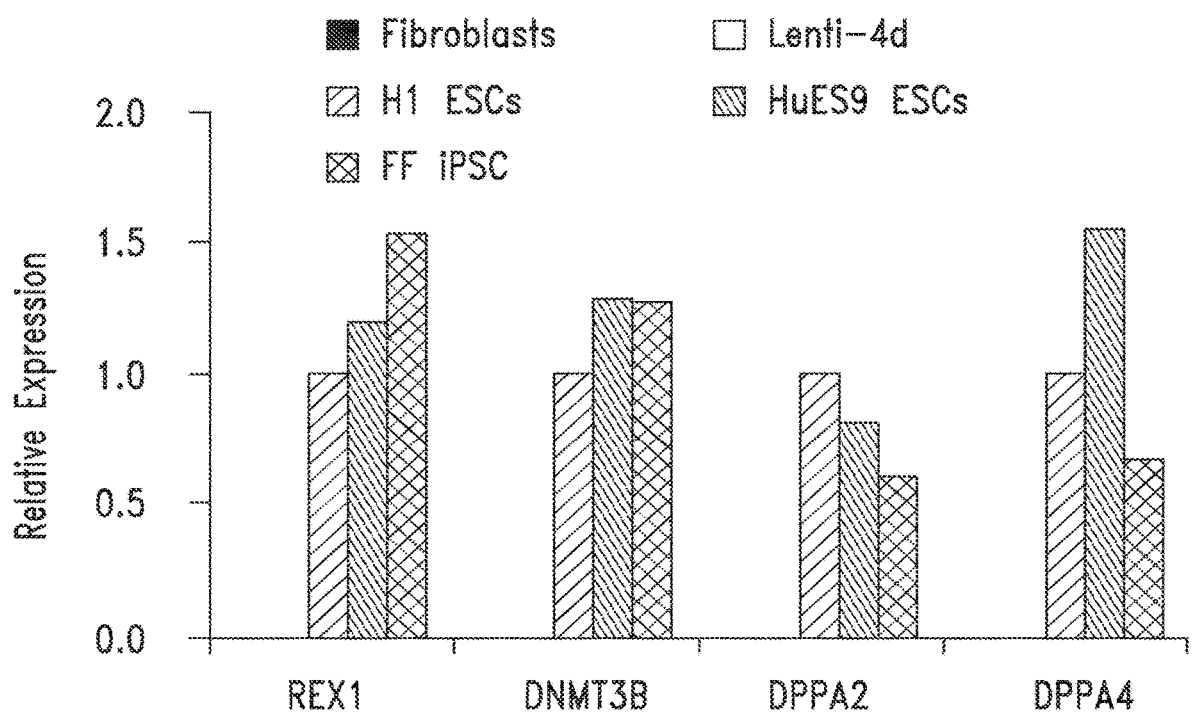
Figure 3F:
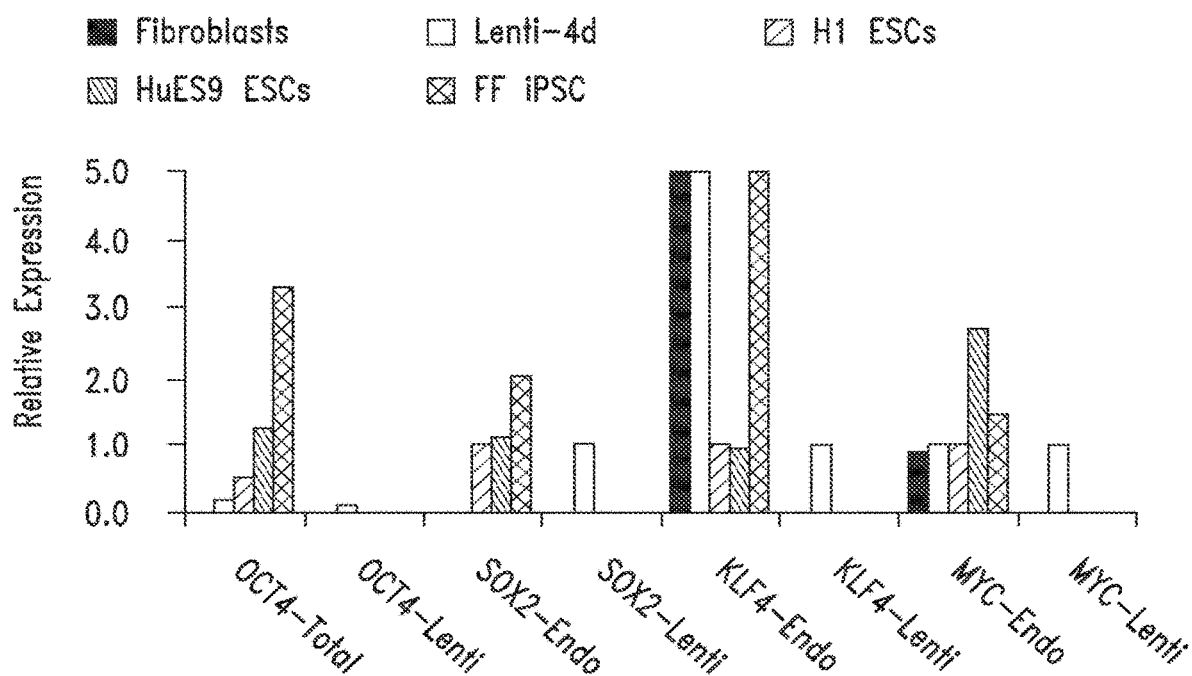
Figure 3G:
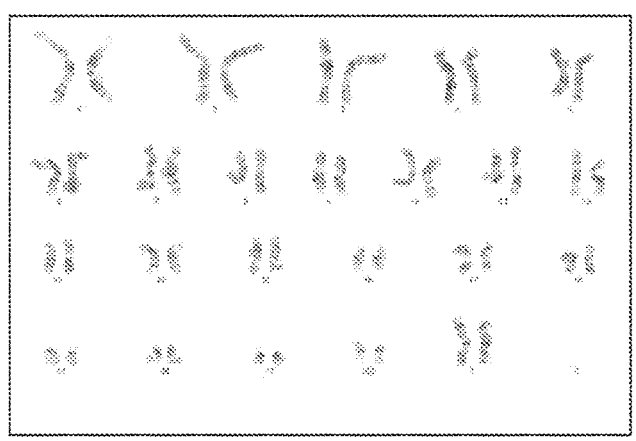

In a specific demonstration, iPSC cells showed a significant drop in viability when enzymatically-passaged and seeded as single cells in feeder-free environments, as can be seen by 7AAD incorporation in FIG. 3B. By using the culture platform of the present invention comprising the media compositions such as those listed in Table 1), pluripotent cell populations were cultured in feeder-free culture and enzymatically dissociated for single cell passage, with vastly improved cell viability and maintenance of pluripotency. More specifically, by using combinations of conventional/basal hESC media formulation and modulators of cellular signaling pathways such as the MAP kinase pathway, TGFβ pathway, Wnt/β-catenin pathway and Rho/Rock pathway, pluripotent stem cell viability and pluripotency were maintained during applications that require single-cell dissociation and feeder-free culture.

Figure 2A:
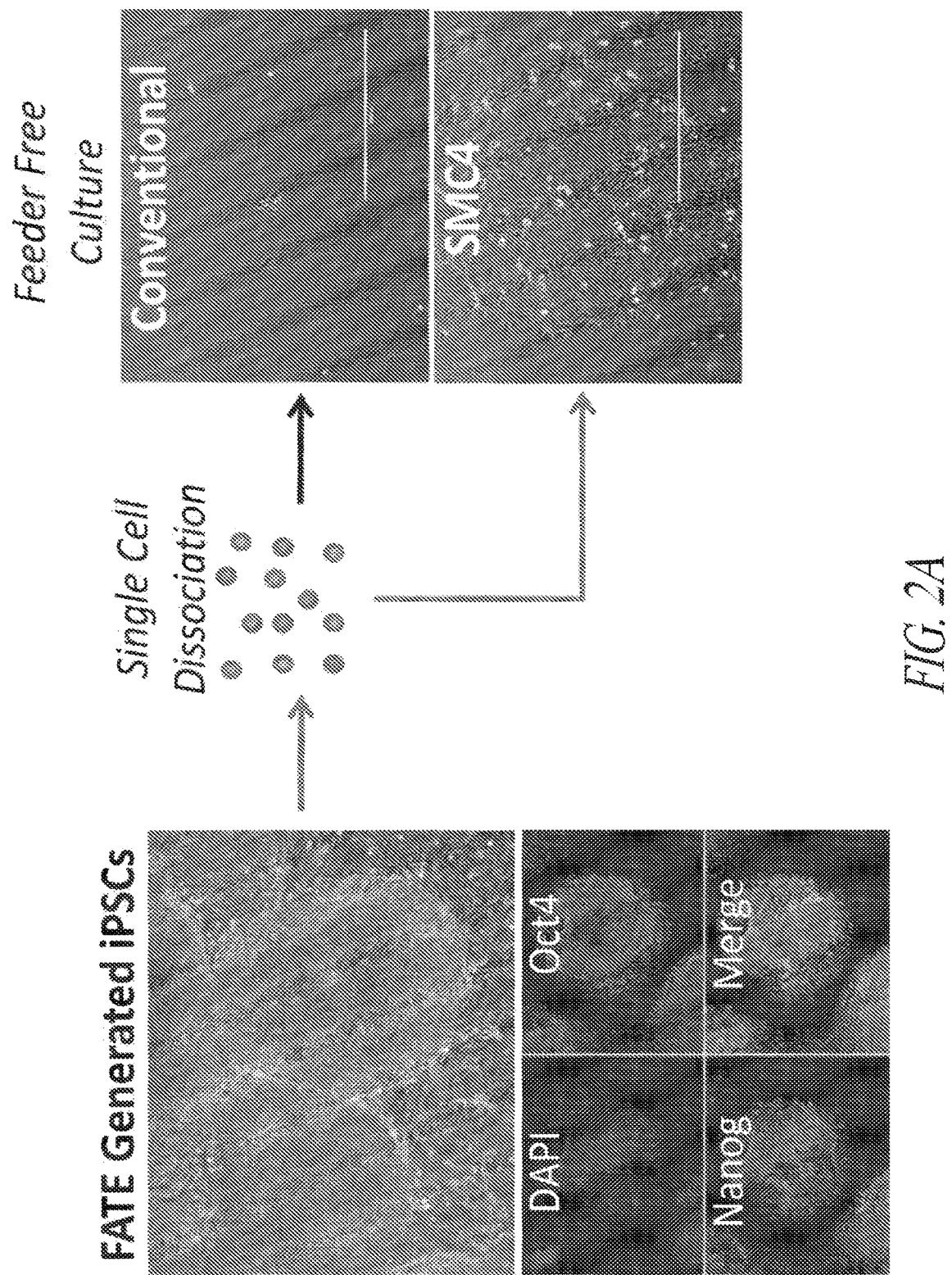
FIGS. 2A-2B. Human pluripotent stem cell adaptation into feeder free and single cell culture.
Figure 2B:
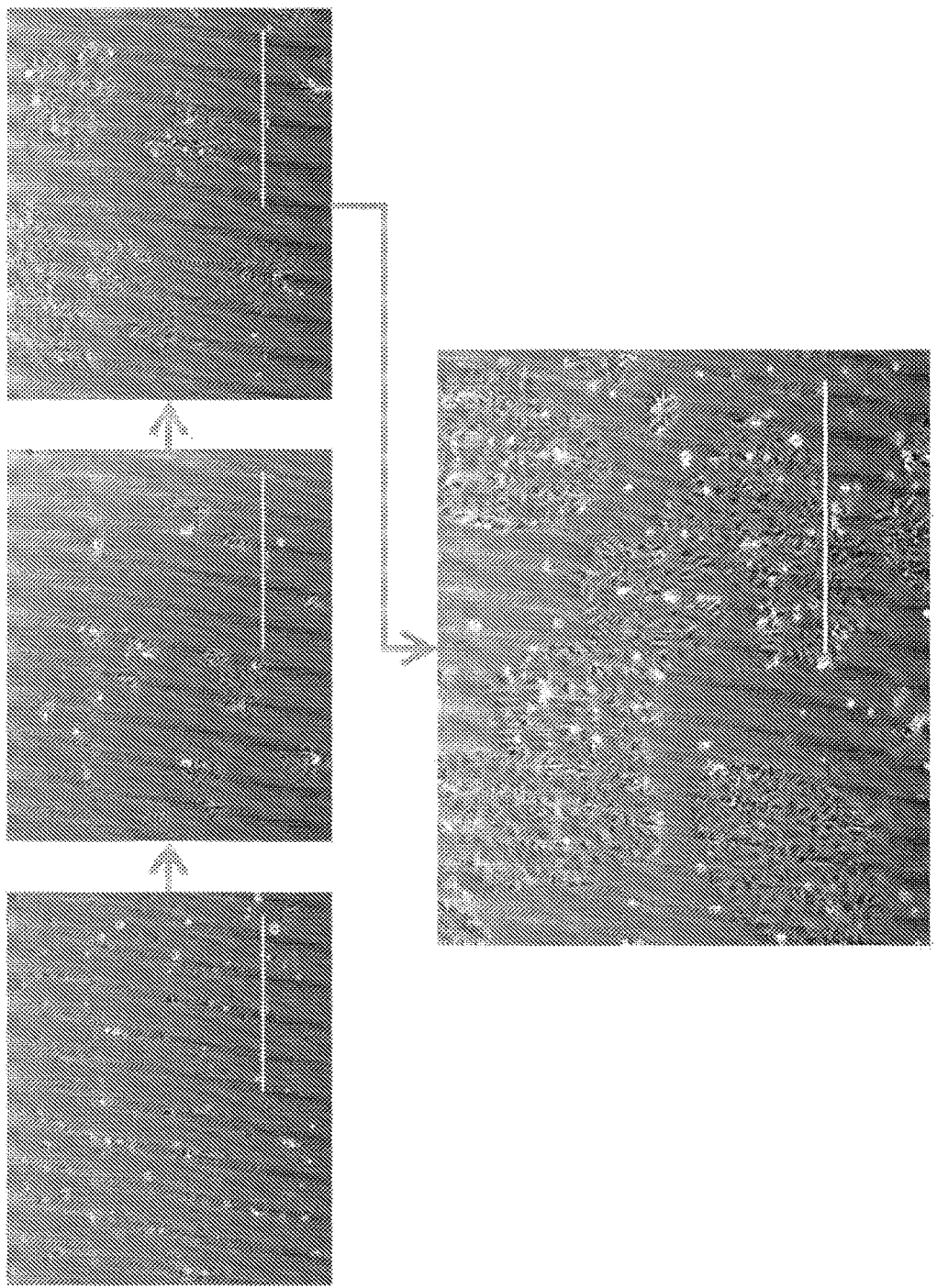
Figure 3H:
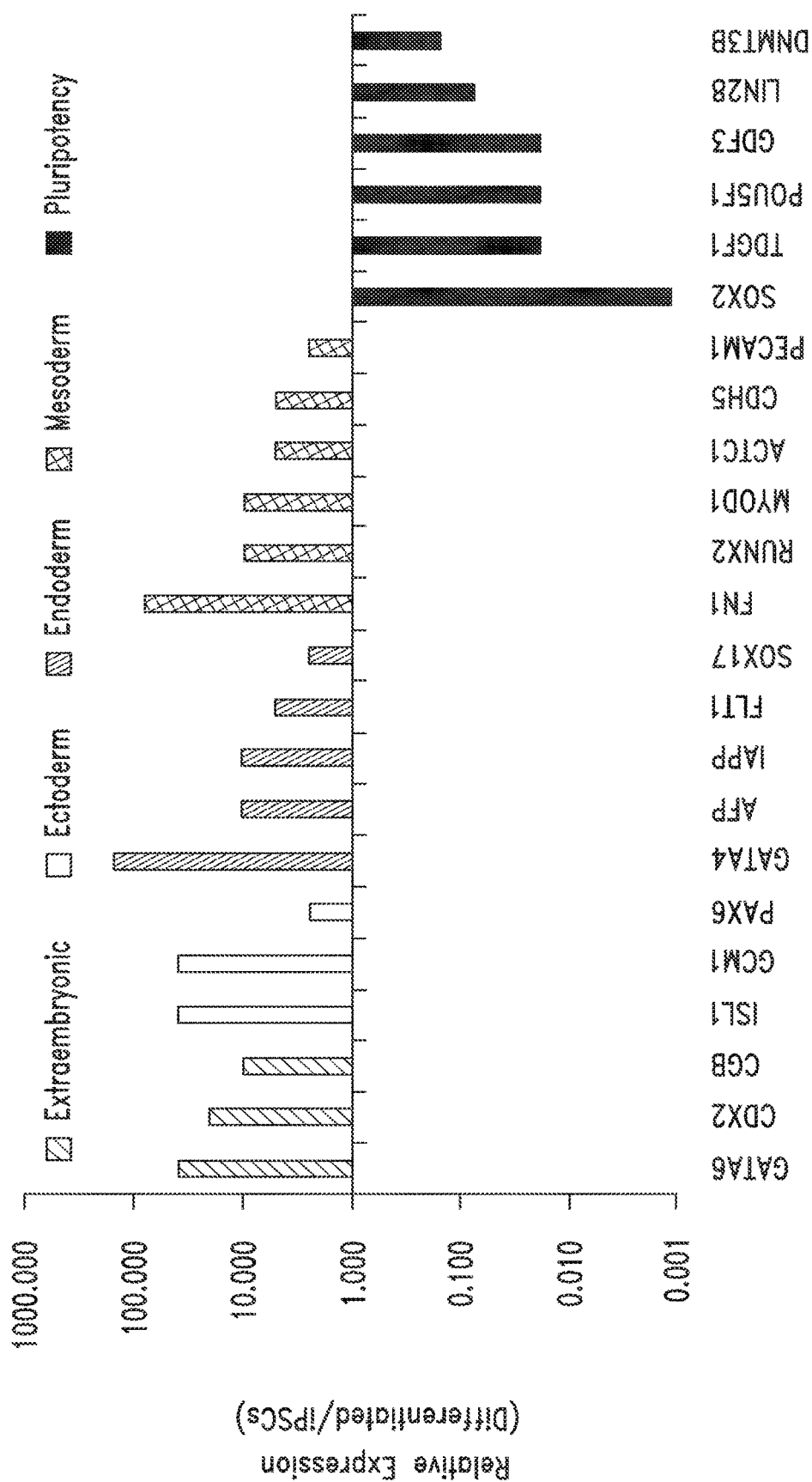
Figure 3I:
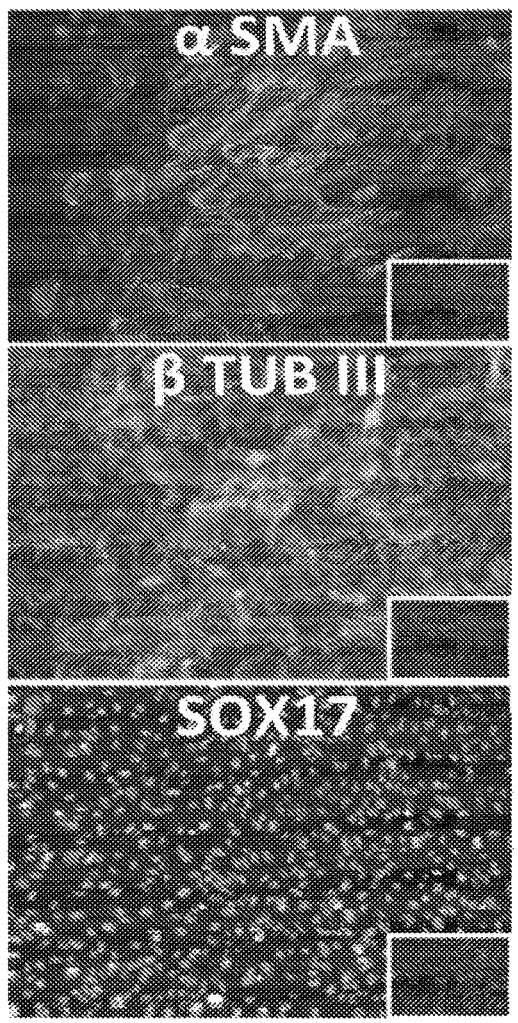
Figure 3J:
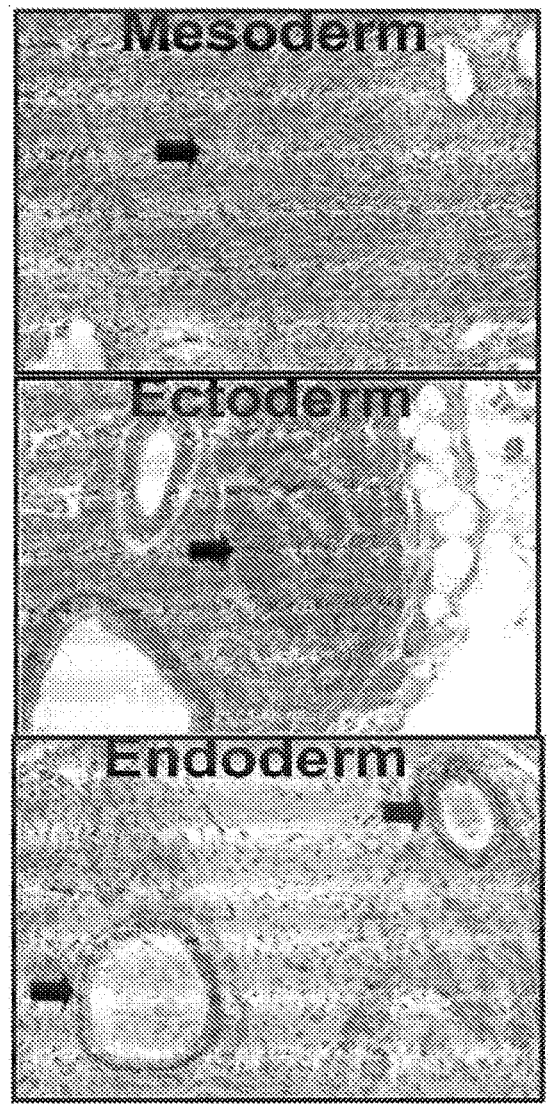

As shown in FIG. 2, iPSCs generated on feeder-cell cultures and using clump passaging were single cell dissociated using enzymes such as accutase and plated as single cells in feeder-free systems such as on Matrigel™ with the use of SMC4 or SMC4+ fibronectin media compositions, as described in Table 1. Cell viability was maintained only when dissociated cells were placed in media containing combinations of the small molecules described in these media are used. The use of conventional medium, resulted in massive cell loss when pluripotent cells are enzymatically dissociated into single cells and plated in feeder-free environments. Once cells are adapted to feeder-free cultures and single cell passaging they were continually maintained in this way with the use of SMC4 medium. Full characterization of hiPSC cells adapted to feeder-free, single cell passaging conditions is shown in FIG. 3. Pluripotent status of these cells was maintained after multiple passages: pluripotent markers were identified by immunofluorescence and gene expression. Further, about 99.8% of cells maintained SSEA4 and Tra1-81 positive staining as measured by flow cytometry. Gene expression profiles of these cells was similar to human ESC cultured on feeders. Transgene silencing in the hiPSC was maintained, karyotype was both normal and identical to the same clone grown in feeder-cell culture. Furthermore, the hiPSCs passaged and maintained in this way differentiated to the three germ layers as demonstrated by both in vitro differentiation and teratoma formation (FIGS. 3I and 3J).

Example 3

Methods and Culture Conditions to Enable Single Cell Sorting of Pluripotent Cells While Maintaining Pluripotency and Cell Viability As described in Example 2, stem cell cultures of ESCs or iPSCs are routinely cultured on feeder cells and passaged by manual selection of cell colonies which are then mechanically dissociated prior to replating. The skilled researcher is able to recognize stem cell colonies having pluripotent, non-differentiated characteristics based on colony morphology and use this as a method of selecting pluripotent cells. Thus, pluripotent populations or populations with the desired characteristics can be picked and manually enriched from a population of cells where some cells have less desirable characteristics, such as cells showing signs of differentiation in culture or clumps of dead cells. This process is laborious and dependent upon skilled researchers to pick the desired cell populations. The use of a cell-enrichment or sorting technology where cells are selected individually on the basis of a desired characteristic would therefore be of great benefit to the field. Such an enrichment step using currently available techniques such as magnetic activated cell sorting (MACS) or Fluorescent Activated Cell Sorting (FACS) would require the enzymatic passaging of pluripotent cell populations into single cell format prior to enrichment and seeding back into culture. Further, the use of feeder-supported cultures would be less desirable for these techniques, necessitating the use of feeder-free culture systems.

In particular embodiments, using media compositions of the invention as described in Table 1, and methods described in Examples 1 and 2, pluripotent cell populations were single cell dissociated, enriched using cell sorting processes such as Magnetic Activated Cell Sorting (MACS) or Fluorescent Activated cell sorting (FACS), and seeded on feeder-free culture without loss of pluripotency or cellular viability.

In a specific example, as shown in FIG. 4, a population of single cell dissociated pluripotent cells maintained in SMC4 medium (Table 1) was selected and sorted by FACS based on cells positive for the cell surface markers SSEA4$^+$/Tra181$^+$. These surface antigens are commonly used as markers for pluripotency. The sorted double-positive population was then transferred to feeder-free culture (Matrigel™ ECM coating) and allowed to grow in either SMC4 medium (Table 1) or SMC4+fibronectin medium for 2-4 days prior to switching back to SMC4 medium (Table 1). Cell division was seen within 24 hours of the sort and cells were near confluent by day 5 post sort. The sorted cells were single cell cultured for an additional 5 passages and shown to not only express markers of undifferentiated status but also represented a substantially pure population of pluripotent cells as judged by double staining flow cytometry for SSEA4$^+$/Tra181$^+$ cells (FIGS. 4B and 4C).

In an example of enriching and sorting of pluripotent stem cells during culture, cultures containining both pluripotent and differentiated cells were enriched for cells positive for Tra181, and then passaging of Tra181$^+$ cells was continued to maintain a pure population of pluripotent stem cells (FIG. 17C).

Figure 4A:
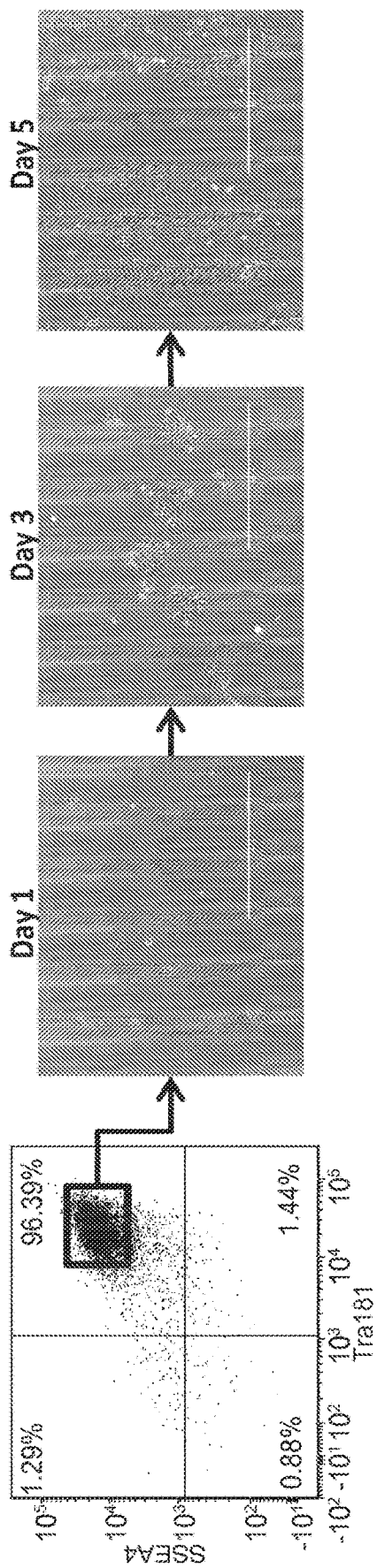
FIGS. 4A-4G. Enhanced single cell sorting and subsequent feeder-free culture of human pluripotent stem cells. Demonstration of sorting of human pluripotent stem cells based on pluripotent marker expression and subsequent maintenance of sorted cells in feeder free culture supplemented with an optimized SMC4 or SMC4+ fibronectin medium.
Figure 4B:
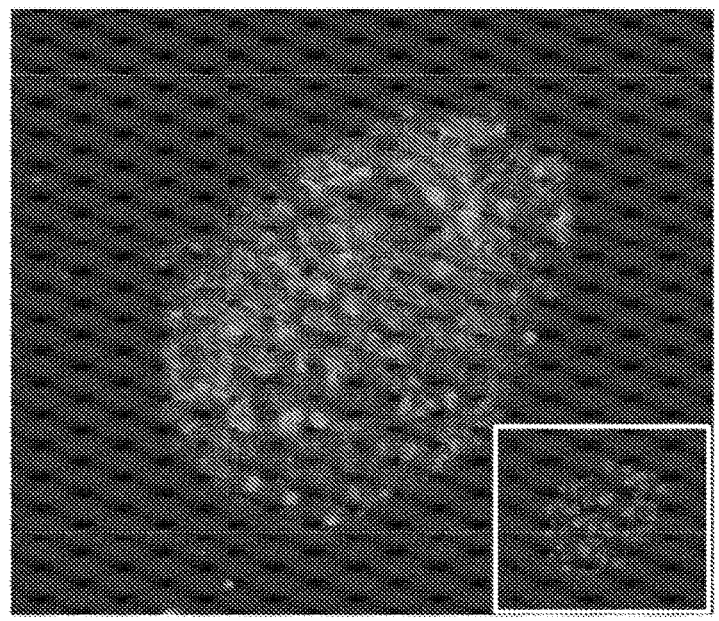
Figure 4C:
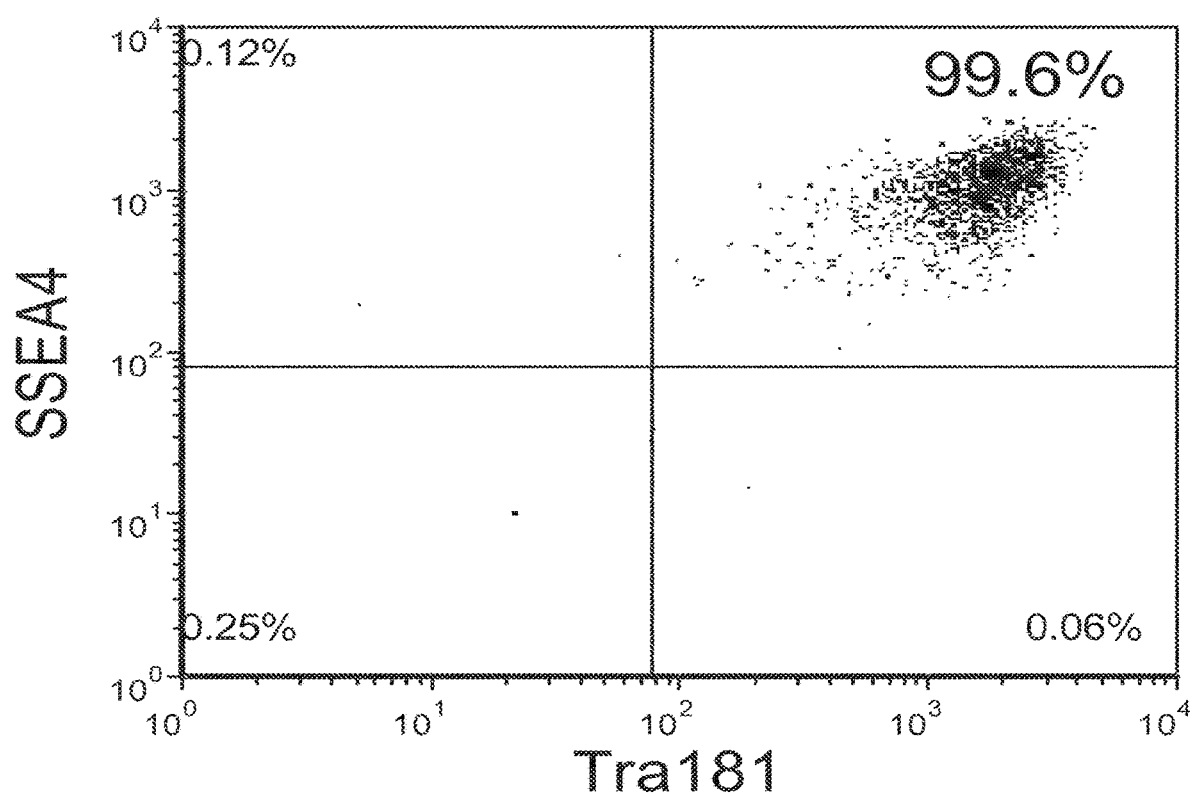
Figure 4D:
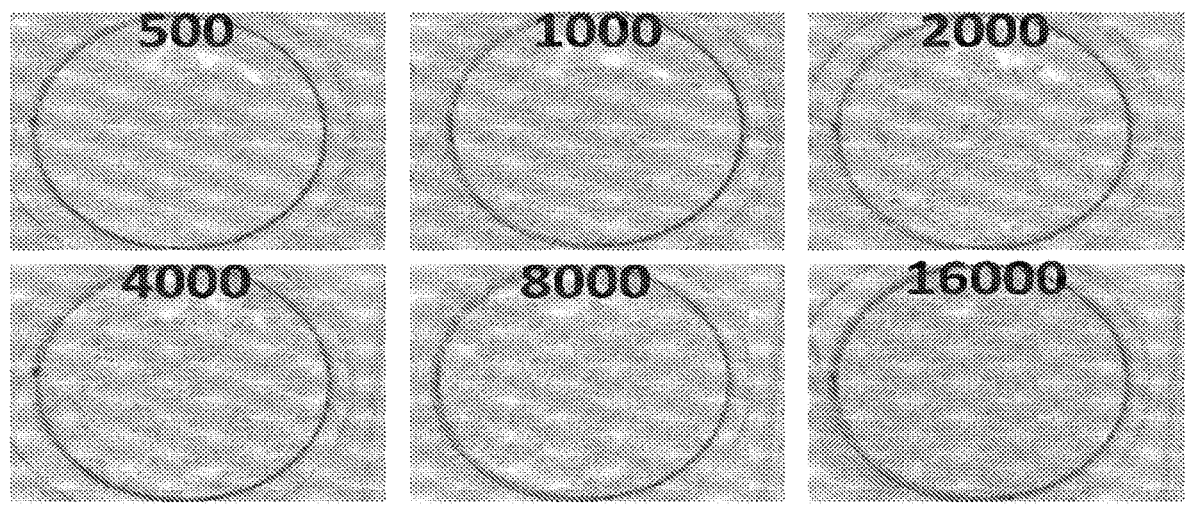
Figure 4E:
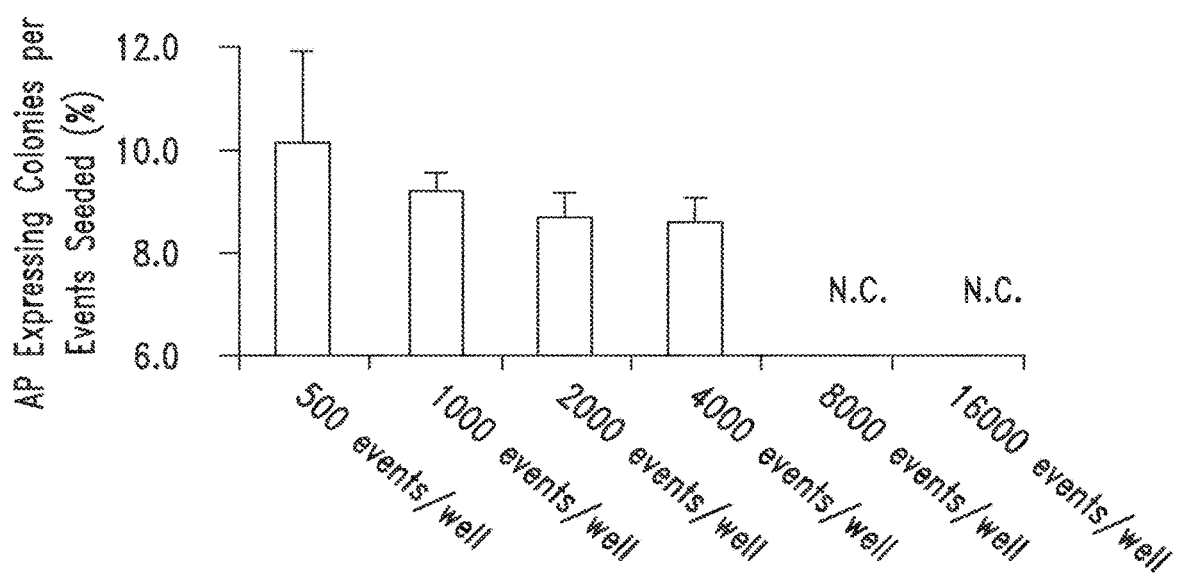
Figure 4F:
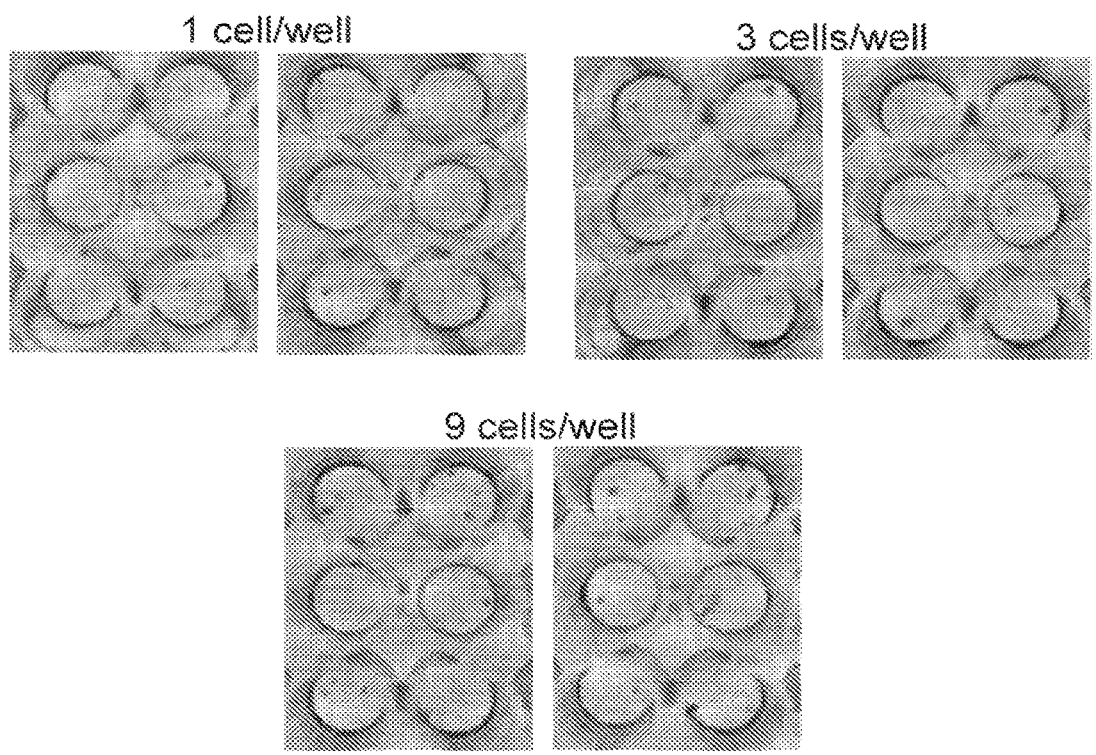
Figure 4G:
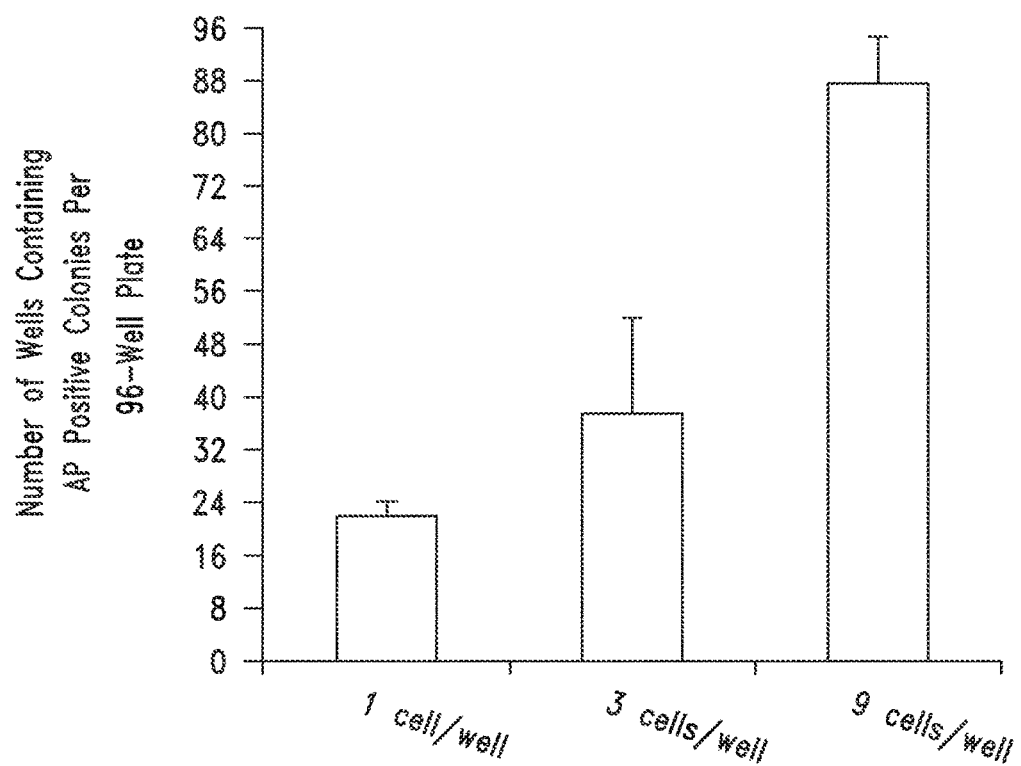
Figure 5A:
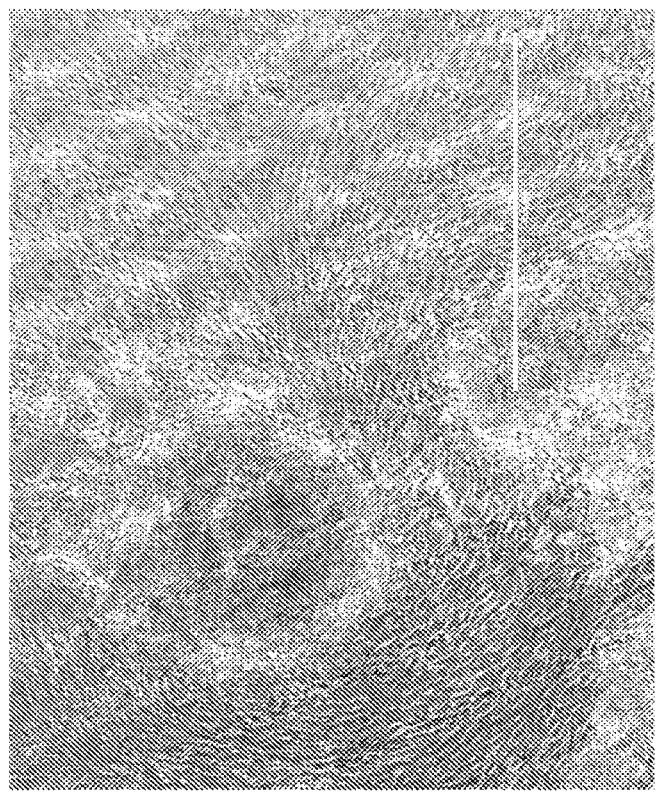
FIGS. 5A-5B. Reprogramming kinetics in the absence and presence of SMC4 medium.
Figure 5A:
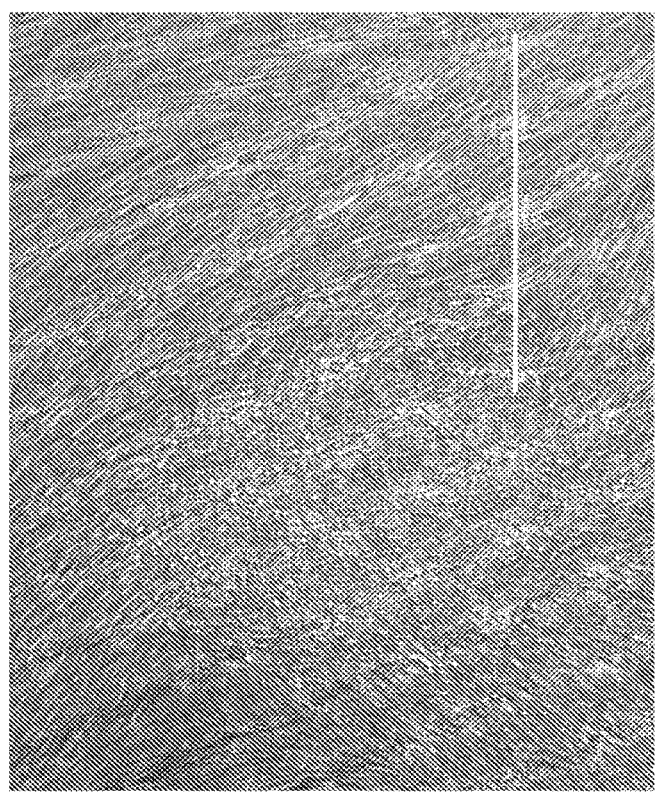
Figure 5B:
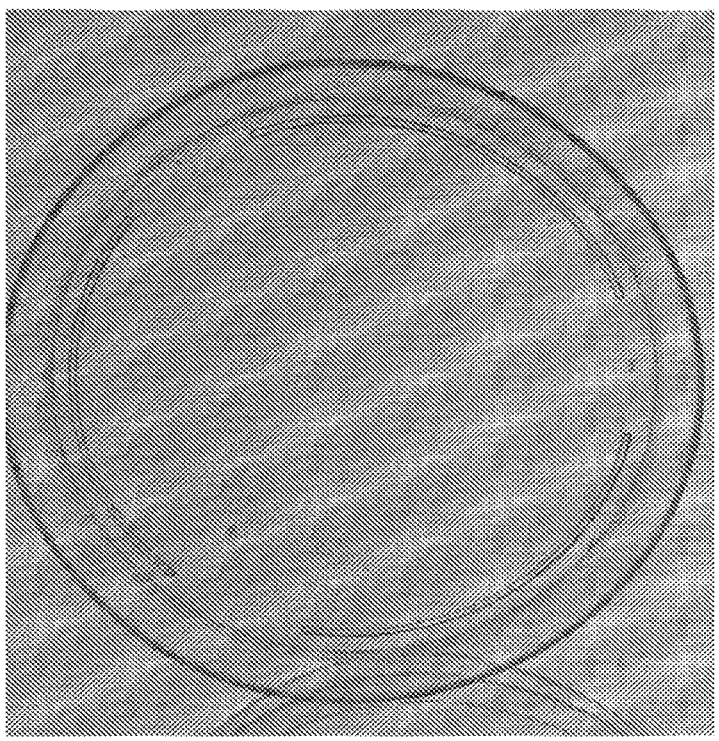
Figure 5B:
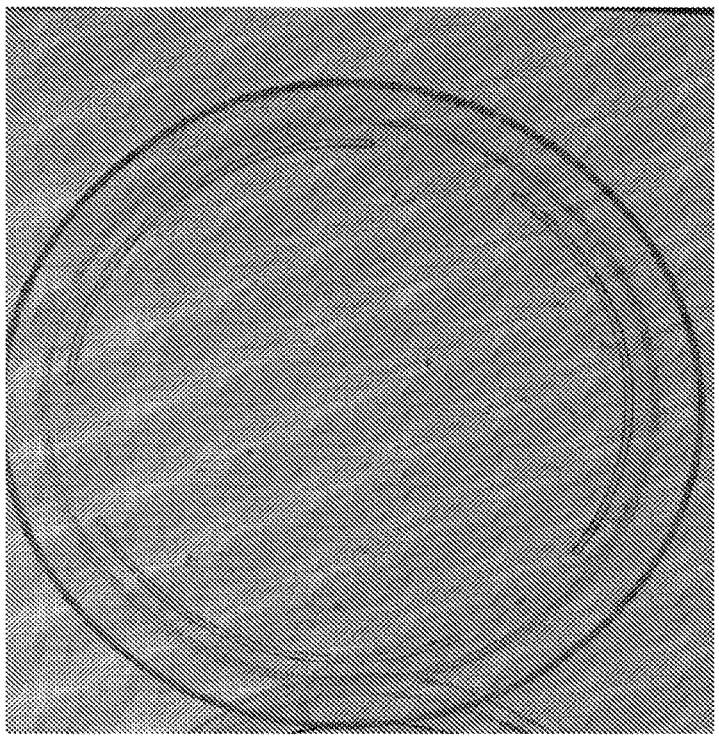

The efficiency of single cell sorting of pluripotent cells was investigated. As can be seen in FIGS. 4D and E various numbers of post-sort events, as measured by the FACS instrument, were plated in feeder-free culture systems using either SMC4 medium or SMC4+ fibronectin medium, and the numbers of alkaline phosphatase-positive cells were scored. Alkaline phosphatase is an early indicator of pluripotent colony formation. The quantified post-sort seeding efficiency, as shown by the number of alkaline positive colonies per number of cells seeded, was seen to be approximately 8-10% in this system (FIG. 4E). In a further demonstration of the potential of single cell sorting in the maintenance of pluripotent cell populations, an iPSC culture was single cell dissociated, labeled with fluorescently-conjugated antibodies specific for the pluripotency markers SSEA4 and Tra181, applied to a FACS and selected based on these markers. The selected SSEA4$^+$/Tra181$^+$ cells were plated directly from the FACS instrument into a 96-well plate at events/well from 1 to 9. As few as 1 event per well produced clonal alkaline phosphatase-positive colonies (FIGS. 4F and 4G). Thus, such a single cell sorting system was used for the clonal selection of pluripotent cells based on preferred characteristics associated with certain cell surface markers.

Example 4

Methods and Conditions to Enable Efficient Reprogramming of Cells to a Pluripotent State in Feeder-Free Culture Systems The use of iPSCs for industrial and/or clinical applications necessitates the generation, selection and maintenance of the cells in fully defined culture conditions, specifically xenogeneic-free conditions. Thus, cellular reprogramming in feeder-free culture conditions is highly desirable. However, while fibroblasts and keratinocytes are the most commonly used cell type for reprogramming due to access via skin biopsy or hair follicle, the efficiency of reprogramming for these cell types is extremely low, and an efficient method for reprogramming these cells in feeder-free cultures has yet to be demonstrated.

As described in Example 2, the use of conventional hESC stem cell media in the presence of inhibitors of cell signaling pathways—specifically the MAP kinase pathway, TGFβ pathway, Wnt/β-catenin pathway and Rho/Rock pathways enabled the growth and maintenance of pluripotent cultures in the absence of feeder-cells and expansion of these cultures using enzymatic, single-cell passaging. In the present example, iPSC cells were generated in culture systems devoid of feeder-cells. Specifically, human fibroblasts were infected with virus expressing the pluripotency factors Oct4, KLF4, Sox2 and C-myc. Reprogramming protocols were carried out as described in Example 1 with cells plated on Matrigel™ rather than feeder cells.

Figure 13A:
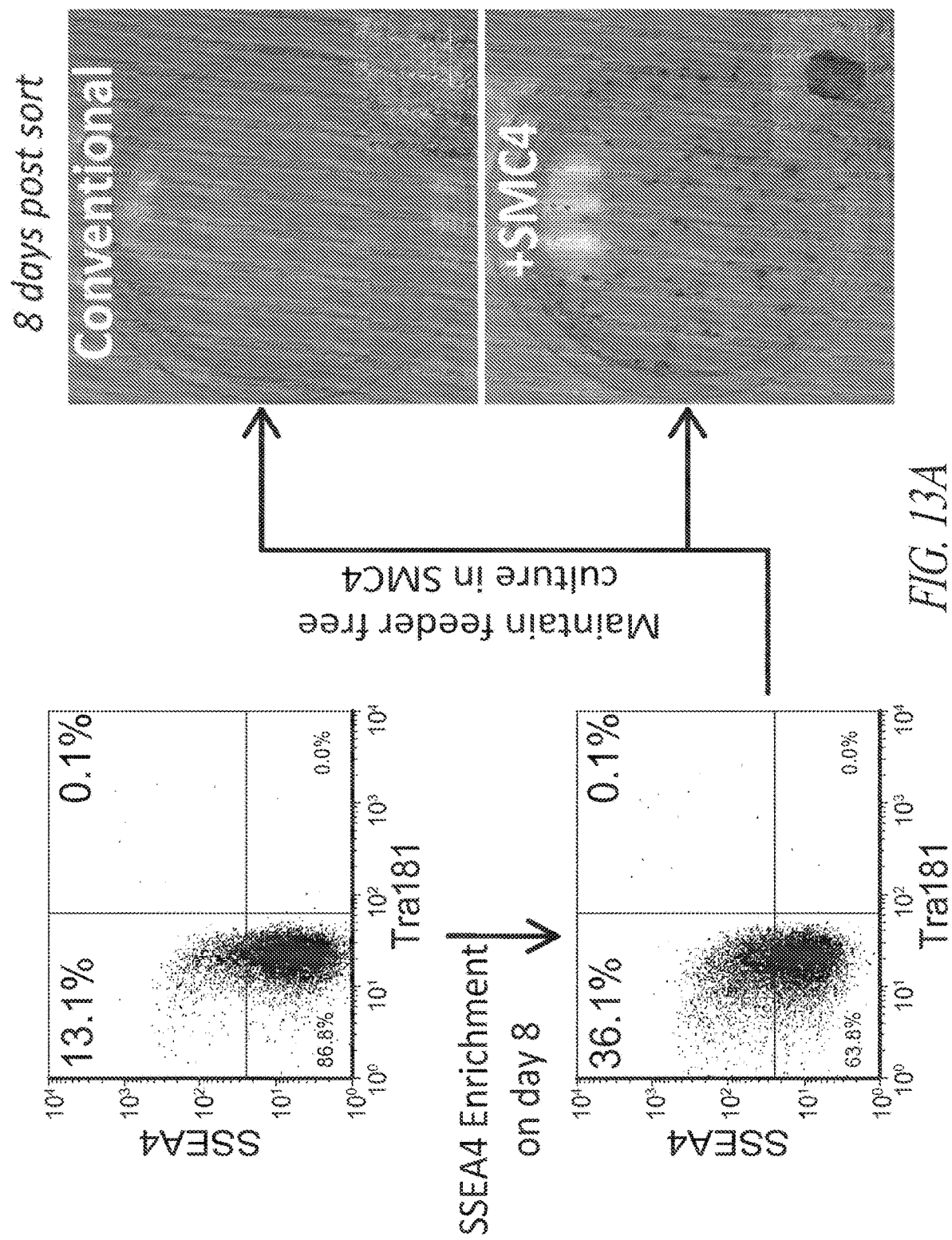
FIGS. 13A-13G. Enhanced cellular reprogramming by single cell sorting and enrichment of pluripotent stem cells from various sources including IMR90 and ASC.

A comparison was made of feeder-free cellular reprogramming using either conventional hESC stem cell medium or conventional hESC medium supplemented with the specific pathway modulators listed in the SMC4 medium (Table 1). As can be seen in FIG. 5, 20 days after the induction of reprogramming using individual lentivirus expression Oct4, Klf4, Sox2 and Myc many iPSC-like colonies were seen in the feeder-free cultures supplemented with the SMC4 medium whereas few or no colonies were seen in the cultures maintained in conventional hESC medium alone. Subsequent characterization of the colonies generated in SMC4 medium showed many of them to be true iPSC colonies. The cells were determined to be pluripotent by expression of pluripotency markers Oct4, Nanog, Sox2, KLF4, SSEA4 and TRA 1-81 using immunofluorescence, flow cytometry and gene expression profiling (FIGS. 13C-E). Further, cells were shown to effectively differentiate to all three germ layers when cultured in differentiation medium. Thus, the efficient generation of iPSCs in a feeder-free culture system was demonstrated by the current invention. The efficiency of this approach in comparison to other methods of reprogramming is described in Example 8 and Table 4.

Example 5

Cell Culture Compositions Used in the Generation and Maintenance of Naïve-State Pluripotent Cells Recent studies have demonstrated that through epigenetic reprogramming, terminally differentiated cells have the ability to recourse into a progenitor-like state (Xie, H., Ye, M., Feng, R., and Graf, T. 2004), into a different differentiated-cell state (Szabo, Bhatia 2010) or even back into an embryonic-like state (Takahashi et al., 2006), such as iPSCs. Although the generation of iPSCs has become more routine, only a very small percentage of the somatic cells in a given experiment reprogram into iPSCs. Several parameters attribute to this low efficiency including the proliferative state of the somatic cell, additional mutagenesis leading to gene activation or suppression, the format of gene delivery and environmental cues. It has also been reported that not all cells identified as iPSCs behave similarly to ESCs. For example, gene expression profiling has demonstrated that many iPSCs display significant differences in expression profiles to their ESC counterparts. In addition, studies of Xist activity and X-chromosome reactivation analysis show that while some ESCs are in a naïve state (i.e., a grounded state of pluripotency) the majority, if not all derived iPSCs are in a primed state (i.e., primed to differentiate). Combined, these differences may contribute to reduced pluripotency and low efficiency in the differentiation of iPSCs towards specific cell types, reducing the value of iPSCs in regenerative medicine.

Figure 6A:
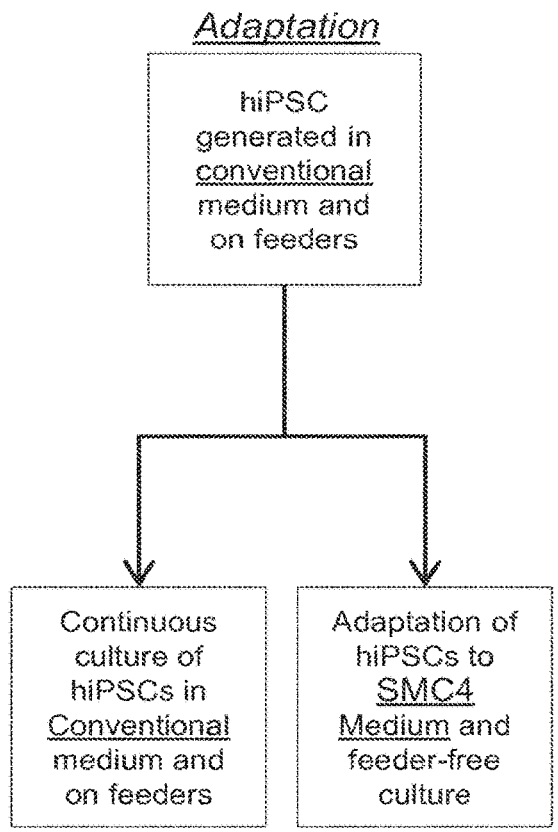
Figure 6B:
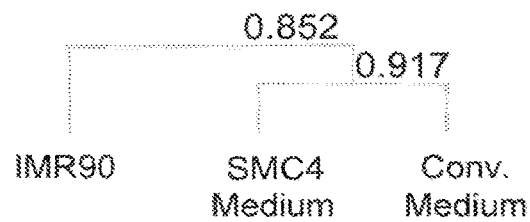
Figure 6C:
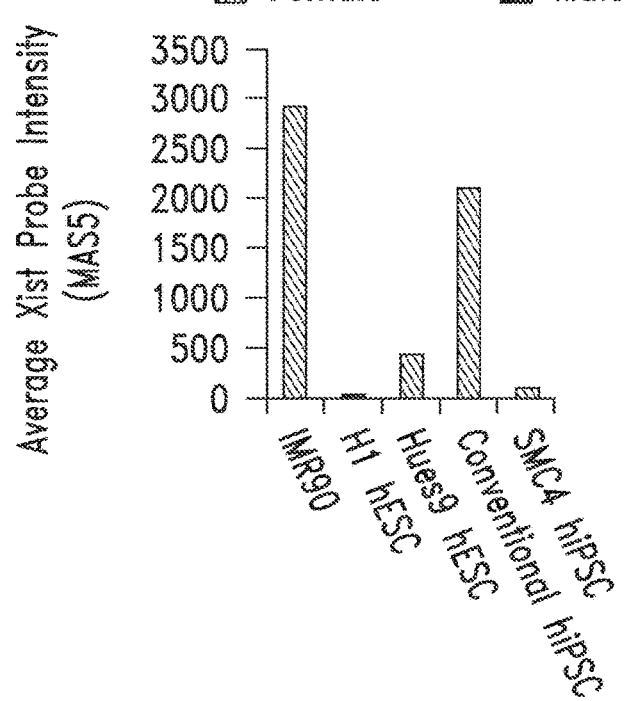

By targeting key cellular pathways involved in the mechanisms behind naïve and primed states, the inventors have demonstrated the ability to transform pluripotent stem cells that exist in a primed state, including conventional iPSCs, into a naïve state. Using the media compositions listed in Table 1, it was possible to further reprogram such primed pluripotent cells and conventional iPSCs to a naïve state. More specifically, by reprogramming somatic cells or culturing iPSCs in a medium containing modulators of cellular signaling pathways, such as the MAP kinase pathway, TGFβ pathway, and/or Wnt/β-catenin pathways, the gene expression signature of the generated or cultured iPSCs become more ESC-like than conventional iPSCs (iPSCs generated and/or cultured in conventional culture medium and not contacted with the modulators of cellular signaling pathways). As demonstrated in hierarchical clustering, both conventional medium and SMC4 medium derived hiPSCs were similar to each other and different from their parental line IMR90 (FIG. 6B). However, when iPSCs cultured in SMC4 medium were plated back onto feeder cells they more closely resembled mouse ESCs than conventionally cultured iPSCs, another demonstration of naïve status (FIG. 6E). Furthermore, iPSCs cultured in SMC4 medium had significantly reduced Xist activity and enhanced expression of genes of the X-chromosome (FIGS. 6C and 6D). Finally, iPSCs cultured in SMC4 medium not only differentiated into all three germ layers but also demonstrated the ability to reactivate genes associated with extraembryonic cells, an ability only reserved for cells in the naïve state (FIG. 3H). Thus, culturing pluripotent stem cells, including iPSCs existing in a primed state, in SMC4 medium promoted naïve status and enhanced differentiation potential.

Figure 7A:
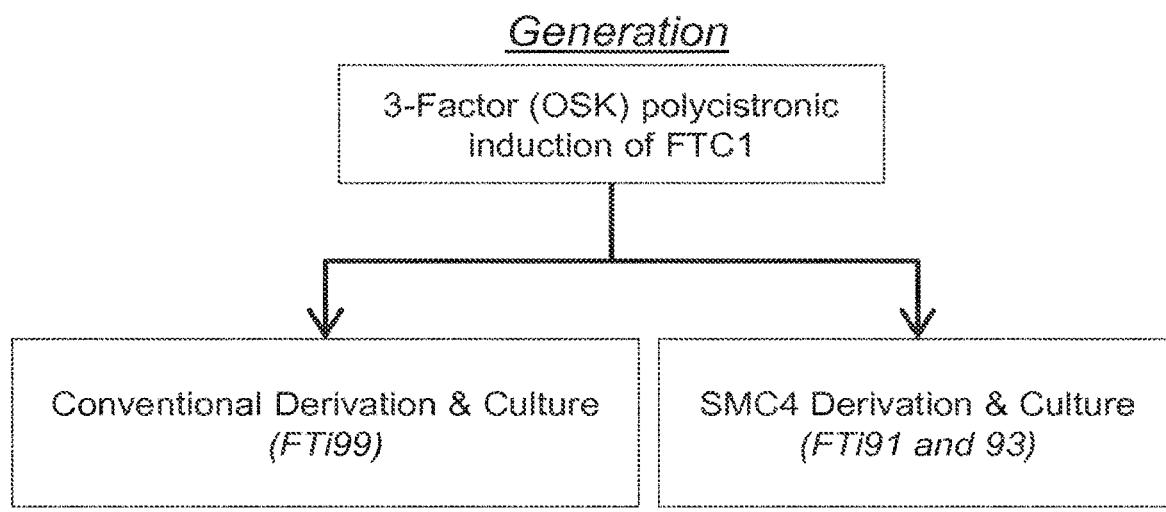
FIGS. 7A-7E. Generation and maintenance in SMC4 medium improves the undifferentiated state of human pluripotent stem cells.
Figure 7B:
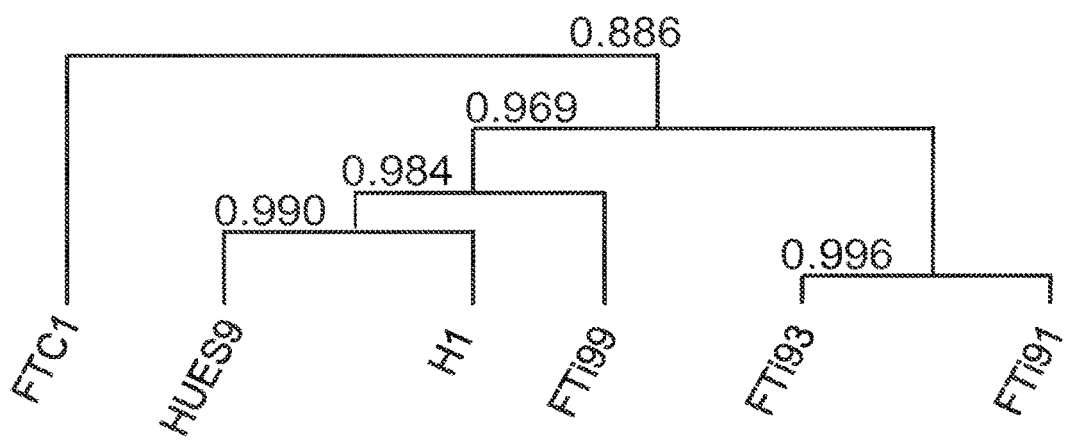
Figure 7C:
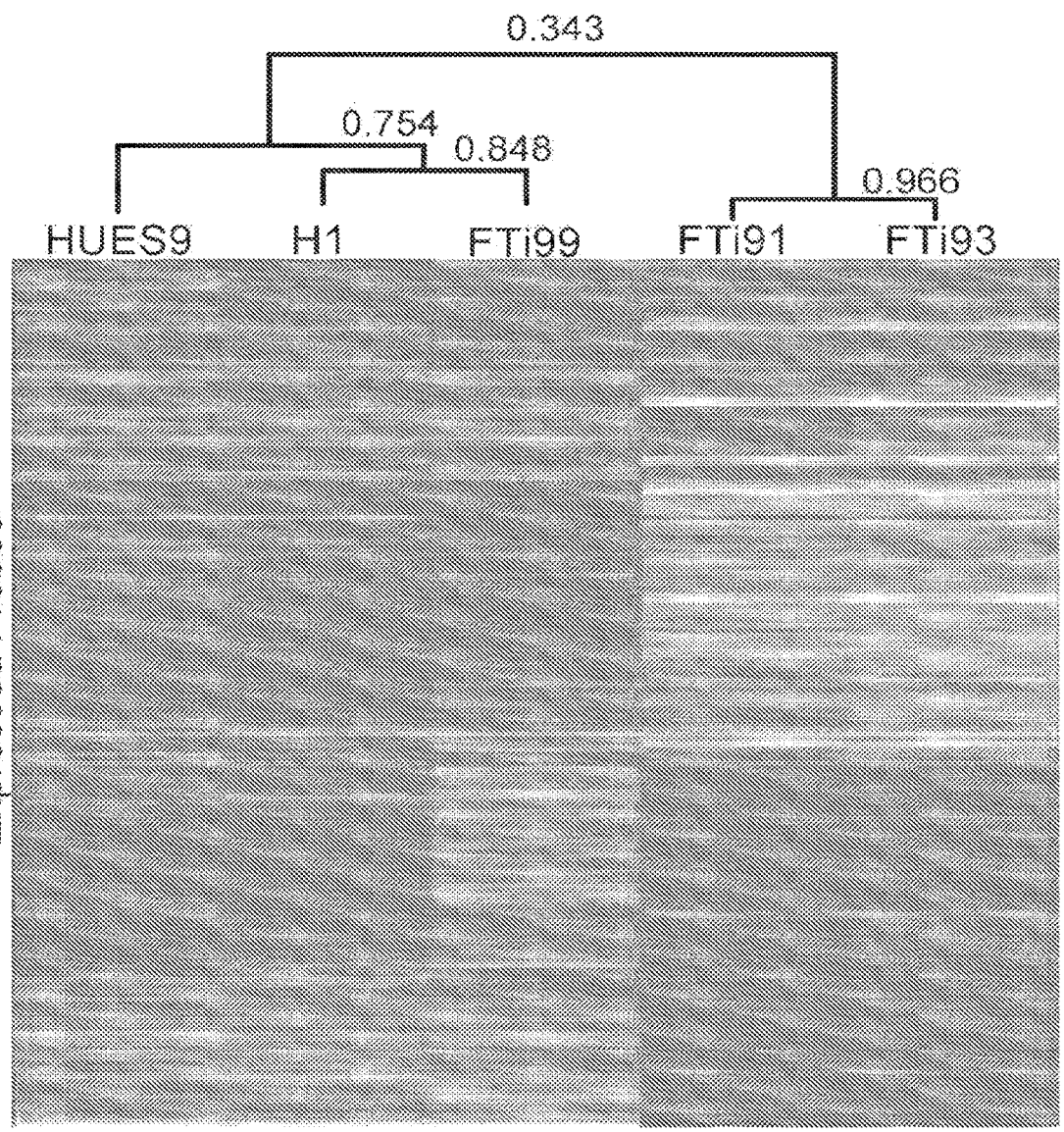
Figure 7D:
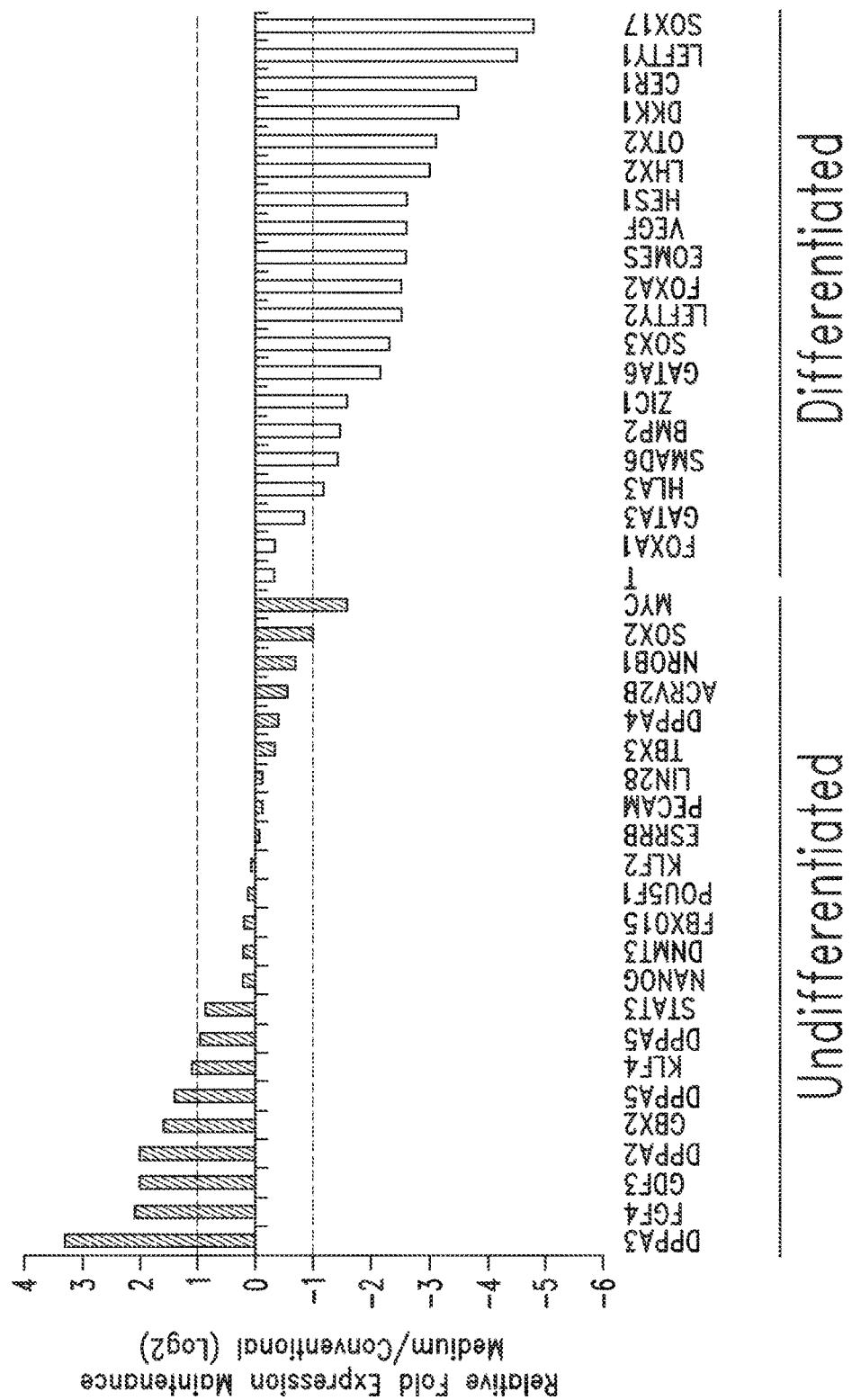
Figure 7E:
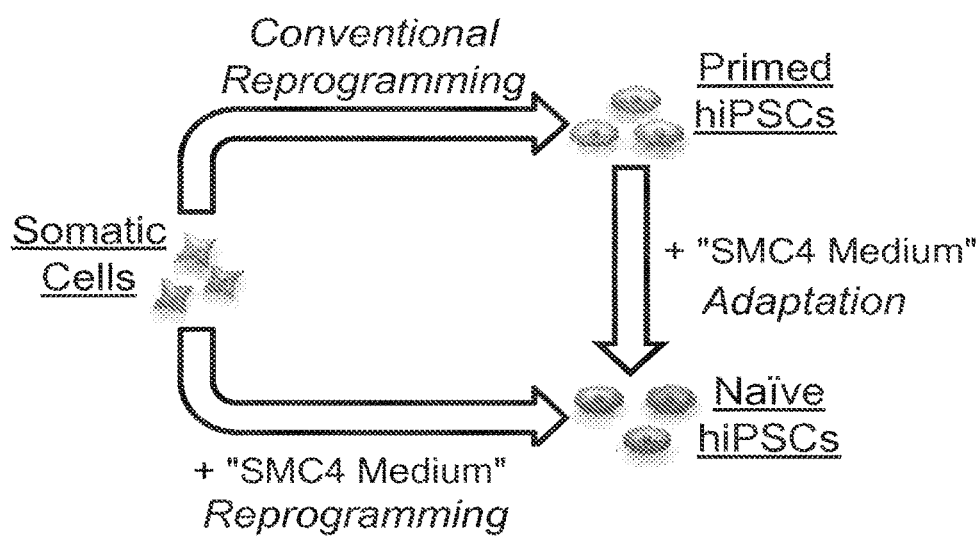

To determine the pluripotent state of hiPSC clones generated using SMC4 supplemented medium and the cell sorting platform (FIG. 7), hiPSCs were derived from the same starting fibroblast line and 3-factor polycistronic vector expressing Oct4, Klf4 and Myc but maintained under conventional culture, including clump passage and feeder cells (FTi99). Affymetrix global gene expression analysis of the various clones as well as mRNA from hESCs was conducted (FIG. 7B). All pluripotent lines were seen to have a different profile from the control fibroblast line (FTC1, Pearson score 0.886) and essentially similar expression profiles to each other (Pearson score 0.969). A heat map signature was generated to represent the 1,739 probes that were differentially expressed by 4-fold between the hESCs/FTi99 (hESCs or hiPSCs generated and maintained on feeder cells and conventional medium) and FTi91/FTi93 (hiPSCs generated and maintained on feeder-free and SMC4 medium) groups (FIG. 7C). In depth analysis of the genes within the 1,739 differentially expressed transcripts identified an interesting trend: while several pluripotency genes commonly associated with naïve state were upregulated in the FTi91/FTi93 group, more significantly, many differentiated genes associated with the prime state were repressed within the this group (FIG. 7D). Our overall analysis of the SMC4 medium generated hiPSCs suggests that culture conditions play a more influential role in deciding the undifferentiated state relative to the starting cell line or the derivation strategy. The data also suggest that clones derived in or adapted to SMC4 culture conditions demonstrate naïve characteristics with preferred qualities such as a highly undifferentiated state with reduced expression of early lineage markers (FIG. 7E).

Example 6

The Identification of Antibody Cocktail to Identify Bona Fide Hipscs

Figure 10:
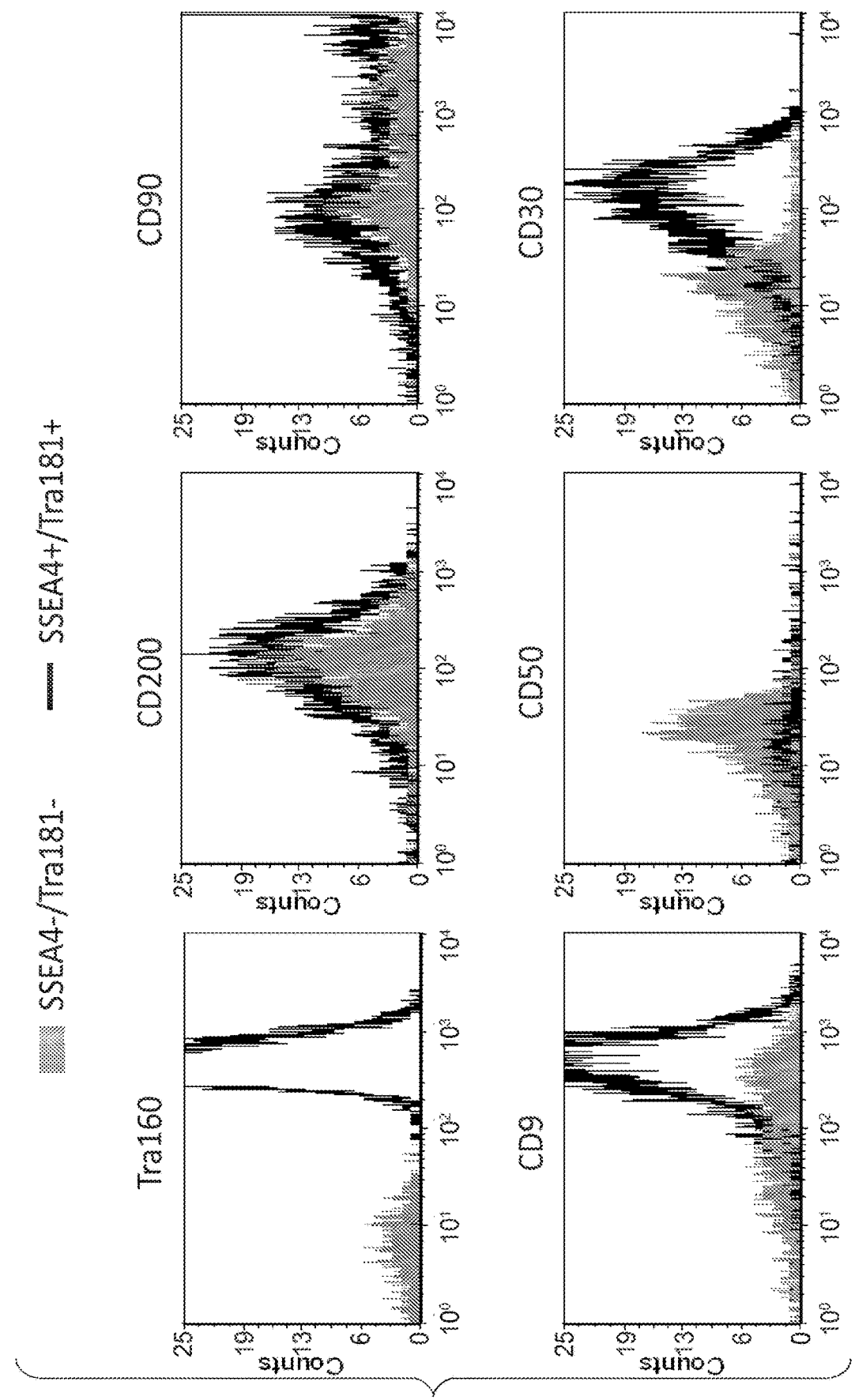
FIG. 10. Identification of pluripotent markers. To survey for additional markers specific to SSEA4$^+$/Tra181$^+$ cells, various surface markers were assessed. Detection of Tra160 expression was used as a positive control as it has been demonstrated to correlate well with Tra181 expression. CD200 and CD90 do not appear to be specific for pluripotent cells as they similarly stain both SSEA$^-$/Tra181$^-$ and SSEA$^+$/Tra181$^+$ populations, while little specificity for and the SSEA$^+$/Tra181$^+$ population is seen with CD9. However, CD50 and CD30 appear to preferentially identify the SSEA4$^+$/Tra181$^+$ population over the SSEA$^-$/Tra181$^-$ population.
Figure 11A:
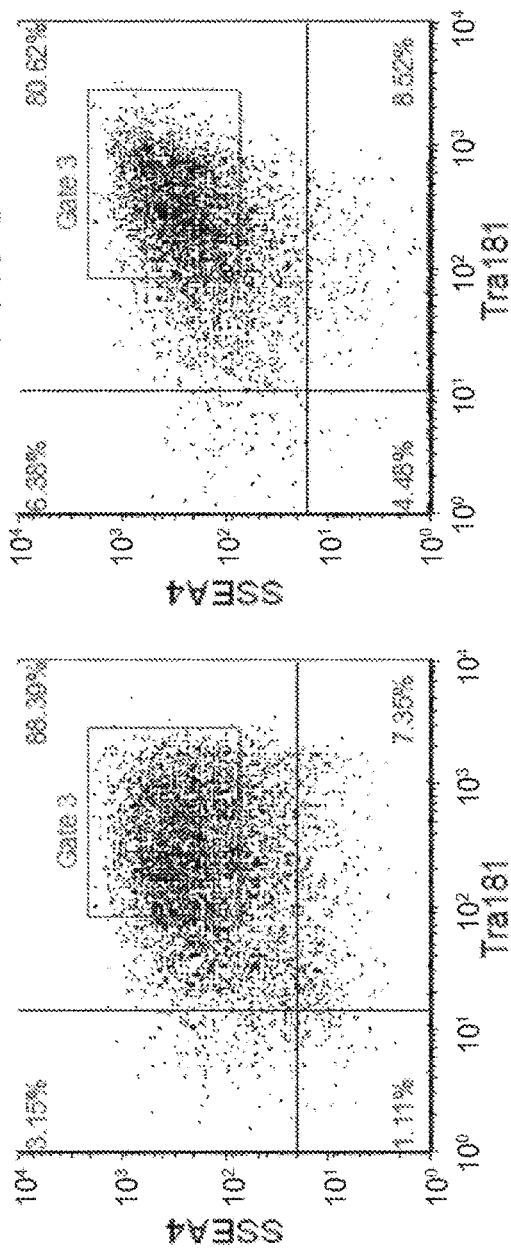
FIGS. 11A-11D. CD30 is specific to Nanog expressing clones.
Figure 11A:
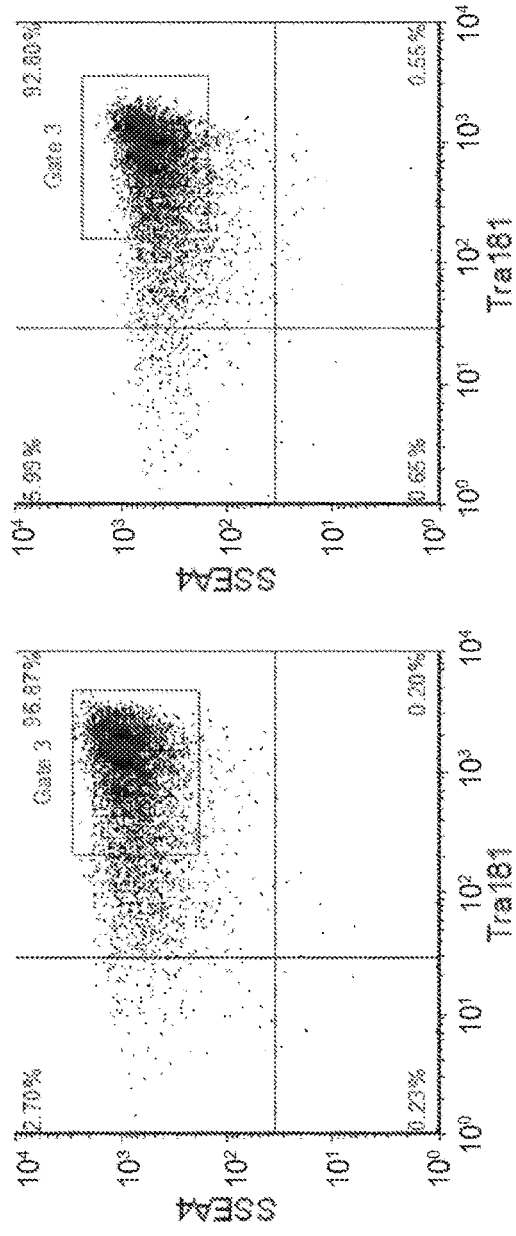
Figure 11B:
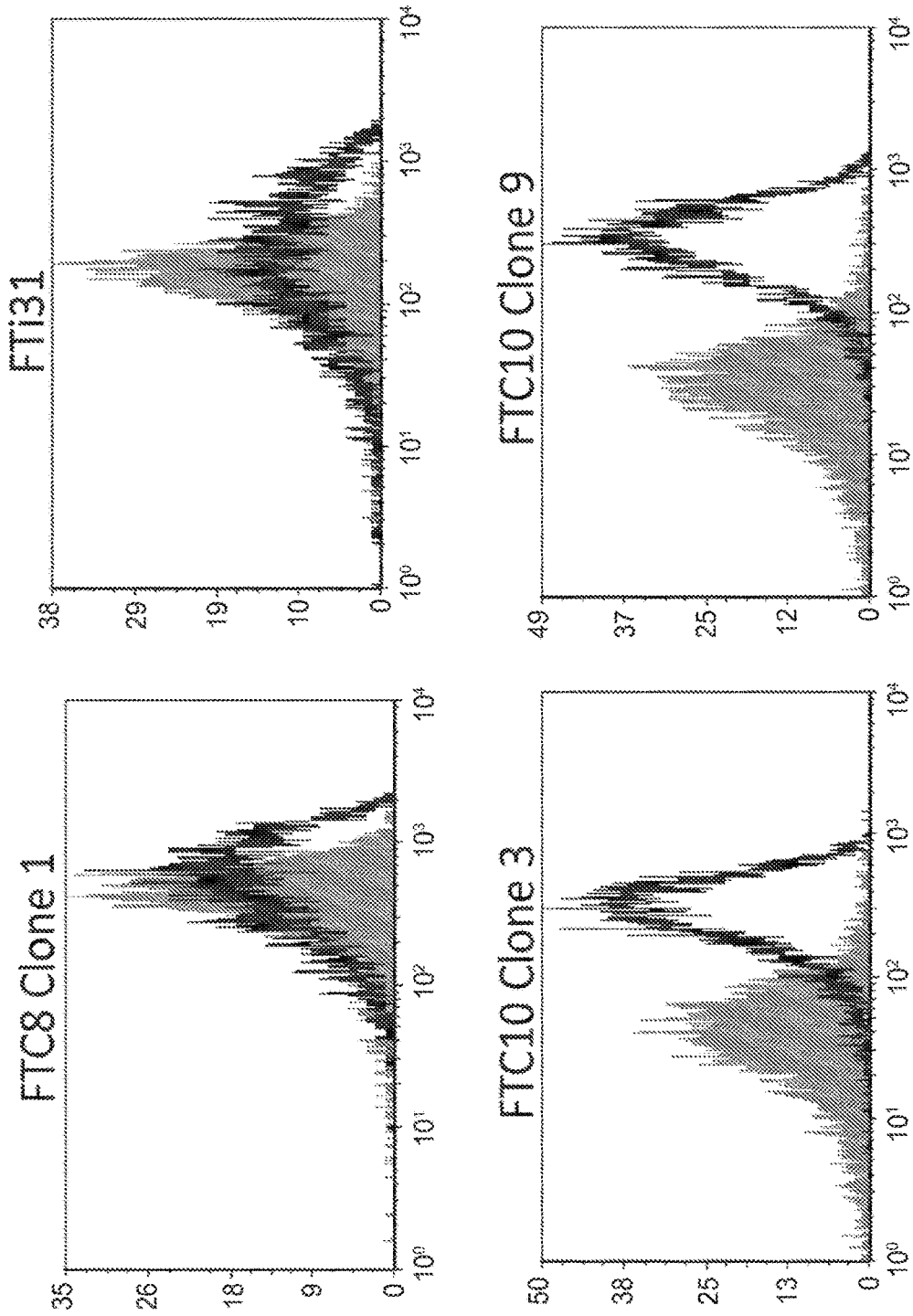
Figures 11C, 11D:
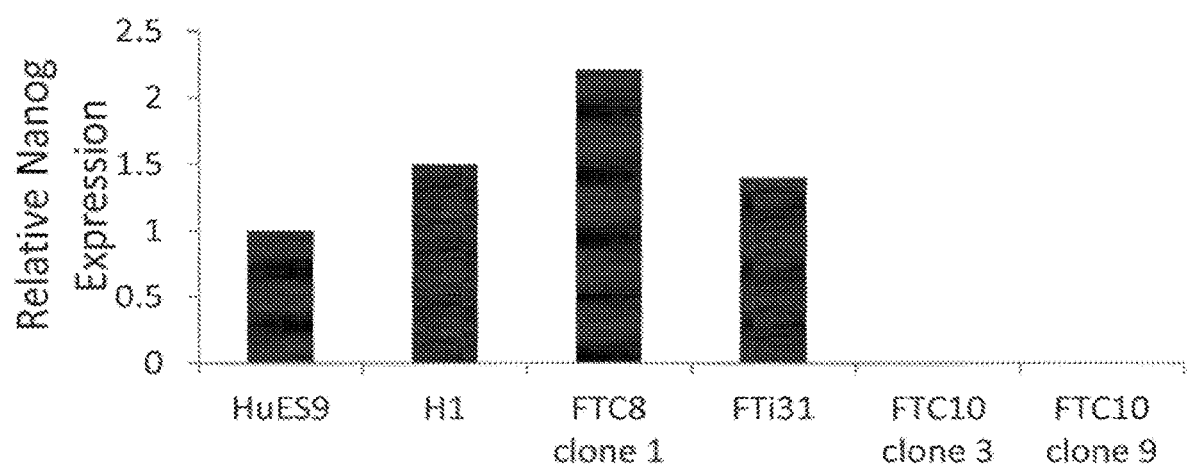

Pluripotent stem cell surface markers were surveyed. In addition to SSEA4 and Tra181 expression, expression of CD30 and CD50 was also identified and deemed to represent additional surface markers of pluripotency (FIG. 10). Cells reprogrammed using polycistronic lentivirus expressing Oct4, Klf4 and Sox2 represent a variety of potency states, and are identified with few cells bearing the markers of true pluripotency, such as Nanog expression. To date, there is no reliable method of identifying truly pluripotent hiPSCs based on surface marker expression. For example, as seen in FIG. 11, some clonal populations that were identified as positive for SSEA4, Tra181 and CD9 did not express Nanog, and would have been incorrectly identified as hiPSCs.

The current invention provides a combination of cell surface markers that identify populations of cells expressing Nanog, a marker of truly pluripotent cells. Specifically, cells positive for surface markers of CD30, SSEA4 and Tra181 identify cells expressing Nanog (FIG. 11).

Figure 12:
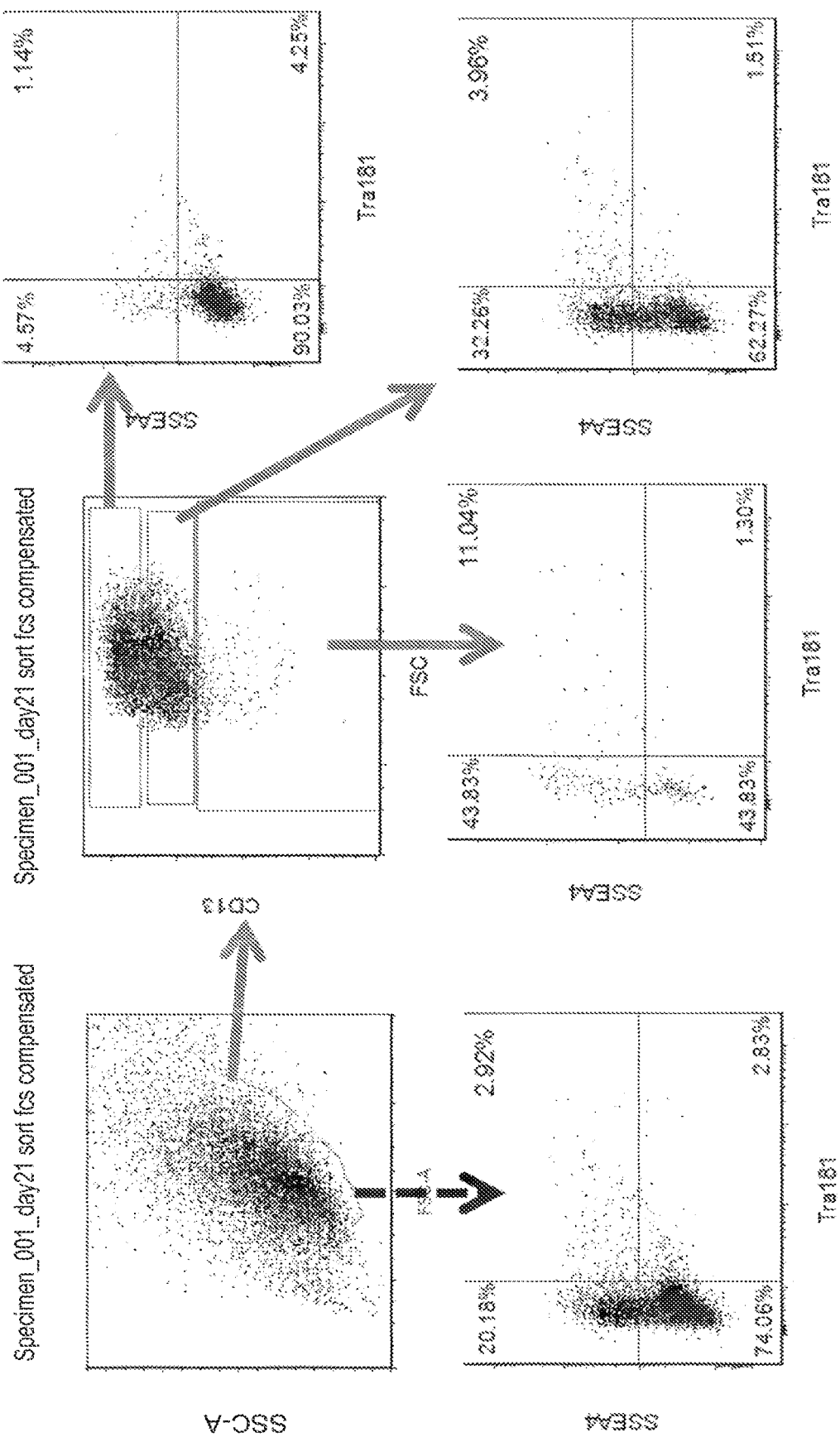
FIG. 12. Depletion of non-reprogrammed cells during the reprogramming process enriches for reprogrammed cells. During a reprogramming process, a mixed population of reprogramming and non-reprogramming cells existed, with only a minor population of cells representing cells reprogrammed to full pluripotency, as indicated by SSEA4 and Tra181 expression (indicated by black colored dotted lined arrow). However, when non-reprogrammed cells were removed or depleted from the mixed population, a significant enrichment of SSEA4 and Tra181 positive population was demonstrated. As indicated by the gray colored solid line arrows, the CD13 negative cell population represented a significantly enriched population of SSEA4 and Tra181 positive cells over CD13 low and high population cells.

In a further example of added enrichment, a cell population undergoing reprogramming was sorted to identify cells positive for CD13 surface marker expression and these CD13+ cells were removed from the reprogramming cell population. The CD13+ population correlated to somatic cells and nonreprogrammed cells, and depleting the reprogramming population of cells of CD13+ cells enhanced enrichment of SSEA4/Tra181 positive cells (FIG. 12). As demonstrated in FIG. 12, when somatic cells were reprogrammed using a polycistronic vector expressing Oct4, Klf4 and Sox2 for 21 days, various cell populations with diverse surface marker expression patterns were created, with only a minor subset of cells representing SSEA4 and Tra181 positive cells (dotted arrow, FIG. 12). However, when the same population was first assessed based on CD13 expression (solid arrows, FIG. 12), the population subset that was negative for CD13 (i.e., depleted of CD13 cells) represented a population that had been significantly enriched for SSEA4 and Tra181 expressing cells (11.04%, FIG. 12). On the contratry, the subset of cells that expressed high levels of CD13 represented few cells that expressed both SSEA4 and Tra181 (1.14%, FIG. 12).

Example 7

Figure 8A:
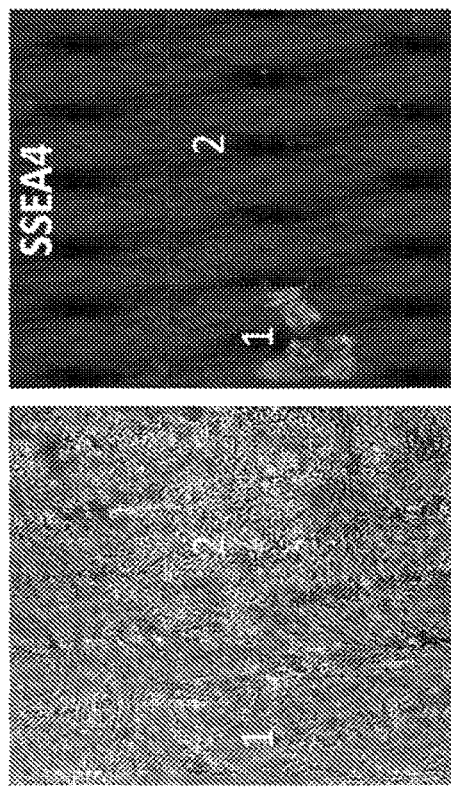
FIGS. 8A-8B. non-iPSC colonies generated during reprogramming process.
Figure 8B:
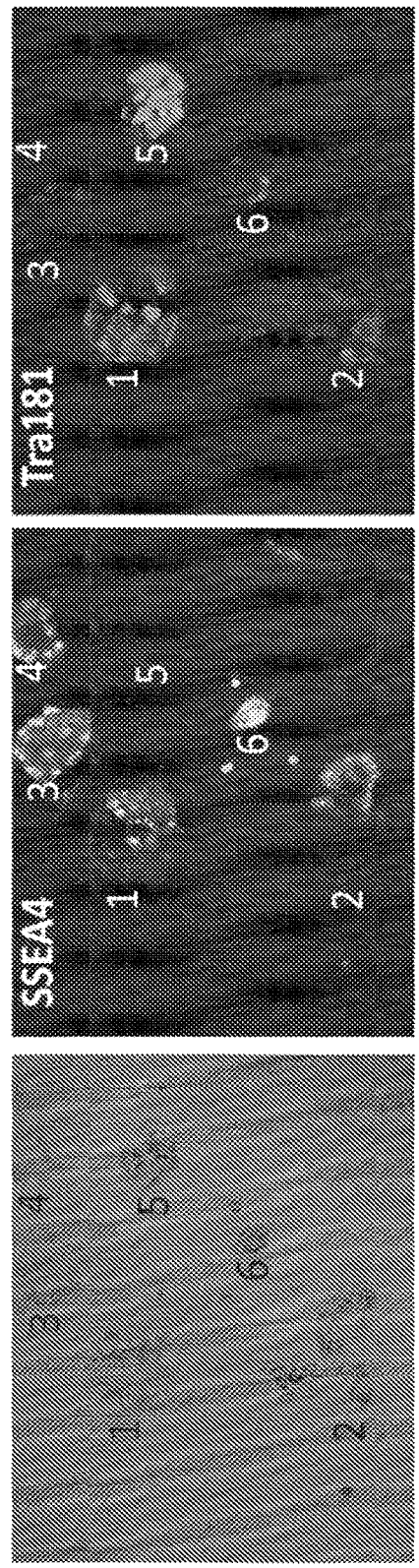

The Use of Single Cell Sorting in the Generation of Induced Pluripotent Stem Cells From Differentiated Cells As can be seen in FIG. 8A, a fibroblast cell culture early in the reprogramming process, where reprogramming was induced using individual lentivirus expressing Oct4, Klf4, Sox2 and myc, contained colonies of morphologically different cells. Some of these cells stained positive for markers of pluripotency whereas others were merely transformed, fast growing cells. At this stage in the reprogramming process it is not clear by cell morphology alone which cell colonies will go on to form iPSCs. The faster growing, transformed but not pluripotent cells quickly took over the culture. It would therefore be advantageous to have an enrichment step that selected for iPSCs early in the reprogramming process. Further, and as shown in FIG. 8, some colonies expressed several pluripotency markers during the reprogramming process, and were true iPSCs, whereas some colonies were not fully reprogrammed and only expressed some markers of pluripotency. Colony 1 in FIG. 8B was positive for both SSEA4 and Tra181, whereas colonies 4 and 5 were only positive for one or the other marker. It would therefore be more efficient and less technically challenging to select for pluripotent cells using cell surface markers of pluripotency or several markers simultaneously rather than by colony morphology.

Using cell culture compositions described herein combined with cell enrichment and/or sorting methodologies also provided herein, it was possible to derive iPSCs in greater numbers and in shorter periods of time by selecting for individual cells that showed surface markers of pluripotency during the reprogramming process. More specifically, and as shown schematically in FIGS. 9A and B, two paths for the generation of iPSCs using single cell sorting and enrichment based on markers of pluripotency during reprogramming were carried out using the methods of the invention.

Figure 9:
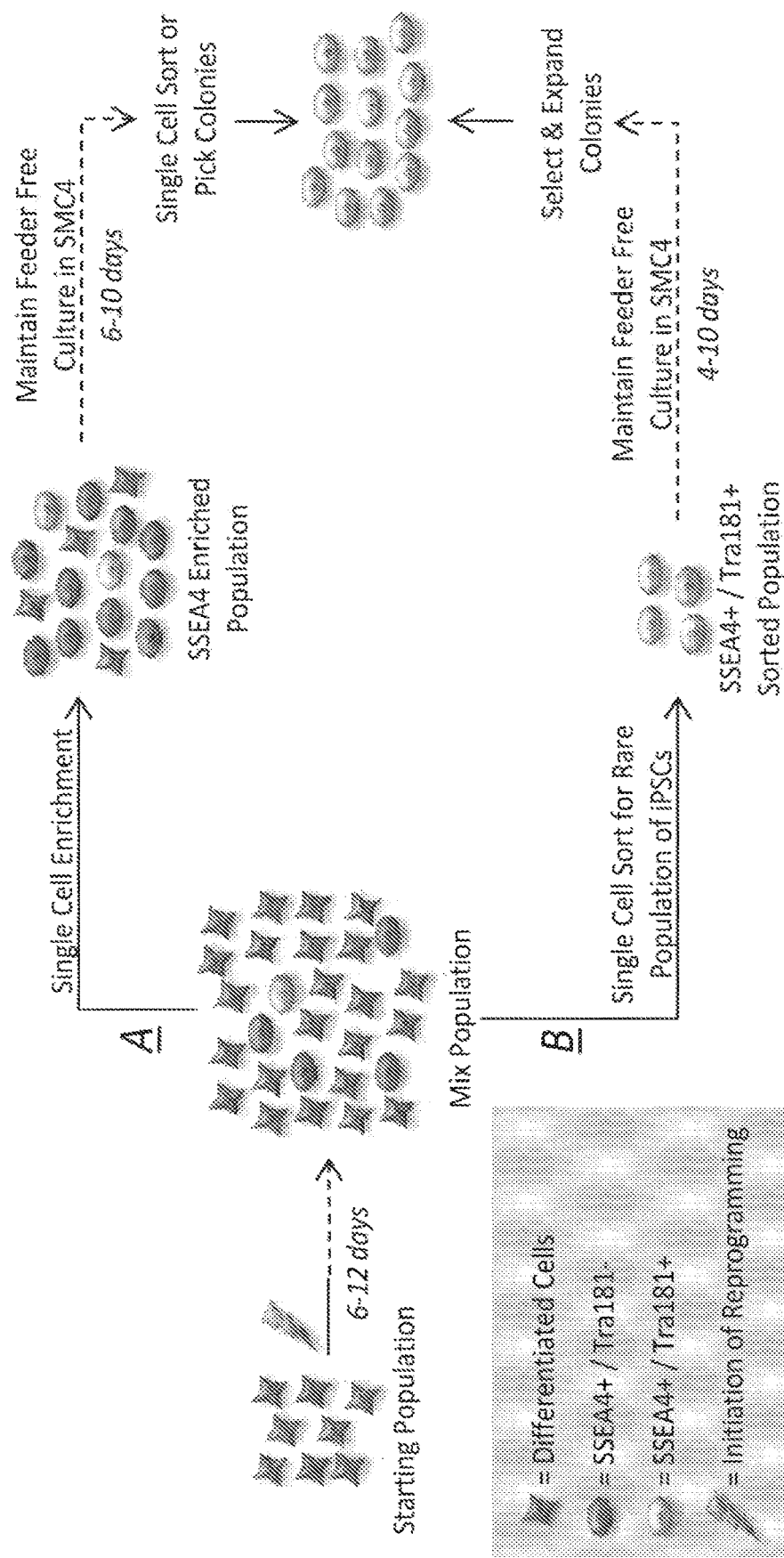
FIG. 9. Selection of pluripotent cells such as iPSCs with the use of cell sorting. A schematic depiction of single cell culture systems and cell sorting methodologies used for the enrichment and selection of pluripotent cells from a mixture of pluripotent and non-pluripotent cells.

In path A, after the initiation of reprogramming, a mixed population of cells at various states of potency was generated. The mixed population of cells contained differentiated cells, partially-reprogrammed cells, reprogrammed cells, and cells undergoing reprogramming. The cell population was enriched using methods such as magnetic bead sorting or flow-cytometry sorting (see Example 1 for methodologies) for cells that expressed pluripotent markers such as SSEA4. Upon enrichment, the cells were maintained in SMC4 medium (Table 1) or, in particular embodiments, SMC4+ fibronectin medium for approximately 3 days followed by replacement with SMC4 medium, and after a culture period of approximately 6-10 days, iPSC colonies were identified based on live culture staining of markers such as SSEA4 and TRA181, and were picked or sorted for clonal expansion (FIG. 9).

Under the path B schematic (FIG. 9), early after the initiation of reprogramming, the mixed population of cells was sorted to obtain the rare population of cells positive for two or more markers of pluripotency. Such markers include but are not limited to SSEA4 and TRA181. The selected cells expressing a combination of pluripotency markers were transferred to feeder cell supplemented culture systems or feeder-free culture systems, specifically those supplemented with cell culture media compositions described in Table 1. In this way iPSC colonies were generated with significantly reduced timelines and technical barriers compared with previously described methodologies.

In a specific demonstration of this technology, IMR90 fibroblast cells were infected with lentivirus expressing Oct4 and Sox2 and Klf4 and c-Myc (OSKM). After several days of feeder-free culture, the reprogramming cells were switched from their somatic cell culture medium to feeder-free culture supplemented with SMC4 medium (Table 1). At 8 days post initiation of reprogramming, the infected cell population was seen by flow-cytometry analysis to contain a modest sub-population of cells that expressed the pluripotency marker SSEA4 (FIG. 13A). Using magnetic activated cell sorting as described in Example 1, the pluripotent population was enriched 3-fold for cells expressing SSEA4 (FIG. 13A). After enrichment of cells for SSEA4 expressing cells, the sorted cells were transferred to feeder-free culture containing Matrigel™ and supplemented with either conventional hESC medium or SMC4 medium or in particular embodiments, SMC4+fibronectin medium. Alkaline phosphatase staining of the cultures shows that use of small molecule inhibitors of MEK, GSK3, Rock kinase and TGFβ supported the enrichment of pluripotent cells using single cell sorting whereas conventional basal medium did not (FIG. 13A).

Figure 13B:
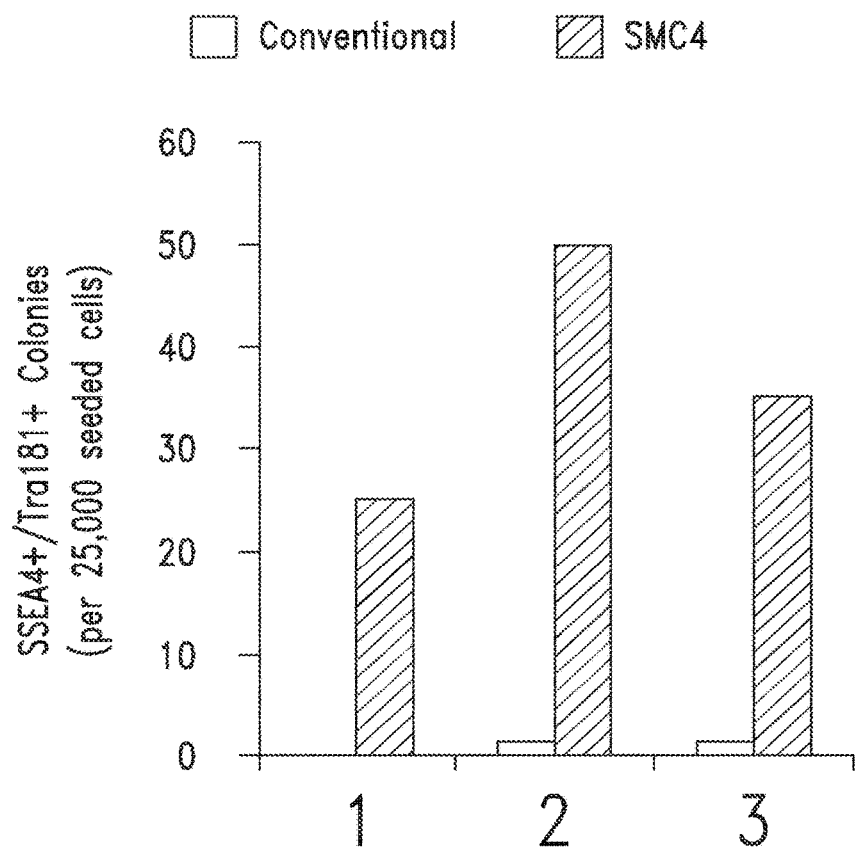
Figure 13C:
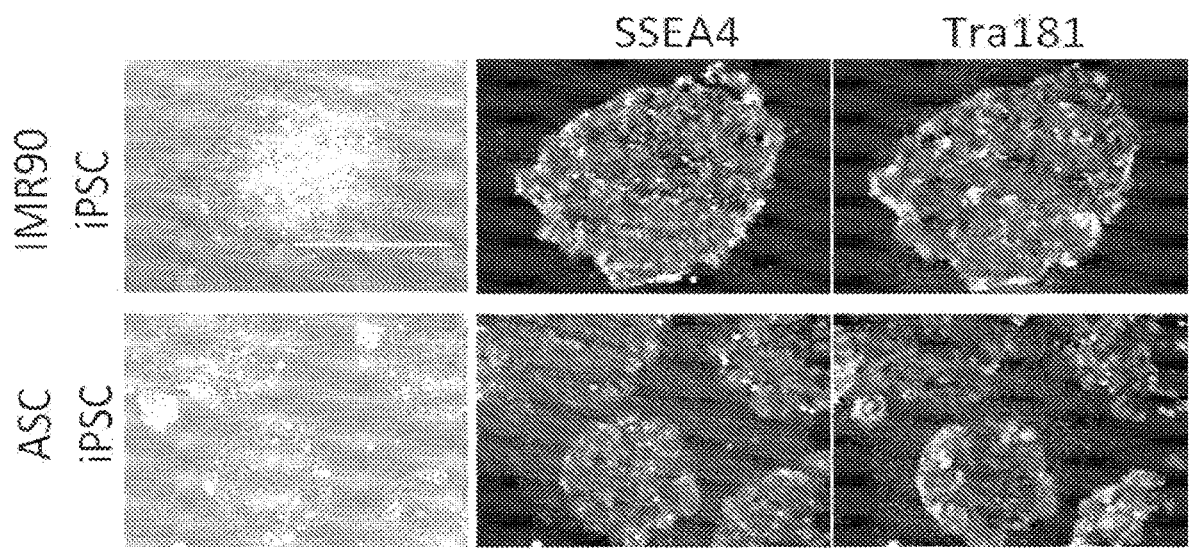
Figure 13D:
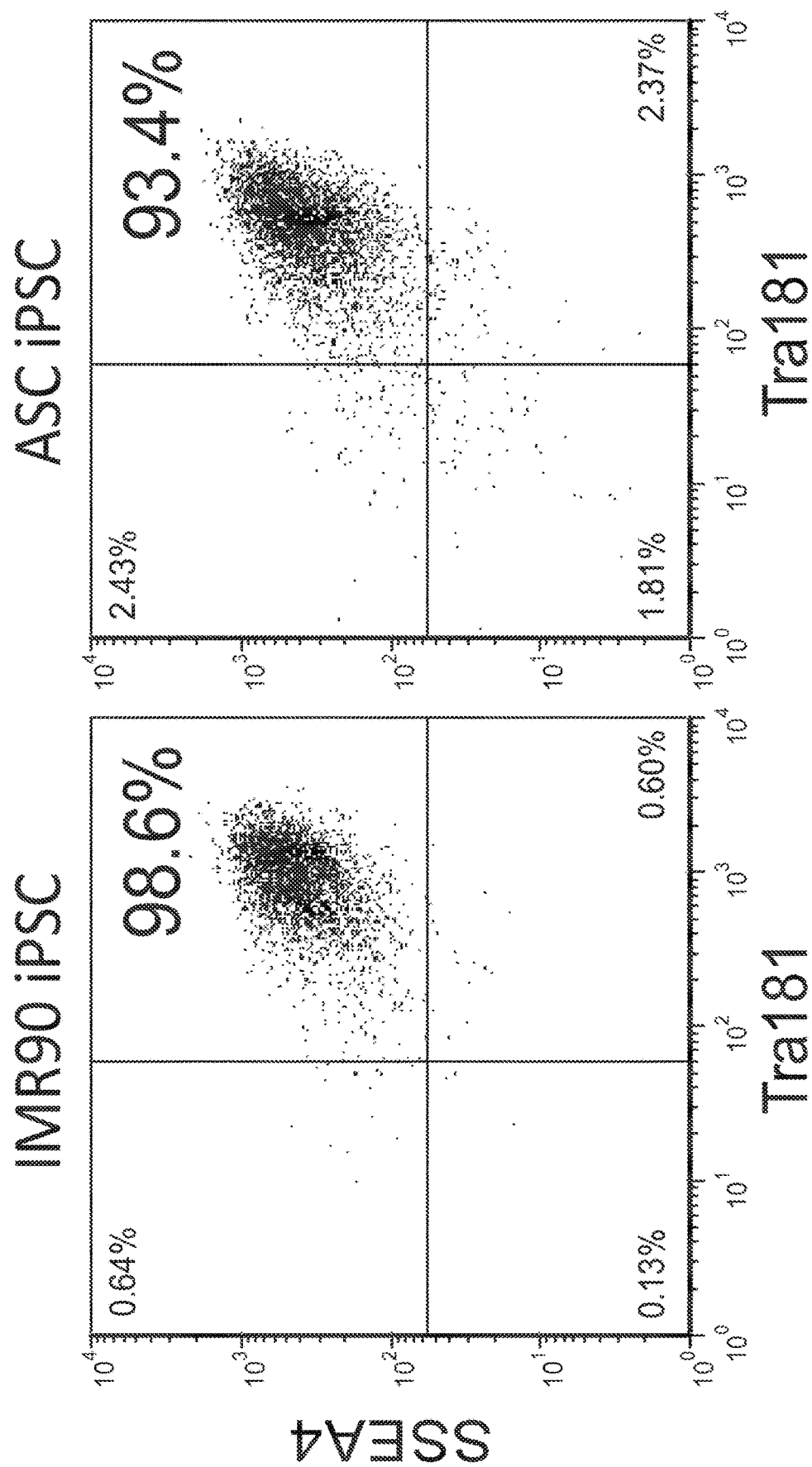
Figure 13E:
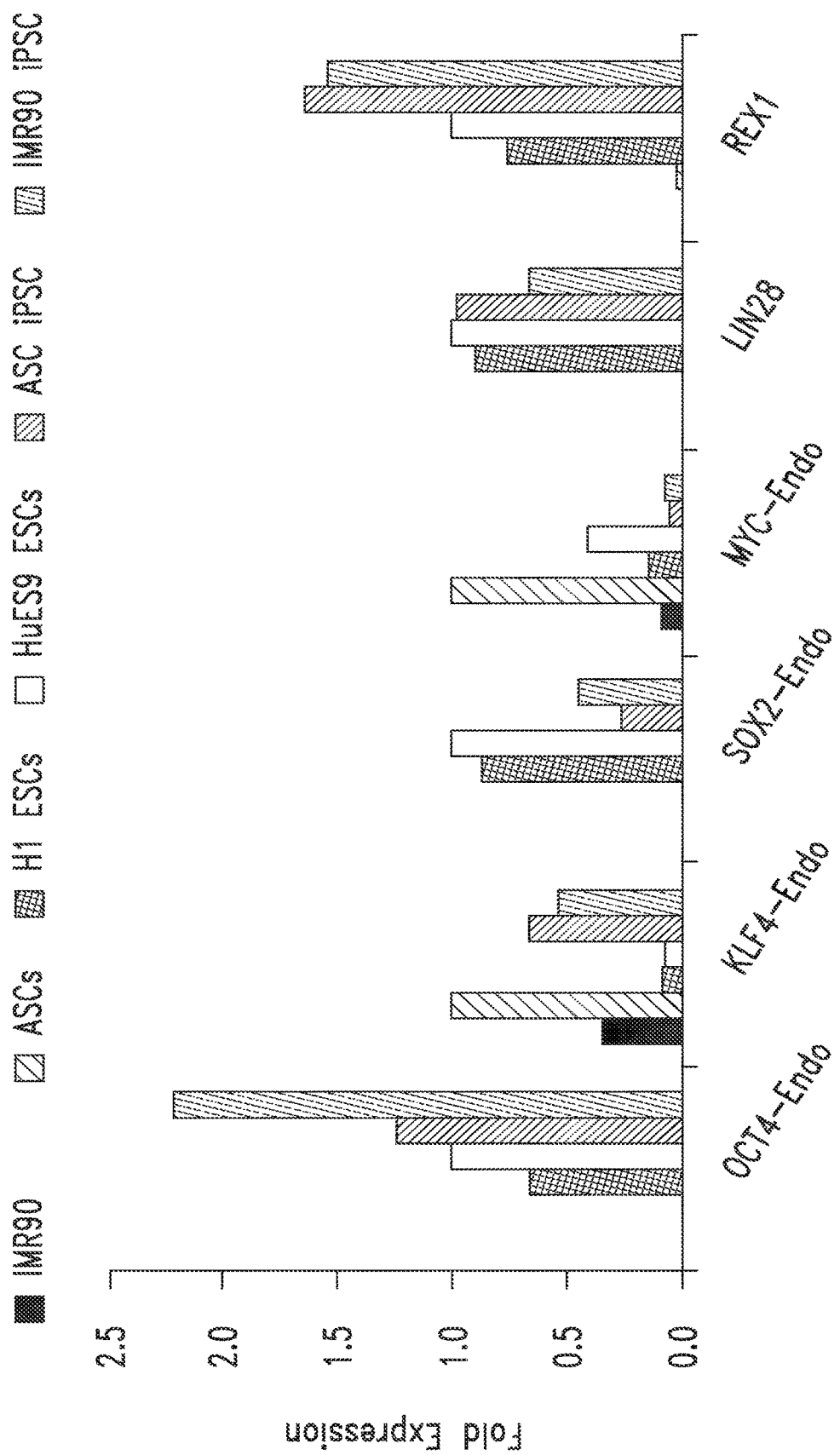
Figure 13F:
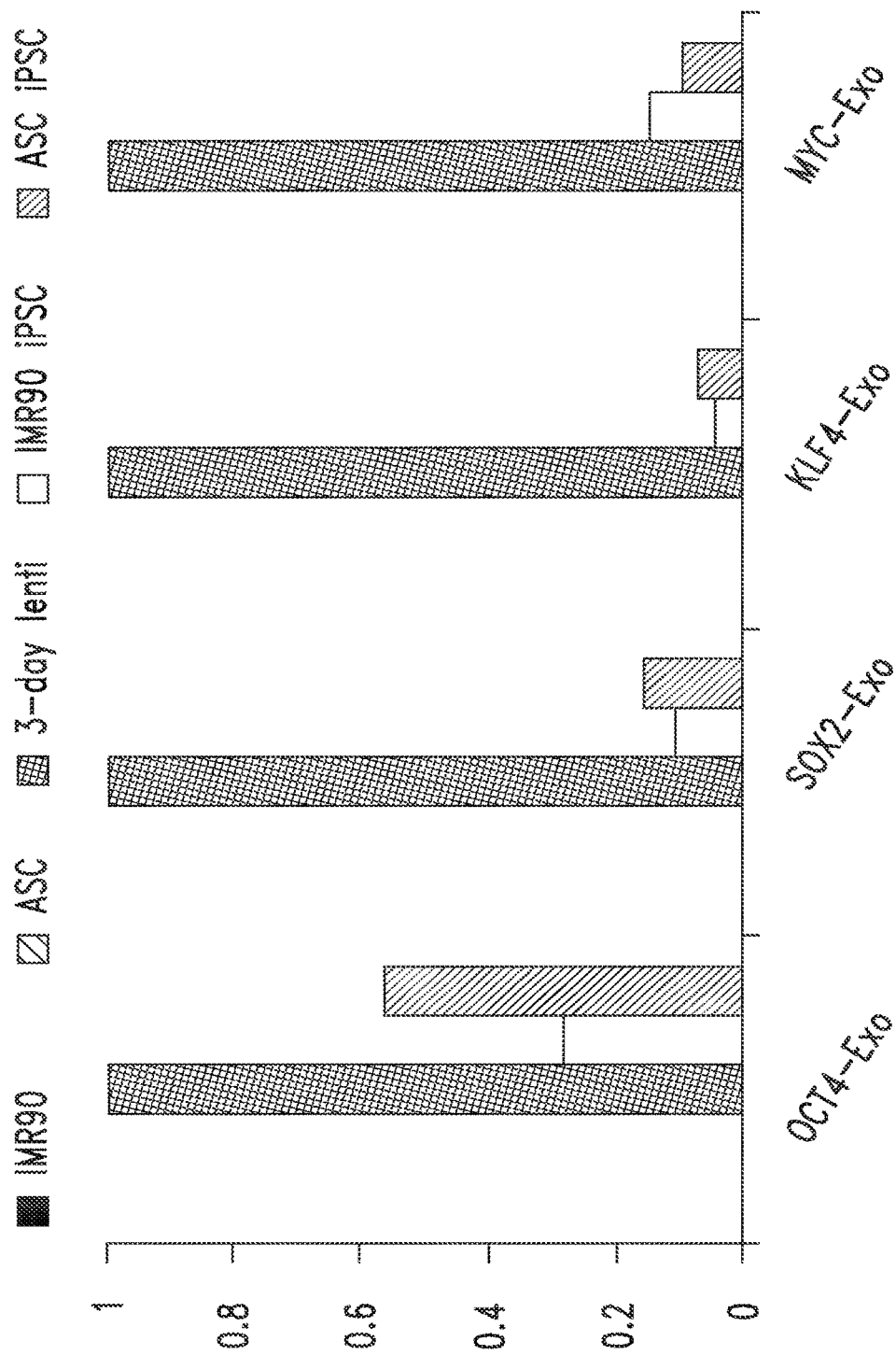
Figure 13G:
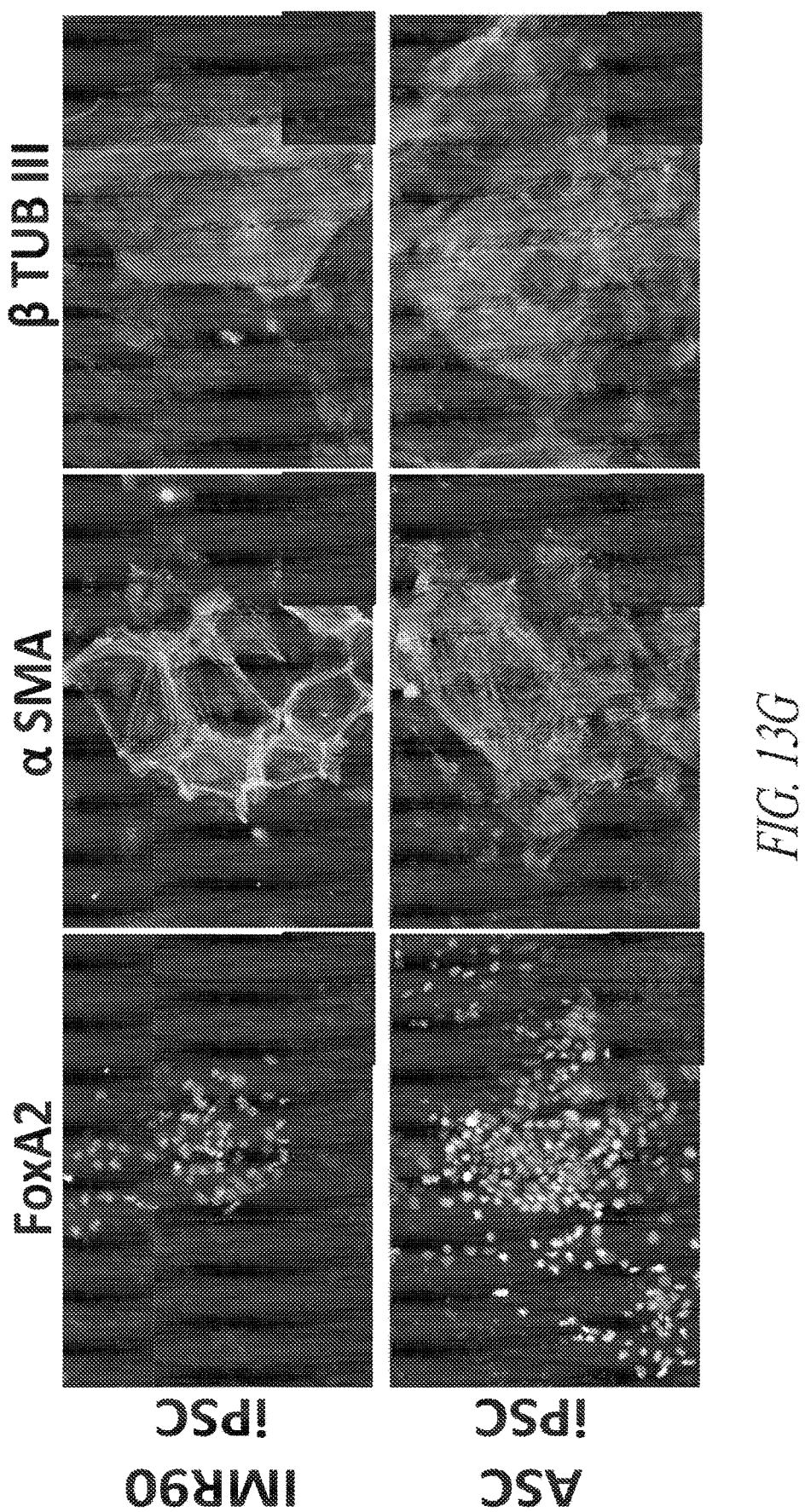

Quantification of three independent experiments clearly demonstrated pluripotent cell selection by single cell sorting only in the presence of the small molecule inhibitors (FIG. 13B). Colonies from cells enriched in this way were cultured further in SMC4 medium and characterized as true iPSCs: the true iPSCs stained positive for pluripotency markers SSEA4 and Tra181 in immunofluorescence and flow cytometry (FIGS. 13C and D); showed similar gene expression profiles to human ESC (FIG. 13E); showed significant silencing of exogenous transgenes (FIG. 13F) and were able to differentiate into all three germ layers (FIG. 13G). Pluripotent cell colonies were rarely observed when the same protocol was used but with conventional culture conditions (consisting of conventional culture medium containing feeder cells and lacking SMC4). Thus the ability to robustly enrich a pluripotent cell population during cellular reprogramming using single cell sorting based on cell surface markers of pluripotency was dependent on the use of the cell signaling pathway inhibitors and additives listed in Table 1. Additionally, improved post-sort seeding was observed when the additive fibronectin was used in the culture system for 3 days. This reprogramming process was also completed for other starting cell types including human adipose-derived stem cells.

Figure 14A:
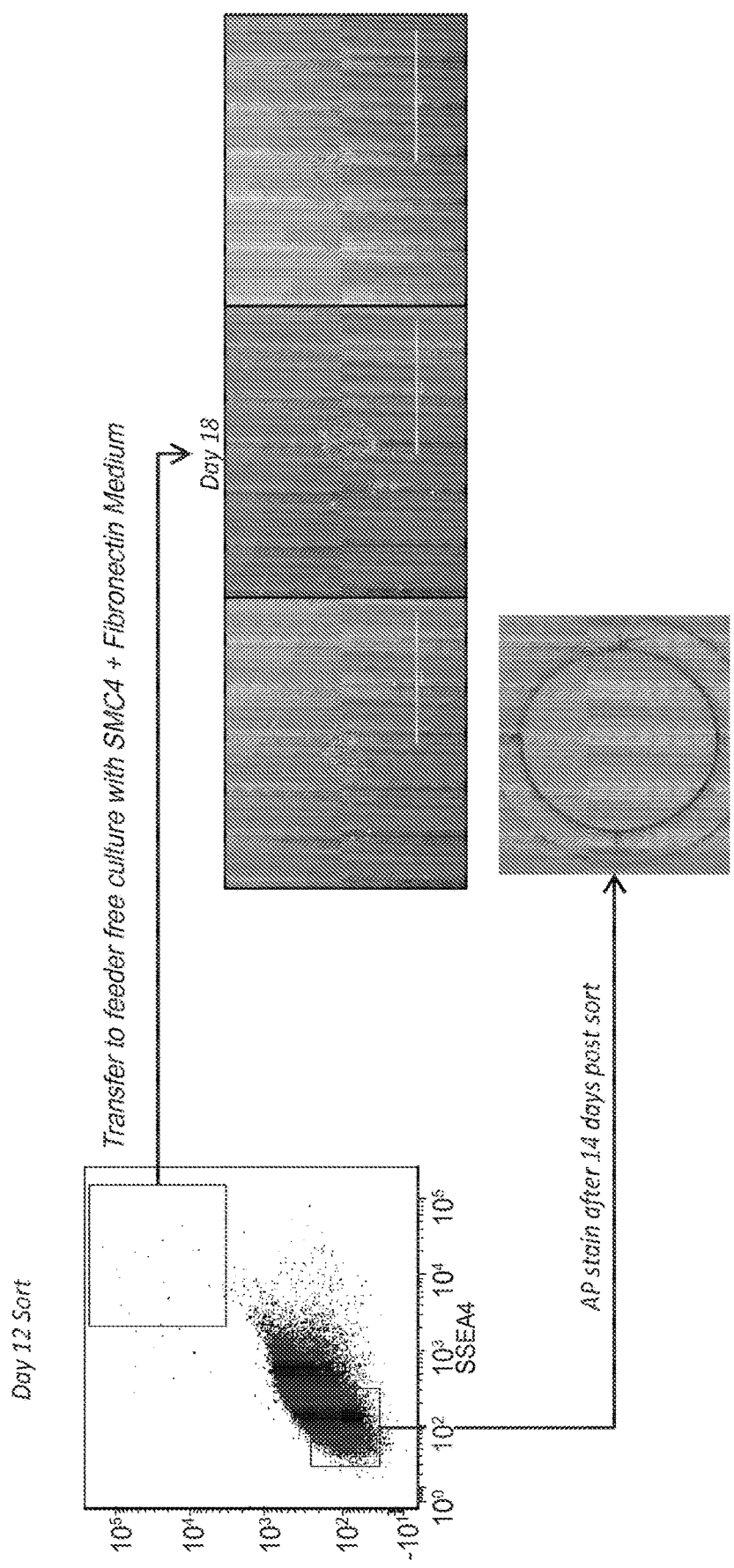
FIGS. 14A-14B. Single cell sorting for the selection of a unique population of pluripotent stem cells.

In a further example of the technology, FACS was used for the enrichment of a pluripotent population of cells from a mixture of non-reprogrammed, partially reprogrammed and fully reprogrammed cells. As with the previous examples, IMR90 fibroblast cells were infected with lentivirus expressing Oct4 and Sox2 and Klf4/c andMyc (OSKM). Several days following fibroblast infection the cell culture was switched to feeder-free culture in SMC4 medium. The infected cell population contained a modest population of cells positive for both SSEA4 and Tra181 markers of pluripotentcy (FIG. 14A). The cells that were positive for both pluripotency markers were selected and sorted away from cells that were either negative for both makers or positive for only one marker. Comparison of subsequent feeder free cultures with media supplemented as described in Table 1, in some embodiments containing fibronectin, showed that cultures from cells positive for both markers formed colonies that were subsequently characterized as pluripotent iPSCs whereas cells gated by FACS to be negative for the markers of pluripotency did not produce alkaline phosphatase-positive colonies (FIG. 14A,B). More specifically, inhibitors of the signaling molecules MEK, GSK, Rock and TGFβ as additives to the basal media formulation facilitated the use of FACS in the sorting selection and enrichment of pluripotent cells early in the reprogramming process. Additionally, improved post-sort seeding was observed when the additive fibronectin was used in the culture system for 3 days.

The advantages of SMC4 medium and culture systems were next used to develop a high-throughput method for generating feeder-free and clonally derived hiPSCs. A scheme was devised to treat cells induced to reprogram with SMC4 medium and select for rare individual cells that have faithfully reprogrammed as indicated by a combination of pluripotency markers. Furthermore, we coupled the reprogramming process with a multiplex platform to effectively select for the top tier clones based on selection assays of dual marker flow-cytometry, qRTPCR and immunofluorescence (FIG. 15).

Figure 15:
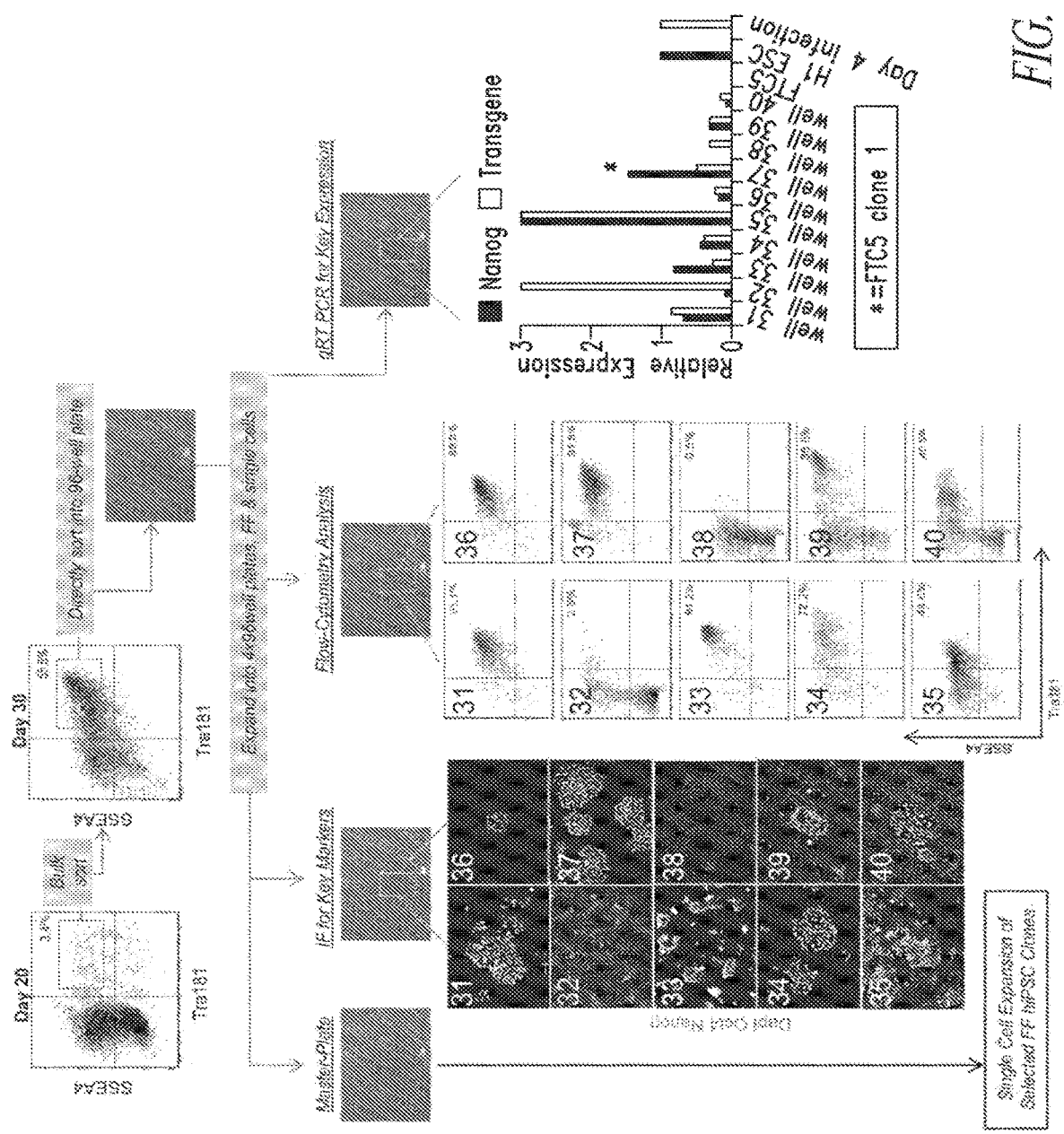
FIG. 15. High-throughput approach for the generation and primary characterization of iPSCs under feeder-free conditions. Three-factor (Oct, Sox, Klf) induced fibroblast cells were sorted in a two-step fashion to deliver an efficient 96-well plating platform using SMC4 medium (and using SMC4+ fibronectin medium during sorting). Wells containing individual colonies were marked and expanded into 4×96-well plates. While one set was designated as the master-plate and expanded, the other three plates were processed for characterization including flow-cytometry analysis for surface marker expression including SSEA4 and Tra181, qRT PCR for expression of key markers including Nanog and transgene silencing and immunofluorescence for pluripotent markers including Oct4 and Nanog. Based on the characterization readouts, selected hiPSC clones were expanded for further analysis and banked. The data panels represent snapshots of the clones surveyed (marked by wells 31-40 of the 96-well plate) during the high-throughput platform hiPSC generation of FTC5. In the qPCR panel, expression was normalized to Gapdh. Nanog expression is relative to H1 hESC while transgene expression is relative to day 4 post infection of FTC5 (Day 4 infection). Based on the characterization readouts, selected hiPSC clones were expanded for further analysis and banked. In the highlighted example, well 37 was identified as a candidate for expansion based on its multi-parameter pluripotency profile and termed FTC5 clone 1. Immuno-fluorescence images were taken at 5× magnification.
Figure 16A:
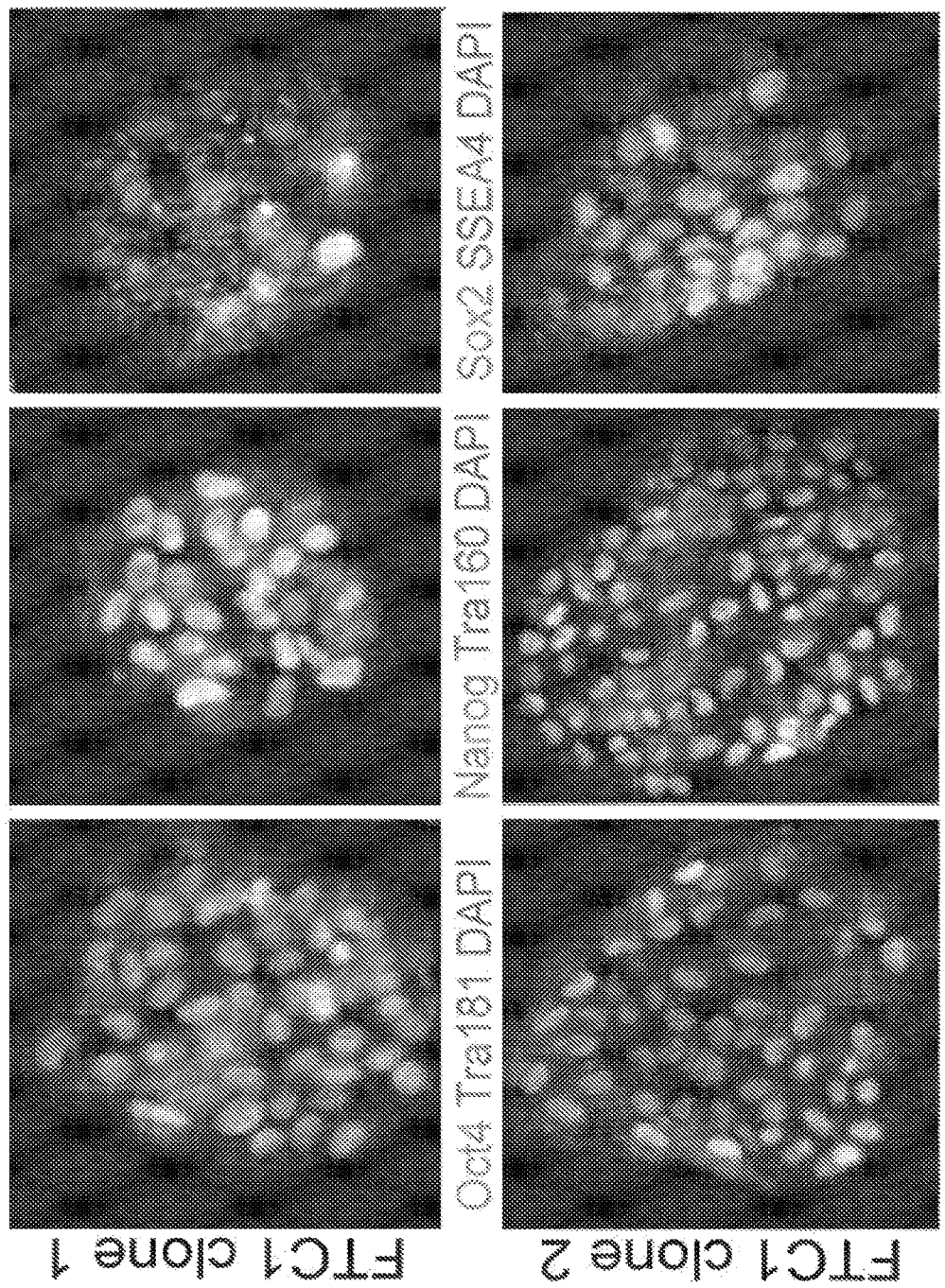
FIGS. 16A-16E. High-throughput platform, clonal and FF derivation of 3-factor (polycistronic-OKS) hiPSCs in the presence of SMC4 medium.
Figure 16B:
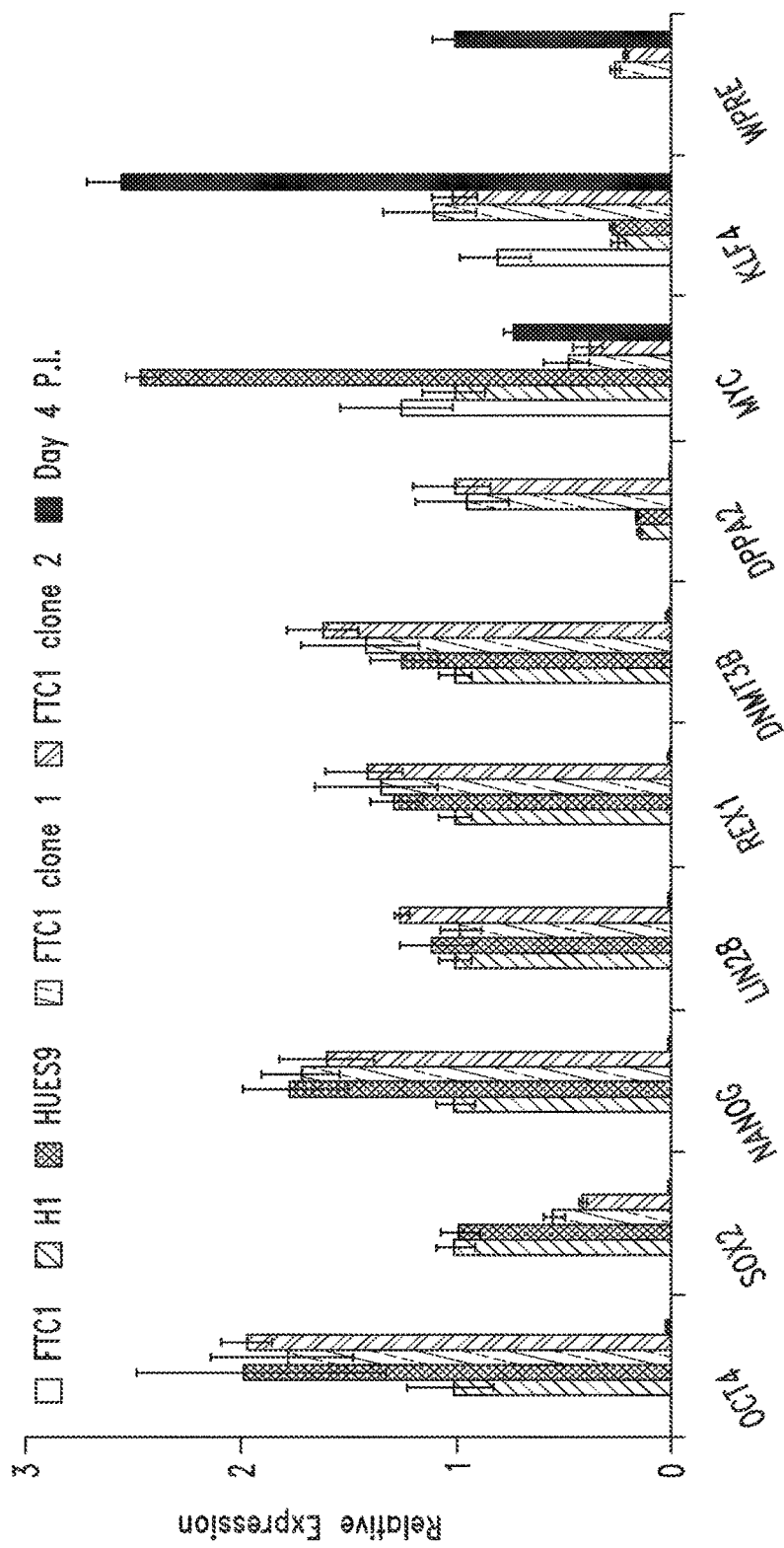
Figure 16C:
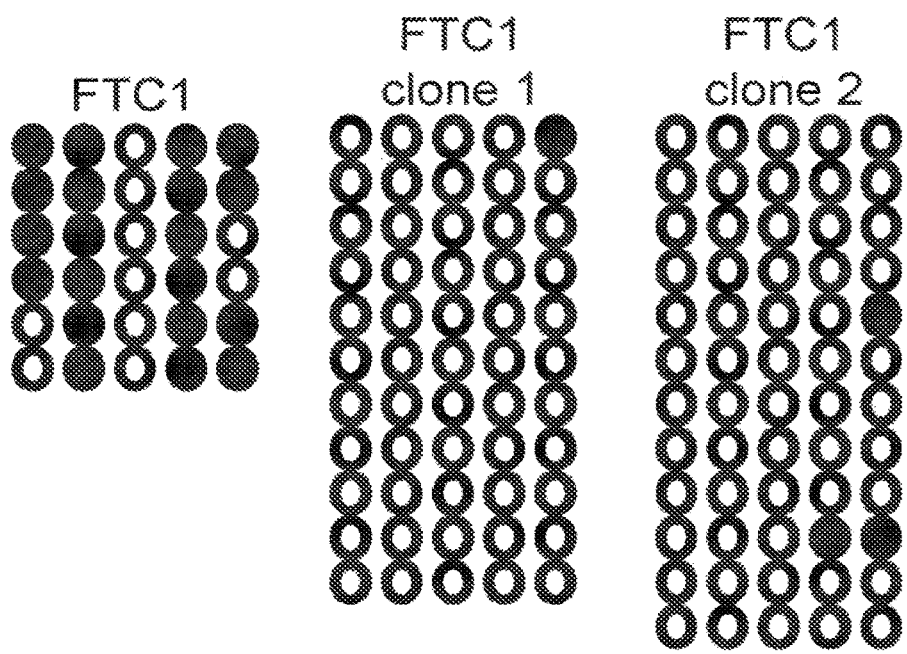
Figure 16D:
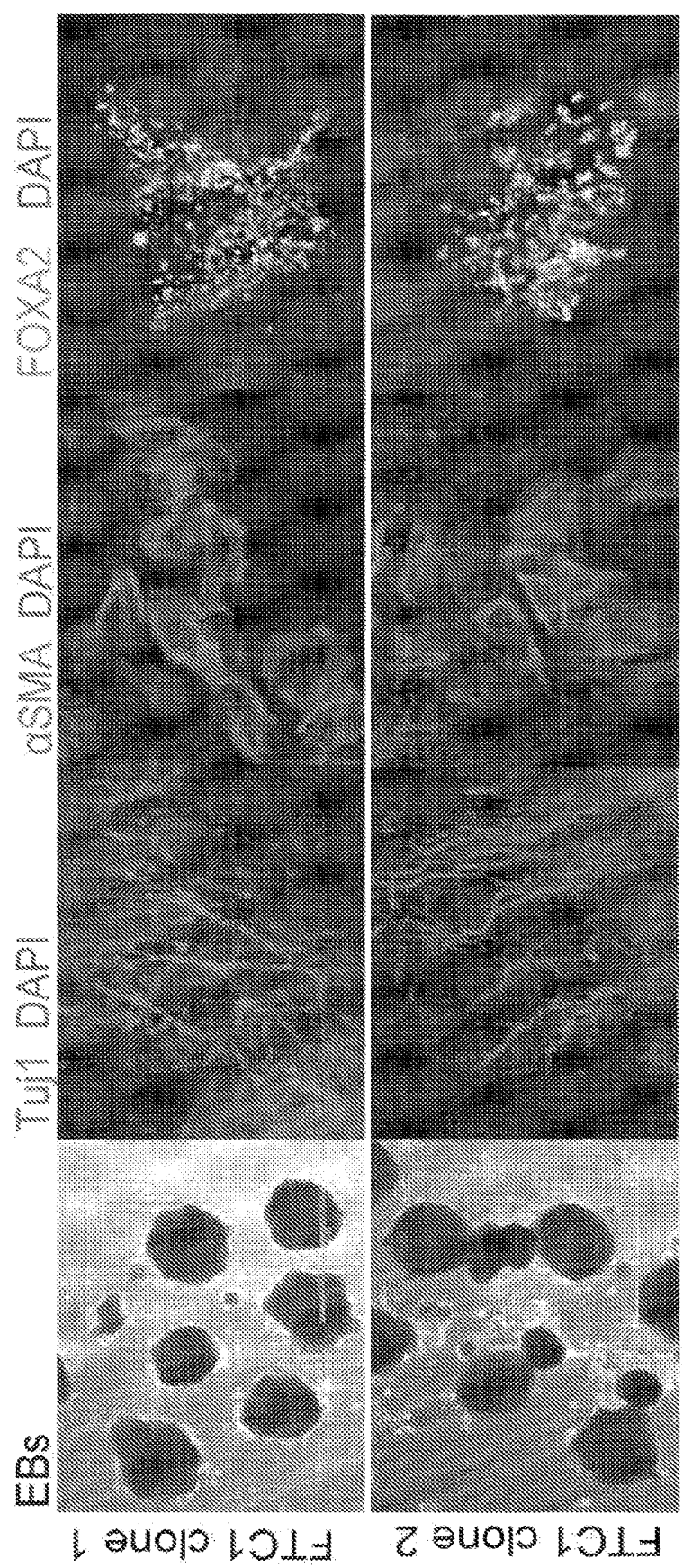
Figure 16E:
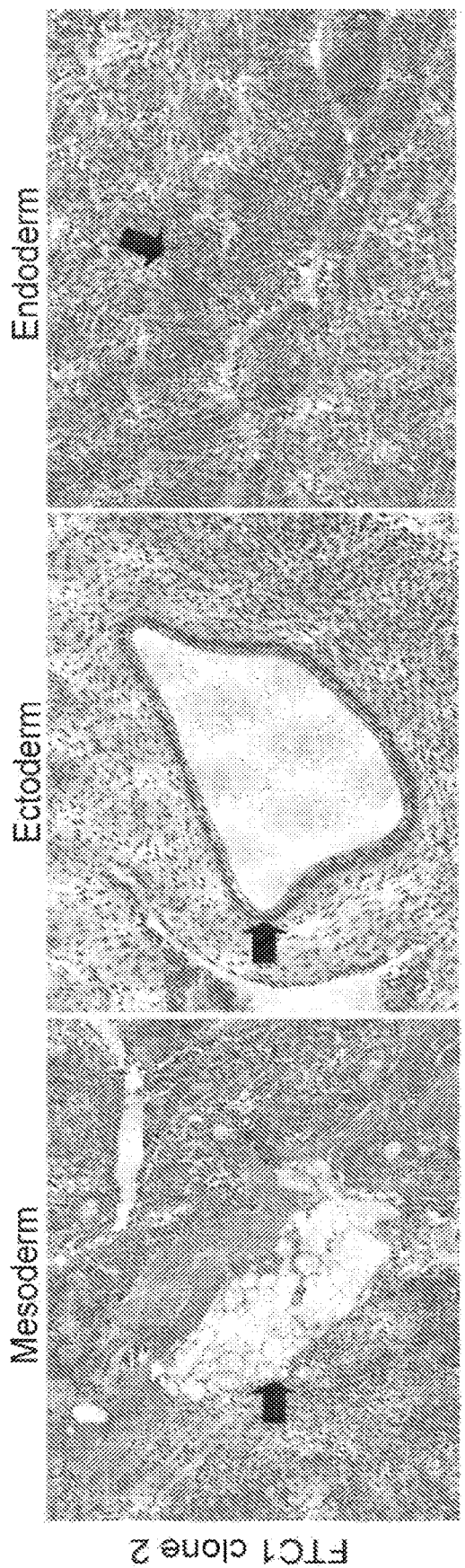

In an optimized multiplex protocol, reprogramming was initiated using the 3-factor (OKS) polycistronic virus, and an initial bulk FACS sort of the SSEA4$^+$/Tra181$^+$ population was completed on day 20 post infection followed by FACS resorting of SSEA4$^+$/Tra181$^+$ cells into 96 well-plates on day 30 (FIG. 15 and B). This strategy allowed for the derivation of numerous clones and led to the generation of clones FTC1 clone 1 and 2 that expressed pluripotent markers, exhibited attenuation of exogenous gene activity and de-methylation of the Oct4 promoter (FIG. 15A-C). FTC1 clone 1 and 2 were also shown to be pluripotent by differentiating into the three somatic lineages in vitro and in vivo (FIG. 15D, E). The selected clones were also assessed for chromosomal integrity and demonstrated to have minimal copy number variations from their parental line and normal karyotype even after 20 continuous single cell passages in FF culture, a marked improvement over other reprogramming strategies (FIG. 17).

Figure 18A:
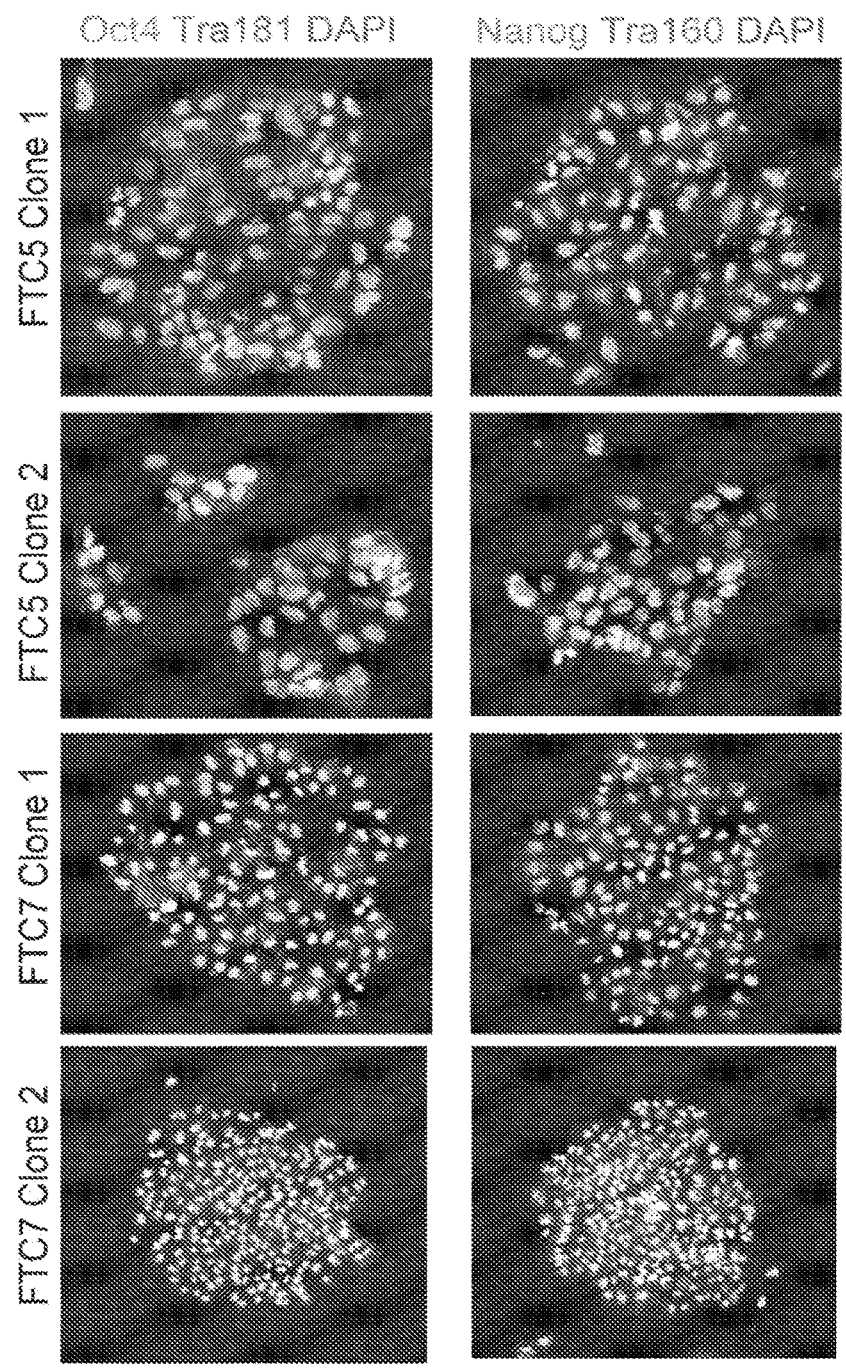
FIGS. 18A-18C. Characterization of FTC5 and FTC7 derived clonal hiPSCs under FF and SMC4 culture. To determine reproducibility of the high-throughput platform, additional patient consented lines FTC5 and FTC7 were tested for hiPSC generation.
Figure 18B:
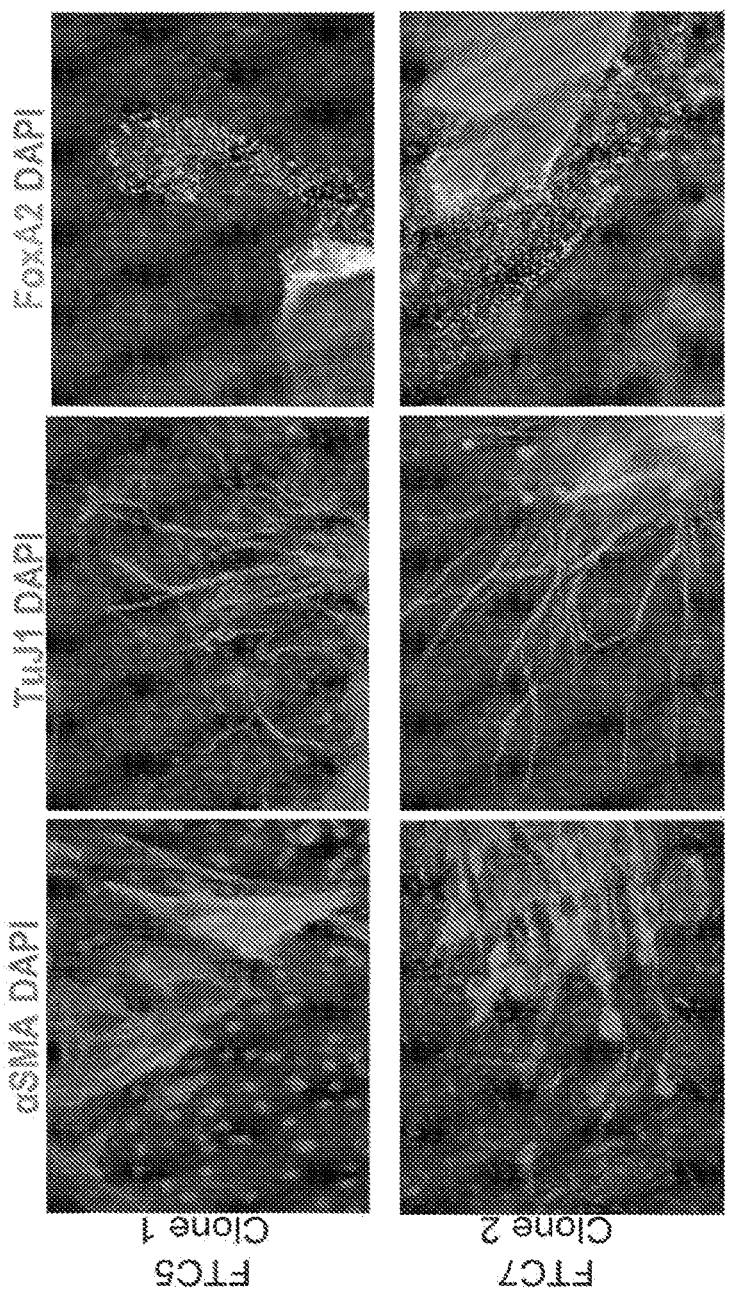
Figure 18C:
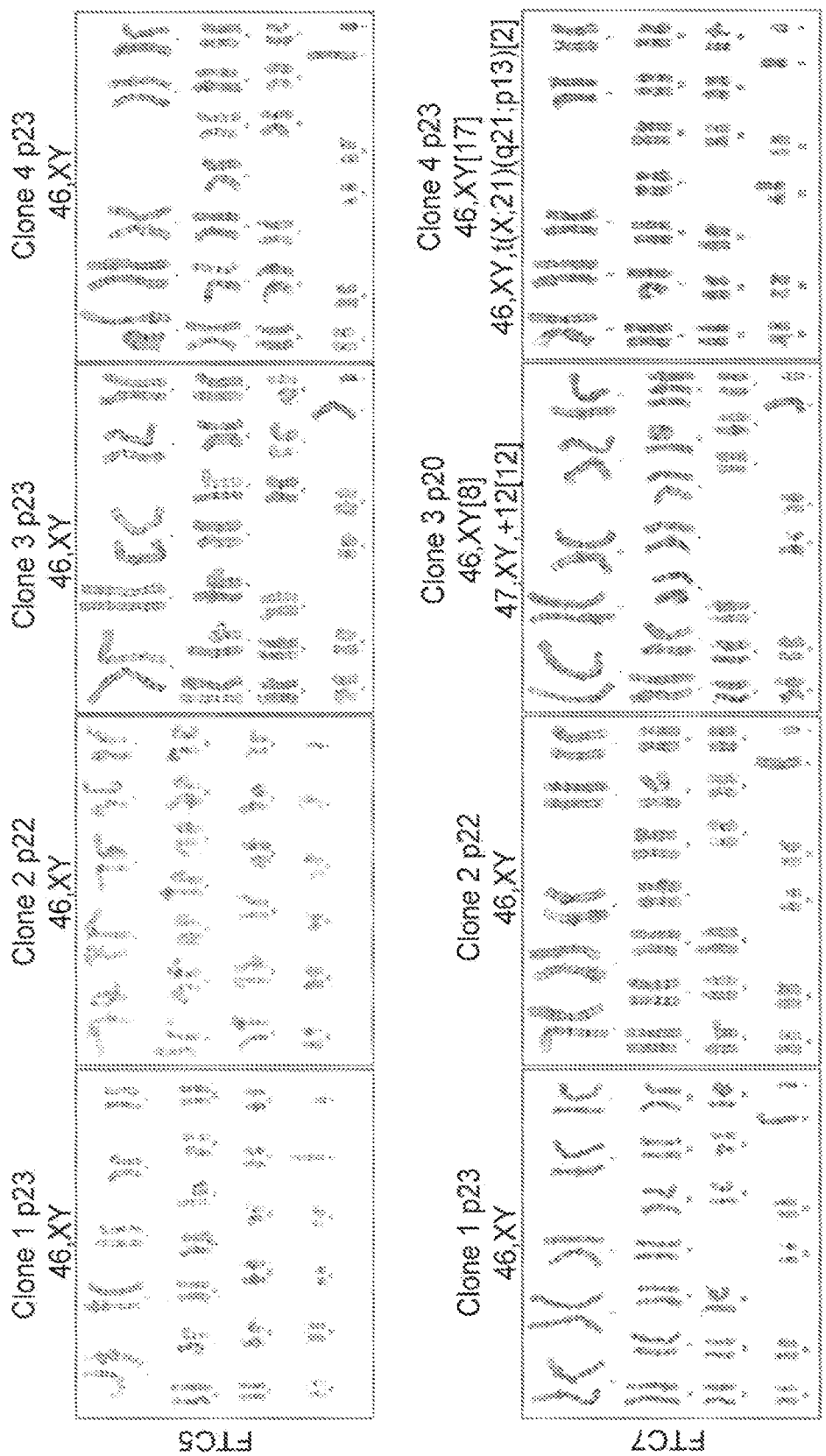

To determine the reproducibility of the platform, additional fibroblast lines, FTC5 and FTC7, were induced to reprogram using a polycistronic vector expressing Oct4, Klf4 and Sox2, and applied to the high-throughput platform as described in FIG. 15. As described in FIG. 18, the colonies derived from FTC5 and FTC7 fibroblast lines were shown to maintain their undifferentiated state, retain their pluripotency and genomic stability. Thus, the combination of 3 pluripotency factors, SMC4 culture medium and a multiplex characterization platform significantly enhances the kinetics of feeder-free reprogramming while enabling the identification, selection and expansion of clonally derived and genomically stable hiPSCs in a high-throughput manner.

Example 8

Methods and Culture Compositions for The Rapid Generation of Multiple iPSC Clones The generation of human iPSCs by the ectopic expression of pluripotency genes such as Oct4, Sox2, Klf4, c-myc, Lin28 and Nanog is an inefficient and technically demanding process. Strategies involving lentiviral or retroviral integration of pluripotency factor transgenes into the host cell genome in combination with culture systems including feeder cell support have traditionally been the most efficient methods for iPSC generation. A literature review of historical studies using virus and feeder cell methodologies for human iPSC generation shows an efficiency of 0.001%-0.01% of infected cells becoming iPS cells, where potential pluripotent cells are seen at the 21-30 day period post infection and these are clonally derived by manual "clump" passaging between 30 and 45 days post infection (Table 4).

Other methods for introducing the pluripotency genes include episomal vector systems and transduction of modified protein. Such methods are regarded as important developments towards the ultimate clinical application of iPSC technology. However, these methodologies are of even lower efficiency than reprogramming using viral systems. Further, the efficiency of the reprogramming process is also reduced, or in some conditions is impossible, when feeder cell-free systems are used in combination with conventional stem cell media formulations, hindering the development of iPSCs for industrial and therapeutic use. Somatic cell reprogramming has been characterized as a stochastic process; the majority of cells will eventually reprogram over time. However a robust, technically easy, efficient and scalable method for producing multiple iPSC clones in a single reprogramming has yet to be described.

The present invention provides cell culture conditions and methodologies to derive clonal iPSC colonies in a relatively short time and with lower technical barriers than current methods. Specifically, and as can be seen in FIG. 13B, the use of small molecule inhibitors of specific signaling pathways as additives in SMC4 medium allowed the generation of iPSC colonies in feeder free culture environments at an efficiency vastly greater than when SMC4 medium is not used. Inhibitors of MEK, GSK, Rock and TGFβ signaling pathways were used to allow efficient reprogramming in feeder-free environments.

As can be seen from FIG. 13 and Table 4, in three independent reprogramming experiments either none or one colony was seen when conventional hESC medium was used in the reprogramming process in a feeder-free environment, whereas the small molecule culture additives (i.e., SMC4 medium) enhanced the feeder-free reprogramming event to an efficiency of 0.035%, and resulted in colonies on days 14-21 post infection and the derivation of clonal iPSCs by days 28-35. Thus, the use of small molecule inhibitors increased the efficiency of reprogramming with respect to the time to reprogram and the percent of cells reprogrammed. The colonies that were generated using this approach were characterized as pluripotent using standard procedures such as immunofluorescence and gene expression profiling.

Figure 14B:
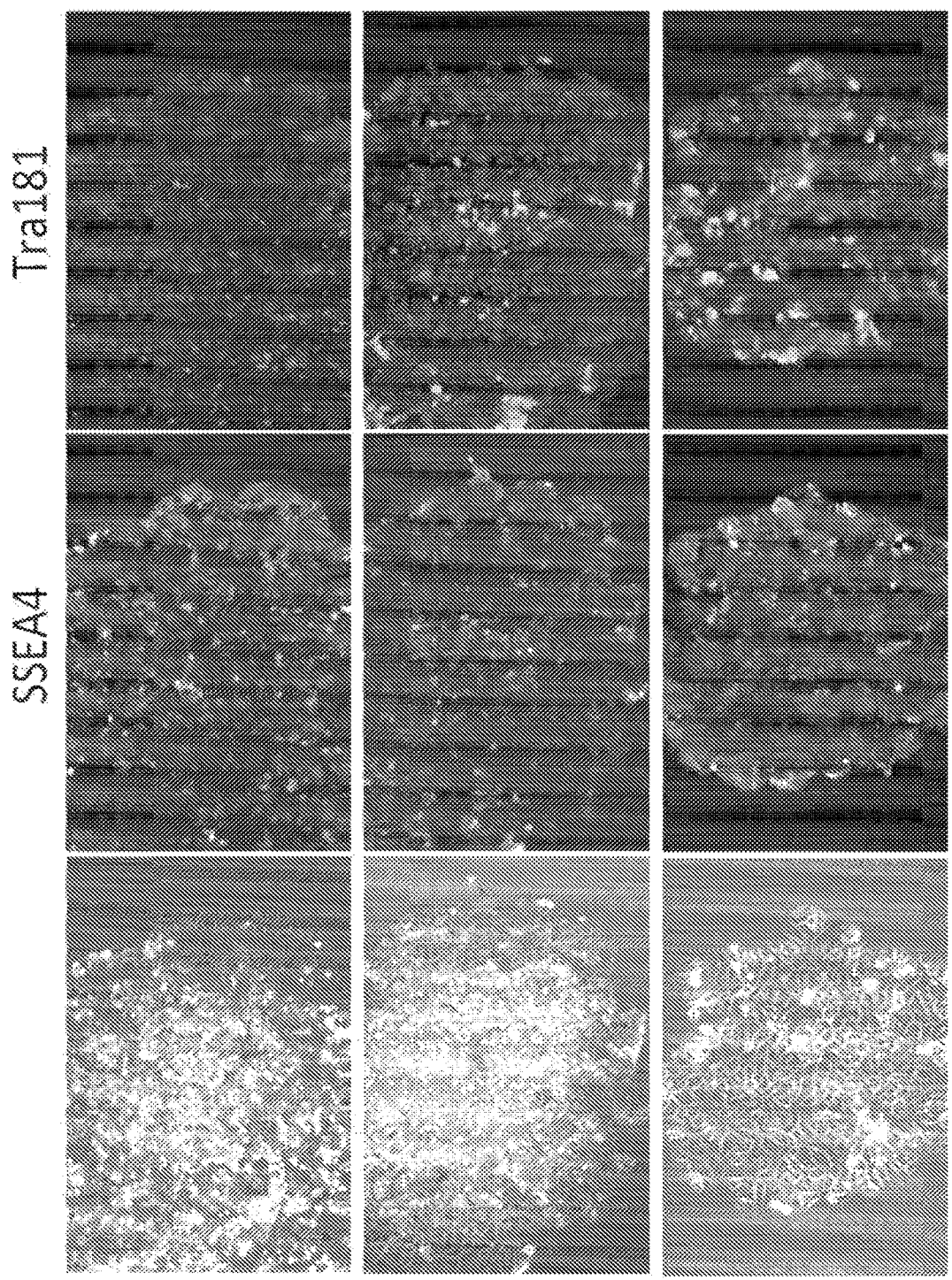

In a further demonstration of this technology, differentiated cells were infected with virus expressing individual pluripotency genes Oct4, Klf4, Sox2, and Myc, and were cultured in SMC4 medium and feeder-free culture environments (Table 1) for 8-12 days. At this time point, and as described in Example 6 and FIGS. 13 and 14, the cells were enriched using FACS or MACS single cell sorting to obtain the small population of pluripotent cells defined by positive staining for pluripotency markers such as SSEA4 and Tra181. Using this approach the timelines for iPSC production were greatly reduced: an efficiency of 0.22% in terms of the percent of cells reprogrammed was demonstrated, with colonies appearing in days immediately post sort (day 10-16). This efficiency of reprogramming allowed the derivation of clonal iPSCs by days 21-28 post infection.

In a further demonstration of the improved efficiency of reprogramming, a polycistronic vector system in which 3 (Oct4, Klf4, and Sox2) or 4 (Oct4, Klf4, Sox2, and myc) pluripotency factors were expressed from the same promoter element was used in combination with the optimized SMC4 medium, feeder-free culture and single cell sorting system using SSEA4 and TRA181, resulting in reprogramming efficiencies of 0.756% with colonies first seen at days 6-8 post infection. This method was so efficient that iPSC colonies were present just 4 days after infection. These techniques represent a significant improvement over traditional methods of iPSC generation.

TABLE 4

Kinetics of reprogramming in various strategies.

| Reprogramming strategy | Appearance of colonies (Days)* | Efficiency (%)** | Derivation of clonal population (Days)*** |
|---|---|---|---|
| Individual 4 Factors Virus +Feeder Cells +Conventional Medium | 21-30 | 0.001-0.01 | 30-45 |
| Individual 4 Factors Virus +Feeder Cells +Conventional Medium +TGFβi + MEKi | 14-21 | 0.01-0.1 | 28-42 |
| Individual 4 Factors Virus | 14-21 | 0.035 ± 0.015 | 28-35 |

TABLE 4-continued

Kinetics of reprogramming in various strategies.

| Reprogramming strategy | Appearance of colonies (Days)* | Efficiency (%)** | Derivation of clonal population (Days)*** |
|---|---|---|---|
| Individual 4 Factors Virus<br>−Feeder Cells<br>+Enrichment<br>+Conventional Medium | N.I. | — | — |
| Individual 4 Factors Virus<br>−Feeder Cells<br>+Enrichment<br>+SMC4 | 10-16 | 0.220 ± 0.120 | 21-28 |
| Individual 3 Factors Virus<br>−Feeder Cells<br>+Enrichment<br>+SMC4 | 18-24 | 0.032 ± 0.018 | 24-35 |
| Polycistronic 4 Factors Virus<br>−Feeder Cells<br>+Enrichment<br>+SMC4 | 6-8 | 0 756 ± 0.238 | 18-24 |
| Polycistronic 3 Factors Virus<br>−Feeder Cells<br>+Enrichment<br>+SMC4 | 10-14 | 0.276 ± 0.084 | 21-28 |

N.I., not identified;
*Morphological appearance of iPSC-like colony;
**Calculated as number of SSEA4+/Tra181+ per seeded cells;
***Time required for an iPSC colony to be expanded and maintained as a clonal line (based on Tra181/SSEA4 staining).
The first two rows following the header represent data from literature search.
Individual Factors Virus; infection conducted by combining individual virus each expressing one of the key transcription factors, 3 represents combination Oct4/Klf4/Sox2 and 4 represents combination Oct4/Klf4/Sox2/cMyc.

Example 9

Figure 20:
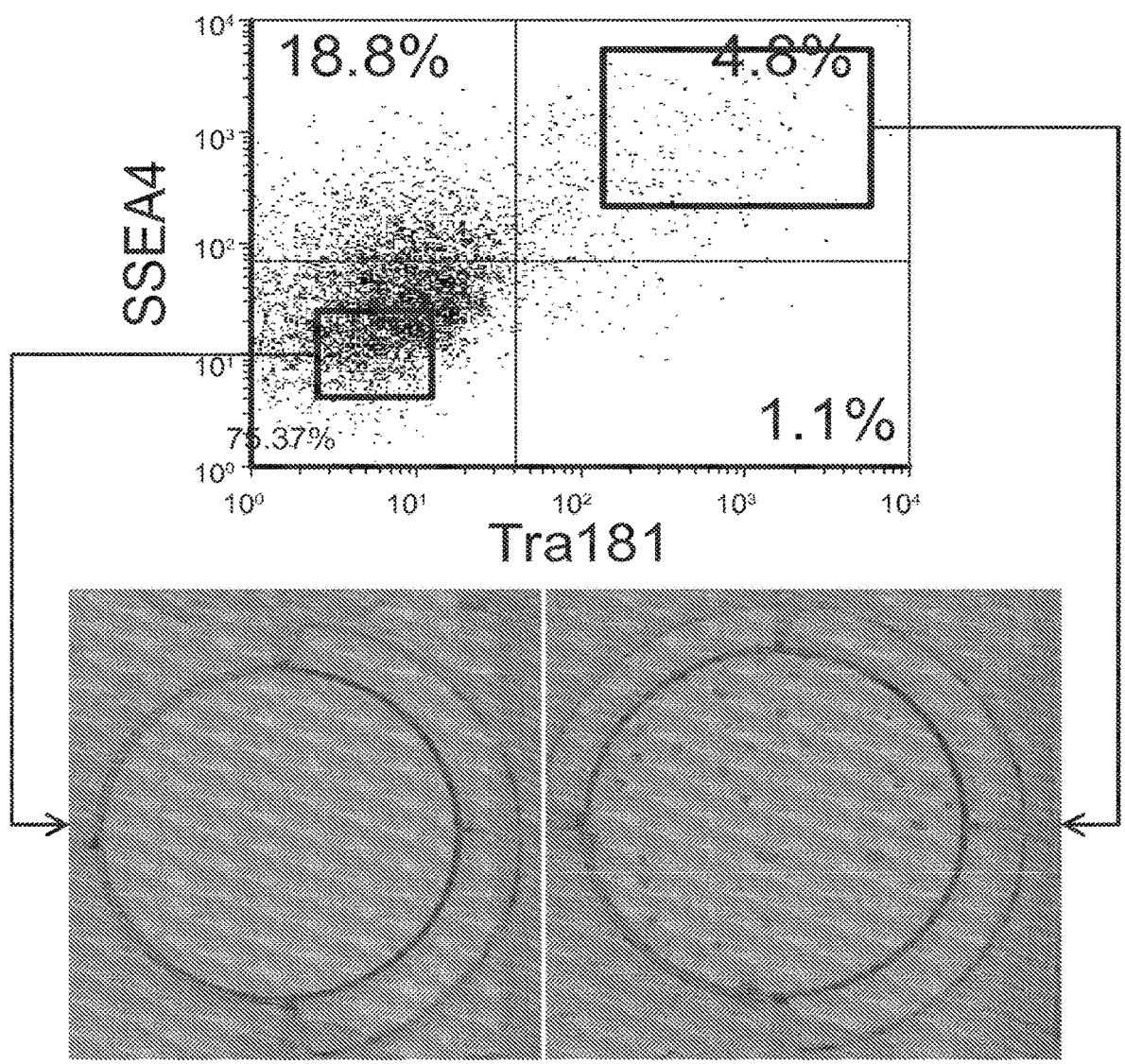
FIG. 20. Separation of differentiated cells from a heterogeneous population of non-, semi- and fully-pluripotent stem cells. FACS sorting of a population of reprogrammed human fibroblast cells: when cells double negative for pluripotency markers SSEA4−/Tra181− (blue box; lower left box) were sorted, no alkaline phosphatase (AP) positive colonies were detected, indicating a loss in pluripotency and potential tumorigenecity after one week of culture, whereas the sorting of a double positive population SSEA4+/Tra181+ (orange box; upper right box) resulted in the selection and enrichment of the population for pluripotent cells, as evidenced by the formation of AP+ colonies.

Methods of Depleting a Pluripotent Cell Population From a Differentiated Cell Population Using Single Cell Sorting and Enrichment Drug screening and some clinical applications of stem cell biology require the generation of homogeneous populations of cells differentiated to a specific lineage from pluripotent cells such as ESCs or iPSCs. Contamination of a differentiated cell population with pluripotent cells could lead to misleading screening results or even tumor/teratoma formation in vivo. Methods of either enriching a population of cells for differentiated cells or depleting pluripotent cells from a cell population could include the sorting technologies described in Examples 3 and 6 herein. The use of small molecule additives in cell culture media to specifically prevent differentiation or partial differentiation of pluripotent cells during the single cell sorting process, as provided by the present invention, allows pluripotent cells to be negatively selected out of a population of fully differentiated cells. Inversely, the positive selection of differentiated cells from a cell population by cell sorting can be more effective under culture conditions where pluripotent cells remain fully positive for surface markers of pluripotency. As can be seen in FIG. 20, a mixed population of fully differentiated fibroblasts and pluripotent cells was effectively separated using FACS when the cells were pre-cultured in culture environments described in Table 1. The small molecule culture additives can also be used during the sorting procedure, stabilizing the single cell suspension. It can be seen from FIG. 20 that cells selected as negative for pluripotency markers were seen to be completely free of pluripotent cells on subsequent culturing and staining for alkaline phosphatase.

Example 10

Cytokine and Growth Factor Free Culture of Pluripotent Stem Cells on Feeder-Free Culture As discussed in Example 2, conventional human pluripotent culture systems include feeder cells and cytokines, such as bFGF, which serve as extrinsic stimuli for the maintenance of human pluripotent stem cells in an undifferentiated state. Feeder cells and the process for producing recombinant cytokines serve as a source of xenogeneic contaminants, however. In addition, the key factor(s) secreted from feeder cells and the exact cellular pathways stimulated by cytokines are yet to be identified. Thus, the conventional culture of human pluripotent stem cells represents an ill-defined system and may impede transition to clinical-grade manufacturing.

To address this issue, the present invention includes a further embodiment wherein the feeder-free and single cell passage system discussed in Example 2 was further modified by removing bFGF and other cytokines and growth factors from the SMC4 medium formulation. Further, in one embodiment of the invention, Matrigel™ was replaced with gelatin, since Matrigel™ represents an extracellular matrix that is animal derived and not fully characterized. These embodiments of the invention provided a fully defined and cytokine free culture system that allows for intrinsic self-renewal and maintenance of pluripotent stem cells, including iPSCs.

As demonstrated in FIGS. 21A and 21B, human pluripotent stem cells, such as iPSCs generated with a polycistronic vector system containing Oct4, Klf4, and Sox2 and maintained in a feeder free environment, were readily single cell passaged onto a gelatin coated culture surface with SMC4 medium devoid of additional cytokines or growth factors such as bFGF. After several passages in this fully defined system, iPSCs maintained their pluripotent status as demonstrated by co-expression of Tra181 and SSEA4 (FIG. 21C). Further, we have demonstrated the generation of iPSCs in this fully defined and cytokine free system. Thus, in one embodiment the invention provides a fully defined culture system absent of growth factor and cytokines comprising a combination of SMC4 medium and gelatin.

Example 11

Genomic Stability in the Generation and Maintenance of Pluripotent Stem Cells

Figure 17A:
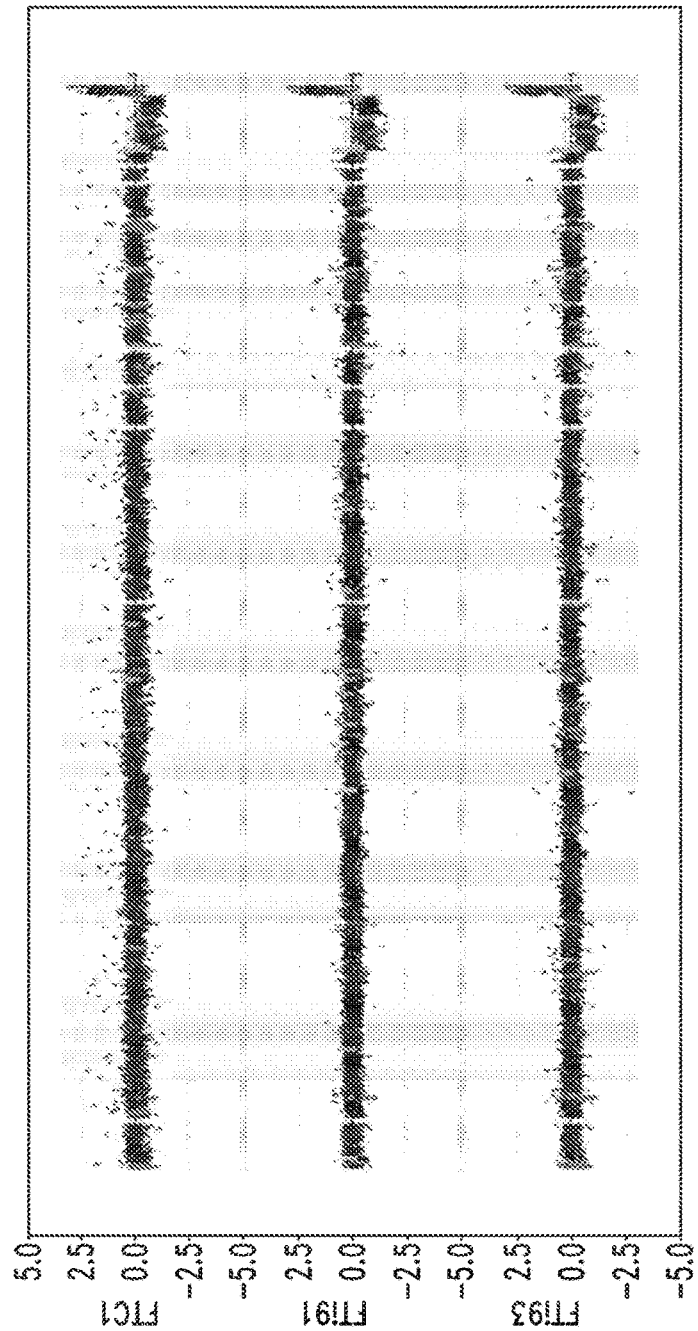
FIGS. 17A-17B. Generation and maintenance of pluripotent stem cells in SMC4 medium maintain genomic integrity and can be enriched for pluripotent cells.
Figure 17B:
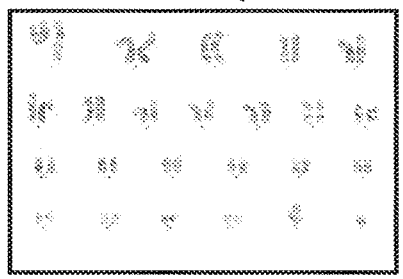
Figure 17B:
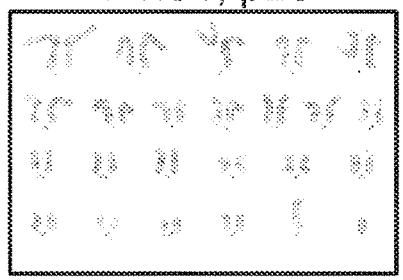
Figure 17B:
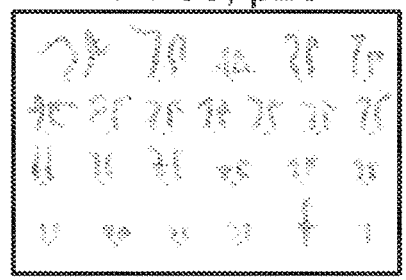

Studies suggest that the reprogramming process and subsequent culture of pluripotent stem cells may result in a higher propensity for genomic abnormalities. In addition, feeder-free culture has been shown to give rise to clonal outgrowth of karyotype abnormal cells. As demonstrated in FIGS. 17A, 17B and 18C, the invention provides a method of reprogramming to obtain cells having genomic stability as well as a method of maintaining reprogrammed cells having genomic stability. In the method of the invention, genomic stability was maintained during both the reprogramming process as well as during long-term feeder-free culture when cells were reprogrammed using our 3-factor polycistronic construct containing Oct4, Klf4 and Sox2 and cultured in SMC4 medium. As seen in FIG. 17A, high resolution comparative genomic hybridization demonstrated that minimal copy number variations were detected when hiPSCs were generated and maintained in long-term feeder-free culture using SMC4 medium. In addition, genomic stability was maintained during routine long-term feeder-free and single cell culture as demonstrated in FIGS. 17B and 18C.

Example 12

Maintaining a Cell Population of Pluripotent Cells During Culturing Using Cell Surface Markers It is often useful to remove differentiated cells from pluripotent cell culture to maintain the pluripotency of a stem cell culture. To date, this process requires manual picking of differentiated cells away from the cell culture or collecting the undifferentiated cells from a substantially differentiated population. Both processes are labor intensive, require skilled training, and rely on selection of cells based on morphology, which may not always be indicative of the true pluripotency status of the cells in the culture (FIG. 8).

Figure 19A:
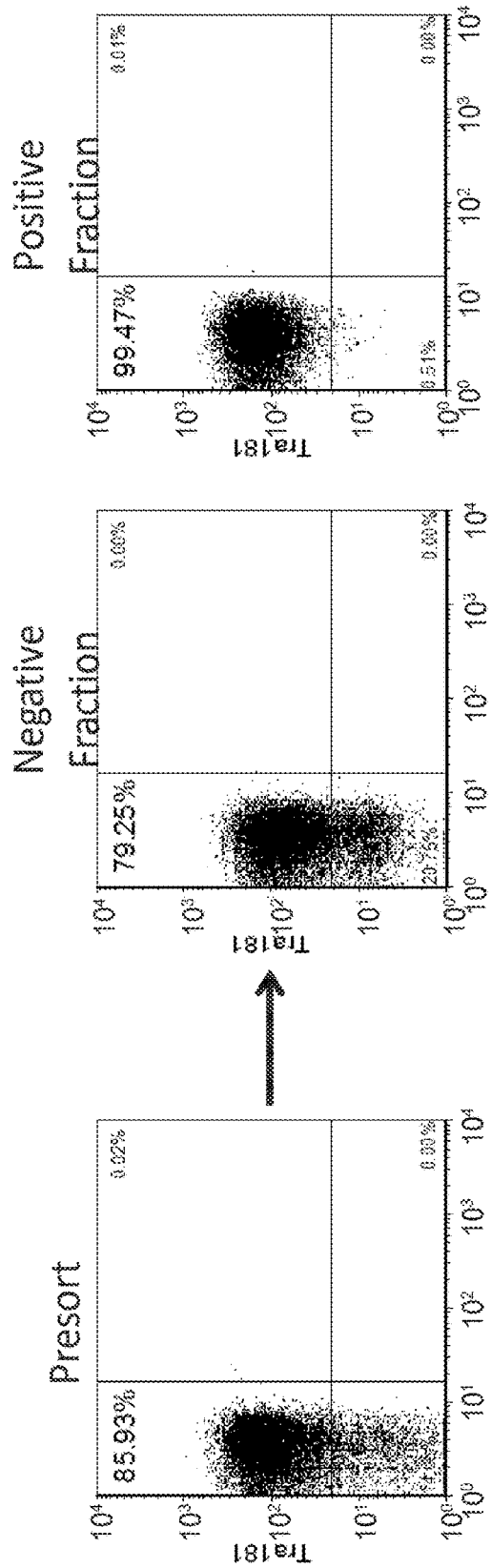
FIGS. 19A-19B. Method of maintaining pluripotent culture using cell surface markers.
Figure 19B:
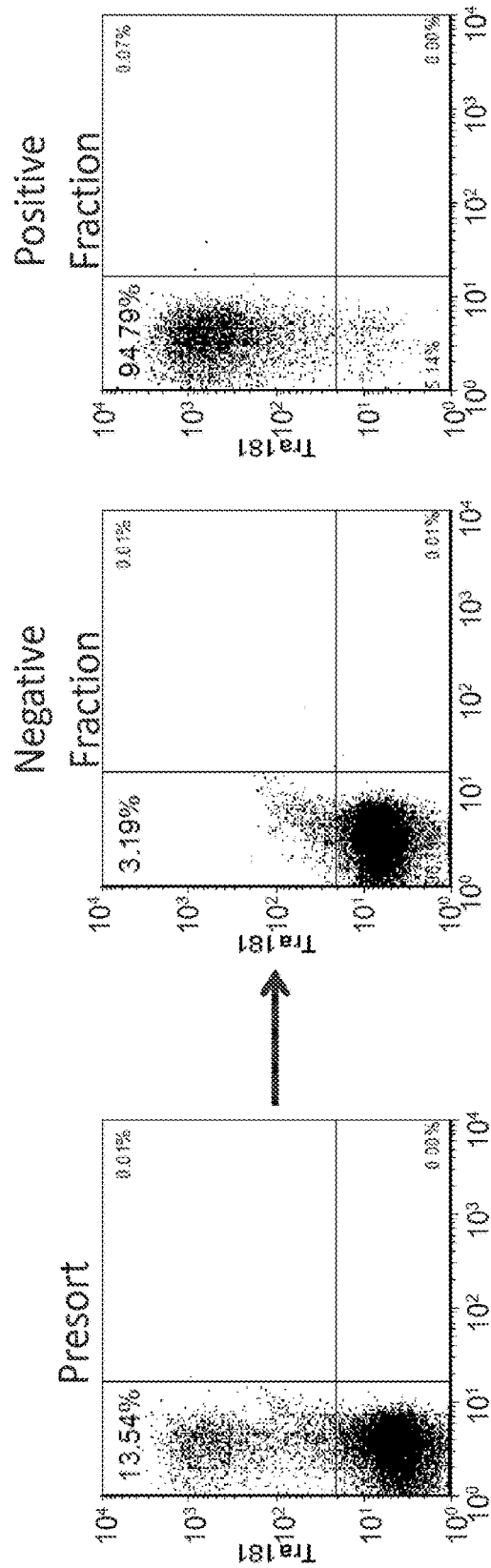

In an improved process, the present invention provides the ability to efficiently and precisely select for undifferentiated cells during routine culture. As demonstrated in FIG. 19A, a population of hiPSCs maintained in SMC4 medium and FF culture was readily enriched or sorted to maintain a cell culture of undifferentiated pluripotent cells. In another example, as described in FIG. 19B, a population of mostly differentiated cells, which would normally be discarded, can be removed from the cell culture to achieve mostly undifferentiated pluripotent cells as described by Tra181 expression.

The invention claimed is:

1. An isolated induced pluripotent cell, a cell line thereof, or a population thereof, wherein: (a) the cell is in contact with a feeder-free culture medium composition comprising a Rock inhibitor, and one or more of a GSK3 inhibitor, a MEK inhibitor and a TGFβ inhibitor; (b) the induced pluripotent cell is a naïve human induced pluripotent stem cell (iPSC) with ground state pluripotency; and (c) the iPSC (i) exhibits reactivated expression of one or more of GATA6, CDX2, or CGB, or (ii) is a cell in a colony having a domed morphology.

2. The induced pluripotent cell, cell line thereof, or population thereof of claim 1, wherein the pluripotent cell is a suspended pluripotent cell.

3. The induced pluripotent cell, cell line thereof, or population thereof of claim 1, wherein the pluripotent cells comprise a population of cells enriched for cells expressing one or more markers of pluripotency obtained by selecting and isolating the pluripotent cells expressing the one or more markers.

4. The induced pluripotent cell, cell line thereof, or population thereof of claim 3, wherein the enriched pluripotent cells maintain pluripotency for at least 5, 10, 15, or 20 passages when cultured in the feeder-free culture medium composition comprising a Rock inhibitor, and one or more of a GSK3 inhibitor, a MEK inhibitor and a TGFβ inhibitor.

5. The induced pluripotent cell, cell line thereof, or population thereof of claim 1, wherein the pluripotent cell comprises reactivated expression of one or more of GATA6, CDX2, or CGB.

6. The induced pluripotent cell, cell line thereof, or population thereof of claim 1, wherein the pluripotent cell has reduced Xist activity and/or enhanced expression of genes of the X chromosome in comparison to pluripotent cells not cultured in the feeder-free culture medium composition.

7. The induced pluripotent cell, cell line thereof, or population thereof of claim 1, wherein the feeder-free culture medium composition is free of additional cytokines and growth factors.

8. The induced pluripotent cell, cell line thereof, or population thereof of claim 1, wherein the feeder-free culture medium composition comprises a GSK3 inhibitor, a MEK inhibitor and a TGFβ inhibitor.

9. The induced pluripotent cell, cell line thereof, or population thereof of claim 1, wherein the induced pluripotent cell is a single cell dissociated induced pluripotent cell.

10. The induced pluripotent cell, cell line thereof, or population thereof of claim 1, wherein the Rock inhibitor is thiazovivin.

11. The induced pluripotent cell, cell line thereof, or population thereof of claim 1, wherein the induced pluripotent cell is an isolated cell expressing one or more markers of pluripotency.

12. The induced pluripotent cell, cell line thereof, or population thereof of claim 11, wherein the induced pluripotent cell has a higher clonality than pluripotent cells not cultured in the feeder-free culture medium composition.

13. The induced pluripotent cell, cell line thereof, or population thereof of claim 11, wherein the population of induced pluripotent cells is an isolated clonal population of a single induced pluripotent cell.

14. An isolated induced pluripotent cell, a cell line thereof, or a population thereof, wherein the cell:
   (a) is in contact with a feeder-free culture medium composition comprising a Rock inhibitor, and one or more of a GSK3 inhibitor, a MEK inhibitor and a TGFβ inhibitor;
   (b) comprises one or more exogenous polynucleotides encoding proteins comprising Oct4, and optionally, one or more of Sox2 and Klf4;
   (c) is a naïve human induced pluripotent stem cell (iPSC) with ground state pluripotency; and
   (d) the iPSC (i) exhibits reactivated expression of one or more of GATA6, CDX2, or CGB, or (ii) is a cell in a colony having a domed morpholgy.

15. The pluripotent cell, cell line thereof, or population thereof of claim 14, wherein the induced pluripotent cell has a higher clonality than pluripotent cells not cultured in said feeder-free culture medium composition; or wherein the population of induced pluripotent cells is a clonal population.

16. The induced pluripotent cell, cell line thereof, or population thereof of claim 1, wherein (a) the ROCK inhibitor is thiazovivin or Y27632; (b) the GSK3 inhibitor is CHIR99021 or BIO; (c) the MEK inhibitor is PD98059 or PD0325901, and (d) the TGFβ inhibitor is A-83-01 or SB431542.

17. The induced pluripotent cell, cell line thereof, or population thereof of claim 14, wherein (a) the ROCK inhibitor is thiazovivin or Y27632; (b) the GSK3 inhibitor is CHIR99021 or BIO; (c) the MEK inhibitor is PD98059 or PD0325901, and (d) the TGFβ inhibitor is A-83-01 or SB431542.

18. The induced pluripotent cell, cell line thereof, or population thereof of claim 11, wherein (a) the ROCK inhibitor is thiazovivin or Y27632; (b) the GSK3 inhibitor is CHIR99021 or BIO; (c) the MEK inhibitor is PD98059 or PD0325901, and (d) the TGFβ inhibitor is A-83-01 or SB431542.

19. The induced pluripotent cell, cell line thereof, or population thereof of claim 1, wherein the induced pluripotent cell has improved genomic stability, as indicated by a lower propensity for genomic abnormalities compared to pluripotent cells that have not been contacted with the feeder-free culture medium composition.

20. The induced pluripotent cell, cell line thereof, or population thereof of claim 1, wherein the iPSC is a cell in a colony having a domed morphology.

* * * * *

UNITED STATES PATENT AND TRADEMARK OFFICE
CERTIFICATE OF CORRECTION

PATENT NO. : 10,844,356 B2
APPLICATION NO. : 15/639628
DATED : November 24, 2020
INVENTOR(S) : Bahram Valamehr, Ramzey Abujarour and Peter Flynn It is certified that error appears in the above-identified patent and that said Letters Patent is hereby corrected as shown below:

In the Claims

Column 66, Line 37, in the last line of Claim 14, delete "domed morpholgy" and insert --domed morphology--

Signed and Sealed this
Fourth Day of February, 2025

Coke Morgan Stewart
*Acting Director of the United States Patent and Trademark Office*